(12) United States Patent
Harada et al.

(10) Patent No.: US 8,193,378 B2
(45) Date of Patent: Jun. 5, 2012

(54) 2H-CHROMENE COMPOUND AND DERIVATIVE THEREOF

(75) Inventors: Hironori Harada, Tokyo (JP); Kazuyuki Hattori, Tokyo (JP); Kazuya Fujita, Tokyo (JP); Sunao Imada, Tokyo (JP); Tatsuaki Morokata, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 13/131,343

(22) PCT Filed: Dec. 4, 2009

(86) PCT No.: PCT/JP2009/070398
§ 371 (c)(1),
(2), (4) Date: May 26, 2011

(87) PCT Pub. No.: WO2010/064707
PCT Pub. Date: Jun. 10, 2010

(65) Prior Publication Data
US 2011/0230463 A1    Sep. 22, 2011

(30) Foreign Application Priority Data
Dec. 5, 2008    (JP) .............................. P2008-311445

(51) Int. Cl.
*C07D 311/00* (2006.01)
(52) U.S. Cl. ....................................... 549/407
(58) Field of Classification Search .................... 549/407
See application file for complete search history.

(56) References Cited

U.S. PATENT DOCUMENTS 6,124,347 A * 9/2000 Ishii et al. ..................... 514/456

FOREIGN PATENT DOCUMENTS

| | | |
|---|---|---|
| JP | 11-106381 | 4/1999 |
| WO | 98/38156 | 9/1998 |
| WO | 01/21577 | 3/2001 |
| WO | 03/061567 | 7/2003 |
| WO | 2005/000833 | 1/2005 |
| WO | 2005/020882 | 3/2005 |
| WO | 2006/001463 | 1/2006 |
| WO | 2006/064757 | 6/2006 |
| WO | 2007/129473 | 11/2007 |

* cited by examiner

*Primary Examiner* — Nizal Chandrakumar
(74) *Attorney, Agent, or Firm* — Fitzpatrick, Cella, Harper & Scinto

(57) ABSTRACT

Provided is a compound which has an excellent $S1P_1$ agonist action, and is useful particularly as an active ingredient for an agent for preventing and/or treating a disease induced by undesirable lymphocyte infiltration or a disease induced by abnormal proliferation or accumulation of cells. According to the present invention, a 2H-chromene compound or a derivative thereof which has an excellent $S1P_1$ agonist action, and is useful particularly as an active ingredient of an agent for preventing and/or treating a disease induced by undesirable lymphocyte infiltration or a disease induced by abnormal proliferation or accumulation of cells can be provided. The 2H-chromene compound and a derivative thereof which are the compounds of the present invention have an $S1P_1$ agonist action, and can be used particularly for prevention and/or treatment of a disease induced by undesirable lymphocyte infiltration or a disease induced by abnormal proliferation or accumulation of cells.

14 Claims, No Drawings

2H-CHROMENE COMPOUND AND DERIVATIVE THEREOF

TECHNICAL FIELD

The present invention relates to a 2H-chromene compound and a derivative thereof, which are useful as an active ingredient for a pharmaceutical composition, particularly a pharmaceutical composition for preventing or treating diseases induced by undesirable lymphocyte infiltration or diseases induced by abnormal proliferation or accumulation of cells.

BACKGROUND ART

Sphingosine 1-phosphate is a metabolite of sphingolipid which is a physiologically active substance secreted from an activated platelet (Annual Review Biochemistry, 2004, Vol. 73, pp. 321-354). The sphingosine 1-phosphate receptor is a G-protein-binding type, and belongs to an Edg-family which is the endothelial differentiation gene. Up to now, five receptors of $S1P_1$ (Edg1), $S1P_2$ (Edg5), $S1P_3$ (Edg3), $S1P_4$ (Edg6), and $S1P_5$ (Edg8) have been found. All of these receptors are broadly distributed in cells and tissues throughout the body, but $S1P_1$, $S1P_3$, and $S1P_4$ are predominantly expressed in lymphocyte and endothelial cells, $S1P_2$ is predominantly expressed in vascular smooth muscle cells, $S1P_5$ is predominantly expressed in brain and spleen, and amino acid sequences thereof are well-conserved among humans and rodents (Annual Review Biochemistry, 2004, Vol. 73, pp. 321-354).

Many receptors bind to G-proteins by stimulation of sphingosine 1-phosphate. $S1P_1$ binds to $G_{i/o}$, $S1P_2$ and $S1P_3$ binds to $G_{i/o}$, $G_q$, $G_{12/13}$, and $G_s$, $S1P_4$ binds to $G_{i/o}$ $G_{12/13}$, and $G_s$, $S1P_5$ binds to $G_{i/o}$ and $G_{12/13}$, and cell proliferation caused by activation of MAPK, changes in the cytoskeletal system and cell infiltration caused by activation of Rac (and/or Rho), and production of cytokine and mediators caused by activation of PLC and calcium influx into cell, and the like (Annual Review Biochemistry, 2004, Vol. 73, pp. 321-354) are induced.

It has been known that through the stimulating action of $S1P_1$ of sphingosine 1-phosphate, migration of lymphocyte, inhibition of apoptosis, production of cytokine, and sequestration of lymphocytes in the thymus and other secondary lymphoid tissues are induced, and angioplasty in vascular endothelial cells is promoted (Nature Review Immunology, 2005, Vol. 5, pp. 560-570). On the other hand, expression of $S1P_3$ is also found on cardiomyocyte, and a transient decrease in the heart rate (infrequent pulse) or in the blood pressure through the stimulation of sphingosine 1-phosphate is observed (Japanese Journal of Pharmacology, 2000, Vol. 82, pp. 338-342). Infrequent pulse is not observed through the stimulation of sphingosine 1-phosphate in knockout mice wherein $S1P_3$ is genetically deficient (Journal of Pharmacology and Experimental Therapeutics, 2004, Vol. 309, pp. 758-768).

It has been known that FTY720 and an FTY720 phosphate which is an active main body thereof have an excellent $S1P_1$ agonist action and thus induce lymphocyte sequestration, and their effects on skin graft or multiple sclerosis, which are autoimmune diseases, is reported (Cellular & Molecular Immunology, 2005, Vol. 2, No. 6, pp. 439-448; and The New England Journal of Medicine, 2006, Vol. 355, pp. 1124-40). However, there have also been reported side effects such as infrequent pulse, reduced lung function (Transplantation, 2006, 82, pp. 1689-1967). It is reported that the FTY720 phosphate has a non-selective agonist action on $S1P_3$, $S1P_4$, and $S1P_5$ (Science, 2002, Vol. 296, pp. 346-349), and between them, a clinical trial result that infrequent pulse induced by a stimulating action through $S1P_3$ is expressed with high frequency as an undesirable side-effect has been reported (Journal of American Society of Nephrology, 2002, Vol. 13, pp. 1073-1083).

As a compound having an $S1P_1$ agonist action, Patent Document 1 discloses a compound of the following general formula (A):

[Chem. 1]

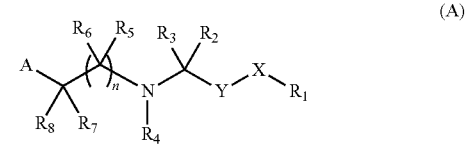

(A)

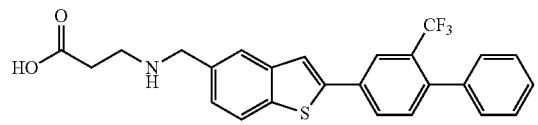

(Example 1)

[wherein n represents 1 or 2; A represents —C(O)OR$_9$ or the like; R$_9$ represents hydrogen or alkyl; X represents a bond, $C_{1-4}$ alkylene, —X$_1$OX$_2$—, or the like, in which X$_1$ and X$_2$ are independently selected from a bond and $C_{1-3}$ alkylene; Y represents a condensed 5,6- or 6,6-hetero bicyclic ring system containing at least one aromatic ring, in which the condensed bicyclic ring system of Y may be substituted, if desired; R$_1$ is selected from $C_{6-10}$ aryl and $C_{2-9}$ heteroaryl, in which any aryl or heteroaryl is substituted with $C_{6-10}$ aryl $C_{0-4}$ alkyl, $C_{2-9}$ heteroaryl, $C_{0-4}$ alkyl, $C_{1-6}$ alkyl, or the like, if desired, R$_2$, R$_3$, R$_5$, R$_6$, R$_7$, and R$_8$ independently represent hydrogen, $C_{1-6}$ alkyl, halo, or the like; R$_4$ represents hydrogen or $C_{1-6}$ alkyl; or R$_7$ and any one of R$_2$, R$_4$ or R$_5$ are combined with an atom to which they bind to form a 4- to 7-membered ring; in which the 4- to 7-membered ring is saturated or partially unsaturated] and a pharmaceutically acceptable salt, a hydrate, a solvate, an isomer, and a prodrug thereof (for details, refer to Patent Document 1), and as a specific compound thereof, for example, the benzothienyl compound above is disclosed as Example 1.

Furthermore, Patent Document 2 discloses that a compound of the following general formula (B):

[Chem. 2]

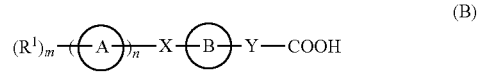

(B)

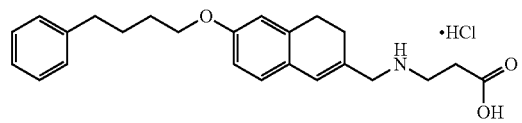

(Example 31-06)

[in the general formula, Ring A represents a cyclic group; Ring B represents a cyclic group which may have a substituent; X represents a spacer having one to eight atoms in the main chain, or the like; Y represents a spacer having one to ten atoms in the main chain, or the like; n represents 0 or 1; in the case where n is 0, m represents 1, and further, $R^1$ represents a hydrogen atom or a substituent; in the case where n is 1, m represents 0 or an integer of 1 to 7, and further, $R^1$ represents a substituent (when m is 2 or more, a plurality of $R^1$ may be the same as or different from each other)], a salt thereof, a solvate thereof, or a prodrug thereof (for details, refer to Patent Document 2) has an S1P receptor-binding ability, and as a specific compound thereof, for example, a tetrahydronaphthalene derivative is disclosed as Example 31-06.

Moreover, Patent Document 3 discloses that a compound of the following general formula (C):

[Chem. 3]

(C)

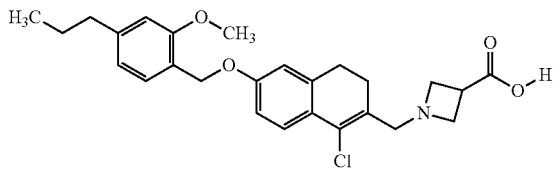

(Example 37-6)

[wherein Ring A represents a cyclic group, Ring B represents a cyclic group which may further have a substituent, X represents a binding arm or a spacer having one to eight atoms in the main chain, in which one atom of the spacer may be combined with a substituent of the Ring B to form a ring which may have a substituent, Y represents a binding arm or a spacer having one to ten atoms in the main chain, in which one atom of the spacer may be combined with a substituent of the Ring B to form a ring which may have a substituent, Z represents an acidic group which may be protected, and n represents 0 or 1, provided that in the case where n is 0, m represents 1, and further, $R^1$ represents a hydrogen atom or a substituent, in the case where n is 1, m represents 0 or an integer of 1 to 7, and further, $R^1$ represents a substituent (when m is 2 or more, a plurality of $R^1$s may be the same as or different from each other)], a salt thereof, an N-oxide thereof, a solvate thereof, or a prodrug thereof as a compound having an S1P receptor-binding ability. As a specific compound thereof, for example, a tetrahydronaphthalene derivative represented by Example 37-6 is disclosed.

However, up to now, there has been a desire for a novel and highly stable $S1P_1$ agonist having the potent $S1P_1$ agonist action of a sphingosine 1-phosphate, and correspondingly, having an excellent lymphocyte sequestering action, and further, having no undesirable actions such as infrequent pulse, reduced lung function, and the like, which have been reported with regard to conventional $S1P_1$ agonists.

PRIOR ART DOCUMENT

Patent Document

[Patent Document 1] Pamphlet of International Publication WO 2005/000833

[Patent Document 2] Pamphlet of International Publication WO 2005/020882

[Patent Document 3] Pamphlet of International Publication WO 2006/064757

DISCLOSURE OF INVENTION

Problems to Be Solved by the Invention

A compound which is useful as an active ingredient of a pharmaceutical composition, particularly a pharmaceutical composition for preventing or treating diseases induced by undesirable lymphocyte infiltration or diseases induced by abnormal proliferation or accumulation of cells, on the basis of an $S1P_1$ agonist action, is provided.

Means for Solving the Problems

The present inventors have made extensive studies on a compound having an $S1P_1$ agonist action, and as a result, they have found that a 2H-chromene compound represented by the formula (I) below or a derivative thereof has an excellent $S1P_1$ agonist action and is useful as an active ingredient of a pharmaceutical composition for preventing or treating diseases induced by lymphocytic infiltration or diseases induced by abnormal proliferation or accumulation of cells, thereby completing the present invention.

Thus, the present invention relates to a 2H-chromene compound represented by the following formula (1):

[Chem. 4]

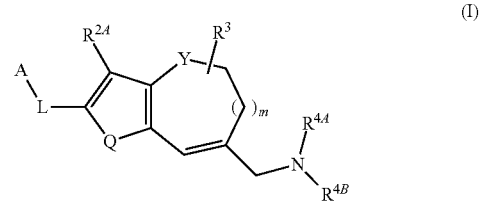

(I)

(wherein

A represents lower alkyl, cycloalkyl, aryl, or heteroaryl, wherein aryl and heteroaryl may respectively be substituted with one to five $R^1$s which are the same as or different from each other, $R^1$ represents halogen, —CN, —$NO_2$, lower alkyl, lower alkenyl, lower alkynyl, halogeno-lower alkyl, aryl, heteroaryl, cycloalkyl, —OH, —O-(lower alkyl), —O-(halogeno-lower alkyl), —O-(aryl), —O-(cycloalkyl), —O-(heteroaryl), —$NH_2$, —NH(lower alkyl), —NH(halogeno-lower alkyl), —N(lower alkyl)$_2$, or cyclic amino, wherein aryl, heteroaryl, cycloalkyl, and cyclic amino may respectively be substituted with one to five substituents which are the same as or different from each other and selected from the group consisting of halogen, —CN, lower alkyl and halogeno-lower alkyl, L represents lower alkylene, lower alkenylene, lower alkynylene, -(lower alkylene)-O—, —O-(lower alkylene)-, or -(lower alkylene)-O-(lower alkylene)-, Q represents S or —C($R^{2B}$)═C($R^{2C}$)—, $R^{2A}$, $R^{2B}$, and $R^{2C}$ are the same as or different from each other and represent —H, halogen, lower alkyl, halogeno-lower alkyl, —O-(lower alkyl), or —O-(halogeno-lower alkyl), Y represents O, S, or —$CH_2$—, provided that wherein Y is —$CH_2$—, Q is S, m represents 0 or 1, $R^3$ represents —H, halogen, lower alkyl, or aryl, $R^{4A}$ represents —H or lower alkyl, $R^{4B}$ represents lower alkyl substituted with a group selected from Group G or cycloalkyl substituted with a group selected from Group G, or $R^{4A}$ and $R^{4B}$ are combined with N to which they bind to form cyclic amino substituted with a group selected from Group G, in which the cyclic amino may further contain one to four substituents which are the same as or different from each other and selected from the group consisting of halogen, lower alkyl, and halogeno-lower alkyl, and Group G represents, —C(=O)OH, tetrazolyl, —C(=O)NHS(=O)₂(lower alkyl), -(lower alkylene)-C(=O)OH, or

[Chem. 5]

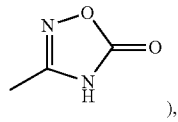

), or a derivative thereof, or a salt thereof.

In this regard, in a case where the symbols in any of the chemical formulae in the present specification are also used in other chemical formulae, the same symbols denote the same meanings, unless specifically described otherwise.

Further, the present invention relates to a pharmaceutical composition, which includes the 2H-chromene compound of the formula (I), or a derivative thereof or a salt thereof and a pharmaceutically acceptable excipient, in particular, (1) an S1P₁ agonist, (2) a pharmaceutical composition for preventing or treating diseases induced by undesirable lymphocyte infiltration associated with S1P₁, (3) a pharmaceutical composition for preventing or treating rejection or graft-versus-host diseases during organ, bone marrow, or tissue transplantation, autoimmune diseases, or inflammatory diseases in humans or animals, (4) a pharmaceutical composition for preventing or treating rejection or graft-versus-host diseases during organ, bone marrow, or tissue transplantation in humans or animals, (5) a pharmaceutical composition for preventing or treating multiple sclerosis, (6) a pharmaceutical composition for preventing or treating diseases induced by abnormal proliferation or accumulation of cells associated with S1P₁, and (7) a pharmaceutical composition for preventing or treating cancer or leukemia.

Furthermore, the present invention relates to a method for preventing or treating diseases induced by undesirable lymphocyte infiltration associated with S1P₁, particularly, rejection or graft-versus-host diseases during organ, bone marrow, or tissue transplantation, or multiple sclerosis in humans or animals, which involves administering to a patient an effective amount of the 2H-chromene compound of the formula (I) or a derivative thereof or a salt thereof. Further, the present invention includes use of the 2H-chromene compound of the formula (I) or a derivative thereof or a salt thereof for prevention or treatment of diseases induced by undesirable lymphocyte infiltration associated with S1P₁, particularly rejection or graft-versus-host diseases during organ, bone marrow, or tissue transplantation, or multiple sclerosis in humans or animals, and the 2H-chromene compound of the formula (I) or a derivative thereof or a salt thereof to be used for prevention or treatment of diseases induced by undesirable lymphocyte infiltration associated with S1P₁, particularly rejection or graft-versus-host diseases during organ, bone marrow, or tissue transplantation, or multiple sclerosis in humans or animals.

Effects of the Invention

The compound of the formula (I) or a salt thereof of the present invention has an S1P₁ agonist action and can be used for prevention or treatment of diseases induced by undesirable lymphocyte infiltration, for example, autoimmune diseases or inflammatory diseases such as rejection or graft-versus-host diseases during organ, bone marrow, or tissue transplantation, rheumatoid arthritis, multiple sclerosis, systemic lupus erythematosus, nephrotic syndrome, encephalomeningitis, myasthenia gravis, pancreatitis, hepatitis, nephritis, diabetes, lung disorders, asthma, atopic dermatitis, inflammatory bowel disease, arteriosclerosis, ischemic reperfusion disorder, and diseases induced by abnormal proliferation or accumulation of cells, for example, cancer, leukemia, and the like.

BEST MODE FOR CARRYING OUT THE INVENTION

Hereinbelow, the present invention will be explained in detail.

In the specification, the "halogen" means F, Cl, Br, or I. Preferably, examples thereof include F and Cl.

In the present specification, the "lower alkyl" is linear or branched alkyl having one to six carbon atoms (hereinafter simply referred to as $C_{1-6}$), and examples thereof include methyl, ethyl, n-propyl, isopropyl, n-butyl, isobutyl, sec-butyl, tert-butyl, n-pentyl, n-hexyl, and the like, in another embodiment, $C_{1-4}$ alkyl, and in a further embodiment, methyl, ethyl, and isopropyl.

The "lower alkenyl" is linear or branched $C_{2-6}$ alkenyl, and examples thereof include vinyl, propenyl, butenyl, pentenyl, 1-methylvinyl, 1-methyl-2-propenyl, 1,3-butadienyl, 1,3-pentadienyl, and the like, and in another embodiment, $C_{2-4}$ alkenyl.

The "lower alkylene" is linear or branched $C_{2-6}$ alkylene and examples thereof include methylene, ethylene, trimethylene, tetramethylene, pentamethylene, hexamethylene, propylene, methylmethylene, ethylethylene, 1,2-dimethylethylene, 1,1,2,2-tetramethylethylene, and the like, in another embodiment, $C_{1-4}$ alkylene, and in a further embodiment, methylene and ethylene.

The "lower alkenylene" is linear or branched $C_{2-6}$ alkenylene and examples thereof include vinylene, ethylidene, propenylene, butenylene, pentenylene, hexenylene, 1,3-butadienylene, 1,3-pentadienylene, and the like, in another embodiment, $C_{2-4}$ alkenylen, and in a further embodiment, vinylene and ethylidene.

The "lower alkynylene" is linear or branched $C_{2-6}$ alkynylene and examples thereof include ethynylene, propynylene, butynylene, pentynylene, hexynylene, 1,3-butadiynylene, 1,3-pentadiynylene, and the like, in another embodiment, $C_{2-4}$ alkynylene, and in a further embodiment, ethynylene, propynylene, butynylene, and pentynylene.

The "halogeno-lower alkyl" is $C_{1-6}$ alkyl substituted with one or more halogen atoms, in another embodiment, lower alkyl substituted with one to five halogen atoms, in a further embodiment, $C_{1-3}$ lower alkyl substituted with one to five halogen atoms, and in an even further embodiment, examples thereof include —CF₃, —CH₂CF₃, —CH(CH₃)CF₃, and —CH(CH₂F)₂.

The "cycloalkyl" is a $C_{3-10}$ saturated hydrocarbon ring group, which may have a bridge. Examples thereof include cyclopropyl, cyclobutyl, cyclopentyl, cyclohexyl, cycloheptyl, cyclooctyl, adamantyl, and the like, in another embodiment, $C_{3-8}$ cycloalkyl, in a further embodiment, $C_{3-6}$ cycloalkyl, and in an even further embodiment, cyclopropyl, cyclopentyl, and cyclohexyl.

The "aryl" is a $C_{6-14}$ monocyclic to tricyclic aromatic hydrocarbon ring group, and examples thereof include phenyl and naphthyl, and in another embodiment, phenyl.

The "heteroaryl" is 5- to 6-membered monocyclic heteroaryl containing one to four hetero atoms selected from N, S, and O, and bicyclic heteroaryl formed by condensation thereof with a benzene ring or 5- to 6-membered monocyclic heteroaryl, and may be partially saturated. In another embodiment, examples thereof include pyridyl, pyrrolyl, pyrazinyl, pyrimidinyl, pyridazinyl, imidazolyl, triazolyl, triazinyl, tetrazolyl, thiazolyl, pyrazolyl, isothiazolyl, oxazolyl, isoxazolyl, thiadiazolyl, oxadiazolyl, thienyl, furyl, benzothiazolyl, and indolyl, in another embodiment, heteroaryl of a 5-membered ring, which may be condensed with a benzene ring, and in an even further embodiment, pyrrolyl, imidazolyl, thiazolyl, thienyl, benzothiazolyl, and indolyl.

The "nitrogen-containing monocyclic heteroaryl" means monocyclic heteroaryl, in which one of the ring-constituting atoms is necessarily N and may have one to two hetero atoms selected from N, S, and O as the ring-constituting atom, and in another embodiment, examples thereof include a 5- to 6-membered ring, in a further embodiment, pyridyl, pyrrolyl, pyrazinyl, pyrimidinyl, pyridazinyl, imidazolyl, triazolyl, tetrazolyl, thiazolyl, pyrazolyl, isothiazolyl, oxazolyl, isoxazolyl, thiadiazolyl, oxadiazolyl, and the like, in an even further embodiment, 5-membered ring, and in an even further embodiment, pyrrolyl and imidazolyl.

The "cyclic amino" means monocyclic to tricyclic heterocycloalkyl, in which one of the ring-constituting atoms is necessarily N, may have one to two hetero atoms selected from N, S, and O as the ring-constituting atom, and may have a partially unsaturated bond. In another embodiment, it is a ring having a reduction number of 4 to 9, in a further embodiment, examples thereof include azetidinyl, pyrrolidinyl, piperidinyl, morpholinyl, homopiperidinyl, 3-azabicyclo[3.1.0]hexanyl, tetrahydropyridyl, octahydrocyclopenta[c]pyrrolyl, quinuclidinyl, and the like, in an even further embodiment, examples thereof include cyclic amino of a 6-membered ring, in an even further embodiment, examples thereof include piperidinyl, piperazinyl, morpholinyl, and tetrahydropyridyl, and in an even further embodiment, examples thereof include azetidinyl, pyrrolidinyl, piperidinyl, and tetrahydropyridyl.

In the present specification, the expression "which may be substituted with one to five $R^1$s which are the same as or different from each other" means non-substitution or having one to five $R^1$s as the substituents. Further, in the case where a plurality of Ws are present, the $R^1$s may be the same as or different from each other.

Embodiments of the present invention will be described below.

(1) The 2H-chromene compound or a salt thereof, wherein Y is O, Q is —C($R^{2B}$)=C($R^{2C}$)—, and m is 0.

(2) The 2H-chromene compound or a salt thereof, wherein $R^{4A}$ and $R^{4B}$ are combined with N to which they bind to form cyclic amino selected from azetidinyl, pyrrolidinyl, piperidinyl, and tetrahydropyridyl, which is substituted with group(s) selected from Group G and may be substituted with lower alkyl or halogen.

(3) The 2H-chromene compound or a salt thereof, wherein the group represented by Group G is —C(=O)OH or —C(=O) NHS(=O)$_2$CH$_3$.

(4) The 2H-chromene compound or a salt thereof, wherein A is phenyl, pyridyl, or thienyl, which may be substituted with one to three $R^1$s which may be the same as or different from each other.

(5) The 2H-chromene compound or a salt thereof, wherein L is -(lower alkylene)-O—, lower alkenylene, or lower alkynylene.

(6) The 2H-chromene compound or a salt thereof, wherein $R^{2A}$ is —H or lower alkyl, $R^{2B}$ is —H, $R^{2C}$ is —H or halogen, $R^3$ is —H or halogen, $R^1$ is halogen, lower alkyl, halogeno-lower alkyl, phenyl, pyrrolyl, cycloalkyl, —O-(lower alkyl), or —O-(halogeno-lower alkyl), and further, L is —CH$_2$—O—, —CH=CH—, or 3-butynylene.

(7) The 2H-chromene compound or a salt thereof, wherein $R^{4A}$ and $R^{4B}$ are combined with N to which they bind to form piperidinyl or tetrahydropyridyl, which is substituted with —C(=O)OH, L is —CH$_2$—O—, $R^{2A}$ is —H, $R^{2B}$ is —H, $R^{2C}$ is —H or halogen, $R^3$ is —H, and A is phenyl or pyridyl, which is substituted with two $R^1$s which are the same as or different from each other, in which $R^1$ is halogen, halogeno-lower alkyl, —O-(lower alkyl), or —O-(halogeno-lower alkyl).

(8) The 2H-chromene compound or a salt thereof, wherein $R^{4A}$ and $R^{4B}$ are combined with N to which they bind to form piperidinyl which is substituted with —C(=O)OH and A is phenyl which is substituted with two $R^1$s which are the same as or different from each other.

(9) The 2H-chromene compound or a salt thereof, wherein $R^{4A}$ and $R^{4B}$ are combined with N to which they bind to form tetrahydropyridyl which is substituted with —C(=O)OH, A is pyridyl which is substituted with two $R^1$s which are the same as or different from each other.

Examples of the specific compound included in the present invention include the following compounds or the salts thereof:

1-{[7-({3-chloro-4-[(1S)-2,2,2-trifluoro-1-methylethoxy]benzyl}oxy)-2H-chromen-3-yl]methyl}-1,2,5,6-tetrahydropyridine-3-carboxylic acid, 1-({7-[(3-chloro-4-isopropylbenzyl)oxy]-2H-chromen-3-yl}methyl)-1,2,5,6-tetrahydropyridine-3-carboxylic acid, 1-[(7-{[4-isopropoxy-3-(trifluoromethyl)benzyl]oxy}-2H-chromen-3-yl)methyl]-1,2,5,6-tetrahydropyridine-3-carboxylic acid, 1-{[7-({3-chloro-4-[2-fluoro-1-(fluoromethyl)ethoxy]benzyl}oxy)-2H-chromen-3-yl]methyl}-1,2,3,6-tetrahydropyridine-4-carboxylic acid, 1-{[7-({5-chloro-6-[(1S)-2,2,2-trifluoro-1-methylethoxy]pyridin-3-yl}methoxy)-2H-chromen-3-yl]methyl}-1,2,5,6-tetrahydropyridine-3-carboxylic acid, (3R)-1-{[7-({4-[(1,3-difluoropropan-2-yl)oxy]-3-(trifluoromethyl)benzyl}oxy)-5-fluoro-2H-chromen-3-yl]methyl}piperidine-3-carboxylic acid, 1-[(7-{[4-cyclopentyl-3-(trifluoromethyl)benzyl]oxy}-2H-chromen-3-yl)methyl]-1,2,5,6-tetrahydropyridine-3-carboxylic acid, (3R)-1-[7-({3-chloro-4-[(1,3-difluoropropan-2-yl)oxy]benzyl oxy)-5-fluoro-2H-chromen-3-yl]methyl}piperidine-3-carboxylic acid, (3S)-1-{[7-({4-[(1,3-difluoropropan-2-yl)oxy]-3-(trifluoromethyl)benzyl}oxy)-5-fluoro-2H-chromen-3-yl]methyl}piperidine-3-carboxylic acid, (3R)-1-[(7-{[4-(2,2,2-trifluoroethoxy)-3-(trifluoromethyl)benzyl}oxy]-2H-chromen-3-yl)methyl]piperidine-3-carboxylic acid, (3R)-1-[(7-[3-(trifluoromethyl)-4-{[(2S)-1,1,1-trifluoropropan-2-yl]oxy]benzyl}oxy)-2H-chromen-3-yl)methyl]piperidine-3-carboxylic acid, (3S)-1-[(7-{[4-(2,2,2-trifluoroethoxy)-3-(trifluoromethyl)benzyl]oxy}-5-fluoro-2H-chromen-3-yl)methyl]piperidine-3-carboxylic acid, (3R)-1-{[7-({4-[(1,3-difluoropropan-2-yl)oxy]-3-(trifluoromethyl)benzyl}oxy)-5-fluoro-2H-chromen-3-yl]methyl}-N-(methylsulfonyl)piperidine-3-carboxamide, or 1-[(7-{[4-(2,2,2-trifluoroethoxy)-3-(trifluoromethyl)benzyl]oxy}-2H-chromen-3-yl)methyl]piperidine-4-carboxylic acid.

The compound of the formula (I) may exist in the form of tautomers or geometrical isomers depending on the kind of the substituents. In the present specification, the compound of the formula (I) shall be described in only one form of isomer, yet the present invention includes other isomers, isolated forms of the isomers, or a mixture thereof.

In addition, the compound of the formula (I) may have asymmetric carbon atoms or axial chirality in some cases, and correspondingly, it may exist in the form of optical isomers. The present invention includes both an isolated form of the optical isomers of the compound of the formula (I) or a mixture thereof.

Moreover, the present invention also includes a pharmaceutically acceptable prodrug of the compound represented by the formula (I). The pharmaceutically acceptable prodrug is a compound having a group which can be converted into an amino group, a hydroxyl group, a carboxyl group, or the like through solvolysis or under physiological conditions. Examples of the group forming the prodrug include the groups described in Prog. Med., 5, 2157-2161 (1985) and Pharmaceutical Research and Development, Drug Design, Hirokawa Publishing Company (1990), Vol. 7, 163-198.

Furthermore, the salt of the compound of the formula (I) is a pharmaceutically acceptable salt of the compound of the formula (I) and may form an acid addition salt or a salt with a base depending on the kind of substituents. Specific examples thereof include acid addition salts with inorganic acids such as hydrochloric acid, hydrobromic acid, hydroiodic acid, sulfuric acid, nitric acid, phosphoric acid, and the like, and with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditolyltartaric acid, citric acid, methanesulfonic acid, ethanesulfonic acid, benzenesulfonic acid, p-toluenesulfonic acid, aspartic acid, glutamic acid, and the like, and salts with inorganic bases such as sodium, potassium, magnesium, calcium, aluminum, and the like or organic bases such as methylamine, ethylamine, ethanolamine, lysine, ornithine, and the like, salts with various amino acids or amino acid derivatives such as acetylleucine and the like, ammonium salts, etc.

Moreover, the present invention also includes various hydrates or solvates, and polymorphic crystal substances of the compound of the formula (I) and a salt thereof. In addition, the present invention also includes compounds labeled with various radioactive or non-radioactive isotopes.

In the present specification, the following abbreviations may be used in some cases.

ADDP=1,1'-(azodicarbonyl)dipiperidine, AIBN=2,2'-azobisisobutyronitrile, AcOH=acetic acid, CDI=1,1'-carbonylbis-1H-imidazole, DAST=(diethylamino)sulfur trifluoride, DBU=1,8-diazabicyclo[5.4.0]undec-7-ene, DCC=dicyclohexylcarbodiimide, DCE=dichloroethane, DCM=dichloromethane, DIBAL=diisobutylaluminum hydride, DIBOC=di-tert-butyl dicarbonate, DIC=N,N'-diisopropylcarbodiimide, DIPEA=diisopropylethylamine, DMA=N,N'-dimethylacetamide, DMAP=4-(N,N'-dimethylamino)pyridine, DME=dimethoxyethane, DMF=N,N'-dimethylformamide, DMSO=dimethylsulfoxide, DPPA=diphenylphosphorylazide, DPPP=1,3-bis(diphenylphosphino)propane, EDCI.HCl=N-[3-(dimethylamino)propyl]-N'-ethylcarboxamide hydrochloride, Et=ethyl, Et₂O=diethylether, TEA=triethylamine, EtOAc=ethyl acetate, EtOH=ethanol, HOBt=1-hydroxy-1H-benzotriazole, IPE=diisopropylether, t-BuOK=potassium tertiary butoxide, LAH=lithium aluminum hydride, MS4 Angstrom=molecular sieves 4 Angstrom, MeCN=acetonitrile, MeOH=methanol, MgSO₄=anhydrous magnesium sulfate, NBS=N-bromosuccinimide, NCS=N-chlorosuccinimide, NMP=N-methylpyrrolidone, NT=not tested, Na₂SO₄=anhydrous sodium sulfate, NaBH(OAc)₃=sodium triacetoxyborohydride, NaBH₄=sodium borohydride, NaOEt=sodium ethoxide, NaOH=sodium hydroxide, NaOMe=sodium methoxide, TBP=tri-normal butylphosphine, PDC=pyridinium dichromate, POCl₃=phosphorous oxychloride, PPh₃= triphenylphosphine, Pd(OAc)₂=palladium (II) acetate, Pd(PPh₃)₄=tetrakis(triphenylphosphine)palladium (0), TEA=triethylamine, TFA=trifluoroacetic acid, THF=tetrahydrofuran, TMEDA=N,N,N'N'-tetramethylethylenediamine, Tf=CF₃S(=O)₂—, brine=saturated brine, i-PrOH=2-propanol, n-BuLi=normal butyllithium, n-BuOH=normal butylalcohol, t-BuOH=tertiary butylalcohol, and tert=tertiary.

(Preparation Methods)

The compound of the formula (I) and a salt thereof can be prepared using the characteristics based on the basic structure or the type of substituents thereof and by applying various known synthesis methods. During the preparation, replacing the relevant functional group with a suitable protective group (a group that can be easily converted into the functional group) at the stage from starting material to an intermediate may be effective depending on the type of the functional group in production technology in some cases. The protective group for such a functional group may include, for example, the protective groups described in "Greene's Protective Groups in Organic Synthesis (4ᵗʰ Ed., 2006)" written by P. G. M. Wuts and T. W. Greene, and one of these may be selected and used as necessary depending on the reaction conditions. In this kind of method, a desired compound can be obtained by introducing the protective group, by carrying out the reaction and by eliminating the protective group, as necessary.

In addition, the prodrug of the compound of the formula (I) can be prepared by introducing a specific group or by carrying out the reaction using the obtained compound of the formula (I) at the stage from a starting material to an intermediate, just as in the case of the above-mentioned protective group. The reaction can be carried out using methods known to those skilled in the art, such as ordinary esterification, amidation, dehydration, and the like.

Hereinbelow, the representative preparation methods for the compound of the formula (I) will be described. Each of the production processes may also be carried out with reference to the References appended in the present description. Further, the preparation methods of the present invention are not limited to the examples as shown below.

<Production Process 1>

[Chem. 6]

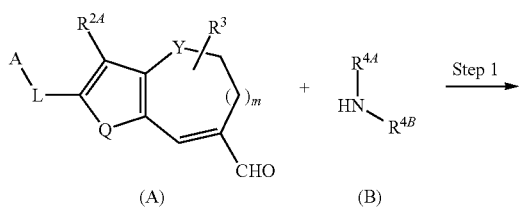

-continued

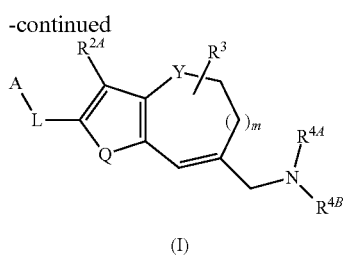

(I)

The compound (I) of the present invention can be obtained by subjecting a compound (A) and a compound (B) to reductive amination.

The process in Step 1 is reductive amination. The compound (A) and the compound (B) are used in equivalent amounts or with either thereof in an excess amount, and the mixture is stirred under any condition from at −45° C. to under refluxing, particularly, from 0° C. to room temperature, usually for 0.1 hour to 5 days, in a vehicle which is inert to the reaction, in the presence of a reducing agent. Examples of the vehicle include alcohols such as MeOH, EtOH, and the like; ethers such as $Et_2O$, THF, dioxane, DME, and the like; halogenated hydrocarbons such as DCM, DCE, chloroform, and the like; and a mixed vehicle thereof. Examples of the reducing agent include $NaBH_3CN$, $NaBH(OAc)_3$, $NaBH_4$, and the like. It may be preferable in some cases to carry out the reaction in the presence of a dehydrating agent such as molecular sieves and the like, or an acid such as acetic acid, hydrochloric acid, a titanium (IV) isopropoxide complex, and the like. An imine that is a reaction intermediate may be isolated as a stable intermediate, and by reducing the imine intermediate, the compound (I) can be obtained. Further, the reaction can be carried out in a vehicle such as MeOH, EtOH, EtOAc, and the like in the presence or absence of an acid such as acetic acid, hydrochloric acid, and the like, using a reduction catalyst (for example, palladium on carbon, Raney nickel, and the like), instead of the reducing agent. In this case, the reaction is carried out under a hydrogen atmosphere from normal pressure to 50 atmospheres, under any temperature condition from cooling to heating.

[References] (1) "Comprehensive Organic Functional Group Transformations II" written by A. R. Katritzky and R. J. K. Taylor, Vol. 2, Elsevier Pergamon, 2005, (2) "Jikken Kagaku Koza (Courses in Experimental Chemistry) ($5^{th}$ Edition)" edited by The Chemical Society of Japan, Vol. 14 (2005) (Maruzen)

<Production Process 2>

[Chem. 7]

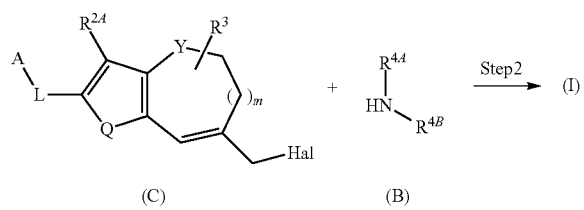

(wherein Hal represents halogen).

The compound (I) of the present invention can be obtained by alkylating the compound (C) with the compound (B).

The process in Step 2 is alkylation. The compound (B) and the compound (C) are used in equivalent amounts or with either thereof in an excess amount, and the mixture is stirred under any temperature condition from cooling to heating and refluxing, preferably from 0° C. to 80° C., usually for 0.1 hour to 5 days, in a vehicle which is inert to the reaction or without a vehicle. Examples of the vehicle include aromatic hydrocarbons; ethers; halogenated hydrocarbons; DMF, DMSO, EtOAc, and MeCN; and a mixed vehicle thereof. It may be advantageous in some cases for the smooth progress of the reaction to carry out the reaction in the presence of an organic base such as TEA, DIPEA, or N-methylmorpholine, and the like, or an inorganic base such as $K_2CO_3$, $Na_2CO_3$ or KOH, and the like. It may be advantageous in some cases for the smooth progress of the reaction to add an inorganic salt such as NaI and the like to a reaction system.

[Reference] "Jikken Kagaku Koza (Courses in Experimental Chemistry) ($5^{th}$ Edition)" edited by The Chemical Society of Japan, Vol. 14 (2005) (Maruzen)

<Intermediate Production Process 1>

[Chem. 8]

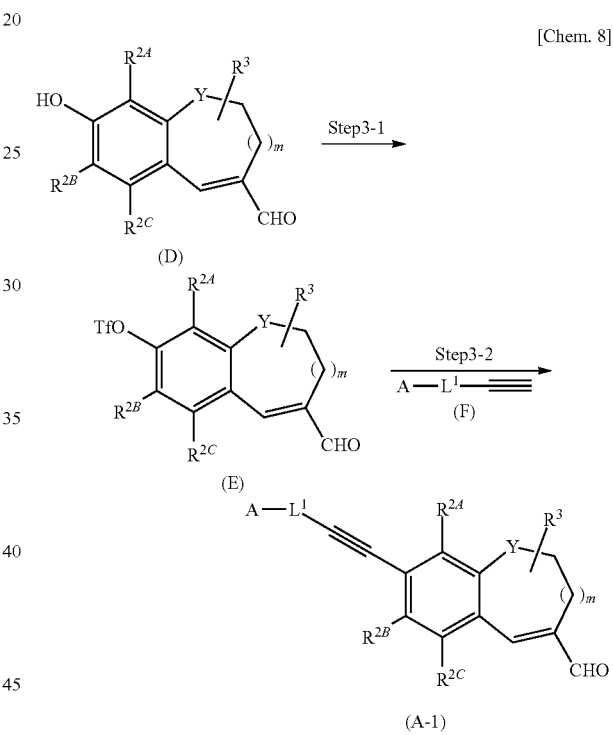

(wherein Tf represents $CF_3S(=O)_2$— and $L^1$ represents lower alkylene or lower alkenylene).

The compound (A-1) can be prepared by a Sonogashira reaction from a compound (D).

The Step 3-1 is triflation. The compound (E) can be prepared by subjecting a compound (D) to undergo a reaction with trifluoromethanesulfonic anhydride. As the vehicle that usually does not disturb the reaction among the halogenated hydrocarbons, the reaction is carried out in the presence of organic bases such as pyridine, TEA, DIPEA, and the like under any temperature condition from −10° C. to ice-cooling. Further, the organic base may be used in combination with a vehicle.

Step 3-2 is a so-called Sonogashira reaction. The compound (A-1) can be prepared by adding a catalytic amount of a Pd(0) catalyst and a base to a compound (E) to allow terminal acetylene to undergo a reaction. It may be advantageous in some cases for the smooth progress of the reaction to add copper iodide to a reaction system. Examples of the vehicle include ethers; aromatic hydrocarbons such as toluene, xylene, and the like; DMF, DMSO, EtOAc; and a mixed vehicle thereof. For example, a base such as TEA, pyrrolidine, and the like may be used in combination with a vehicle. As for a reaction temperature, the reaction can be carried out under any temperature condition from room temperature to under reflux.

[Reference] K. Sonogashira, *Tetrahedron Letters,* 1975, 50, pp. 4467.

<Intermediate Production Process 2>

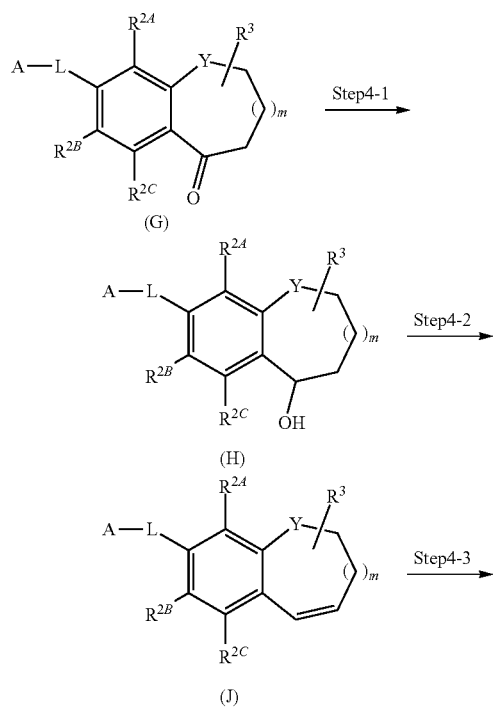

The compound (A-2) can be prepared by reducing a compound (G) and dehydrating it, and formylating the obtained compound (J).

The Step 4-1 is a reduction reaction of a ketone. The compound (G) is treated with an equivalent amount or excess amount of a reducing agent under any temperature condition from cooling to heating, preferably from −20° C. to 80° C., usually for 0.1 hour to 3 days, in a vehicle which is inert to the reaction. Examples of the vehicle include ethers; alcohols; aromatic hydrocarbons; DMF, DMSO, EtOAc, and a mixed vehicle thereof. As the reducing agent, hydride reducing agents such as $NaBH_4$, DIBAL, and the like, metal reducing agents such as sodium, zinc, iron, and the like, and further, the reducing agents in the following References are suitably used.

[References] (1) "Reductions in Organic Chemistry, $2^{nd}$ ed. (ACS Monograph: 188)" written by M. Hudlicky, A C S, 1996, (2) "Comprehensive Organic Transformations" written by R. C. Larock, $2^{nd}$ ed., VCH Publishers, Inc., 1999, (3) "Oxidation and Reduction in Organic Synthesis (Oxford Chemistry Primers 6)" written by T. J. Donohoe, Oxford Science Publications, 2000, (4) "Jikken Kagaku Koza (Courses in Experimental Chemistry) ($5^{th}$ Edition)" edited by The Chemical Society of Japan, Vol. 14 (2005) (Maruzen)

The Step 4-2 is a dehydration reaction. Usually, a starting material is stirred in concentrated sulfuric acid under a warming condition, and then distillation is continued until the eluent no longer exits.

The Step 4-3 is formylation. The compound (A-2) is obtained by the reaction of the compound (J) with a formamide derivative. Here, the formamide derivative means a formamide compound in which lower alkyls or aryls which are the same as or different from each other bind to nitrogen atoms of the formamide. For a Vilsmeier complex prepared by the reaction of the formamide derivative with $POCl_3$, the aromatic ring is subjected to nucleophilic substitution to produce an ammonium salt. This can be hydrolyzed under a basic condition to obtain a formyl product. In this reaction, a compound (J) and a DMF equivalent are used in equivalent amounts or with either thereof in an excess amount, and the mixture is stirred in a vehicle which is inert to the reaction or without a vehicle, in the presence of a halogenating agent. This reaction is carried out under any temperature condition from room temperature to heating and refluxing, usually for 0.1 hour to 5 days. Examples of the vehicle include halogenated hydrocarbons; ethers; or MeCN. The halogenating agent is used so as to derive a DMF derivative into a Vielsmeier complex, and usually, it is not particularly limited as long as it is a reagent used for halogenations of alcohols, but phosphorous pentachloride, $POCl_3$, or the like may be appropriately used.

[Reference] (1) "Strategic Applications of Named Reactions in Organic Synthesis" written by L. Kurti and B. Czako, Elsevier Inc, 2005, pp. 468-469

<Intermediate Production Process 3>

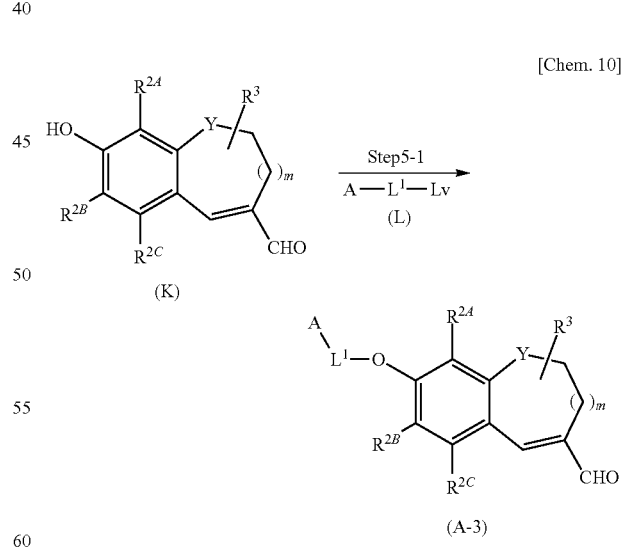

(wherein Lv represents a leaving group).

The compound (A-3) is obtained by the reaction of a compound (K) with a compound (L).

The Step 5-1 is alkylation. Examples of the leaving group Lv include halogen, methanesulfonyloxy, p-toluenesulfonyloxy groups, and the like.

The compound (K) and the compound (L) are used in equivalent amounts or with either thereof in an excess amount, and the mixture is stirred in a vehicle which is inert to the reaction or without a vehicle, under any temperature condition from cooling to heating and refluxing, preferably from 0° C. to 80° C., usually for 0.1 hour to 5 days. Examples of the vehicle include aromatic hydrocarbons; ethers; halogenated hydrocarbons; DMF, DMSO, EtOAc, MeCN; and a mixed vehicle thereof. It may be advantageous in some cases for the smooth progress of the reaction to carry out the reaction in the presence of organic bases such as TEA, DIPEA, N-methylmorpholine, and the like, or inorganic bases such as $K_2CO_3$, $Na_2CO_3$, KOH, and the like. It may be advantageous in some cases for the smooth progress of the reaction to add inorganic salts such as NaI and the like to a reaction system.
[Reference] "Jikken Kagaku Koza (Courses in Experimental Chemistry) (5th Edition)" edited by The Chemical Society of Japan, Vol. 14 (2005) (Maruzen)

<Intermediate Production Process 4>

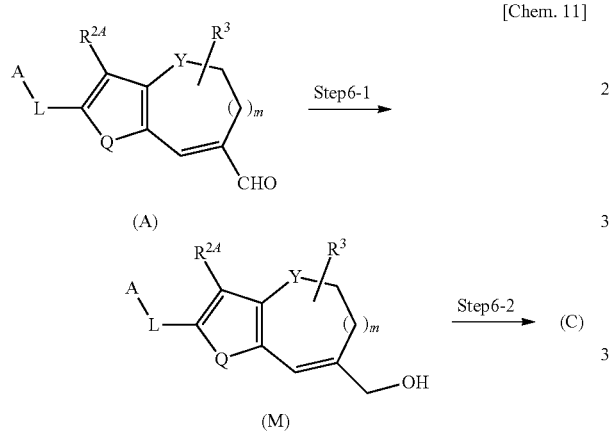

The compound (C) can be obtained from the compound (A) via the compound (M).

The Step 6-1 is reduction. The compound (M) can be obtained by stirring the compound (A) with an equivalent amount or excess amount of a reducing agent in a vehicle which is inert to the reaction, under any temperature condition from cooling to heating, preferably from −20° C. to 80° C., usually for 0.1 hour to 3 days. Examples of the vehicle used are not particularly limited, but include ethers such as diethylether, THF, dioxane, and dimethoxyethane, alcohols such as MeOH, EtOH, 2-propanol, and the like, aromatic hydrocarbons such as benzene, toluene, xylene, and the like, DMF, DMSO, EtOAc, and a mixed vehicle thereof. As the reducing agent, hydride reducing agents such as $NaBH_4$, DIBAL, and the like, metal reducing agents such as sodium, zinc, iron, and the like, and the reducing agents in the following References are suitably used.

[References]
"Reductions in Organic Chemistry, 2nd ed. (ACS Monograph: 188)" written by M. Hudlicky, A C S, 1996
"Comprehensive Organic Transformations" written by R. C. Larock, 2nd ed., VCH Publishers, Inc., 1999
"Oxidation and Reduction in Organic Synthesis (Oxford Chemistry Primers 6)" written by T. J. Donohoe, Oxford Science Publications, 2000
"Jikken Kagaku Koza (Courses in Experimental Chemistry) (5th Edition)" edited by The Chemical Society of Japan, Vol. 14 (2005) (Maruzen)

The Step 6-2 is halogenation. The compound (C) can be obtained by subjecting the compound (M) to halogenation. As the halogenating agent, a halogenating agent for converting a hydroxyl group to halogen is used. The halogenating agent is not particularly limited, but, for example, $PBr_3$, HBr, $BBr_3$, $PCl_3$, $PCl_5$, or the like is used. As the vehicle, ethers are preferable, and for example, THF, diethylether, dimethoxyethane, methyl-t-butylether, dioxane, 2-methyltetrahydrofuran, or the like is used.

<Intermediate Production Process 5>

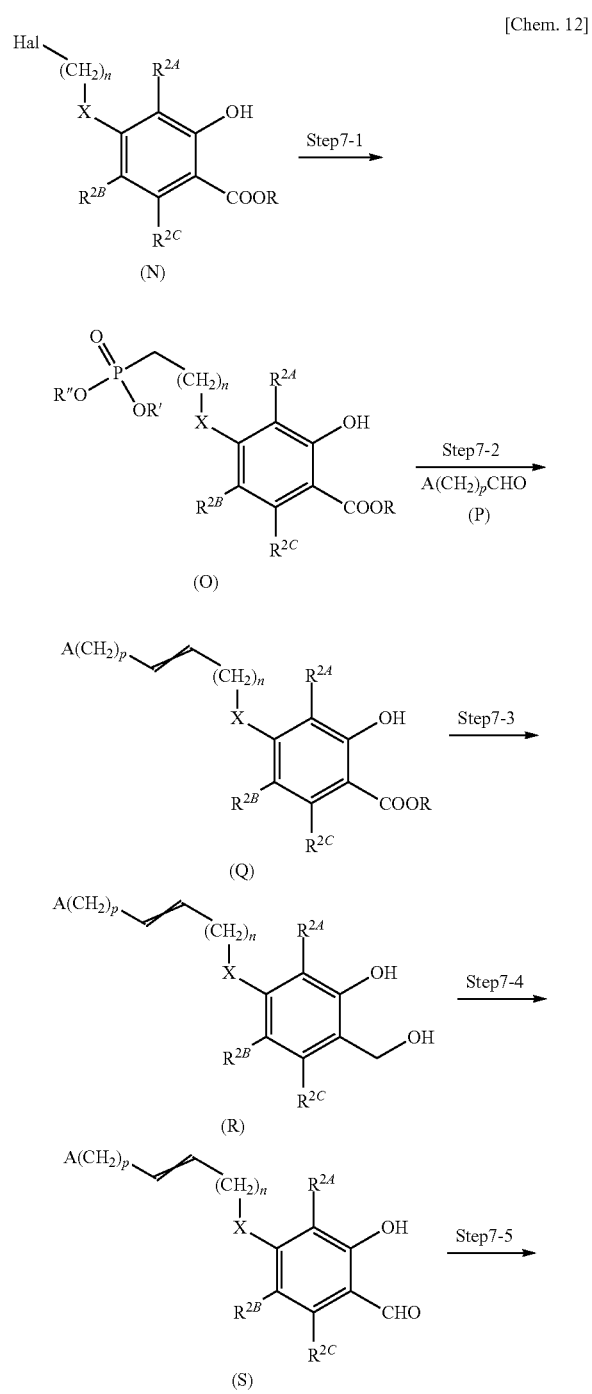

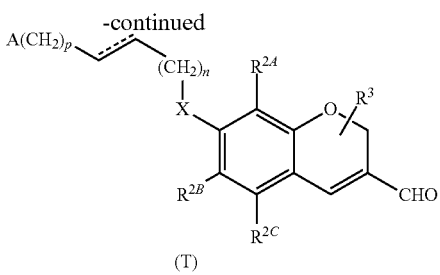

(wherein X represents —O— or a bond, R represents a protecting group of a carboxylic group, R' and R" represent lower alkyl, n and p each represent an integer of 0 to 4, which are the same as or different from each other, and further, a sum of n and p represents 4 or less. ⸺ represents a single bond or a double bond).

The compound (T) can be prepared by sequentially performing a Wittig reaction, reduction, oxidation, and construction of a chromene skeleton from the compound (N). The compound (T) in which ⸺ is a single bond is obtained by carrying out a reduction reaction at a step which does not disturb the reaction.

The Step 7-1 is a phosphorus ylide-forming reaction. The compound (O) is obtained by reacting the compound (N) with, for example, triethyl phosphite or the like, usually in a vehicle which does not disturb the reaction. Examples of the vehicle include aromatic hydrocarbons; ethers; halogenated hydrocarbons; ketones such as acetone, ethylmethylketone, and the like; DMF, DMSO, EtOAc, MeCN; and a mixed vehicle thereof. As for a reaction temperature, the reaction can be carried out under any temperature condition from −20° C. to heating.

The Step 7-2 is a so-called Wittig reaction. The compound (O) can be reacted with an aldehyde compound (P) to prepare a compound (Q). By the aldehyde addition of phosphoryl group-substituting carbanions, olefins can be obtained through a Wittig-like mechanism. The reaction temperature is any of the conditions from 0° C. to warming.

[References] (1) J. Boutagy C R V, 79, 87, 1974, (2) W. S. Wadsworth Jr O R, 25, 73, 1977.

The Step 7-3 is a reduction reaction. As the reducing agent, $LiAlH_4$, $LiAlH(OMe)_3$, or DIBAL is used, and the reaction can be carried out in a vehicle which is inert to the reaction, such as THF, ethers, and the like, usually under any temperature condition from cooling to heating.

The Step 7-4 is an oxidation reaction. As the oxidizing agent, manganese dioxide or PDC is used. Examples of the vehicle usually include halogenated hydrocarbons and the like. As for the reaction temperature, the reaction is carried out under any temperature condition from 0° C. to heating, usually at room temperature. As other methods, there is a method using a $DMSO-POCl_3$-based reagent. A method using a reagent such as DCC, acid anhydrides, chlorine, or $Me_2S$—NCS-based reagents (Corey-Kim oxidation) or using a Dess-Martin Periodinane, instead of $POCl_3$, can also be used. The reaction usually proceeds under any temperature condition from room temperature to warming. Examples of the vehicle are not particularly limited, but include aromatic hydrocarbons; ethers; halogenated hydrocarbons; MeCN, and a mixed vehicle thereof.

The Step 7-5 is a chromene ring-constituting reaction. The compound (T) can be prepared by adding an acrolein derivative to the compound (S), followed by stirring under any temperature condition from room temperature to heating in the presence of an inorganic base such as $K_2CO_3$ and the like.

Examples of the vehicle include aromatic hydrocarbons; ethers; halogenated hydrocarbons; MeCN, and a mixed vehicle thereof. Usually, ether-based vehicles such as THF, DME, dioxane, and the like are used.

The compound in which ⸺ of a compound (T) is a single bond is obtained by reducing some compounds among the compound (P) through the compound (S). This is a so-called reduction reaction of olefins. Usually, the compound is stirred in a vehicle which is inert to the reaction in the presence of a metal catalyst, usually for 1 hour to 5 days, under a hydrogen atmosphere. This reaction is usually carried out under any temperature condition from cooling to heating, preferably at room temperature. Examples of the vehicle are not particularly limited, but include alcohols such as MeOH, EtOH, i-PrOH, and the like; ethers; water, EtOAc, DMF, DMSO; and a mixed vehicle thereof. As the metal catalyst, palladium catalysts such as palladium on carbon, palladium black, palladium hydroxide, and the like, platinum catalysts such as a platinum plate, platinum oxide, and the like, nickel catalysts such as reduced nickel, Raney nickel, and the like, rhodium catalysts, iron catalysts such as reduced iron and the like, etc. are suitably used. Instead of hydrogen gas, formic acid or ammonium formate in an equivalent amount or in an excess amount can also be used as a hydrogen source for the compound.

[References] (1) "Reductions in Organic Chemistry, $2^{nd}$ ed. (ACS Monograph: 188)" written by M. Hudlicky, A C S, 1996, (2) "Jikken Kagaku Koza (Courses in Experimental Chemistry) ($5^{th}$ Edition)" edited by The Chemical Society of Japan, Vol. 19 (2005) (Maruzen)

Furthermore, some compounds represented by the formula (I) can also be prepared by any combination of the steps that can usually be employed by a person skilled in the art, such as known alkylation, acylation, substitution reaction, oxidation, reduction, hydrolysis, deprotection, halogenation, and the like, from the compound of the present invention prepared as above.

For example, for alkylation, an alkylation reaction that is usually used by a person skilled in the art can be employed, and the alkylation can be carried out in an organic vehicle which is inert to the reaction, such as ethers; aromatic hydrocarbons; halogenated hydrocarbons; DMF, MeCN; aprotic polar vehicles, and the like, under cooling, from under cooling to room temperature, or from at room temperature to under heating, in the presence of bases such as NaH; carbonic acid alkali; hydrogen carbonate alkali; alkoxide; tertiary amine; organic bases, and the like.

Further, for example, acylation can employ an acylation reaction that is usually used by a person skilled in the art can be employed, but the acylation is carried out in an organic vehicle which is inert to the reaction, such as ethers; aromatic hydrocarbons; halogenated hydrocarbons; esters such as EtOAc, and the like; MeCN; aprotic vehicles, and the like, using a condensing agent such as EDCI.HCl, CDI, diphenylphosphorylanide, and the like, depending on the reaction condition, but usually under cooling, under any temperature condition from cooling to room temperature, or under any temperature condition room temperature to heating, particularly in the presence of HOBt.

The compounds of the formula (I) can be isolated and purified as their free compounds, salts, hydrates, solvates, or polymorphic crystal substances thereof. The salts of the compound of the formula (I) can be prepared by carrying out a conventional salt-forming reaction.

Isolation and purification are carried out by employing ordinary chemical operations such as extraction, fractional crystallization, various types of fractional chromatography, and the like.

Various isomers can be prepared by selecting an appropriate starting compound or separated by using the difference in the physicochemical properties between the isomers. For example, the optical isomers can be obtained by means of a general method for designing optical resolution of racemic products (for example, fractional crystallization for inducing diastereomer salts with optically active bases or acids, chromatography using a chiral column or the like, and others), and further, the isomers can also be prepared from an appropriate optically active starting compound.

The pharmacological activity of the compound of the formula (I) was confirmed by the tests shown below.

TEST EXAMPLE 1

Evaluation of In Vitro $S1P_1$ Receptor Agonist Activity in Biological Body (Method 1) Method for Evaluation on Receptor Agonist Action by GTP[$\gamma$-$^{35}$S] Binding Assay Using Membrane of Human $S1P_1$ Expressing Cell The in vitro $S1P_1$ agonist action of the compound of the present invention was evaluated by the increase in the functional binding activity of GTP[$\gamma$-$^{35}$S] to G-protein using the membrane of a human $S1P_1$ expressing cell. A cDNA encoding a human $S1P_1$ was cloned from a human colorectal cDNA library and introduced to an expression vector pcDNA3.1 to construct a $S1P_1$-pcDNA3.1. Then, by Lipofectamine 2000 (GIBCO), the $S1P_1$-pcDNA3.1 was transfected into a CHO cell, and cultured in a Ham's F-12 culture medium containing 10% fetal bovine serum, 100 U/mL penicillin, 100 µg/mL streptomycin, and 1 mg/mL G418 disulfate, to obtain a stable, G418-resistant strain. The cultured human $S1P_1$ expressing cells were isolated in a 1 mM EDTA.2Na-containing PBS, and disrupted under ice-cooling by a homogenizer made of glass in a 1 mM Tris HCl (pH 7.4) buffer solution containing 0.1 mM EDTA and a protein inhibitor. It was centrifuged at 1,400×10 mM, and a supernatant was further centrifuged at 4° C. for 60 min at 100,000×g, and suspended in a 10 mM Tris HCl (pH 7.4) buffer solution containing 1 mM EDTA to purify the membrane. The obtained membrane (0.13 mg/mL) and 50 µM GTP[$\gamma$-$^{35}$S] (NEN; inactive 1250 Ci/mmol) were reacted in a 20 mM HEPES (pH 7.0) buffer solution (total amount: 150 µL) containing 100 mM NaCl, 10 mM $MgCl_2$, 0.1% fatty acid-free BSA, and 5 µM GDP for 1 hour together with the compound of the present invention ($10^{-12}$ to $10^{-5}$ M), and then a membrane was recovered on a GF-C filter plate with a Cell Harvester (Packard, FilterMate). The filter plate was dried at 50° C. for 60 min, and Microscinti-o (Packard) was added thereto for measurement by a liquids scintillation counter for a microplate (Packard, TOP count). For evaluation of the human $S1P_1$ agonist action of the compound of the present invention and the comparative compound, the percentages with the rate of a maximum reaction to make the GTP[$\gamma$-$^{35}$S] bonds saturated in the presence of the compound being set at 100%, and the rate of the reaction of the GTP [$\gamma$-$^{35}$S] bonds in the absence of the compound being set at 0% were used, a non-linear regression curve was plotted, and a concentration to cause an agonist action operating 50% of the maximum reaction was defined as an $EC_{50}$ value (nM).

(Method 2) Method for Evaluation of Receptor Agonist Action by $Ca^{2+}$ Influx Assay Using Human $S1P_1$ Expressing Cell The in vitro $S1P_1$ agonist action of the compound of the present invention was evaluated by the increase in the $Ca^{2+}$ concentration in a human $S1P_1$ expressing cell. A cDNA encoding a human $S1P_1$ was cloned from a human colorectal cDNA library and introduced to an expression vector pcDNA3.1 to construct a $S1P_1$-pcDNA3.1. Then, by Lipofectamine 2000 (GIBCO), the $S1P_1$-pcDNA3.1 was transfected into a CHO cell, and cultured in a Ham's F-12 culture medium containing 10% fetal bovine serum, 100 U/mL penicillin, 100 µg/mL streptomycin, and 1 mg/mL G418 disulfate, to obtain a stable, G418-resistant strain. The cultured human $S1P_1$ expressing cells were isolated in a 1 mM EDTA.2Na-containing PBS and suspended in a Ham's F-12 culture medium containing 10% fetal bovine serum, 100 U/mL penicillin, and 100 µg/mL streptomycin. This cell suspension was dispensed to a 96-well plate at 50000 cells/well, and cultured at a $CO_2$ incubator (5% $CO_2$, 37° C.) overnight. The culture medium was replaced with a calcium-sensitive fluorescent reagent (FLIPR (registered trademark) calcium 3 assay kit, molecular device)-containing loading buffer (Hank's balance salt solution, 20 mM HEPES, 2.5 mM probenecid) and left stand at a $CO_2$ incubator (5% $CO_2$, 37° C.) for 1 hour. The plate was set at a Functional Drug Screening System FDSS6000 (Hamamatsu Photonics K. K.), and persistently measured 124 times every 1.02 second at an excitation wavelength of 480 nm. The test compound (final concentration $10^{-12}$ to $10^{-5}$ M) was added at the same time as the $12^{th}$ measurement, and the change in the $Ca^{2+}$ concentration in cells was evaluated by the change in the fluorescent strength. For evaluation of the human $S1P_1$ agonist action of the compound of the present invention and the comparative compound, the percentages with the rate of a maximum reaction to make the increase in the $Ca^{2+}$ concentration in cells saturated after the addition of the compound being set at 100% and the rate of the increase in the $Ca^{2+}$ concentration in cells by the addition of a vehicle alone being set at 0% were used, a non-linear regression curve was plotted, and a concentration to cause an agonist action operating 50% of the maximum reaction was defined as an $EC_{50}$ value (nM).

TEST EXAMPLE 2

Evaluation of Reduction of Number of Peripheral Blood Lymphocytes in Rat

The action on the peripheral blood lymphocytes were evaluated using rats. 6- to 10-week-old male Lewis rats (Japan Charles River Laboratories Japan, Inc.) were randomly divided into groups (n=3), and the compound of the present invention was suspended in 0.5% methyl cellulose-containing distilled water, and orally administered with a sonde. At 4 hours or 24 hours after administration, 0.2 ml of blood was collected from the ocular fundus under ether anesthesia. To the blood sample were immediately added EDTA.4K and heparin to prevent clotting, and the number of the lymphocytes in blood was measured with an automatic hematocyte analyzer (Sysmex Corp.; XT-2000i). For the reduction of the number of the lymphocytes in peripheral blood by the compound of the present invention, the percentage with the number of the lymphocytes in groups administered with 0.5% methyl cellulose-containing distilled water being set at 100%, as performed at the same time, were used, and the dose to cause 50% reduction of the number of the lymphocytes in the peripheral blood by administration of the compound of the present invention was defined as an $ED_{50}$ value (mg/kg).

The results of Test Example 1 and Test Example 2 on some compounds of the formula (I) are shown in Tables 1 and 2. In the tables, Column A shows in vitro $S1P_1$ agonist action, $EC_{50}$ values (nM) by the method 1 of Test Example 1 provided that the value with * shows the $EC_{50}$ values measured by the method 2. Further, Column B shows the action of reducing the number of the lymphocytes in the peripheral blood at 4 hours or 24 hours after administration of the drug of Test Example 2 with $ED_{50}4h$ (mg/kg) or $ED_{50}24h$ (mg/kg), respectively.

As shown in Table 1 and 2, it was confirmed that the compound of the formula (I) of the present invention has an excellent $S1P_1$ agonist action and has a potent action of reducing the number of the lymphocytes in the peripheral blood even at 4 hours or 24 hours after administration in the pharmacological test using rats.

TABLE 1

| No | A: $EC_{50}$ (nM) | B: $ED_{50}$ 4 h (mg/kg) |
|---|---|---|
| Ex 1 | 1.7 | 0.016 |
| Ex 25 | 1.7 | 0.013 |
| Ex 31 | 1.2 | 0.065 |
| Ex 34 | 2 | 0.010 |
| Ex 43 | 6.2 | 0.26 |
| Ex 44 | 3.7 | 0.37 |
| Ex 45 | 1.5 | 0.10 |
| Ex 56 | 2.3 | 0.067 |
| Ex 62 | 2.5 | 0.21 |
| Ex 66 | 10 | 0.21 |
| Ex 69 | 6.3 | 0.087 |
| Ex 74 | 5.6 | 0.59 |
| Ex 81 | 4.6 | 0.25 |
| Ex 85 | 11 | 0.19 |
| Ex 89 | 6.1 | 0.16 |
| Ex 109 | 5.4 | 0.26 |
| Ex 116 | 8.5 | 0.10 |
| Ex 132 | 22 | 0.16 |
| Ex 137 | 9.4 | 0.11 |
| Ex 141 | 5.9 | 0.099 |
| Ex 143 | NT | 0.32 |
| Ex 144 | NT | 0.16 |

TABLE 2

| No | A: $EC_{50}$ (nM) | B: $ED_{50}$ 24 h (mg/kg) |
|---|---|---|
| Ex 149 | 8.7 | 0.12 |
| Ex 151 | 1.1* | 0.35 |
| Ex 152 | 6.3* | 0.28 |
| Ex 156 | 16* | 0.086 |
| Ex 160 | 2.2* | 0.26 |
| Ex 171 | 9.0* | 0.14 |
| Ex 178 | 55 | 0.12 |
| Ex 181 | 0.68* | 0.29 |
| Ex 183 | 5.5* | 0.21 |
| Ex 212 | 1.1* | 0.21 |
| Ex 216 | 7.8* | 0.25 |
| Ex 223 | 1.1* | 0.32 |
| Ex 230 | 7.0* | 0.19 |
| Ex 236 | 32* | 0.10 |

TEST EXAMPLE 3

Evaluation of Increase in Lung Weight in Rats

The increased lung weight in rats, one of the undesirable effects observed for conventional $S1P_1$ agonists, was evaluated. 6- to 10-week-old male Lewis or SD rats (Japan Charles River Laboratories Japan, Inc.) were randomly divided into groups (n=3 to 4), and the compound of the present invention was suspended in 0.5% methyl cellulose-containing distilled water, and orally administered with a sonde. For single-time administration, at 24 hours after administration, the weight of the rat was measured, the blood was removed under anesthesia with pentobarbital, and the lung was taken out and its weight was measured. For repeated administration, the administration was made once a day for 7 days, and at 24 hours after the final administration, the weight and the lung weight were measured. For the increased lung weight, the increase rate of the average of the relative weights of the group administered with a suspension of the compound of the present invention in 0.5% methyl cellulose-containing distilled water to the average of the relative weights of the group administered with 0.5% methyl cellulose-containing distilled water was denoted as a percentage and the administration amount showing 10% or more of the increased lung weight was determined as positive.

It was confirmed that among the compounds of the present invention, the compounds of Examples 31, 43, 44, 45, 56, 62, 66, 69, 74, 81, 85, 89, 109, 116, 137, 143, 149, 151, 152, 160, 171, 178, 181, 183, 212, 216, 223, 230, and 236 had an increased lung weight of less than 10% even at a dose of 1 mg/kg and a weak action on the lung.

TEST EXAMPLE 4

Evaluation of Rejection Inhibiting Action in Heterotopic Rat Abdominal Heart Transplant A heterotopic rat abdominal heart transplant model can be carried out in accordance with the method of Ono and Lindsey (Transplantation, 1969, 517, pp. 225-229). As a donor, 6- to 8-week male ACI rats (CLEA Japan, Inc.) were employed, and the hearts were exposed under anesthesia with pentobarbital. The left and right vena cava other than aorta and pulmonary artery, pulmonary veins, and inferior vena cava were ligated at once and the aorta and the pulmonary vein were detached and removed as a graft. 6- to 8-week male Lewis rats (Japan Charles River Laboratories Japan, Inc.) were used as recipients. Under anesthesia with pentobarbital, the pulmonary artery end of the graft and the abdominal aorta of the recipient were anastomosed and the pulmonary artery end of the graft and the vena cava of the recipient were anastomosed to prepare a model (grouped into 6 to 10 examples per group). The rejection determination of the transplanted heart promotes the recipient's abdominal palpation every 29 days after transplantation, and the presence or absence of the beating of the graft is determined on the rejection. The compound of the present invention is suspended in 0.5% methylcellulose-containing distilled water and orally administered once or twice a day for 14 days from the date of the transplant. As a control, 0.5% methylcellulose-containing distilled water is orally administered the same number of times during the same period. Simultaneously, 0.02 mg/mL/kg of tacrolimus are administered intramuscularly to all of the groups. By this test, the rejection inhibiting action of the compound of the present invention when tacrolimus is used in combination can be determined.

TEST EXAMPLE 5

Evaluation of Infrequent Pulse Expression Using Awake Rats

Male Lewis rats were anesthetized with isoflurane inhalation and a polyethylene tube was intubated into the femoral artery and vein. It was connected to a blood pressure measuring amplifier•heart rate unit via a pressure transducer from an arterial line, and the arterial blood pressure and the heart rate were measured. Intravenous line from Vehicle (10% HCO40/tween80/PEG, 90% saline) and the present compounds were intravenously infused persistently at a rate of 1 mL/kg/min for 10 minutes. The measurement data were read (for a total evaluation time of 20 minutes) from a chart of the values before administration, at 1, 2, 5, and 10 min after the start of constant infusion, and at 1, 2, 5, and 10 min after the completion of infusion, and thus, for the heart rate and the blood pressure before administration, the decrease rates (%) before and after infusion were calculated.

It was confirmed that among the compounds of the present invention, for example, the compound of Example 230 does not have an influence on the heart rate and the blood pressure at 1 mg/kg administration by the present evaluation, and the infrequent pulse is not expressed.

As the results of the tests above, it was confirmed that the compound of the formula (I) of the present invention has an excellent $S1P_1$ agonist action and has a lymphocytic infiltration inhibiting action. Further, as shown in Test Examples 3 and 4 above, Example compounds of some embodiments of the present invention can be an $S1P_1$ agonist action, which has weak undesirable actions in which the undesirable actions are observed in conventional $S1P_1$ agonists, such as increased lung weight, infrequent pulse, and the like and small side-effects.

Accordingly, the compound of the formula (I) of the present invention is useful for preventing or treating diseases induced by undesirable lymphocyte infiltration, for example, rejection or graft-versus-host diseases during organ, bone marrow, or tissue transplantation, autoimmune diseases or inflammatory diseases such as rheumatoid arthritis, multiple sclerosis, systemic lupus erythematosus, nephrotic syndrome, encephalomeningitis, myasthenia gravis, pancreatitis, hepatitis, nephritis, diabetes, lung disorders, asthma, atopic dermatitis, inflammatory bowel disease, arteriosclerosis, ischemic reperfusion disorder, and the like, and diseases induced by abnormal proliferation or accumulation of cells, for example, cancer, leukemia, and the like, particularly for preventing or treating rejection or graft-versus-host diseases during organs, bone marrow, or tissue transplantation, and multiple sclerosis.

In addition, the compound of the present invention can be administered as an $S1P_1$ agonist alone, or in combination with at least one agent, in the same or different doses, through the same or different administration routes. Examples of the agent that can be combined include, but are not limited thereto, cyclosporin A, tacrolimus, sirolimus, everolimus, mycophenolate, azathioprine, brequinar, Leflunomide, fingolimod, an anti-IL-2 receptor antibody (for example, daclizumab and the like), an anti-CD3 antibody (for example, OKT3), anti-T cell immunoglobulin (for example, AtGam and the like), belatacept, abatacept, cyclophosphamide, n-interferon, aspirin, acetaminophen, ibuprofen, naproxen, piroxicam, anti-inflammatory steroid (for example, prednisolone, and dexamethasone), and the like.

A pharmaceutical composition containing one or two or more kinds of the compound of the formula (I) or a salt thereof as an active ingredient can be prepared using excipients that are usually used in the art, that is, excipients for pharmaceutical preparations, carriers for pharmaceutical preparations, and the like, according to the methods usually used.

Administration can be accomplished either by oral administration via tablets, pills, capsules, granules, powders, solutions, and the like, or parenteral administration injections, such as intraarticular, intravenous, or intramuscular injections, and the like, suppositories, ophthalmic solutions, eye ointments, transdermal liquid preparations, ointments, transdermal patches, transmucosal liquid preparations, transmucosal patches, inhalations, and the like.

The solid composition for oral administration is used in the form of tablets, powders, granules, or the like. In such a solid composition, one or more active ingredient(s) are mixed with at least one inactive excipient, for example, lactose, mannitol, glucose, hydroxypropyl cellulose, microcrystalline cellulose, starch, polyvinyl pyrrolidone, magnesium aluminometasilicate, and/or the like. According to a usual method, the composition may contain inactive additives, including lubricants such as magnesium stearate like, disintegrating agents such as carboxymethyl starch sodium, stabilizing agents, and solubilization assisting agents. If necessary, tablets or pills may be coated with sugar or a film of a gastric or enteric coating substance.

The liquid composition for oral administration contains pharmaceutically acceptable emulsions, solutions, suspensions, syrups, elixirs, or the like, and also contains generally used inert diluents, for example, purified water or ethanol. In addition to the inert diluent, the liquid composition may also contain auxiliary agents, such as a solubilization assisting agent, a moistening agent, and a suspending agent, as well as sweeteners, flavors, aromatics, and antiseptics.

The injections for parenteral administration include sterile, aqueous or non-aqueous solutions, suspensions, or emulsions. As the aqueous solvent, for example, distilled water for injection or physiological saline is included. Examples of the non-aqueous solvent include propylene glycol, polyethylene glycol, vegetable oils such as olive oil and the like, alcohols such as ethanol and the like, polysorbate 80 (pharmacopeia), etc. Such a composition may further contain a tonicity agent, an antiseptic, a moistening agent, an emulsifying agent, a dispersing agent, a stabilizer, or a solubilizing aid. These are sterilized, for example, by filtration through a bacteria-retaining filter, blending with bactericides, or irradiation. In addition, these can also be used by producing a sterile solid composition, and dissolving or suspending it in sterile water or a sterile vehicle for injection prior to its use.

Examples of the formulation for external use include ointments, plasters, creams, jellies, patches, sprays, lotions, eye-drops, eye ointments, and the like. The drug contains generally used ointment bases, lotion bases, aqueous or non-aqueous liquid preparations, suspensions, emulsions, or the like. Examples of the ointment bases or lotion bases include polyethylene glycol, propylene glycol, white vaseline, bleached beeswax, polyoxyethylene hydrogenated castor oil, glyceryl monostearate, stearyl alcohol, cetyl alcohol, lauromacrogol, sorbitan sesquioleate, and the like.

Regarding a transmucosal agent such as an inhalation, a transnasal agent, and the like, the transmucosal agents in a solid, liquid or semi-solid state are used, and can be prepared in accordance with a conventionally known method. For example, a known excipient, as well as a pH adjusting agent, an antiseptic, a surfactant, a lubricant, a stabilizer, a thickener, or the like may be appropriately added thereto. For their administration, an appropriate device for inhalation or insufflation may be used. For example, a compound may be administered alone or as a powder of formulated mixture, or as a solution or suspension by combining it with a pharmaceutically acceptable carrier, using a conventionally known device or sprayer, such as a measured administration inhalation device and the like. The dry powder inhaler or the like may be for single or multiple administration use, and a dry powder or a powder-containing capsule may be used. Alternatively, this may be in a form of a pressurized aerosol spray which uses an appropriate ejection agent, for example, chlorofluoroalkane, hydrofluoroalkane, or a suitable gas such as carbon dioxide and the like.

Usually, in the case of oral administration, the daily dose is suitably from 0.001 to 100 mg/kg per body weight, preferably from 0.1 to 30 mg/kg, and more preferably from 0.1 to 10 mg/kg, and this is administered in one portion or dividing it into 2 to 4 portions. In the case of intravenous administration, the daily dose is suitably from about 0.0001 to 10 mg/kg per body weight, and this is administered once a day or two or more times a day. In addition, a transmucosal agent is administered at a dose from about 0.001 to 100 mg/kg per body weight, and this is administered once a day or two or more times a day. The dose is appropriately decided in response to an individual case by taking the symptoms, the age, the gender, and the like into consideration.

The compound of the formula (I) can be used in combination with various agents for treating or preventing the diseases, in which the compound of the formula (I) as described above is considered effective. The combined preparation may be administered simultaneously or separately and persistently or at a desired time interval. The preparations to be administered simultaneously may be a blend or may be prepared individually.

EXAMPLES

Furthermore, the following abbreviations may be used in some cases in the Examples, Preparation Examples, and Tables described later.

Pr=Preparation Example No., Ex=Example No., RefEx=Reference Example No., Str=Structural Formula, MS=Mass Spectrometric Data, ESI (EI)=Electrospray Ionization Analysis Data, FAB=Mass Spectrometric Data according to Fast Atom Bombardment Ionization, Hz=Hertz, $CDCl_3$=deuterated chloroform, DMSO-$d_6$= dimethylsulfoxide $d_6$.

Further, the crossed double bonds in the structural formula mean a mixture of a cis-form and a trans-form. In the $^1$H-NMR data, tetramethylsilane is used as an internal standard unless otherwise specifically described, and δ (ppm) (integrated value, disintegrated pattern) of signals in $^1$H-NMR in which DMSO-$d_6$ is used as a measurement vehicle. In the present specification, NMR represents $^1$H-NMR: Proton Nuclear Magnetic Resonance. Further, the suffixes + and − of MS and ESI (EI) each represents positive mass data and negative mass data.

Preparation Example 1

7-[(5-Bromo-4-phenyl-2-thienyl)methoxy]-2H-chromene-3-carbaldehyde (120 mg) was dissolved in DMF (2.4 mL). To this reaction liquid were added $Zn(CN)_2$ (65 mL) and $Pd(PPh_3)_4$ (65 mg) at room temperature. The reaction mixture was stirred at 100° C. for 5 hours and then poured into 1:1 a mixed vehicle of aqueous $NaHCO_3$ and EtOAc, followed by stirring for 1 hour. The organic layer was washed with brine, dried over $MgSO_4$, and then concentrated under reduced pressure, followed by purification by silica gel column chromatography (hexane:EtOAc=100:0 to 70:30) to obtain 5-{[(3-formyl-2H-chromen-7-yl)oxy]methyl}-3-phenylthiophene-2-carbonitrile (83 mg) as a pale yellow solid.

Preparation Example 2

To a solution of methyl 5-bromo-4-phenylthiophene-2-carboxylate in dioxane were added 2-isopropenyl-4,4,5,5-tetramethyl 1,3,2-dioxaborolane and a 2 M aqueous $Na_2CO_3$ solution. To the reaction mixture were added palladium acetate and $PPh_3$, followed by stirring at 100° C. for 5 hours. After leaving to be cooled, a saturated aqueous $NH_4Cl$ solution was added thereto, followed by extraction with EtOAc. The organic layer was washed with brine, dried over $MgSO_4$, and then concentrated under reduced pressure, followed by purification by silica gel column chromatography (hexane:EtOAc=95:5 to 80:20) to obtain methyl 5-isopropenyl-4-phenylthiophene-2-carboxylate as a colorless liquid.

In the same manner as in Preparation Example 2, the compounds of Preparation Example 2-1 through Preparation Example 2-4 shown in Tables described later were prepared.

Preparation Example 3

To a solution of DMF (2.5 mL) in DCM (3 mL) was added dropwise $POCl_3$ (2 mL) at 0° C., followed by stirring at room temperature for 30 minutes. Subsequently, to the reaction liquid were added dropwise 8-(benzyloxy-3,4-dihydro-1-benzoxepin-5(2H)-one in DCM (4 mL), followed by stirring at room temperature for 1 hour and at 50° C. for 3 hours. To the reaction liquid was added water, followed by extraction with EtOAc twice. The organic layer was combined, washed with water and brine, dried over $MgSO_4$, and then concentrated under reduced pressure. The residue was purified by silica gel column chromatography (automatic purification device; hexane:EtOAc=97:3 to 90:10) to obtain 8-(benzyloxy)-5-chloro-2,3-dihydro-1-benzoxepin-4-carbaldehyde (445 mg).

Preparation Example 4

To a solution of DMF (2 mL) in DCM (7.5 mL) was added dropwise $POCl_3$ (1.39 mL) at 0° C., followed by stirring at room temperature for 30 minutes. Subsequently, to the reaction liquid was added dropwise a solution of 7-{[tert-butyl (diphenyl)silyl]oxy}-2,3-dihydro-4H-chromen-4-one (2.00 g) in DCM (11 mL), followed by stirring at room temperature for 1 hour and at 50° C. for 3 hours. To the reaction liquid was added water, followed by extraction with EtOAc twice. The organic layer was combined, washed with water and brine, and dried over $MgSO_4$, and the liquid was concentrated. The residue was purified by silica gel column chromatography (automatic purification device, hexane:EtOAc=100:0 to 80:20) to obtain 4-chloro-7-hydroxy-2H-chromene-3-carbaldehyde (720 mg).

Preparation Example 5

7-(benzyloxy)-2,3-dihydro-4H-chromen-4-one was dissolved in THF, a solution (0.97 M, 5 mL) of methylmagnesium bromide in THF was added dropwise thereto at 0° C., followed by stirring at room temperature for 1 hour, and a solution (0.97 M, 5 mL) of methylmagnesium bromide in THF was added dropwise thereto, followed by stirring at room temperature for 2 hours. To the reaction liquid was added a saturated aqueous $NH_4Cl$ solution and subsequently 2 M hydrochloric acid (20 mL), followed by stirring at room temperature for 2 hours and then extracting with EtOAc three times. The organic layer was combined, washed with water and brine, dried over $MgSO_4$, and then concentrated under reduced pressure. The residue was purified by silica gel column chromatography (automatic purification device, hexane: EtOAc=95:5 to 90:10) to obtain 7-(benzyloxy)-4-methyl 2H-chromene (445 mg) as a colorless transparent liquid.

In the same manner as in Preparation Example 5, the compound of Preparation Example 5-1 shown in Tables described later was prepared.

Preparation Example 6

To a solution of 2-hydroxy-4-[(2-methoxy-4-propylphenoxy)methyl]benzaldehyde (120 mg) in dioxane (2.4 mL) were added $K_2CO_3$ (55.2 mg) and acrolein (0.267 mL) at 25° C. The reaction mixture was warmed to 100° C., followed by stirring at 100° C. for 15 hours. The reaction mixture was left to be cooled to 25° C., and then filtered through celite, and the filtrate was concentrated. The residue was purified by silica gel column chromatography (automatic purification device, hexane:EtOAc=100:0 to 80:20) to obtain 7-[(2-methoxy-4-propylphenoxy)methyl]-2H-chromene-3-carbaldehyde (104.2 mg) as a colorless liquid.

In the same manner as in Preparation Example 6, the compounds of Preparation Example 6-1 through Preparation Example 6-9 and Preparation Example 6-11 shown in Tables described later were prepared.

Preparation Example 6-10

$K_2CO_3$ (835 mg) was suspended in dioxane (40 mL), and 2-hydroxy-4-(methoxymethoxy)benzaldehyde (1 g) and 3-methyl 2-butanal (0.787 mL) were added thereto, followed by stirring at 110° C. overnight. EtOAc was added thereto, the insoluble materials were removed by filtration through celite, and the filtrate was concentrated under reduced pressure. The residue was purified by silica gel column chromatography (automatic purification device, hexane:EtOAc=95:5 to 70:30) to obtain 7-(methoxymethoxy)-2,2-dimethyl-2H-chromene-3-carbaldehyde (320 mg) as a yellow oil.

Preparation Example 7

At 0° C., to a mixed vehicle of concentrated HCl (8 mL) and AcOH (1.6 mL) was added tert-butyl 3-cyano-3-(fluoromethyl)azetidine-1-carboxylate (800 mg). The liquid was warmed to 25° C., followed by stirring at 25° C. for 1 hour and then at 100° C. for 5 hours. The reaction liquid was concentrated under reduced pressure, followed by azeotroping with toluene (30 mL) three times. The residue was dissolved in a mixed vehicle of acetone (4.8 mL) and water (8.0 mL), and at 0° C., $Na_2CO_3$ (593.7 mg) and DIBOC (1223 mg) were added thereto. The reaction liquid was warmed to 25° C., followed by stirring at 25° C. for 15 hours. Fifteen hours later, the reaction solution was concentrated and acetone was evaporated. The residue was extracted three times (50 mL×3) by the addition of ether (50 mL). The aqueous layer was combined and cooled to 0° C., and at 0° C., 2 M HCl (10 mL) was added thereto to prepare a solution at pH=2 to 3. The precipitated white solid was collected by filtration and washed with hexane (50 mL) to obtain 1-(tert-butoxycarbonyl)-3-(fluoromethyl)azetidine 3-carboxylic acid (801.2 mg) as a white solid.

Preparation Example 8 tert-Butyl 3-cyano-3-(hydroxymethyl)azetidine-1-carboxylate (5.0 g) was dissolved in DCM (100 mL). At 0° C., DAST (3.74 mL) was added thereto, followed by stirring at 0° C. for 3 hours. Three hours later, to the reaction liquid was added an aqueous $NaHCO_3$ solution (100 mL), followed by extraction with DCM (50 mL) three times. The organic layer was washed with brine, dried over $MgSO_4$, and then concentrated. The residue was purified by silica gel column chromatography (automatic purification device, hexane:EtOAc=100:0 to 50:50) to obtain tert-butyl 3-cyano-3-(fluoromethyl)azetidine-1-carboxylate (1.24 g) as a brown solid.

Preparation Example 9

2-Fluoro-4,6-dihydroxybenzaldehyde (12 g) was dissolved in MeCN (250 mL), and cesium carbonate (25.1 g) and chloromethylmethylether (6.95 mL) were added thereto, followed by stirring at room temperature for 1 hour. The insoluble materials were removed by filtration through celite and the filtrate was concentrated. The residue was purified by silica gel column chromatography (automatic purification device, hexane:EtOAc=100:0 to 94:6) to obtain 2-fluoro-6-hydroxy-4-(methoxymethoxy)benzaldehyde (11.89 g) as a white powder.

In the same manner as in Preparation Example 9, the compounds of Preparation Example 9-1 through Preparation Example 9-4 shown in Tables described later were prepared.

Preparation Example 10

7-Hydroxy-2,3-dihydro-4H-chromen-4-one (900 mg) was dissolved in DMF (10 mL), and tert-butyl(chloro)diphenylsilane (1.711 mL) and 1H-imidazole (448 mg) were added thereto, followed by stirring at room temperature overnight. To the reaction liquid was added water, followed by extraction with EtOAc three times. The organic layer was combined, washed with water and brine in this order, dried over $MgSO_4$, and then concentrated under reduced pressure. The residue was purified by silica gel column chromatography (automatic purification device, hexane:EtOAc=90:10 to 80:20) to obtain 7-{[tert-butyl(diphenyl)silyl]oxy}-2,3-dihydro-4H-chromen-4-one (2.08 g) as a colorless transparent syrup.

In the same manner as in Preparation Example 10, the compound of Preparation Example 10-1 shown in Tables described later was prepared.

Preparation Example 11

To a solution of 7-hydroxy-2H-chromene-3-carbaldehyde in DCM was added pyridine at 0° C. To the reaction liquid was added dropwise trifluoromethanesulfonic anhydride at 0° C. After stirring at room temperature for 1 hour, water was added thereto at 0° C. The mixture was extracted with EtOAc. The organic layer was washed with 1 M HCl, water, and brine in this order, dried over $MgSO_4$, and then concentrated under reduced pressure. The residue was purified by silica gel column chromatography (hexane:EtOAc=95:5 to 80:20) to obtain 3-formyl-2H-chromen-7-yl trifluoromethanesulfonate as a yellow oily substance.

In the same manner as in Preparation Example 11, the compound of Preparation Example 11-1 shown in Tables described later was prepared.

Preparation Example 12

To DMF (1 mL) was added dropwise $POCl_3$ (0.25 mL) at 0° C., followed by stirring at room temperature for 30 minutes. To the reaction mixture was added dropwise a solution of 7-(benzyloxy)-4-methyl 2H-chromene (280 mg) in DCM (1 mL), followed by stirring at room temperature for 3 hours. The reaction liquid was poured into ice-water, followed by extraction with EtOAc three times. The organic layer was combined, washed with water and brine in this order, dried over MgSO$_4$, and then concentrated under reduced pressure. The residue was purified by silica gel column chromatography (automatic purification device, hexane:EtOAc=85:15 to 70:30) to obtain 7-(benzyloxy)-4-methyl-2H-chromene-3-carbaldehyde (234 mg) as a pale yellow powder.

In the same manner as in Preparation Example 12, the compound of Preparation Example 12-4 was prepared from the compound of Preparation Example 12-1 shown in Tables described later.

Preparation Example 13

A solution of NaH (105.63 mg) in DMF (5.5 mL) was cooled to 0° C., and methyl 2-{[tert-butyl(dimethyl)silyl] oxy}-4-[(diethoxyphosphoryl)methyl]benzoate (550 mg) was added thereto. The reaction mixture was warmed to 25° C., then stirred for 1 hour, and cooled to 0° C. again, and 2-methoxy-4-propylbenzaldehyde (235.34 mg) was added thereto. The reaction mixture was warmed to 25° C. and then stirred for 15 hours. To the reaction liquid was added a saturated aqueous NH$_4$Cl solution (50 mL), followed by extraction with EtOAc (50 mL) three times. The organic layer was washed with brine, dried over MgSO$_4$, and then concentrated under reduced pressure. The residue was purified by silica gel column chromatography (automatic purification device, hexane:EtOAc=100:0 to 70:30) to obtain methyl 2-hydroxy-4-[(E)-2-(2-methoxy-4-propylphenyl)vinyl]benzoate (304.2 mg) as a white solid.

In the same manner as in Preparation Example 13, the compound of Preparation Example 13-1 shown in Tables described later was prepared.

Preparation Example 14

To DMF (40 mL) was added 60% NaH (634 mg) under ice-cooling, and a solution of 4-fluoro-3-(trifluoromethyl) benzonitrile (2 g) in DMF (20 mL) was slowly added thereto. After stirring at room temperature for 5 hours, the reaction was quenched with a saturated NH$_4$Cl solution, followed by extraction with EtOAc. The organic layer was washed with brine, dried over MgSO$_4$, and then filtered. The filtrate was concentrated to obtain 4-isopropoxy-3-(trifluoromethyl)benzonitrile (2.4 g) as a pale yellow solid.

In the same manner as in Preparation Example 14, the compounds of Preparation Example 14-1 through Preparation Example 14-16 shown in Tables described later were prepared.

Preparation Example 15

To a solution of methyl 4-fluoro-2-(trifluoromethyl)benzoate in DMF were added K$_2$CO$_3$ and piperidine, followed by stirring at 100° C. for 3 hours. The reaction mixture was cooled to 0° C., and water was added thereto, followed by extraction with EtOAc. The organic layer was washed with brine, dried over MgSO$_4$, and then concentrated under reduced pressure. The residue was purified by silica gel column chromatography (hexane:EtOAc=100:0 to 90:10) to obtain methyl 4-piperidin-1-yl-2-(trifluoromethyl)benzoate as a colorless oily substance.

In the same manner as in Preparation Example 15, the compounds of Preparation Example 15-1 through Preparation Example 15-4 shown in Tables described later were prepared.

Preparation Example 16

To a solution of methyl 1H-indole-5-carboxylate (1.5 g) in DMF (30 mL) was added NaH (410 mg) at 0° C. The reaction mixture was warmed to 25° C., followed by stirring for 0.5 hours. Then, the reaction mixture was cooled to 0° C. again, and then methyliodide (1.38 mL) was added thereto. The reaction mixture was warmed to 25° C., followed by stirring for 3 hours. To the reaction liquid was added water (50 mL), followed by extraction with EtOAc (50 mL) three times. The organic layer was washed with brine, dried over MgSO$_4$, and then concentrated under reduced pressure. The residue was purified by silica gel column chromatography (automatic purification device, CHCl$_3$:MeOH=100:0 to 98:2) to obtain methyl 1-ethyl-1H-indole-5-carboxylate (1465 mg) as a white solid.

Preparation Example 17

To a solution of 4-fluoro-2-(trifluoromethyl)benzoic acid in MeOH were added concentrated sulfuric acid at 0° C. The reaction mixture was heated and refluxed for 2 days. The reaction mixture was concentrated under reduced pressure and the residue was diluted with EtOAc. The organic layer was washed with a saturated aqueous NaHCO$_3$ solution, dried over MgSO$_4$, and then concentrated under reduced pressure to obtain methyl 4-fluoro-2-(trifluoromethyl)benzoate as a colorless oily substance.

Preparation Example 18

The suspension of 4-bromo-5-ethylthiophene-2-carboxylic acid (800 mg) in MeOH (4 mL) was added dropwise SOCl$_2$ (0.50 mL) at 0° C. The reaction mixture was stirred at 0° C. for 1 hour, warmed to 60° C., and then stirred for 15 hours. The reaction liquid was concentrated under reduced pressure. The residue was purified by silica gel column chromatography (automatic purification device, hexane: EtOAc=98:2 to 70:30) to obtain methyl 4-bromo-5-ethylthiophene-2-carboxylate (765.0 mg) as a colorless liquid.

In the same manner as in Preparation Example 18, the compounds of Preparation Example 18-1 through Preparation Example 18-6 shown in Tables described later were prepared.

Preparation Example 19

To a solution of N-isopropylpropan-2-amine (165.5 mg) in THF (1 mL) was added dropwise a solution of n-butyllithium in hexane (1.6 M, 0.98 mL) at −78° C., followed by warming to 25° C. and then stirring for 30 minutes. After cooling to −78° C. again, a solution of 1-tert-butyl-3-methylpyrrolidine-1,3-dicarboxylate (300 mg) in THF (1 mL) was added dropwise thereto. The reaction mixture was warmed to −40° C. and then stirred for 1 hour. The reaction mixture was cooled to −78° C. again, and a solution of N-fluoro-N-(phenylsulfonyl) benzenesulfonamide (495.1 mg) in THF (1 mL) was added dropwise thereto. The reaction mixture was stirred at −78° C. for 1 hour, then warmed to 25° C., and stirred for 15 hours. Fifteen hours later, to the reaction liquid was added a saturated aqueous NH$_4$Cl solution (30 mL), followed by extraction with EtOAc (30 mL) three times. The organic layer was washed with brine, dried over MgSO$_4$, and then concentrated under reduced pressure. The residue was purified by silica gel column chromatography (automatic purification device, hexane:EtOAc=100:0 to 80:20) to obtain 1-tert-butyl 3-methyl-3-fluoropyrrolidine-1,3-dicarboxylate (154.3 mg) as a yellow liquid.

Preparation Example 20

To a solution of methyl 4-phenylthiophene-2-carboxylate (1.8 g) in DCM (18 mL) was added portionwise pyridinium tribromide (13.2 g) at 0° C. The reaction liquid was warmed to 25° C. and then stirred for 45 hours. The reaction mixture was cooled to 0° C., and a saturated aqueous $Na_2S_2O_3$ solution (100 mL) was slowly added dropwise. The reaction mixture was extracted with DCM (50 mL) three times. The organic layer was washed with brine, dried over $MgSO_4$, and then concentrated under reduced pressure. The residue was purified by silica gel column chromatography (automatic purification device, hexane:EtOAc=100:0 to 90:10) to obtain methyl 5-bromo-4-phenylthiophene-2-carboxylate (2.06 g) as a colorless liquid.

Preparation Example 21

To a solution of 4-chloro-5,5,5-trifluoro-3-phenylpent-3-en-2-one (950 mg) and methylsulfanylacetate (446 mg) in MeCN (23.8 mL) was added dropwise DBU (0.63 mL) at 25° C., followed by stirring at the same temperature for 15 hours. To the reaction liquid was added a saturated aqueous $NH_4Cl$ solution (50 mL), followed by extraction with diethylether (50 mL) three times. The organic layer was washed with brine, dried over $MgSO_4$, and then concentrated under reduced pressure. The residue was purified by silica gel column chromatography (automatic purification device, hexane: EtOAc=98:2 to 90:0) to obtain methyl 3-methyl-4-phenyl-5-(trifluoromethyl)thiophene-2-carboxylate (1.08 g) as a colorless liquid.

Preparation Example 22

To a solution of benzyl 3-cyanopyrrolidine-1-carboxylate (1.0 g) and TEA hydrochloride (2.99 g) in toluene was added sodium azide (1.41 g) at 25° C., followed by stirring at 115° C. for 5 hours. The reaction liquid was left to be cooled and DCM (10 mL) was added thereto. Then, to a 5% aqueous salicylic acid solution (100 mL) was added dropwise the reaction liquid, followed by stirring at 25° C. for 1 hour. The reaction liquid was extracted with EtOAc (30 mL) three times. The organic layer was washed with brine, dried over $MgSO_4$, and then concentrated under reduced pressure. The residue was purified by silica gel column chromatography (automatic purification device, hexane:EtOAc=100:0 to 80:20) to obtain benzyl 3-(1H-tetrazol-5-yl)pyrrolidine-1-carboxylate (10.8 g) as a colorless liquid.

Preparation Example 23

To a solution of methyl 2-{[tert-butyl(dimethyl)silyl]oxy}-4-methylbenzoate (3.4 g) in carbon tetrachloride (68 mL) were added, and NBS (2.16 g) and AIBN (398 mg) were added thereto at room temperature, followed by stirring at 80° C. for 1 hour. Completion of the reaction was confirmed by means of TLC, and to the reaction liquid was added water to stop the reaction, followed by extraction with EtOAc. The organic layer was washed with brine, dried using $MgSO_4$, and then concentrated under reduced pressure, followed by purification by silica gel column chromatography (automatic purification device, hexane:EtOAc=100:0 to 95:5) to obtain methyl 4-(bromomethyl)-2-{[tert-butyl(dimethyl)silyl]oxy}benzoate (3.79 g) as a colorless liquid.

Preparation Example 23-1

To a solution of (2S)-3-(4-chlorophenyl)-2-methylpropan-1-ol (300 mg) in DCM (20 mL) were added N-bromosuccinimide (347 mg) and triphenylphosphine (511 mg) under ice-cooling. The reaction liquid was stirred at room temperature for 2 hours, and then the reaction liquid was poured into water, followed by extraction with chloroform. The organic layer was washed with brine and dried over $MgSO_4$, and then vehicle was evaporated under reduced pressure. The residue was subjected to silica gel column chromatography (hexane: EtOAc=100:0 to 90:10) to obtain 1-[(2S)-3-bromo-2-methylpropyl]-4-chlorobenzene (373 mg) as a colorless liquid.

Preparation Example 24

To a solution of N-isopropylpropan-2-amine (11.54 mL) in THF (50 mL) was added dropwise a solution of n-butyllithium in hexane (1.6 M, 51.45 mL) at −78° C. The reaction mixture was warmed to 0° C. and then stirred for 30 minutes. The reaction mixture was cooled to −78° C. again, and then a solution of tert-butyl 3-cyanoazetidine-1-carboxylate (5.0 g) in THF (30 mL) was added dropwise, followed by stirring at −78° C. for 1 hour. To the reaction mixture was added dropwise a solution of 1H-benzotriazol-1-yl-methanol (8.19 g) in THF (20 mL) at −78° C., followed by stirring at −78° C. for 3 hours. To the reaction mixture was added a saturated aqueous $NH_4Cl$ solution (100 mL), followed by extraction with EtOAc (50 mL) three times. The organic layer was washed with brine, dried over $MgSO_4$, and then concentrated under reduced pressure. The residue was purified by silica gel column chromatography (automatic purification device, hexane: EtOAc=100:0 to 50:50) to obtain tert-butyl 3-cyano-3-(hydroxymethyl)azetidine-1-carboxylate (5.68 g) as a white solid.

Preparation Example 25

A solution of methyl 4-amino-(2-trifluoromethyl)benzoate hydrochloride (1.24 g) and 2,5-dimethoxytetrahydrofuran (773 mg) in AcOH (20 mL) was stirred at 80° C. for 12 hours. The reaction mixture was concentrated under reduced pressure and azeotroped with toluene, and AcOH was evaporated. The obtained yellowish brown oily substance was dissolved in chloroform, and a saturated aqueous $NaHCO_3$ solution was added thereto. The organic layer was washed with a saturated aqueous $NaHCO_3$ solution, water, and brine in this order, dried over $MgSO_4$, and then concentrated under reduced pressure. The residue was purified by silica gel column chromatography ($CHCl_3$:MeOH=97:3) to obtain methyl 4-(1H-pyrrolo-1-yl)-2-(trifluoromethyl)benzoate (11.8 g).

In the same manner as in Preparation Example 25, the compound of Preparation Example 25-1 shown in Tables described later was prepared.

Preparation Example 26

To a solution of trimethyl(pro-1-pyn-1-yl)silane (877 mg) in THF (60 mL) were added a solution of n-BuLi in hexane (1.58 M, 4.5 mL) was added at −78° C. The reaction mixture was stirred at −78° C. for 3 hours, and then a solution of 1-(bromomethyl)-2,4-bis(trifluoromethyl)benzene (2 g) in THF (10 mL) was added dropwise thereto, followed by stirring for 1 hour. To the reaction liquid was added an aqueous $NH_4Cl$ solution, followed by extraction with ether. The organic layer was washed with brine, dried over $MgSO_4$, and then concentrated under reduced pressure. The residue was purified by silica gel column chromatography (hexane:EtOAc=100:0) to obtain {-4-[2,4-bis(trifluoromethyl)phenyl]but-1-yn-1-yl}(trimethyl)silane (1.8 g) as a colorless liquid.

Preparation Example 27

1-(chloromethyl)-2-methoxy-4-propylbenzene (1.1 g) was dissolved in DMF (20 mL), and 7-hydroxy-2H-chromene-3- carbaldehyde (975 mg) and $K_2CO_3$ (1.15 g) were added thereto, followed by stirring at 80° C. for 1 hour. Further, sodium iodide (416 mg) was added thereto, followed by stirring at 80° C. for 1 hour. After confirming completion of the reaction, to the reaction liquid was added water to stop the reaction, followed by extraction with EtOAc three times. The organic layer was combined, washed with brine, dried over $MgSO_4$, and then concentrated under reduced pressure. The residue was purified by silica gel column chromatography (automatic purification device, hexane:EtOAc=95:5 to 80:20) to obtain 7-[(2-methoxy-4-propylbenzyl)oxy]-2H-chromene-3-carbaldehyde (1.21 g) as a yellow powder.

In the same manner as in Preparation Example 27, the compounds of Preparation Example 27-1 through Preparation Example 27-6 shown in Tables described later were prepared.

Preparation Example 28

7-Hydroxy-2H-chromene-3-carbaldehyde (200 mg) was dissolved in DMF (5 mL), and $K_2CO_3$ (235 mg) and 1-(bromomethyl)-2,4-bis(trifluoromethyl)benzene (0.234 mL) were added thereto, followed by stirring at 80° C. for 30 minutes. The reaction liquid was poured into water, and the resulting powder was collected by filtration and dried under reduced pressure to obtain 7-{[2,4-bis(trifluoromethyl)benzyl]oxy}-2H-chromene-3-carbaldehyde (455 mg) as a pale yellow powder.

In the same manner as in Preparation Example 28, the compounds of Preparation Example 28-1 through Preparation Example 28-27 shown in Tables described later were prepared.

Preparation Example 29

To a solution of 3-formyl-2H-chromen-7-yltrifluoromethanesulfonate (520 mg) in DMF (10.4 mL) were added 1-ethynyl-4-(trifluoromethyl)benzene (330 μL), bis(triphenylphosphine)palladium (II) dichloride (355 mg), and copper iodide (I) (161 mg), and TEA (470 μL) at room temperature. The reaction mixture was stirred at 100° C. for 5 hours. To the reaction mixture was added water under ice-cooling, the insoluble materials were separated by filtration, and the filtrate was extracted with EtOAc. The organic layer was washed with brine, dried over $MgSO_4$, and then concentrated under reduced pressure. The residue was purified by silica gel column chromatography (hexane:EtOAc) to obtain 7-{[4-(trifluoromethyl)phenyl]ethynyl}-2H-chromene-3-carbaldehyde (189 mg).

In the same manner as in Preparation Example 29, the compounds of Preparation Example 29-1 through Preparation Example 29-15 shown in Tables described later were prepared.

Preparation Example 30

To a solution of $Pd(PPh_3)_4$ (542 mg) and TEA (4 mL) in DMF (16 mL) were added 1-bromo-4-isobutylbenzene (1 g) and ethynyl(trimethyl)silane (553 mg) at room temperature, followed by stirring at 60° C. for 4 hours. To the reaction liquid was added 1 M hydrochloric acid, followed by extraction with ether. The insoluble materials were filtered through celite. The organic layer was washed with brine, dried over $MgSO_4$, and then concentrated under reduced pressure. The residue was purified by silica gel column chromatography (hexane) to obtain [(4-isobutylphenyl)ethynyl](trimethyl)silane (459 mg) as a yellow liquid.

In the same manner as in Preparation Example 30, the compound of Preparation Example 30-1 shown in Tables described later was prepared.

Preparation Example 31

To a solution of copper chloride (10 mg) and $Pd(PPh_3)_4$ (60 mg) in DMF (2 mL) were added [((4-isobutylphenyl)ethynyl](trimethyl)silane (288 mg) and 5-fluoro-3-formyl-2H-chromen-7-yl trifluoromethanesulfonate (340 mg) at room temperature, followed by stirring at 80° C. for 12 hours. The reaction liquid was concentrated and the residue was purified by silica gel column chromatography ($CHCl_3$) to obtain 5-fluoro-7-[(4-isobutylphenyl)ethynyl]-2H-chromene-3-carbaldehyde (83 mg) as a yellow solid.

In the same manner as in Preparation Example 31, the compound of Preparation Example 31-1 shown in Tables described later was prepared.

Preparation Example 32

To a solution of 1-[4-phenyl-5-(trifluoromethyl)-2-thienyl]ethanone (1.0 g) in THF (20 mL) was added dropwise DIBAL (0.99 M solution in toluene, 9.34 mL) at −78° C. The reaction mixture was warmed to 25° C. and stirred for 3 hours and a saturated aqueous Rochelle salt solution (50 mL) was added thereto, followed by extraction with EtOAc (50 mL) three times. The organic layer was washed with brine, dried over $MgSO_4$, and then concentrated under reduced pressure. The residue was purified by silica gel column chromatography (automatic purification device, hexane:EtOAc=98:2 to 90:10) to obtain 1-[4-phenyl-5-(trifluoromethyl)-2-thienyl]ethanol (0.99 g) as a colorless liquid.

Preparation Example 33

To a solution of 3-(trifluoromethyl)-4-[(1S)-2,2,2-trifluoro-1-methylethoxy]benzoic acid (1.085 g) in THF (43 mL) was added dropwise a solution of $BH_3.THF$ in THF (1 M, 14 mL) at 0° C. The reaction mixture was warmed to room temperature and then stirred for 15 hours. To the reaction liquid was added 1 M hydrochloric acid at 0° C. to stop the reaction, followed by stirring for 30 minutes and extracting with EtOAc. The organic layer was washed with brine, dried over $MgSO_4$, and then concentrated under reduced pressure to obtain {3-(trifluoromethyl)-4-[(1S)-2,2,2-trifluoro-1-methylethoxy]phenyl}methanol (570 mg) as a white oily substance.

In the same manner as in Preparation Example 33, the compounds of Preparation Example 33-1 through Preparation Example 33-21 shown in Tables described later were prepared.

Preparation Example 34

To a solution of methyl 4-piperidin-1-yl-2-(trifluoromethyl)benzoate (955 mg) in THF (19 mL) were added dropwise a solution of DIBAL in hexane (1 M, 10.0 mL) under ice-cooling, followed by stirring at the same temperature for 2 hours. To the reaction liquid was added dropwise MeOH, and then a saturated aqueous Rochelle salt solution was added thereto, followed by stirring at room temperature for 1 hour. The mixture was extracted with EtOAc, and the organic layer was washed with brine, dried over $MgSO_4$, and then concentrated under reduced pressure. The obtained residue was purified by silica gel column chromatography (hexane:EtOAc) to obtain[4-piperidin-1-yl-2-(trifluoromethyl)phenyl]methanol (846 mg).

In the same manner as in Preparation Example 34, the compounds of Preparation Example 34-1 through Preparation Example 34-30 shown in Tables described later were prepared.

Preparation Example 35

Methyl 2-hydroxy-4-[(2-methoxy-4-propylphenoxy)methyl]benzoate (300 mg) was dissolved in THF (15 mL). To the reaction liquid was added LAH (103.4 mg) at 0° C., followed by warming from 0° C. to 25° C. and then stirring for 3 hours. To the reaction liquid was added a saturated aqueous Rochelle salt solution (30 mL), followed by extraction with EtOAc (30 mL) three times. The organic layer was washed with brine, dried over $MgSO_4$, and then concentrated under reduced pressure. The residue was purified by silica gel column chromatography (automatic purification device, hexane:EtOAc=100:0 to 80:20) to obtain 2-(hydroxymethyl)-5-[(2-methoxy-4-propylphenoxy)methyl]phenol (245.2 mg) as a white solid.

In the same manner as in Preparation Example 35, the compounds of Preparation Example 35-1 through Preparation Example 35-3 shown in Tables described later were prepared.

Preparation Example 36

To a solution of $NaBH_4$ (93.1 mg) in EtOH (15 mL) was added dropwise a solution of 7-{[2,4-bis(trifluoromethyl)benzyl]oxy}-2,3-dihydro-4H-thiochromen-4-one (1.0 g) in EtOH (5 mL) at 0° C. The reaction mixture was warmed to 25° C., followed by stirring for 3 hours. The reaction liquid was concentrated under reduced pressure and to the residue were added DCM (20 mL) and then saturated aqueous $NH_4Cl$ (30 mL) at 0° C., followed by stirring for 1 hour and extracting with DCM three times (30 mL×3). The organic layer was washed with brine, dried over $MgSO_4$, and then concentrated under reduced pressure. The residue was purified by silica gel column chromatography (automatic purification device, hexane:EtOAc=100:0 to 60:40) to obtain 7-{[2,4-bis(trifluoromethyl)benzyl]oxy}thiochroman-4-ol (845 mg) as a white solid.

In the same manner as in Preparation Example 36, the compounds of Preparation Example 36-1 through Preparation Example 36-2 shown in Tables described later were prepared.

Preparation Example 37

At a normal pressure under a hydrogen gas atmosphere, to a solution of methyl 4-phenyl-5-vinylthiophene-2-carboxylate (250 mg) in EtOH (5 mL) was added Pd/C (50% wet) (50 mg) at 25° C., followed by stirring for 5 hours. The reaction mixture was filtered through celite and the filtrate was concentrated under reduced pressure to obtain methyl 5-ethyl-4-phenylthiophene-2-carboxylate (247.3 mg) as a colorless liquid.

In the same manner as in Preparation Example 37, the compounds of Preparation Example 37-1 through Preparation Example 37-3 shown in Tables described later were prepared.

Preparation Example 38

To a solution of 5-fluoro-7-hydroxy-2H-chromene-3-carbaldehyde (275 mg) and 2-(hydroxymethyl)-5-methyl-4-phenyl-thiazole (436 mg) in toluene (8.2 mL) were added ADDP (393 mg) and TBP (315 mg) under ice-cooling. The reaction liquid was stirred at room temperature for 15 hours, then IPE was added thereto, and the solid was removed by filtration. The filtrate was concentrated under reduced pressure and the residue was purified by silica gel column chromatography (hexane:EtOAc=90:20 to 70:30) to obtain 5-fluoro-7-[(5-5-methyl-4-phenyl-1,3-thiazol-2-yl)methoxy]-2H-2H-chromene-3-carbaldehyde (381 mg) as a pale yellow solid.

In the same manner as in Preparation Example 38, the compounds of Preparation Example 38-1 through Preparation Example 38-61 shown in Tables described later were prepared.

Preparation Example 39

To a solution of 5-({[2'-fluoro-2-(trifluoromethyl)biphenyl-4-yl]oxy}methyl)-2-(hydroxymethyl)phenol (520 mg) in chloroform (10 mL) was added manganese dioxide (1 g) at room temperature. The reaction liquid was stirred at room temperature for 16 hours, and then filtered through celite. The filtrate was concentrated under reduced pressure and purified by silica gel column chromatography (hexane:EtOAc=95:5 to 80:20) to obtain 4-({[2'-fluoro-2-(trifluoromethyl)biphenyl-4-yl]oxy}methyl)-2-hydroxybenzaldehyde (180 mg) as a white solid.

In the same manner as in Preparation Example 39, the compounds of Preparation Example 39-1 through Preparation Example 39-6 shown in Tables described later were prepared.

Preparation Example 40

To a solution of [2-({[2-(trifluoromethyl)biphenyl-4-yl]oxy}methyl)-4,5-dihydro-1-benzothien-6-yl]methanol (1.0 g) in DCM (20 mL) were added PDC (1.36 g) and MS4 Angstrom (1.36 g) at 25° C. The reaction liquid was stirred for 3 hours, and then filtered through celite. The filtrate was concentrated under reduced pressure and the residue was purified by silica gel column chromatography (automatic purification device, hexane:EtOAc=100:0 to 80:20) to obtain 2-({[2-(trifluoromethyl)biphenyl-4-yl]oxy}methyl)-4,5-dihydro-1-benzothiophene-6-carbaldehyde (345 mg) as a colorless liquid.

Preparation Example 41

To a solution of [1-(tert-butoxycarbonyl)piperidin-4-yl] acetic acid (200 mg) in dioxane (1 mL) was added a 4 M hydrogen chloride dioxane solution (1 mL). The reaction liquid was stirred at room temperature for 15 hours, and then concentrated under reduced pressure to obtain piperidin-4-yl acetic acid hydrochloride (140 mg) as a white solid.

In the same manner as in Preparation Example 41, the compounds of Preparation Example 41-1 through Preparation Example 41-5 shown in Tables described later were prepared.

Preparation Example 42

Benzyl 3-(1H-tetrazol-5-yl)pyrrolidine-1-carboxylate (300 mg) was added to a mixed solution of concentrated hydrochloric acid (3 mL) and AcOH (0.6 mL), followed by stirring at 100° C. for 5 hours. The reaction liquid was concentrated and then azeotroped with toluene three times (30 mL×3). The residue was dissolved in a mixed solution of acetone (0.9 mL) and water (1.5 mL), and then cooled to 0° C., and Na₂CO₃(174.5 mg) and DIBOC (359.4 mg) were added thereto. The reaction mixture was warmed to 25° C. and then stirred for 15 hours. The reaction liquid was concentrated. To the residue was added diethylether (30 mL) for extraction three times. The organic layer was washed with brine, dried over MgSO₄, and then concentrated under reduced pressure to obtain tert-butyl 3-(1H-tetrazol-5-yl)pyrrolidine-1-carboxylate (102.7 mg) as a colorless liquid.

Preparation Example 43

To 1-tert-butyl 3-methyl 3-fluoropyrrolidine-1,3-dicarboxylate (100 mg) was added a mixed solution of concentrated hydrochloric acid (1 mL) and AcOH (0.2 mL) at 0° C. The reaction mixture was warmed to room temperature, stirred for 1 hour, and then stirred at 100° C. for 5 hours. After confirming that the starting materials were lost, the resultant was concentrated under reduced pressure and then azeotroped with toluene three times. The residue was dissolved in a mixed liquid of acetone (0.6 mL) and water (1 mL), and Na₂CO₃ (64 mg) and DIBOC (132 mg) were added thereto at 0° C., followed by warming to room temperature and then stirring for 15 hours. The reaction mixture was concentrated under reduced pressure and acetone was evaporated. To the residue was added diethylether for liquid separation. The aqueous layer was combined, cooled to 0° C., and adjusted to pH=2 to 3 with 2 M hydrochloric acid. EtOAc was added thereto for extraction. The organic layer was washed with brine, dried over MgSO₄, and then concentrated under reduced pressure to obtain 1-(tert-butoxycarbonyl)-3-fluoropyrrolidine-3-carboxylic acid (70 mg) as a white solid.

Preparation Example 44

5-Fluoro-7-(methoxymethoxy)-2H-chromene-3-carbaldehyde (1.5 g) was dissolved in acetone (25 mL), and 1 M HCl (20 mL) was added thereto, followed by heating and refluxing for 5 hours. The reaction liquid was concentrated and the residue was dissolved in EtOAc, washed with water and brine, and dried over MgSO₄, and the filtrate was concentrated. The residue was washed with chloroform to obtain 5-fluoro-7-hydroxy-2H-chromene-3-carbaldehyde (0.95 g) as a yellow powder.

In the same manner as in Preparation Example 44, the compounds of Preparation Example 44-1 through Preparation Example 44-6 shown in Tables described later were prepared.

Preparation Example 45

7-(Methoxymethoxy)-2,2-dimethyl-2H-chromene-3-carbaldehyde (300 mg) was dissolved in EtOH (10 mL), and (1S)-(+)-10-camphor sulfonic acid (421 mg) was added thereto, followed by stirring at 80° C. overnight. To the reaction liquid was added silica gel, followed by concentration. The residue was purified by silica gel column chromatography (automatic purification device, hexane:EtOAc=90:10 to 70:30) to obtain 7-hydroxy-2,2-dimethyl-2H-chromene-3-carbaldehyde (175 mg) as a red powder.

Preparation Example 46

To a solution of KOH (358 mg) in MeOH (30 mL) was added {4-[2,4-bis(trifluoromethyl)phenyl]but-1-yn-1-yl}(trimethyl)silane (1.8 g), followed by stirring at room temperature for 18 hours. The reaction liquid was neutralized with 1 M hydrochloric acid and extracted with ether. The organic layer was washed with brine, dried over MgSO₄, and then concentrated under reduced pressure. The residue was purified by silica gel column chromatography (hexane:EtOAc=100:0) to obtain 1-but-3-yn-1-yl-2,4-bis(trifluoromethyl)benzene (426 mg) as a colorless liquid.

Preparation Example 47

To 7-(benzyloxy)-4-methyl-2H-chromene-3-carbaldehyde (230 mg) and 1,2,3,4,5-pentamethylbenzene (608 mg) was added TFA (3 mL), followed by stirring at room temperature overnight. The reaction liquid was poured into an aqueous NaHCO₃ solution, followed by extraction with EtOAc three times. The organic layer was combined, washed with brine, dried over MgSO₄, and then concentrated under reduced pressure. The residue was purified by silica gel column chromatography (automatic purification device, hexane:EtOAc=80:20 to 20:80) to obtain 7-hydroxy-4-methyl-2H-chromene-3-carbaldehyde (130 mg) as a pale yellow powder.

In the same manner as in Preparation Example 47, the compounds of Preparation Example 47-1 through Preparation Example 47-2 shown in Tables described later were prepared.

Preparation Example 48

2-Fluoro-4,6-dimethoxybenzaldehyde (22 g) was dissolved in DCM (110 mL), and a solution of BBr₃ in DCM (1 M, 300 mL) was added dropwise thereto under ice-cooling, followed by stirring at room temperature overnight. After confirming completion of the reaction, the reaction liquid was poured into ice-water (100 mL), followed by stirring for 1 hour and then extracting with EtOAc three times. The organic layer was combined, washed with water and brine in this order, dried over MgSO₄, and concentrated under reduced pressure. The residue was purified by silica gel column chromatography (automatic purification device, hexane:EtOAc=80:20 to 60:40) to obtain 2-fluoro-4,6-dihydroxybenzaldehyde (12 g) as a white powder.

Preparation Example 49

To a solution of 7-{[2,4-bis(trifluoromethyl)benzyl]oxy}thiochroman-4-ol (800 mg) in toluene (16 mL) was added 4-methylbenzenesulfonic acid (33.7 mg), followed by stirring at 120° C. for 3 hours. To the reaction liquid was added a saturated aqueous NaHCO₃ solution (50 mL), followed by extraction with EtOAc (50 mL) three times. The organic layer was washed with brine, dried over MgSO₄, and then concentrated under reduced pressure. The residue was purified by silica gel column chromatography (automatic purification device, hexane:EtOAc=100:0 to 80:20) to obtain 2,4-bis(trifluoromethyl)benzyl 2H-thiochroman-7-yl ether (753.2 mg) as a colorless liquid.

Preparation Example 50

A mixture of methyl 4-(bromomethyl)-2-{[tert-butyl(dimethyl)silyl]oxy}benzoate (0.30 g) and triethylphosphite (0.17 g) was mixed at 25° C. and then stirred at 130° C. for 24 hours. The reaction liquid was concentrated under reduced pressure and azeotroped with toluene twice (30 mL×2). The residue was purified by silica gel column chromatography (automatic purification device, hexane:EtOAc=40:60 to 10:90) to obtain methyl 2-{[tert-butyl(dimethyl)silyl]oxy}-4-[(diethoxyphosphoryl)methyl]benzoate (0.23 g) as a colorless liquid Preparation Example 51

To a solution of 7-[(4-bromo-5-ethyl-2-thienyl)methoxy]-2H-chromene-3-carbaldehyde (150 mg) in dioxane (4.5 mL) were added [2-(trifluoromethyl)phenyl]boric acid and a 2 M aqueous $Na_2CO_3$ solution at 25° C. Then, to the reaction mixture were added palladium acetate (4.44 mg) and $PPh_3$ (20.75 mg), followed by warming to 100° C. and stirring for 5 hours. To the reaction liquid was added a saturated aqueous $NH_4Cl$ solution (30 mL), followed by extraction with EtOAc (30 mL) three times. The organic layer was washed with brine, dried over $MgSO_4$, and then concentrated under reduced pressure. The residue was purified by silica gel column chromatography (automatic purification device, hexane:EtOAc=95:5 to 80:20) to obtain 7-({5-ethyl-4-[2-(trifluoromethyl)phenyl]-2-thienyl}methoxy)-2H-chromene-3-carbaldehyde (134.8 mg) as a pale yellow liquid.

In the same manner as in Preparation Example 51, the compounds of Preparation Example 51-1 through Preparation Example 51-5 shown in Tables described later were prepared.

Preparation Example 52

Under a nitrogen atmosphere, to a solution of [3-chloro-4-(trifluoromethyl)phenyl]methanol (800 ng) and phenylboric acid (1.90 g) in toluene (16 mL) were added potassium phosphate (1.61 g), palladium acetate (42.6 mg), and dicyclohexyl (2',6'-dimethoxybiphenyl-2-yl)phosphine (195.0 mg) at 25° C. The reaction mixture was warmed to 100° C. and then stirred for 15 hours. To the reaction liquid was added water (30 mL), followed by extraction with EtOAc (30 mL) three times. The organic layer was washed with brine, dried over $MgSO_4$, and then concentrated under reduced pressure. The residue was purified by silica gel column chromatography (automatic purification device, hexane:EtOAc=70:30 to 50:50) to obtain [6-(trifluoromethyl)biphenyl-3-yl]methanol (678.3 mg) as a yellow solid.

In the same manner as in Preparation Example 52, the compounds of Preparation Example 52-1 through Preparation Example 52-4 shown in Tables described later were prepared.

Preparation Example 53

A solution of {3-chloro-4-[(1S)-2,2,2-trifluoro-1-methylethoxy]phenyl}methanol (284 mg) and $SOCl_2$ (179 µL) in DCM (7 mL) was stirred at room temperature for 2 hours. The reaction liquid was poured into water, followed by extraction with chloroform. The organic layer was washed with brine, dried over $MgSO_4$, and then concentrated under reduced pressure to obtain 2-chloro-4-(chloromethyl)-1-[(1S)-2,2,2-trifluoro-1-methylethoxy]benzene (285 mg) as a colorless liquid.

In the same manner as in Preparation Example 53, the compounds of Preparation Example 53-1 through Preparation Example 53-4 shown in Tables described later were prepared.

Preparation Example 54

To a solution of methyl 4-bromo-3-benzoate (300 mg) in THF (1 mL) were added cyclopentylzinc bromide (9.6 mL) and palladium-tri-tert-butylphosphine (1:2) (123 mg). The reaction liquid was stirred at room temperature for 20 hours. A saturated aqueous $NH_4Cl$ solution was added thereto at 0° C., followed by filtration through celite and extraction with EtOAc. The organic layer was washed with brine and dried over $MgSO_4$. The vehicle was evaporated under reduced pressure and the residue was purified by silica gel column chromatography (hexane:EtOAc=100:0 to 90:10) to obtain methyl 3-chloro-4-cyclopentyl benzoate (280 mg) as a yellow solid.

Preparation Example 55

To a solution of (7-{[2,4-bis(trifluoromethyl)benzyl]oxy}-5-fluoro-2H-chromen-3-yl)methanol (200 mg) in MeCN (5 mL) was added triphenylphosphine dibromide (240 mg). The reaction liquid was stirred at room temperature for 2 hours and concentrated under reduced pressure. To the residue were added EtOAc and IPE, the resulting solid was removed by filtration, and the filtrate was concentrated to obtain 7-{[2,4-bis(trifluoromethyl)benzyl]oxy}-3-(bromomethyl)-5-fluoro-2H-chromene (230 mg) as a brown liquid. 60% sodium hydride (24 mg) was added to a DMF solution (5 mL) at 0° C., and subsequently, ethyl 1H-pyrazole-4-carboxylate (76 mg) was added thereto. The mixture was stirred at room temperature for 0.5 hours, and a solution of 7-{[2,4-bis(trifluoromethyl)benzyl]oxy}-3-(bromomethyl)-5-fluoro-2H-chromene (220 mg) in DMF (5 mL) was added thereto at 0° C. The reaction liquid was stirred at room temperature for 13 hours, quenched with a saturated $NH_4Cl$ solution, and then extracted with EtOAc. The organic layer was washed with brine, dried over $MgSO_4$, and concentrated under reduced pressure. The residue was purified by silica gel column chromatography (hexane:EtOAc=100:0 to 70:30) to obtain ethyl 1-[(7-{[2,4-bis(trifluoromethyl)benzyl]oxy}-5-fluoro-2H-chromen-3-yl)methyl]-1H-pyrazole-4-carboxylate (111 mg) as a pale yellow solid.

In the same manner as in Preparation Example 55, the compound of Preparation Example 55-1 shown in Tables described later was prepared.

Preparation Example 56

A solution of 4-isopropoxy-3-(trifluoromethyl)benzonitrile (2.4 g) and 5 M NaOH (50 mL) in EtOH (50 mL) was heated and refluxed for 18 hours. The solution was cooled to room temperature, acidified by hydrochloric acid, and then extracted with chloroform. The organic layer was washed with brine, dried over $MgSO_4$, and concentrated under reduced pressure. The residue was purified by silica gel column chromatography (chloroform:MeOH=100:0 to 95:5). The product was washed with hexane to obtain 4-isopropoxy-3-(trifluoromethyl)benzoic acid (2.2 g) as a white solid.

In the same manner as in Preparation Example 56, the compounds of Preparation Example 56-1 through Preparation Example 56-6 shown in Tables described later were prepared.

Preparation Example 57

5-Bromo-3-(trifluoromethyl)-2-{[(2S)-1,1,1-trifluoropropan-2-yl]oxy}pyridine (500 mg) was dissolved in a mixed vehicle of DMSO (5 mL) and MeOH (5 mL). Then, TEA (0.42 mL) was added thereto at 25° C., and then $Pd(OAc)_2$ (17 mg) and DPPP (60 mg) were added thereto at 25° C., followed by stirring at 70° C. for 15 hours under a CO atmosphere. To the reaction solution was added water (30 mL), followed by extraction with EtOAc (20 mL) three times. The organic layer was washed with brine, dried over MgSO$_4$, and then filtered, and the filtrate was concentrated. The residue was purified by silica gel column chromatography (automatic purification device, developing solution; hexane:EtOAc=100:0 to 80:20) to obtain methyl 5-(trifluoromethyl)-6-{[(2S)-1,1,1-trifluoropropan-2-yl]oxy}nicotinate (403 mg) as a yellow solid.

Preparation Example 58

To a solution of ethyl (1-methyl-1,2,3,6-tetrahydropyridin-4-yl)acetate (2.05 g) in dichloroethane (14 mL) was added 1-chloroethyl-chloroformate (1.5 mL) at 0° C. The reaction liquid was heated and refluxed for 2.5 hours, and then concentrated under reduced pressure. The residue was dissolved in MeOH (14 mL), and heated and refluxed for 1 hour. After concentration under reduced pressure, the residue was purified by amino column chromatography (chloroform:methanol=100:0 to 80:20) to obtain ethyl 1,2,3,6-tetrahydropyridin-4-ylacetate (130 mg) as a brown liquid.

In the same manner as in Preparation Example 58, the compound of Preparation Example 58-1 shown in Tables described later was prepared.

Preparation Example 59

Methyl 5,6-dichloronicotinate (1.5 g) and 60% sodium hydride (640 mg) were dissolved in THF (45 mL). 1,3-Difluoropropan-2-ol (1.5 g) was added thereto at 0° C., followed by stirring at 0° C. for 3 hours, and the reaction solution was quenched with aqueous NH$_4$Cl. After extraction with EtOAc, the organic layer was dried over MgSO$_4$ and then filtered, and the desiccant was removed. The vehicle was evaporated under reduced pressure, followed by purification by silica gel column chromatography (hexane:AcOEt=100:0 to 50:50) to obtain methyl 5-chloro-6-[(1,3-difluoropropan-2-yl)oxy]nicotinate (1.56 g) as a colorless liquid.

To a solution of methyl 5-chloro-6-[(1,3-difluoropropan-2-yl)oxy]nicotinate (1 g) in THF (20 mL) was added dropwise a 0.99 M solution of DIBAL in toluene (11.3 mL) at 0° C., followed by stirring at 0° C. for 2 hours. Then, the reaction solution was poured into an aqueous Rochelle salt solution, followed by stirring at room temperature for 1 hour. After extraction with an EtOAc-water system, the organic layer was washed with brine, dried over MgSO$_4$, and then filtered, and the desiccant was removed. The vehicle was evaporated under reduced pressure, followed by purification by silica gel column chromatography (Hex:AcOEt=98:2 to 70:30) to obtain {5-chloro-6-[(1,3-difluoropropan-2-yl)oxy]pyridin-3-yl}methanol (650 mg) as a colorless liquid.

Preparation Example 60

To 5,6-dichloronicotinic acid (2.2 g) was added 1,1,1-trimethoxyethane (4.3 mL), followed by irradiation with microwave at 120° C. for 15 minutes. The reaction mixture was dissolved in EtOAc and washed with water. The organic layer was dried over MgSO$_4$ and the vehicle was evaporated under reduced pressure. The residue was purified by silica gel column chromatography (hexane:EtOAc=85:15 to 80:20) to obtain methyl 5,6-dichloronicotinate (2.2 g) as a white solid.

Preparation Example 61

To a solution of ethyl 4-pyridyl acetate (2 g) in MeCN (20 mL) was added methyliodide (2.3 mL). The reaction liquid was stirred at room temperature overnight and then concentrated under reduced pressure. To the residue was added IPE and the resulting solid was collected by filtration. The solid was dissolved in MeOH, and sodium borohydride (916 mg) was added there at 15° C. or lower.

The reaction liquid was stirred at room temperature for 6 hours, and then water was added thereto, followed by extraction with chloroform. The organic layer was washed with brine, dried over MgSO$_4$, and concentrated under reduced pressure. The residue was purified by column chromatography (chloroform:MeOH=100:0 to 90:10) to obtain ethyl (1-methyl-1,2,3,6-tetrahydropyridin-4-yl)acetate (2.08 g) as a pale yellow liquid.

Preparation Example 62

To a solution of {3-(trifluoromethyl)-4-[(1S)-2,2,2-trifluoro-1-methylethoxy]phenyl}methanol (200 mg) in dichloroethane (5 mL) were added thionyl chloride (111 µL) and a catalytic amount of DMF, followed by stirring at 60° C. for 2 hours. The reaction liquid was concentrated under reduced pressure and then to the residue were added a solution of ethyl (3R)-1-[(7-hydroxy-2H-chromen-3-yl)methyl]piperidine-3-carboxylate (175 mg) in DMF (8.75 mL) and potassium carbonate (152 mg) in this order, followed by stirring at 80° C. for 2 hours. The reaction liquid was cooled to room temperature and poured into water, followed by extraction with EtOAc. The organic layer was washed with water and brine in this order and then dried over anhydrous sodium sulfate, and the vehicle was evaporated. The residue was purified by silica gel column chromatography to obtain ethyl (3R)-1-[(7-{[3-(trifluoromethyl)-4-{[(2S)-1,1,1-trifluoropropan-2-yl]oxy}benzyl]oxy}-2H-chromen-3-yl)methyl]piperidine-3-carboxylate (271 mg) as a yellow oily substance.

In the same manner as in Preparation Example 62, the compounds of Preparation Example 62-1 through Preparation Example 62-19 shown in Tables described later were prepared.

Preparation Example 63

To a solution of 4-chloro-3-(trifluoromethyl)benzonitrile (1.5 g), iron (III) acetylacetonate (130 mg), and 1-methylpyrrolidin-2-one (4 mL) in THF (45 mL) was added a 1 M solution of cyclopentyl magnesium bromide in THF (8.8 mL) at 5° C., followed by stirring at room temperature for 0.5 hours and diluting with diethylether. 1 M hydrochloric acid was slowly added thereto, followed by extraction with EtOAc. The organic layer was washed with brine, dried over MgSO$_4$, and concentrated under reduced pressure. The residue was purified by silica gel column chromatography (hexane:EtOAc=100:0 to 95:5) to obtain 4-cyclopentyl-3-(trifluoromethyl)benzonitrile (367 mg) as a white solid.

Preparation Example 64

To a solution of 7-(methoxymethoxy)-2H-chromene-3-carbaldehyde (5.00 g) and ethyl (3R)-piperidine-3-carboxylate (4.20 mL) in dichloroethane (150 mL) was added sodium triacetoxyborohydride (12.0 g), followed by stirring at 80° C. for 4 hours. The reaction liquid was cooled to room temperature and then saturated aqueous NaHCO$_3$ was added thereto, followed by extraction with chloroform. The organic layer was washed with brine and dried over anhydrous sodium sulfate, and the vehicle was evaporated. The residue was purified by silica gel column chromatography (hexane:EtOAc=4:1) to obtain ethyl (3R)-1-{[7-(methoxymethoxy)-2H-chromen-3-yl]methyl}piperidine-3-carboxylate (7.30 g) as a yellow oily substance.

43

In the same manner as in Preparation Example 64, the compounds of Preparation Example 64-1 through Preparation Example 64-7 shown in Tables described later were prepared.

For the Preparation Example Compounds, the structures are shown in Tables 3 to 57, and the physicochemical data and preparation methods are shown in Tables 99 to 107.

Example 1

To a solution of 1-[(7-{[2,4-bis(trifluoromethyl)benzyl]oxy}-5-fluoro-2H-chromen-3-yl)methyl]pyrrolidine-3-carboxylic acid (98 mg) in DMF (2 mL) was added CDI (46 mg), followed by stirring at 70° C. for 12 hours. To the reaction liquid were added methanesulfonamide (27 mg) and DBU (43 mg) in this order, followed by stirring for 12 hours. To the reaction liquid was added AcOH, followed by concentration under reduced pressure, and the residue was purified by reverse phase column chromatography (H$_2$O:MeCN=100:0 to 90:10) to obtain a yellow amorphous substance (70 mg). This yellow amorphous substance was dissolved in dioxane (1 mL), and a 4 M HCl/dioxane solution (1 mL) was added thereto, followed by stirring and then concentrating under reduced pressure. The residue was washed with hexane to obtain 1-[(7-{[2,4-bis(trifluoromethyl)benzyl]oxy}-5-fluoro-2H-chromen-3-yl)methyl]-N-(methylsulfonyl)pyrrolidine-3-carboxamide hydrochloride (60 mg) as a pale yellow solid.

Example 2

To a solution of pyrrolidine-3-carboxylic acid hydrochloride in MeOH was added TEA, followed by stirring at room temperature for 10 minutes. The reaction mixture was concentrated under reduced pressure, and a solution of 7-{[4-phenyl-5-(trifluoromethyl)-2-thienyl]methoxy}-2H-chromene-3-carbaldehyde in MeOH and AcOH were added thereto at room temperature. The reaction mixture was heated to 70° C., stirred for 2 hours, and left to be cooled to 25° C., and NaBH$_3$CN was added thereto at room temperature, followed by stirring at 70° C. for 5 hours. The reaction liquid was purified by reverse phase column chromatography (MeCN:H$_2$O=20:80 to 50:50) and the resulting white solid was washed with diisopropylether to obtain 1-[(7-{[4-phenyl-5-(trifluoromethyl)-2-thienyl]methoxy}-2H-chromen-3-yl)methyl]pyrrolidine-3-carboxylic acid as a white solid.

Example 3

Pyrrolidine-3-carboxylic acid hydrochloride (165 mg) was dissolved in MeOH, and TEA was added thereto, followed by stirring at room temperature for 1 hour. The reaction mixture was concentrated under reduced pressure, and then a solution of 7-{[2,4-bis(trifluoromethyl)phenyl]ethynyl}-5-fluoro-2H-chromene-3-carbaldehyde in MeOH (8 mL) and AcOH (0.5 mL) were added thereto at room temperature, followed by stirring at 70° C. for 0.5 hours. After leaving to be cooled to room temperature, to the reaction mixture was added NaBH$_3$CN (57 mg) at room temperature, followed by stirring at 50° C. for 2 hours. After confirming completion of the reaction by means of LC, the reaction liquid was purified by reverse phase chromatography (MeCN:H$_2$O=20:80 to 50:50), the resulting amorphous substance (233 mg) was dissolved in dioxane (1 mL), and a 4 M HCl/dioxane solution (1 mL) was added thereto. The reaction liquid was concentrated under reduced pressure and the residue was washed with MeCN to obtain 1-[(7-{[2,4-bis(trifluoromethyl)phe-

44 nyl]ethynyl}-5-fluoro-2H-chromen-3-yl)methyl]pyrrolidine-3-carboxylic acid hydrochloride (185 mg) as a pale yellow solid.

Example 154

A solution of ethyl 1-[(7-{[2,4-bis(trifluoromethyl)benzyl]oxy}-5-fluoro-2H-chromen-3-yl)methyl]-1H-pyrazole-4-carboxylate (100 mg) and a 1 M aqueous NaOH solution (0.55 mL) in EtOH/THF (3 mL/1 mL) was stirred at 100° C. for 2 hours, neutralized with 1 M HCl, and extracted with chloroform. The organic layer was washed with brine, dried over MgSO$_4$, and concentrated under reduced pressure. The residue was purified by silica gel column chromatography (chloroform:methanol=100:0 to 90:10) and the obtained solid was washed with IPE to obtain 1-[(7-{[2,4-bis(trifluoromethyl)benzyl]oxy}-5-fluoro-2H-chromen-3-yl)methyl]-1H-pyrazole-4-carboxylic acid (71 mg) as a white solid.

Example 156

To a solution of ethyl (3R)-1-[(7-{[3-(trifluoromethyl)-4-{[(2S)-1,1,1-trifluoropropan-2-yl]oxy}benzyl]oxy}-2H-chromen-3-yl)methyl]piperidine-3-carboxylate (271 mg) in EtOH (5.4 mL)-THF (2.7 mL) was added a 1 M aqueous NaOH solution (923 µL), followed by stirring at 50° C. for 2 hours. The reaction liquid was cooled to room temperature, then 1 M hydrochloric acid (923 µL) was added thereto, and the vehicle was evaporated. The residue was purified by reverse phase chromatography (H$_2$O:MeCN=100:0 to 30:70) to obtain a yellow oily substance, which was dissolved in dioxane (3 mL), treated with 4 N HCl/dioxane (1 mL), and washed with IPE to obtain (3R)-1-[(7-{[3-(trifluoromethyl)-4-{[(2S)-1,1,1-trifluoropropan-2-yl]oxy}benzyl]oxy}-2H-chromen-3-yl)methyl]piperidine-3-carboxylic acid hydrochloride (215 mg) as a white powder.

In the same manner as the methods of Examples 1 to 3, 154, or 156, the compounds of Examples shown in Tables described later were prepared. For the Example Compounds, the structures are shown in Tables 58 to 98, and the physicochemical data and the preparation methods are shown in Tables 108 to 131.

TABLE 3

| No | Str |
|---|---|
| Pr1 | 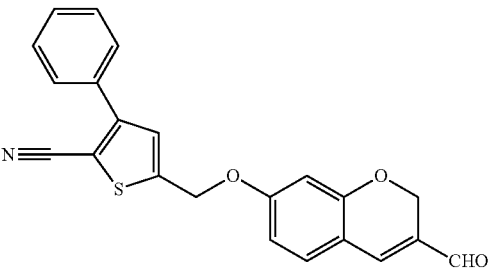 |
| Pr2 | 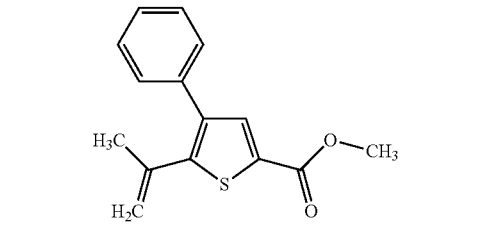 |

TABLE 3-continued
| No | Str |
|---|---|
| Pr2-1 | 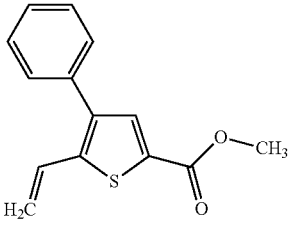 |
| Pr2-2 | 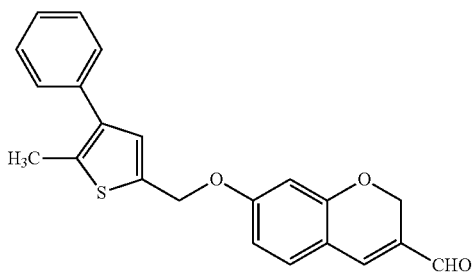 |
| Pr2-3 | 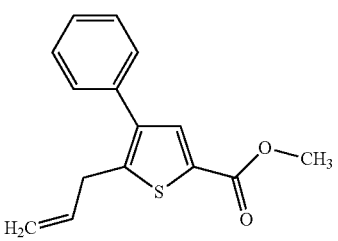 |
TABLE 4
| Pr2-4 | 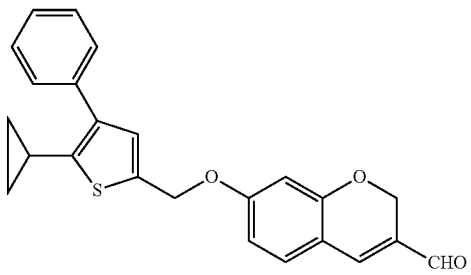 |
|---|---|
| Pr3 | 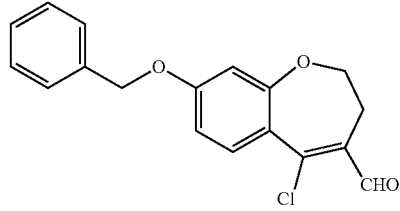 |
| Pr4 | 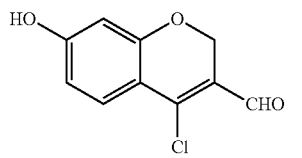 |
TABLE 4-continued
| Pr5 | 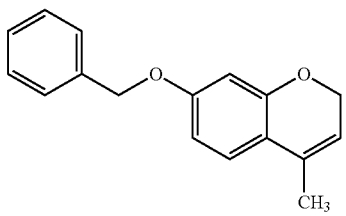 |
|---|---|
| Pr5-1 | 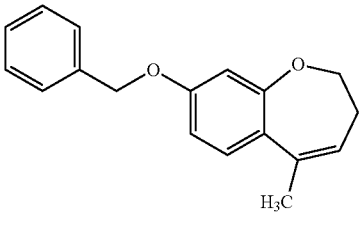 |
| Pr6 | 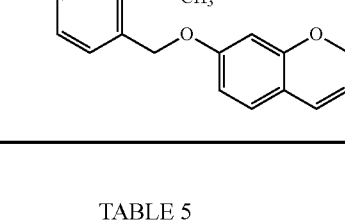 |
TABLE 5
| Pr6-1 | 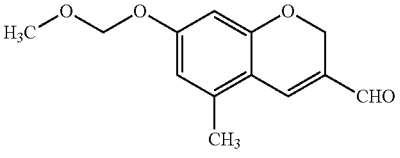 |
|---|---|
| Pr6-2 | 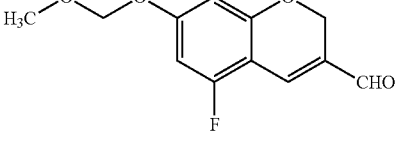 |
| Pr6-3 | 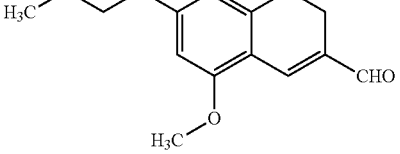 |
| Pr6-4 | 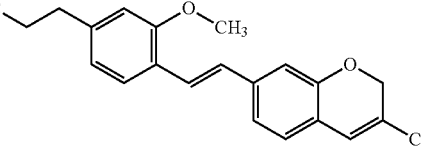 |
| Pr6-5 | 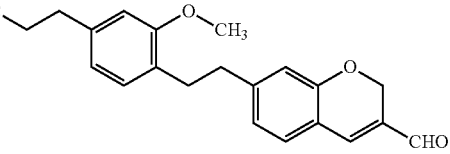 |

TABLE 5-continued
Pr6-6 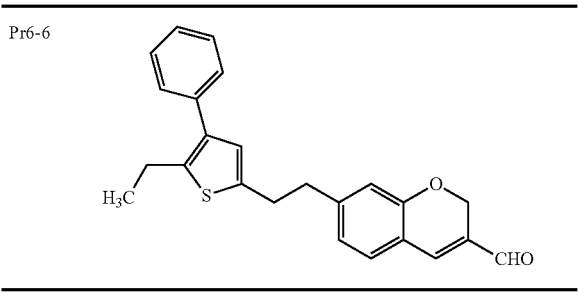
TABLE 6
Pr6-7 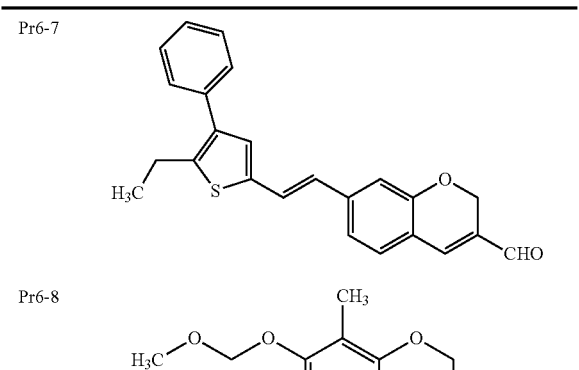
Pr6-8
Pr6-9
Pr6-10
Pr6-11
Pr7 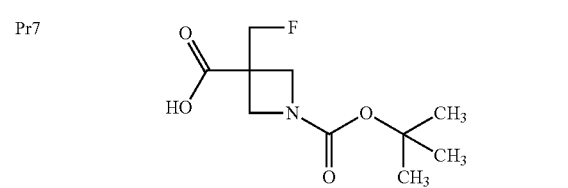
Pr8 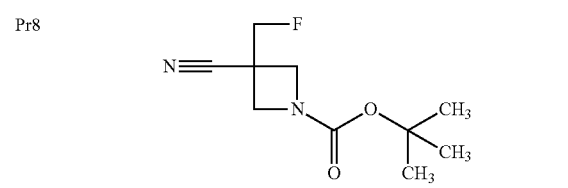
TABLE 7
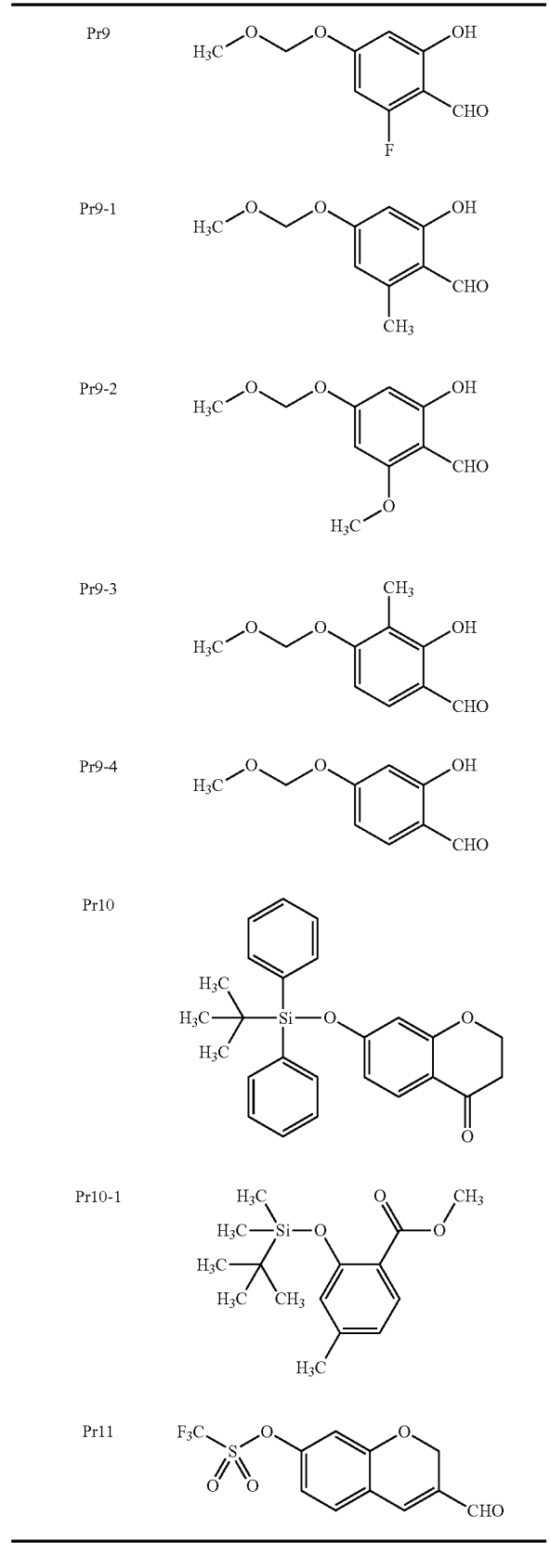
Pr9
Pr9-1
Pr9-2
Pr9-3
Pr9-4
Pr10
Pr10-1
Pr11

TABLE 8
| | |
|---|---|
| Pr11-1 | 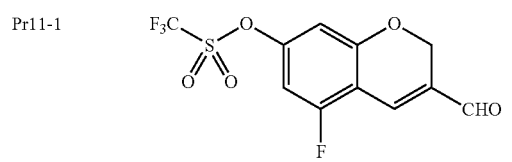 |
| Pr12 | 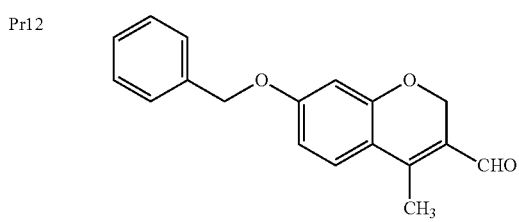 |
| Pr12-1 | 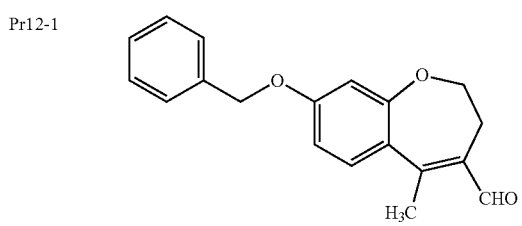 |
| Pr12-2 | 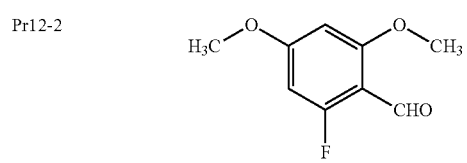 |
| Pr12-3 | 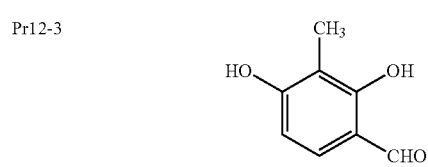 |
| Pr12-4 | 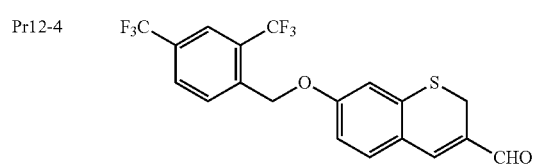 |
| Pr13 | 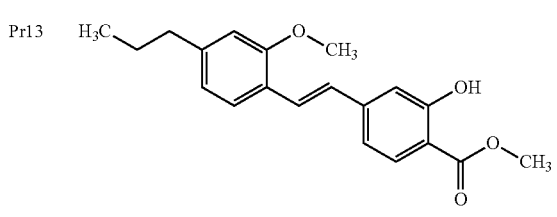 |
TABLE 9
| | | |
|---|---|---|
| Pr13-1 | 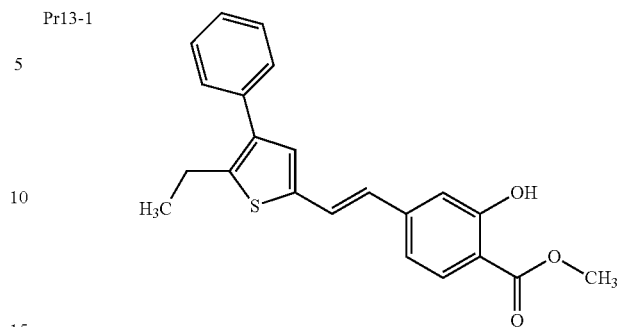 | |
| Pr14 | 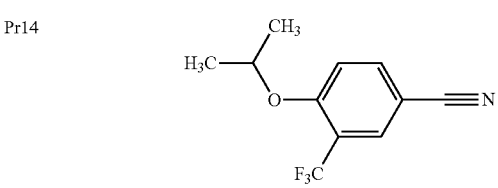 | |
| Pr14-1 | 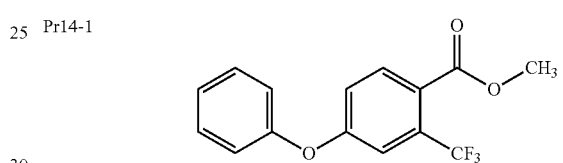 | |
| Pr14-2 | 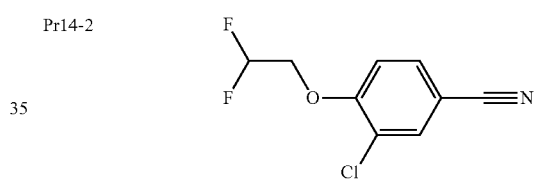 | |
| Pr14-3 | 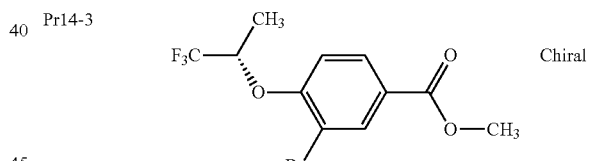 | Chiral |
| Pr14-4 | 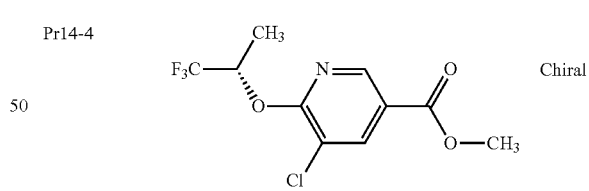 | Chiral |
TABLE 10
| | | |
|---|---|---|
| Pr14-5 | 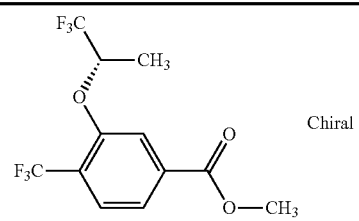 | Chiral |

TABLE 10-continued
| Pr14-6 | 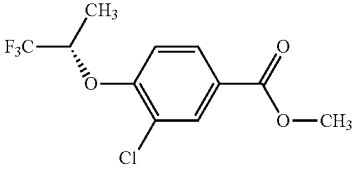 | Chiral |
| --- | --- | --- |
| Pr14-7 | 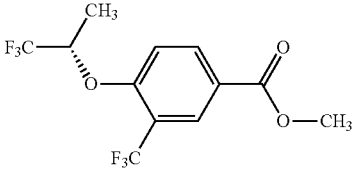 | Chiral |
| Pr14-8 | 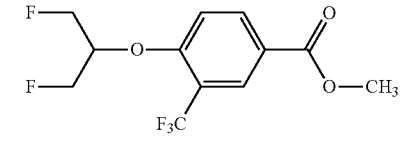 | |
| Pr14-9 | 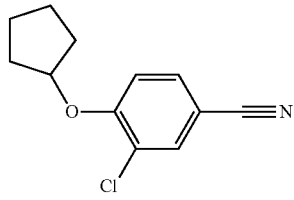 | |
| Pr14-10 | 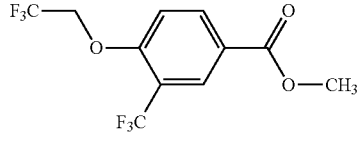 | |
| Pr14-11 | 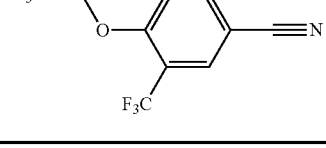 | |
TABLE 11
| Pr14-12 | 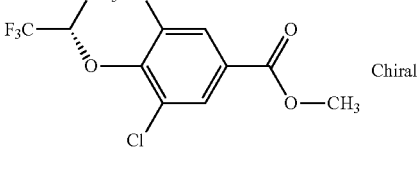 | Chiral |
| --- | --- | --- |
| Pr14-13 | 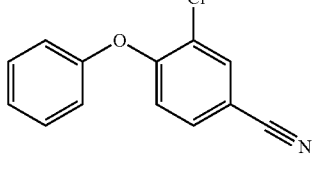 | |
| Pr14-14 | 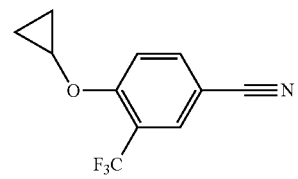 | |
| Pr14-15 | 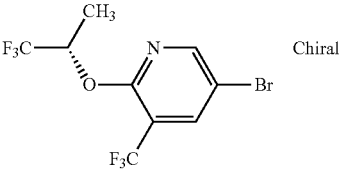 | Chiral |
| Pr14-16 | 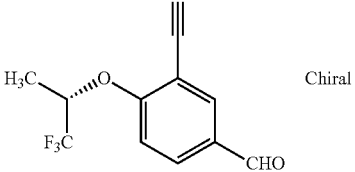 | Chiral |
| Pr15 | 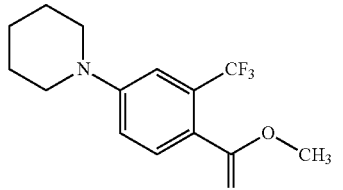 | |
| Pr15-1 | 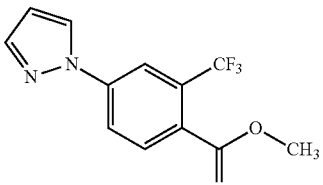 | |
TABLE 12
| Pr15-2 | 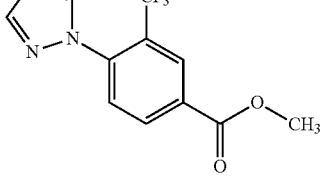 |
| --- | --- |
| Pr15-3 | 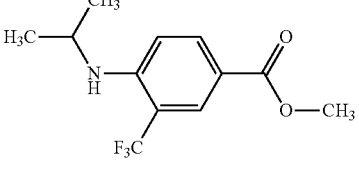 |
| Pr15-4 | 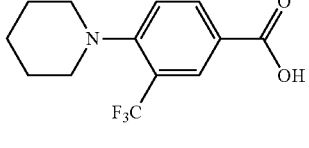 |

TABLE 12-continued
| Pr16 | 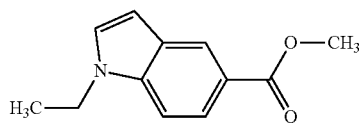 |
| Pr17 | 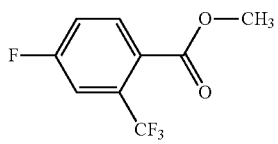 |
| Pr18 | 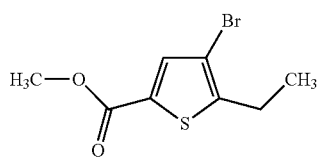 |
| Pr18-1 | 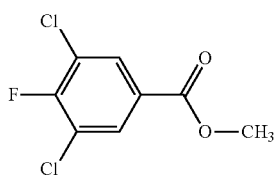 |
TABLE 13
| Pr18-2 | 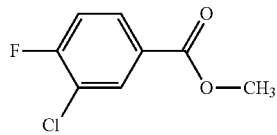 |
| Pr18-3 | 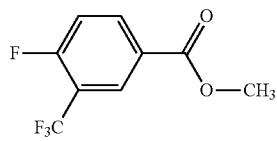 |
| Pr18-4 | 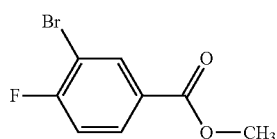 |
| Pr18-5 | 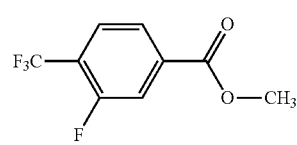 |
| Pr18-6 | 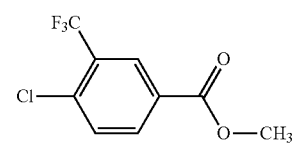 |
| Pr19 |  |
TABLE 13-continued
| Pr20 | 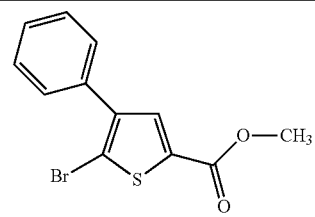 |
TABLE 14
| Pr21 | 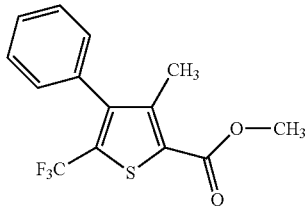 |
| Pr22 | 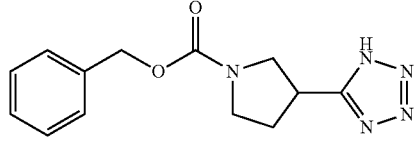 |
| Pr23 | 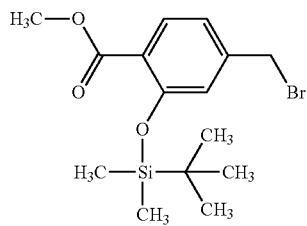 |
| Pr23-1 | 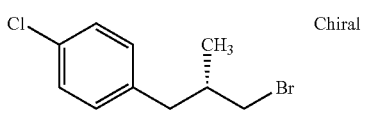 Chiral |
| Pr24 | 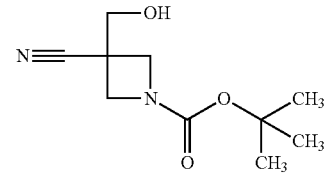 |
| Pr25 | 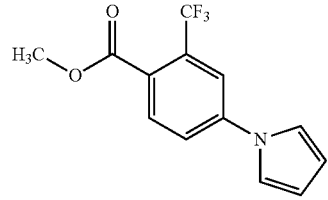 |
| Pr25-1 | 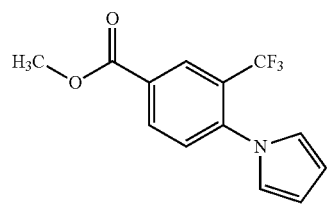 |

TABLE 15
Pr26, Pr27, Pr27-1, Pr27-2, Pr27-3, Pr27-4
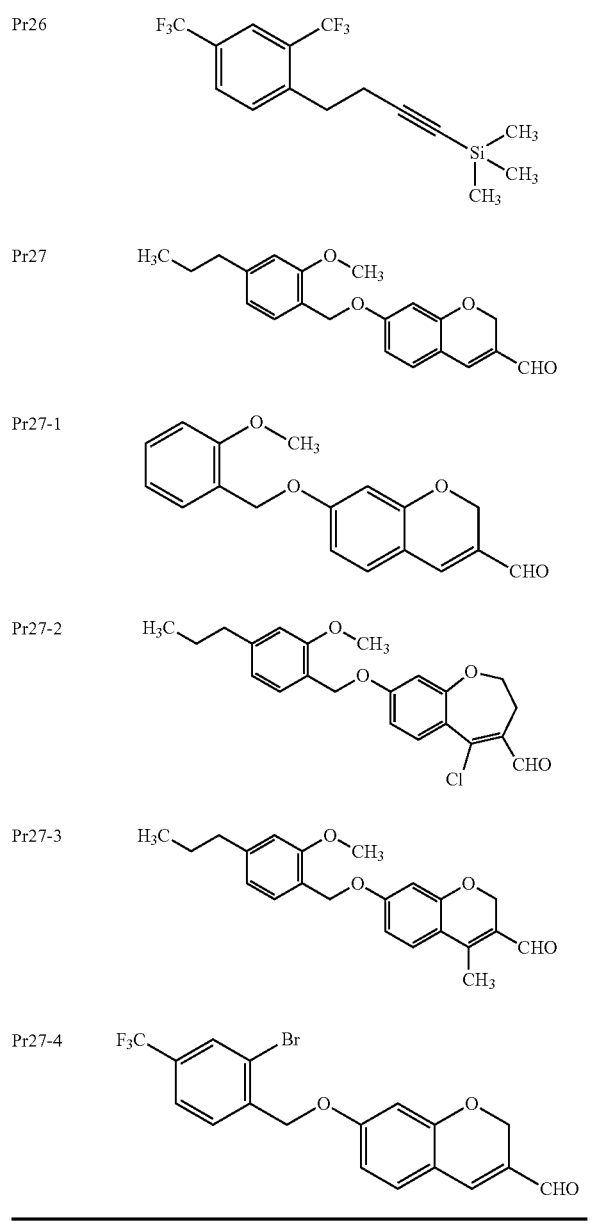
TABLE 16
Pr27-5, Pr27-6
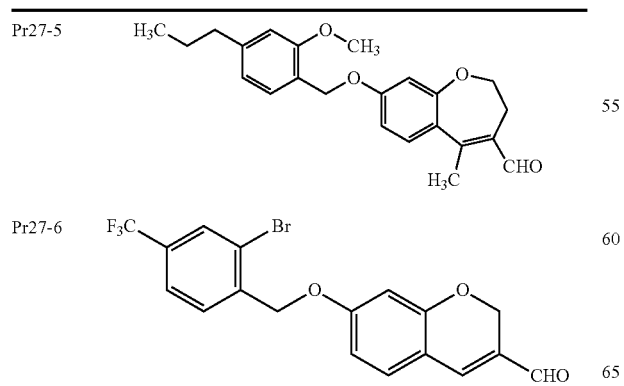
TABLE 16-continued
Pr28, Pr28-1, Pr28-2, Pr28-3, Pr28-4
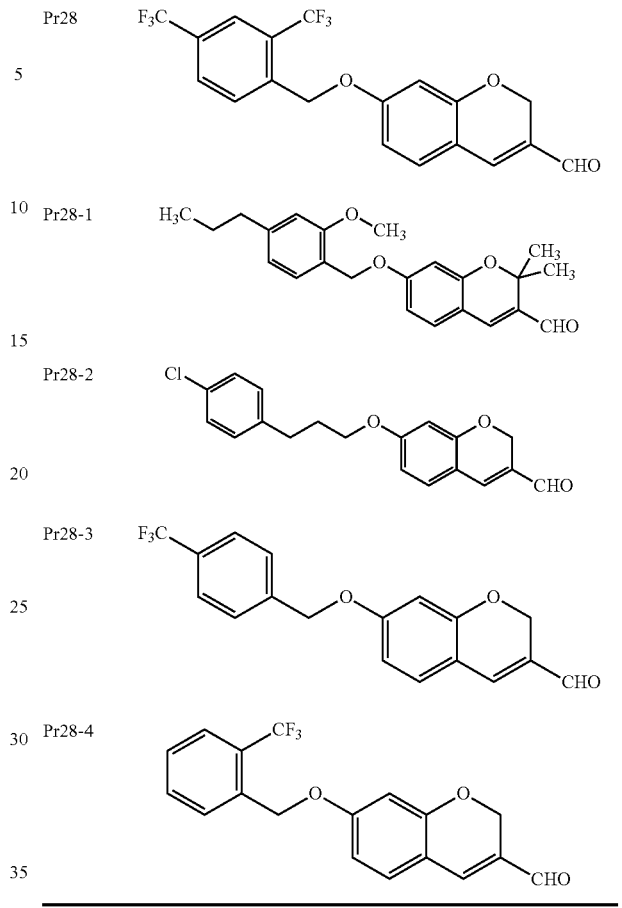
TABLE 17
Pr28-5, Pr28-6, Pr28-7
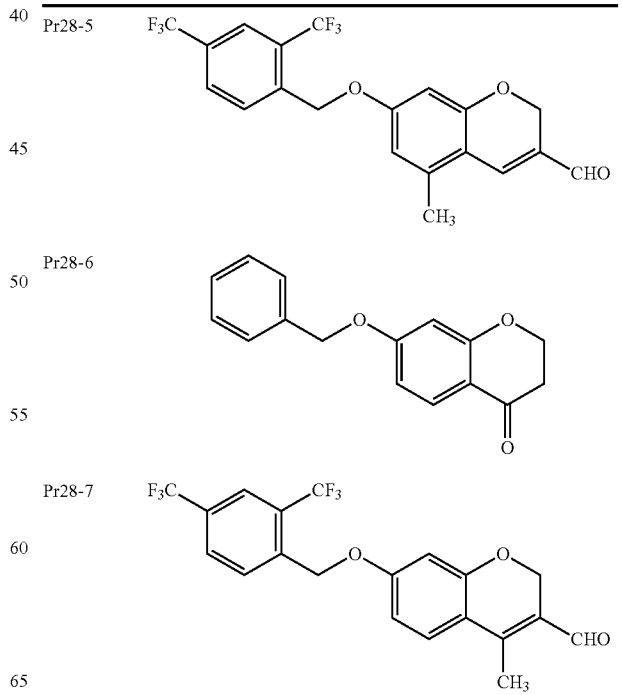

TABLE 17-continued
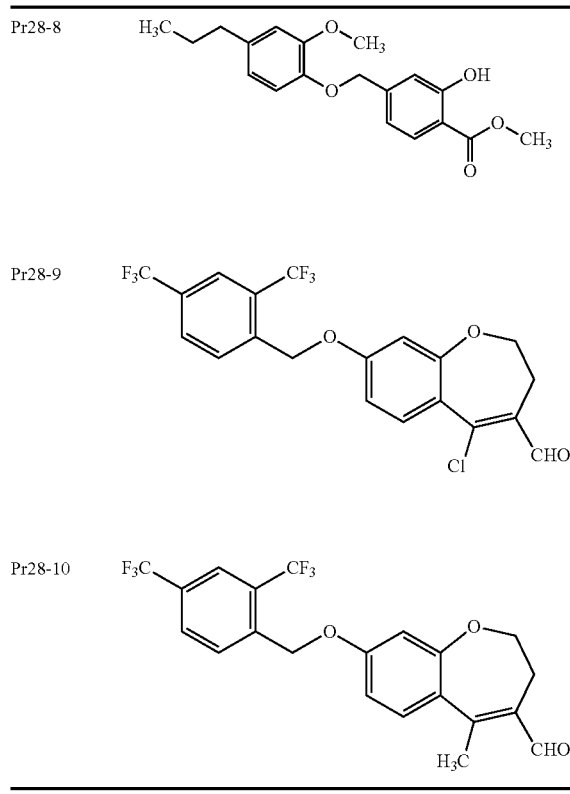
TABLE 18
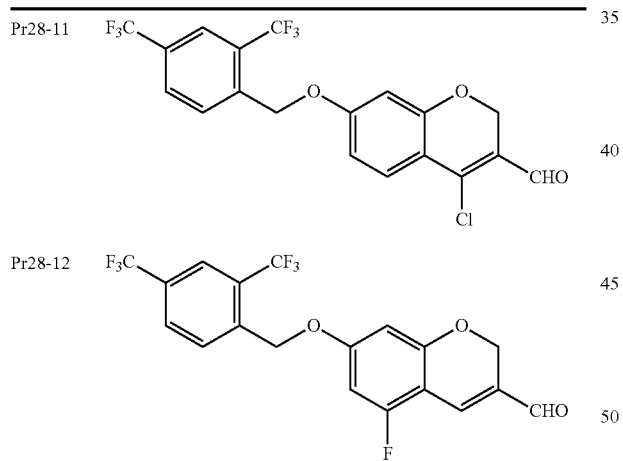
TABLE 18-continued
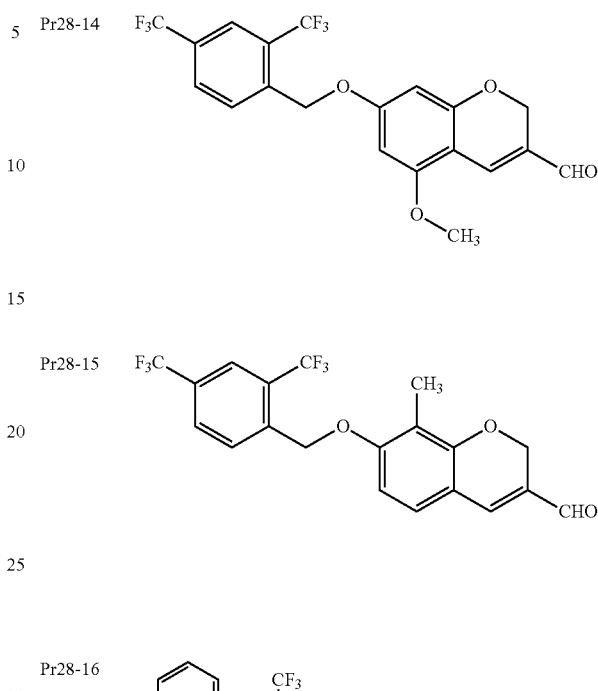
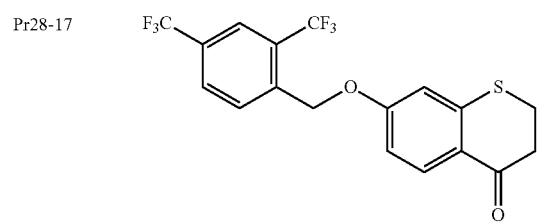
TABLE 19
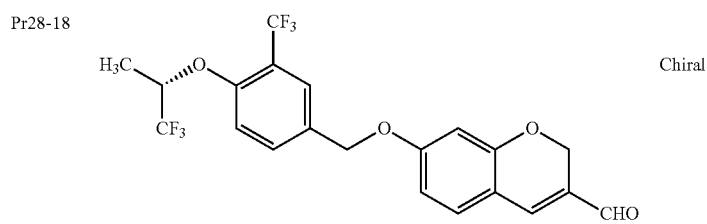

TABLE 19-continued
| Pr28-19 | 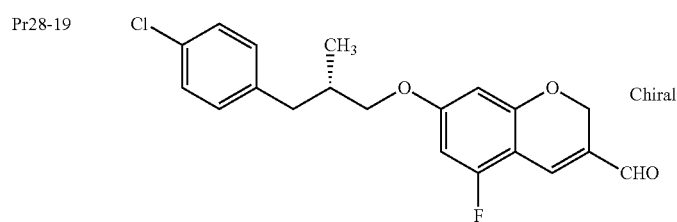 |
| Pr28-20 | 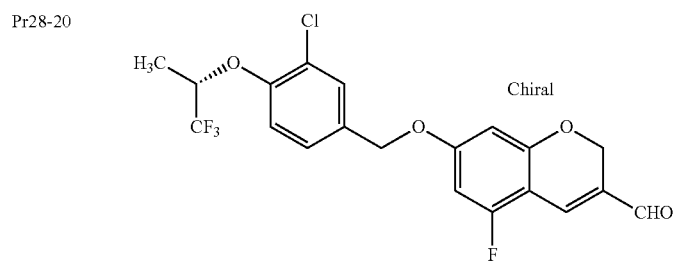 |
| Pr28-21 | 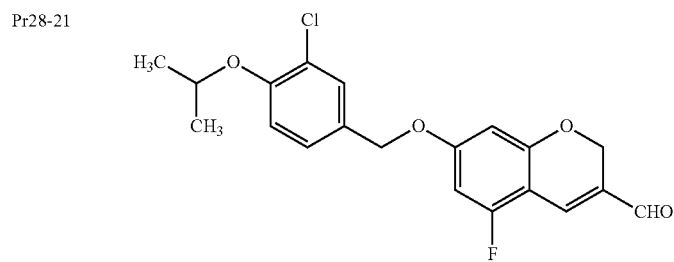 |
| Pr28-22 | 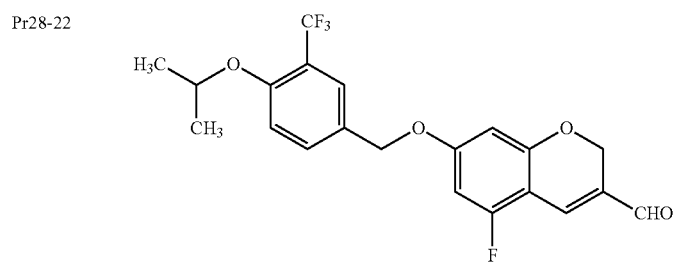 |
| Pr28-23 | 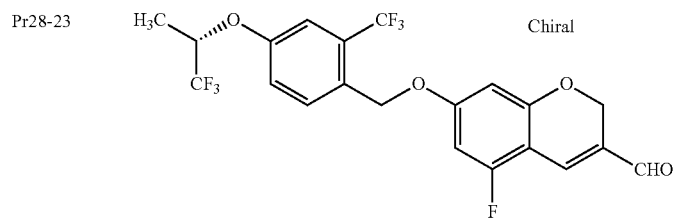 |
TABLE 20
| Pr28-24 | 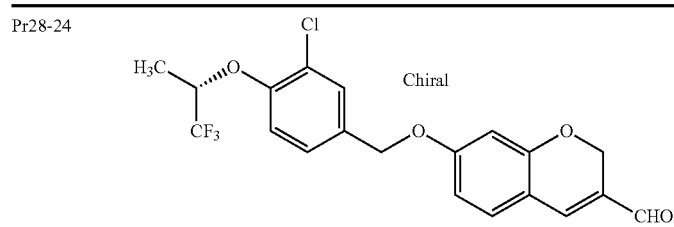 |

TABLE 20-continued
Pr28-25 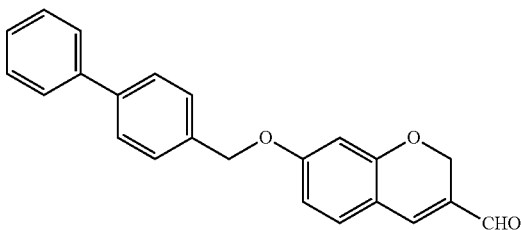
Pr29-26 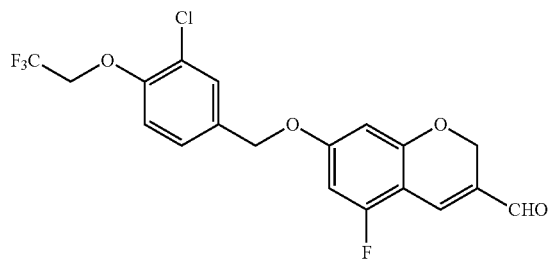
Pr28-27 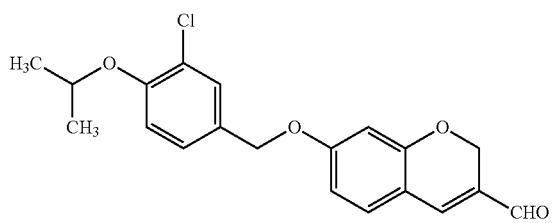
Pr29 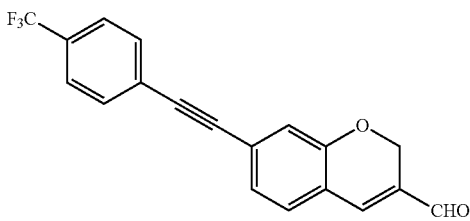
Pr29-1 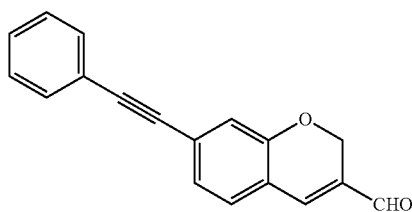
TABLE 21
Pr29-2 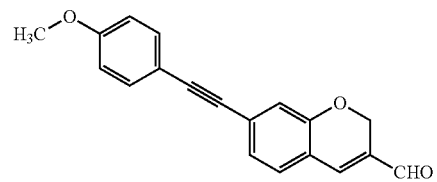
TABLE 21-continued
Pr29-3 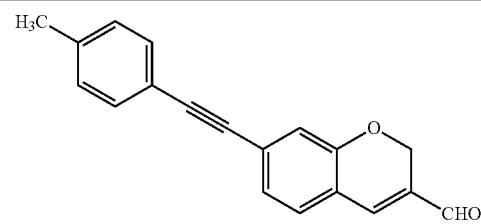

TABLE 21-continued
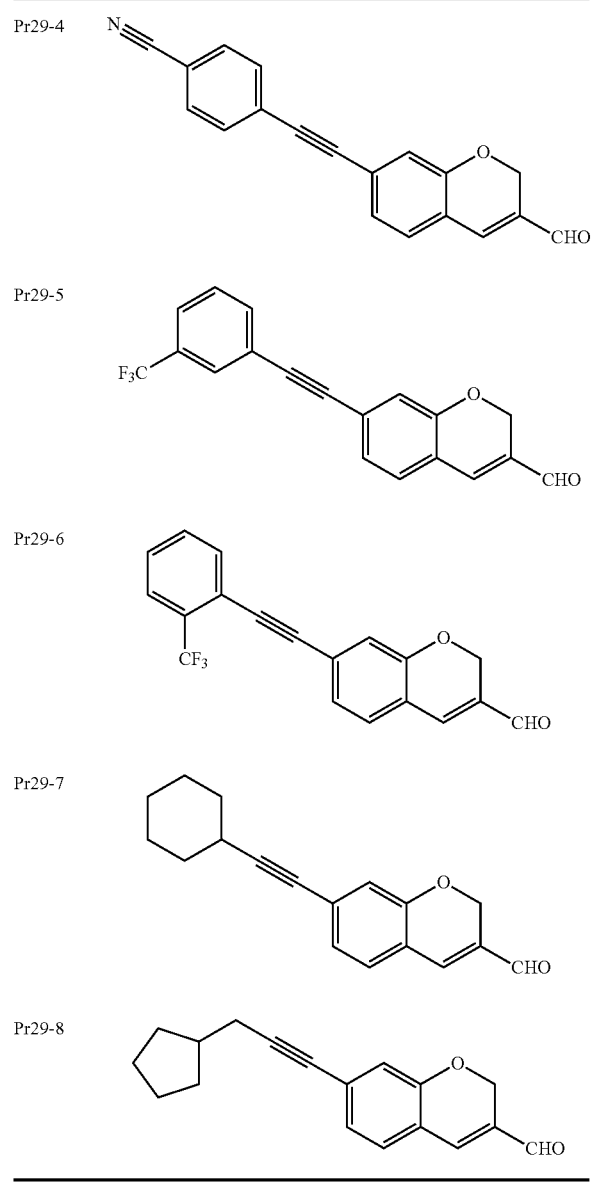
TABLE 22
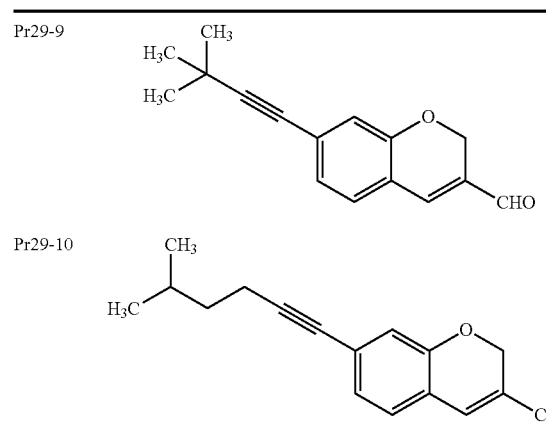
TABLE 22-continued
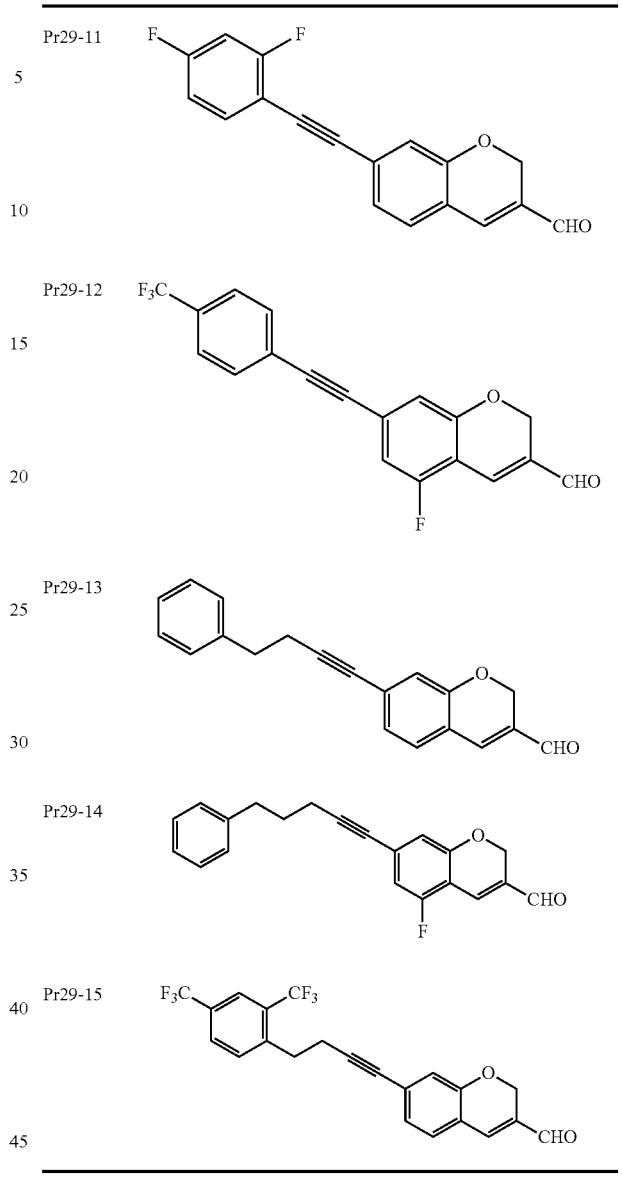
TABLE 23
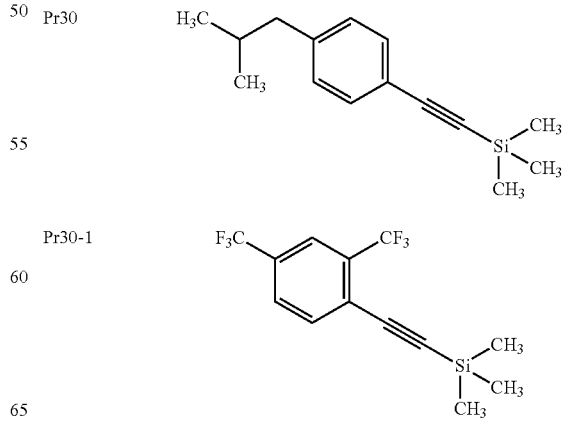

TABLE 23-continued
| | |
|---|---|
| Pr31 | 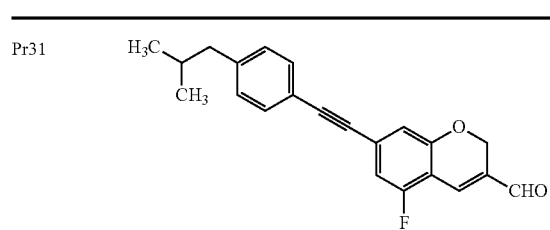 |
| Pr31-1 | 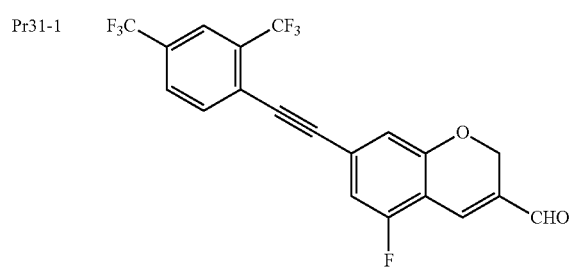 |
| Pr32 | 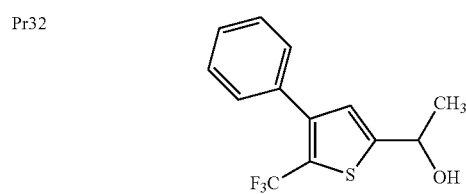 |
| Pr33 | 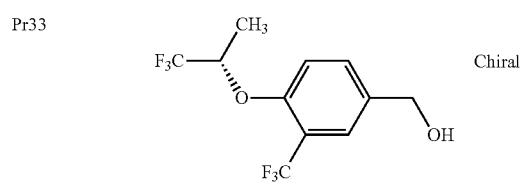 Chiral |
TABLE 24
| | |
|---|---|
| Pr33-1 | 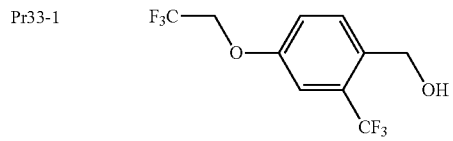 |
| Pr33-2 | 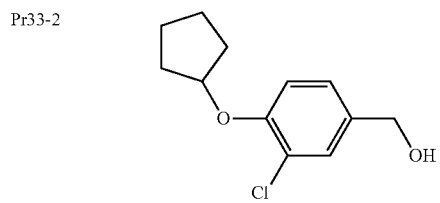 |
| Pr33-3 | 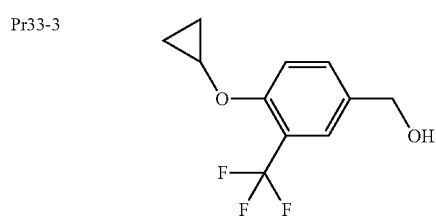 |
| Pr33-4 | 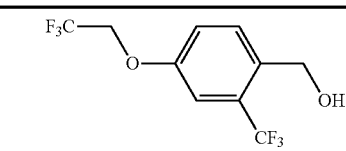 |
| Pr33-5 | 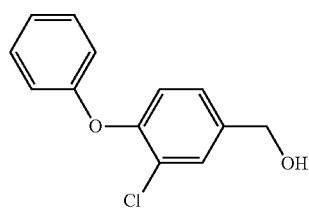 |
| Pr33-6 | 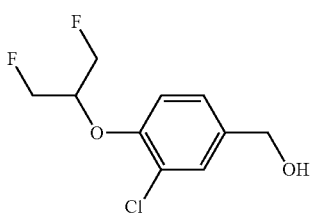 |
| Pr33-7 | 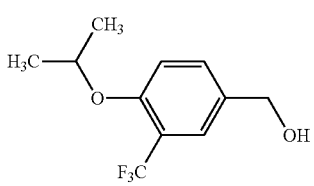 |
TABLE 25
| | |
|---|---|
| Pr33-8 | 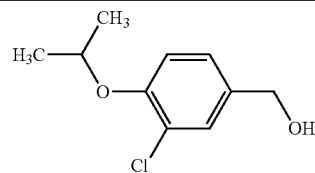 |
| Pr33-9 | 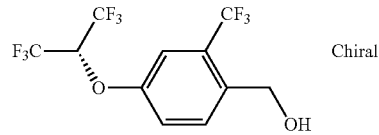 Chiral |
| Pr33-10 | 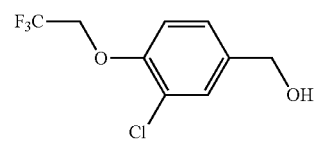 |
| Pr33-11 | 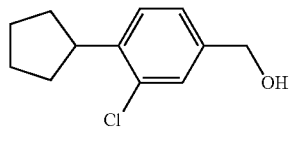 |
| Pr33-12 | 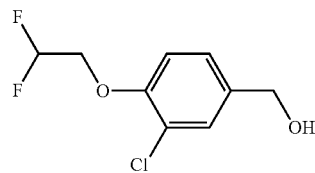 |

TABLE 25-continued
| Pr33-13 | 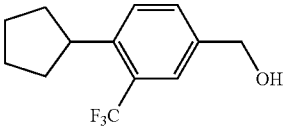 |
| Pr33-14 | 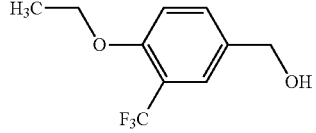 |
| Pr33-15 | 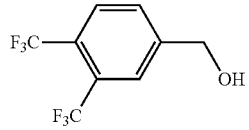 |
TABLE 26
| Pr33-16 | 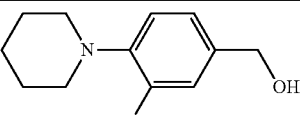 |
| Pr33-17 | 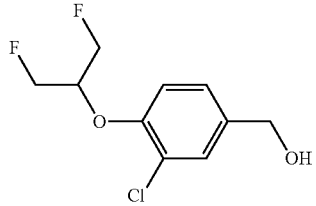 |
| Pr33-18 | 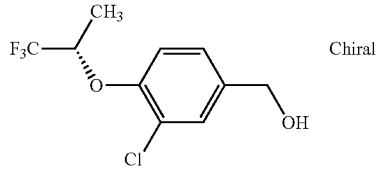 Chiral |
| Pr33-19 | 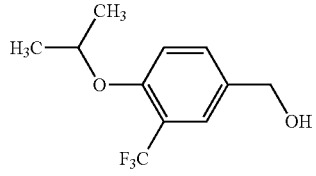 |
| Pr33-20 | 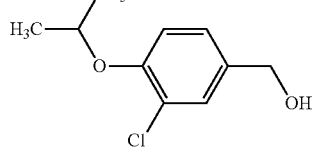 |
| Pr33-21 | 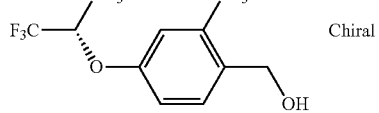 Chiral |
TABLE 26-continued
| Pr34 | 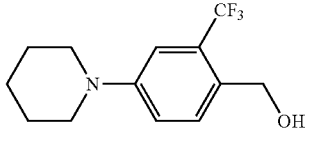 |
TABLE 27
| Pr34-1 | 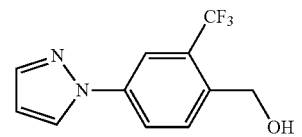 |
| Pr34-2 | 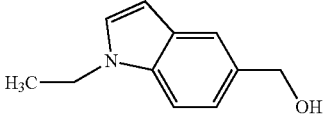 |
| Pr34-3 | 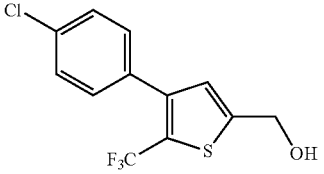 |
| Pr34-4 | 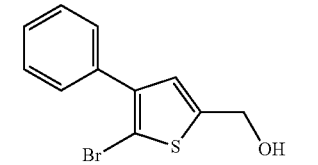 |
| Pr34-5 | 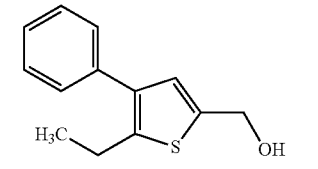 |
| Pr34-6 | 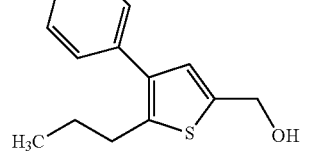 |
| Pr34-7 | 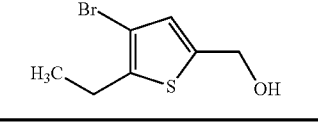 |

TABLE 28
Pr34-8 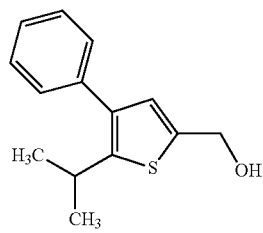
Pr34-9 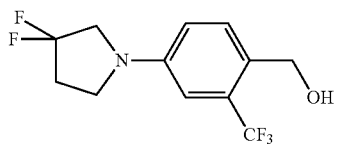
Pr34-10 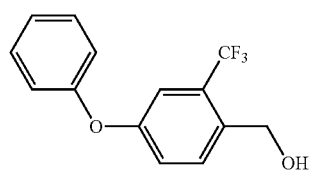
Pr34-11 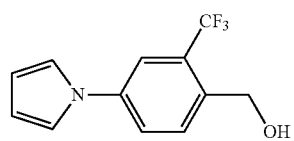
Pr34-12 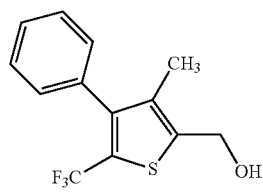
Pr34-13 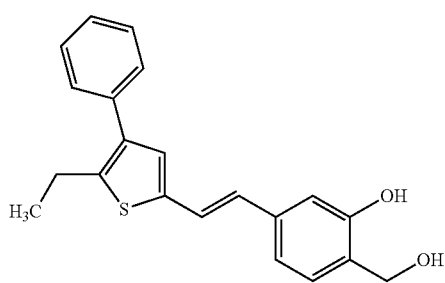
TABLE 29
Pr34-14 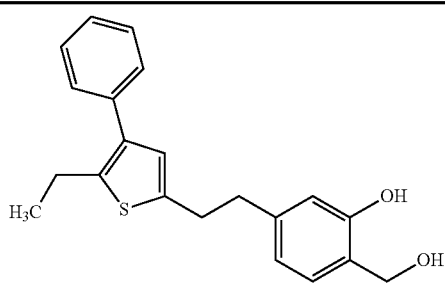
TABLE 29-continued
Pr34-15 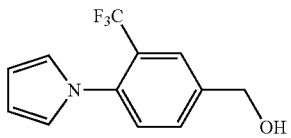
Pr34-16 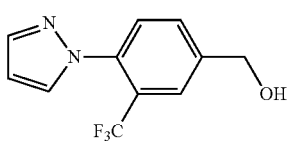
Pr34-17 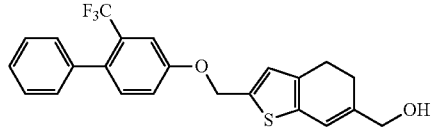
Pr34-18 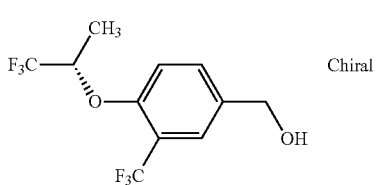 Chiral
Pr34-19 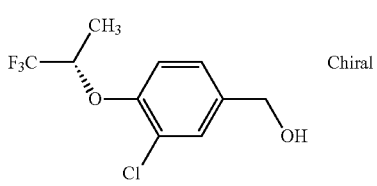 Chiral
Pr34-20 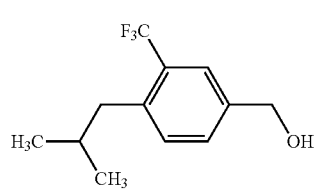
TABLE 30
Pr34-21 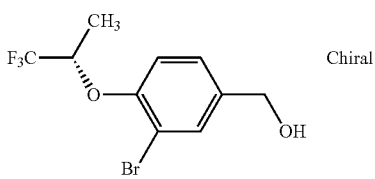 Chiral
Pr34-22 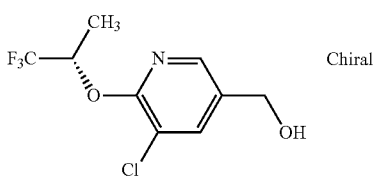 Chiral TABLE 30-continued
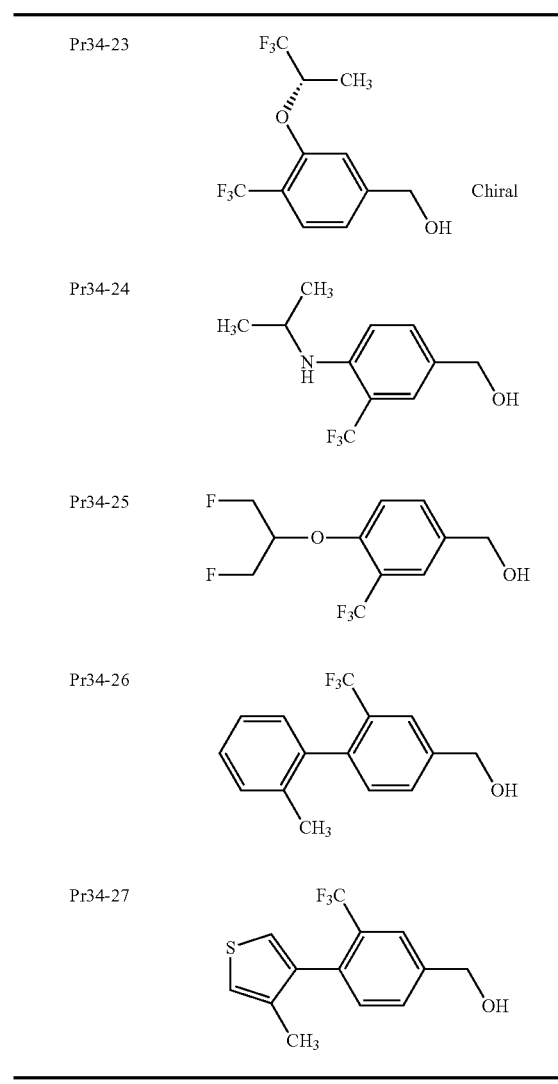
TABLE 31
TABLE 31-continued
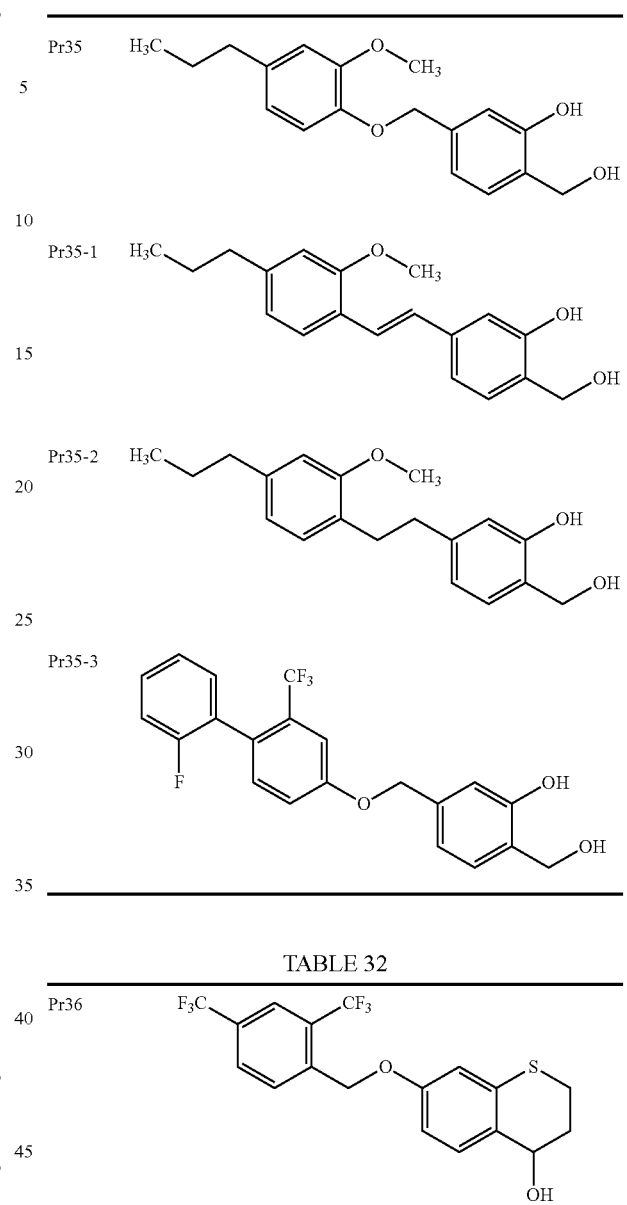
TABLE 32

TABLE 32-continued
Pr37 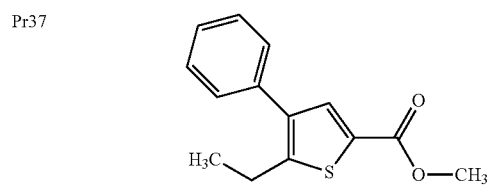
Pr37-1 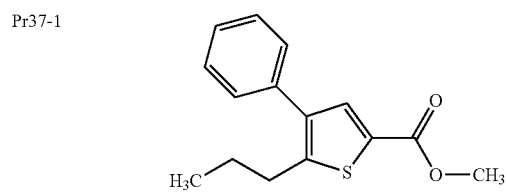
Pr37-2 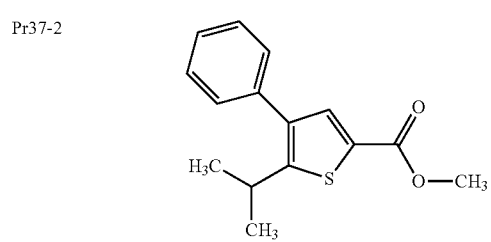
TABLE 33
Pr37-3 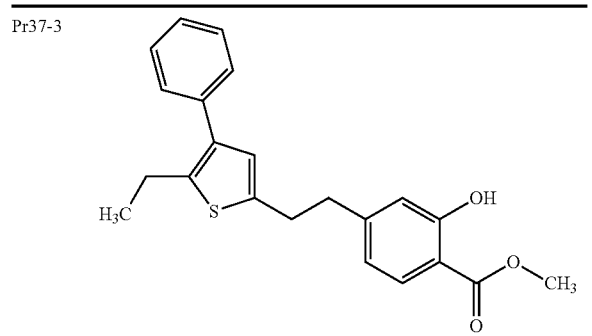
Pr38 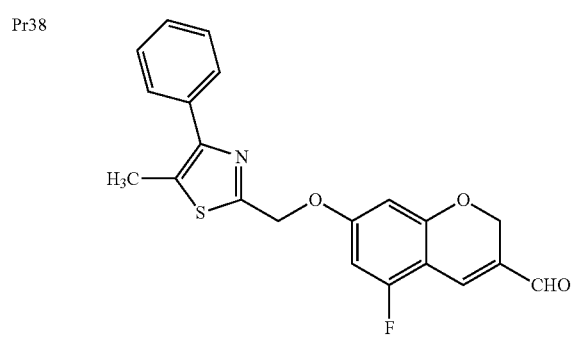
Pr38-1 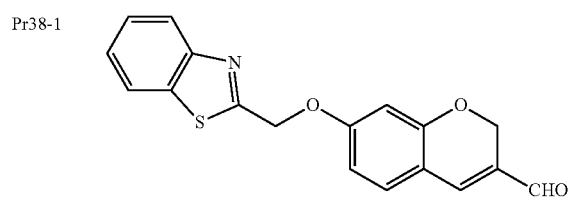
TABLE 33-continued
Pr38-2 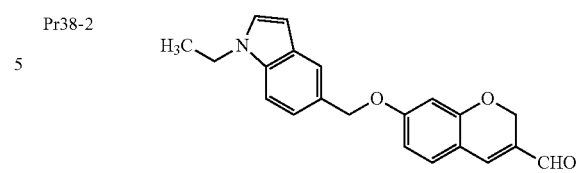
Pr38-3 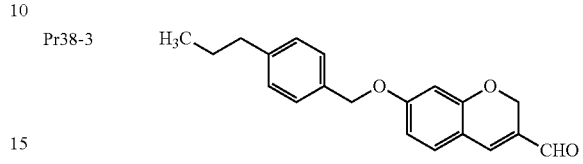
TABLE 34
Pr38-4 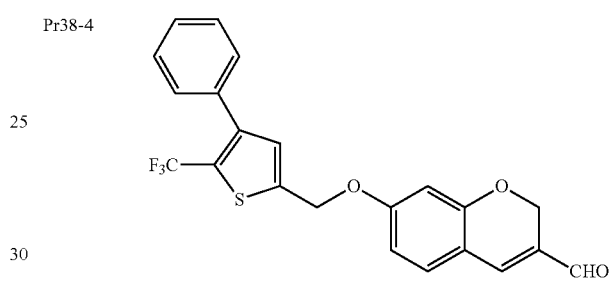
Pr38-5 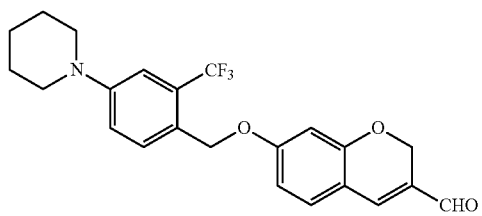
Pr38-6 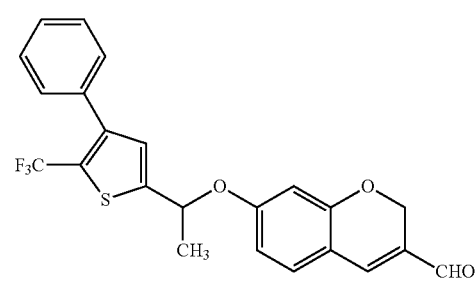
Pr38-7 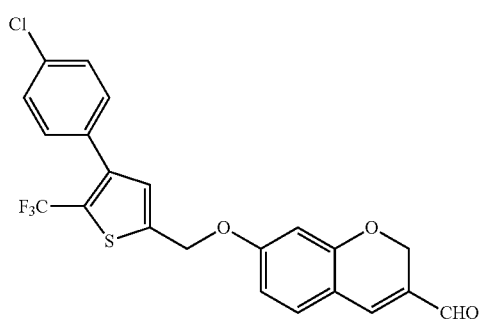

TABLE 34-continued
Pr38-8 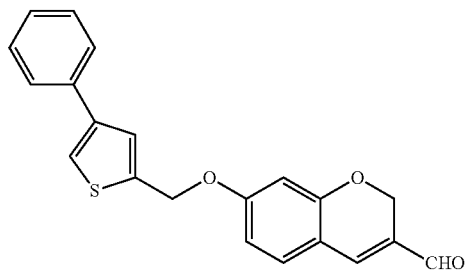
TABLE 35
Pr38-9 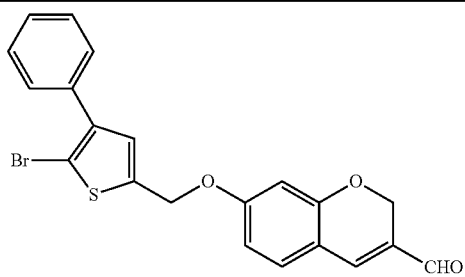
Pr38-10 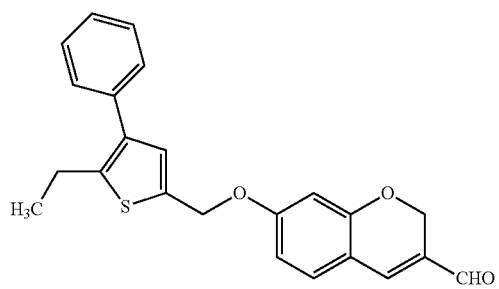
TABLE 35-continued
Pr38-11 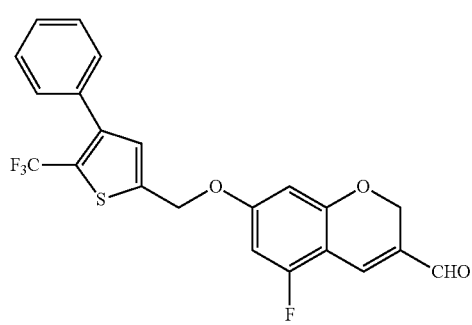
Pr38-12 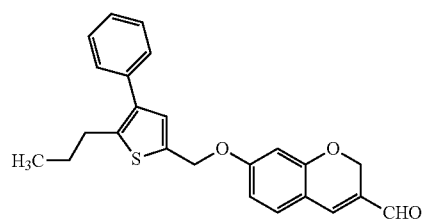
Pr38-13 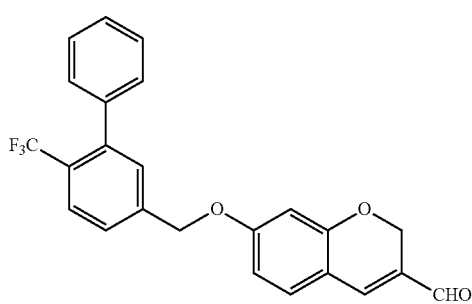
TABLE 36
Pr38-14 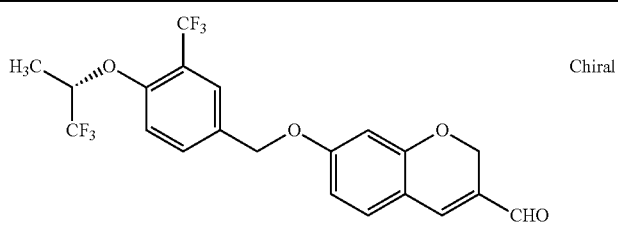 Chiral
Pr38-15 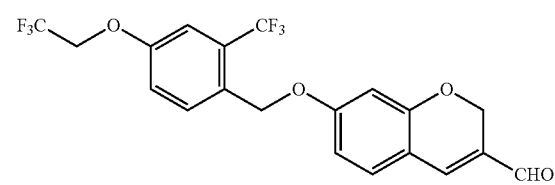
Pr38-16 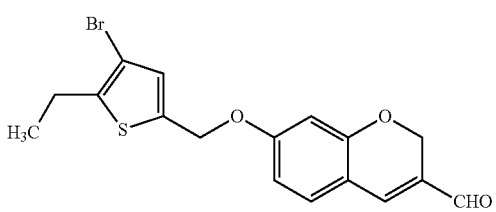

TABLE 36-continued
Pr38-17
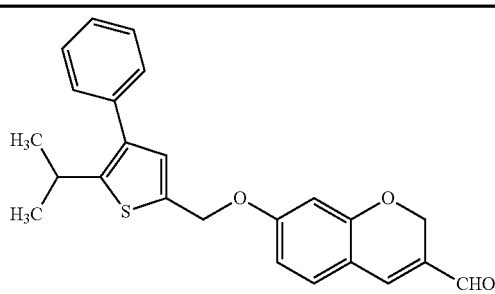
Pr38-18
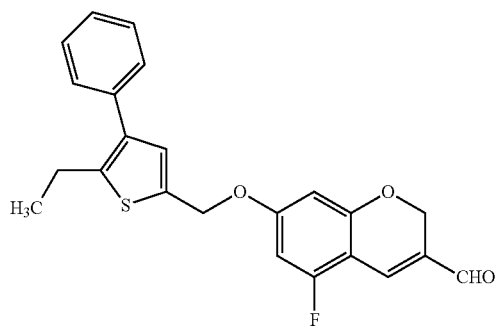
Pr38-19
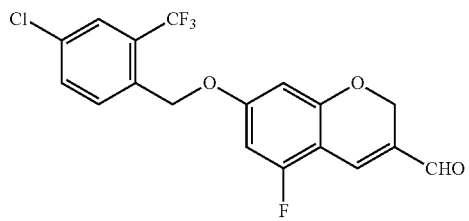
TABLE 37
Pr38-20
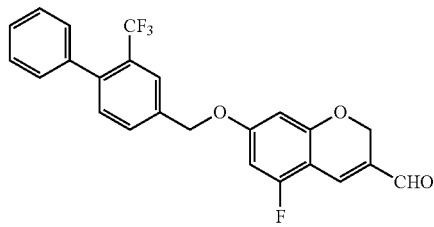
Pr38-21
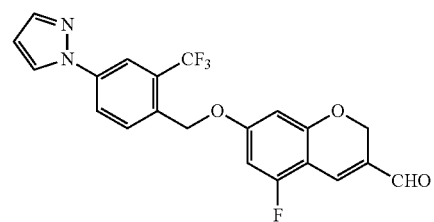
Pr38-22
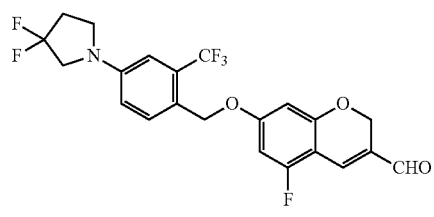
TABLE 37-continued
Pr38-23
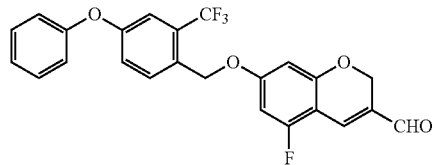
Pr38-24
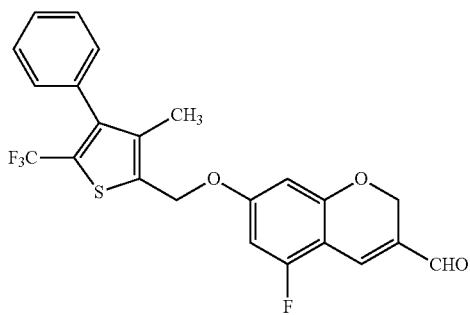

TABLE 38
Pr38-25 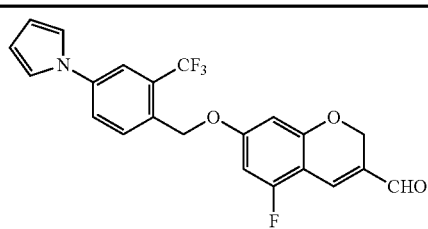
Pr38-26 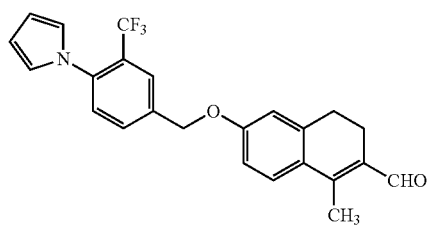
Pr38-27 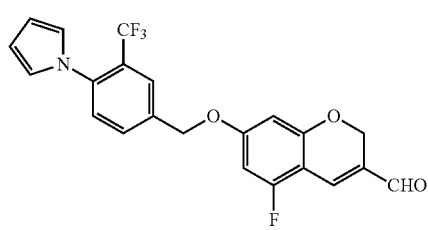
TABLE 38-continued
Pr38-28 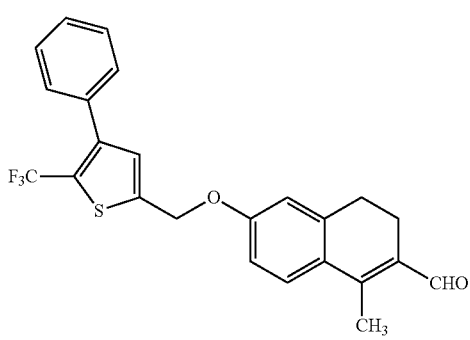
Pr38-29 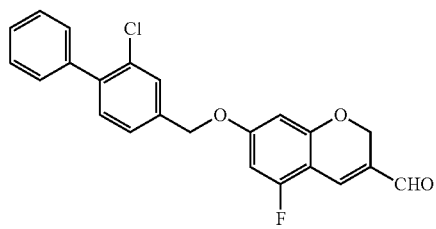
TABLE 39
Pr38-30 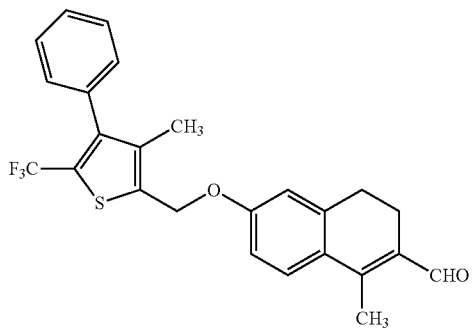
Pr38-31 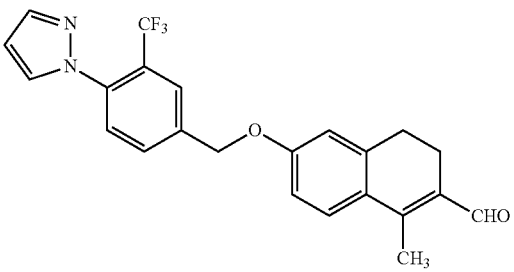
Pr38-32 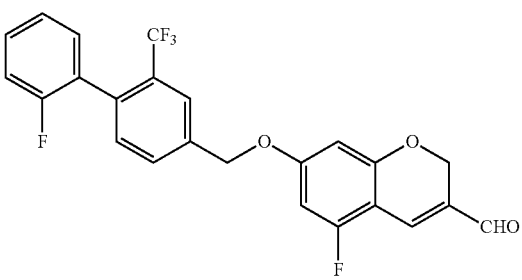

TABLE 39-continued
Pr38-33 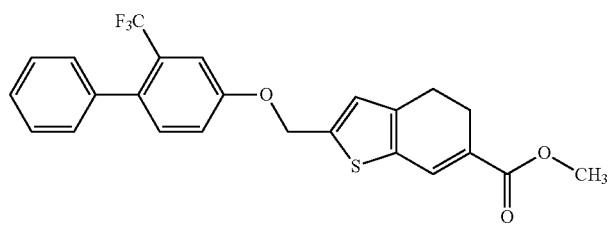
Pr38-34 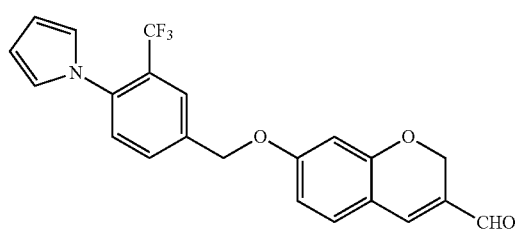
TABLE 40
Pr38-35 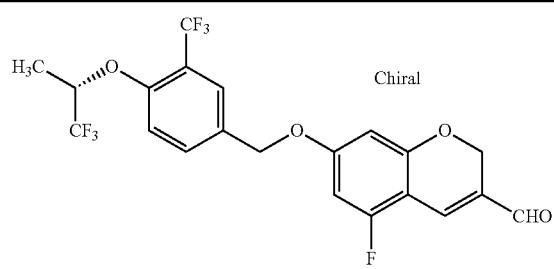
Pr38-36 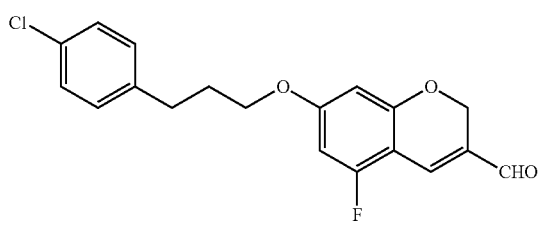
Pr38-37 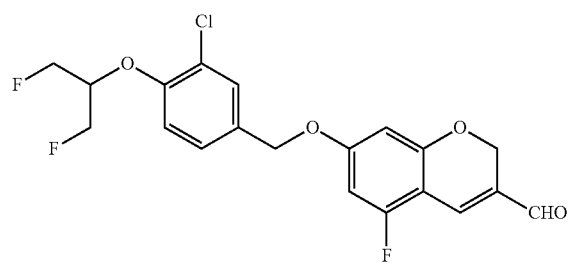
Pr38-38 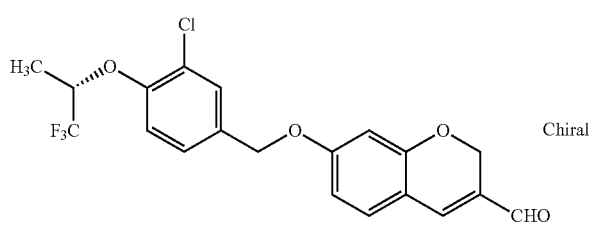

TABLE 40-continued
Pr38-39
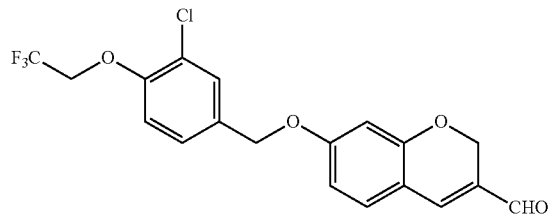
Pr38-40
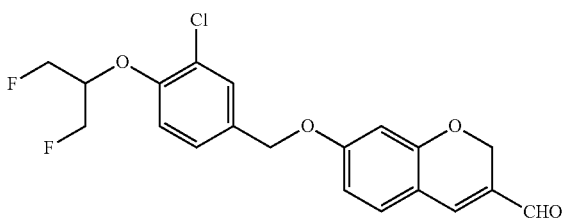
Pr38-41
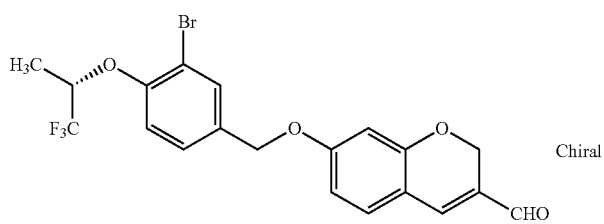
Chiral
Pr38-42
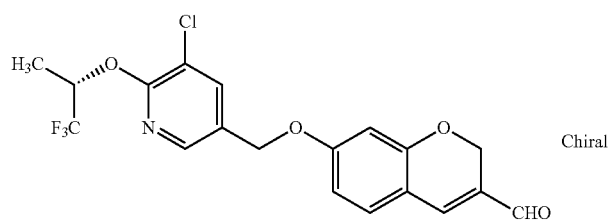
Chiral
Pr38-43
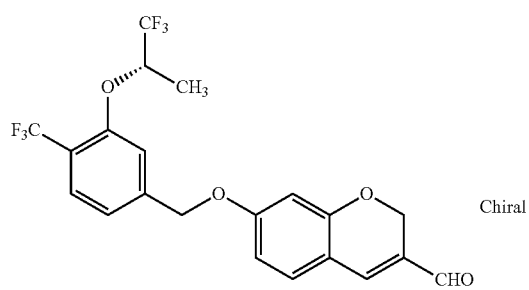
Chiral
Pr38-44
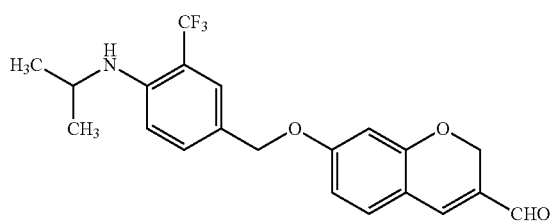

-continued
Pr38-45 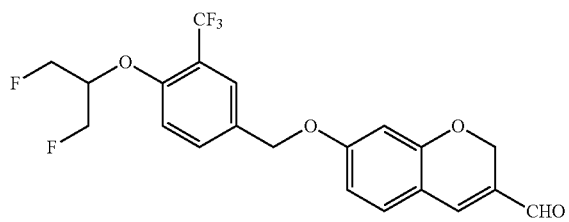
Pr38-46 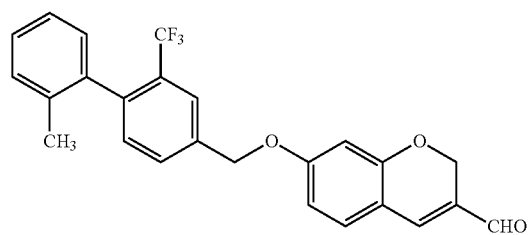
Pr38-47 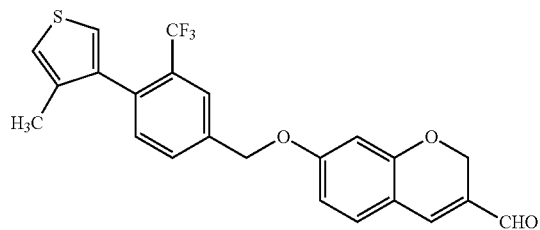
TABLE 42
Pr38-48 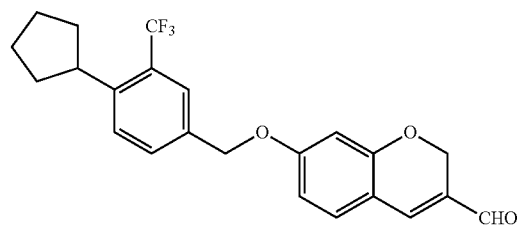
Pr38-49 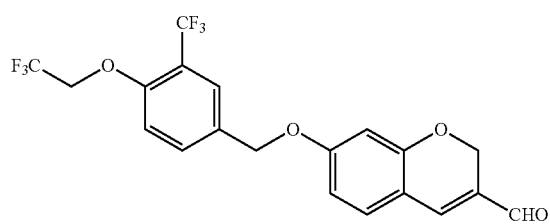
Pr38-50 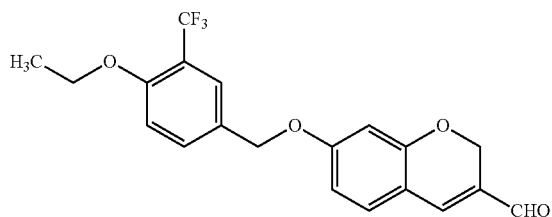

TABLE 42-continued
Pr38-51 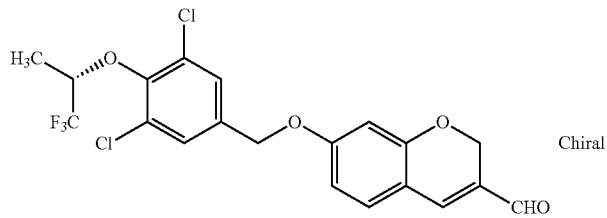 Chiral
Pr38-52 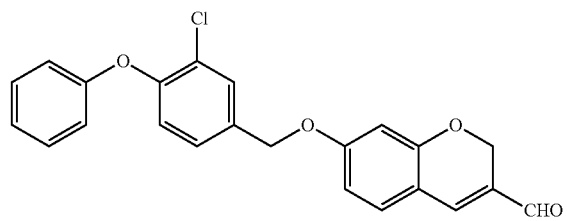
Pr38-53 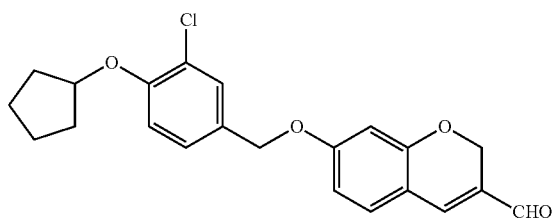
Pr38-54 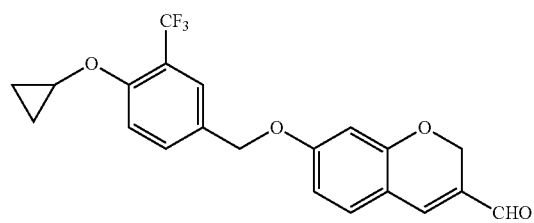
TABLE 43
Pr38-55 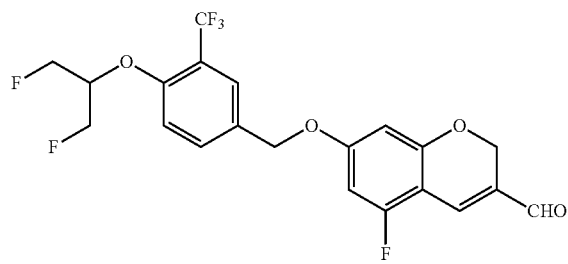
Pr38-56 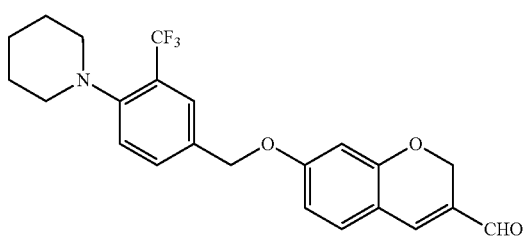

TABLE 43-continued
Pr38-57 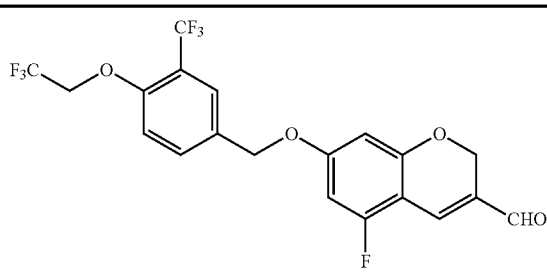
Pr38-58 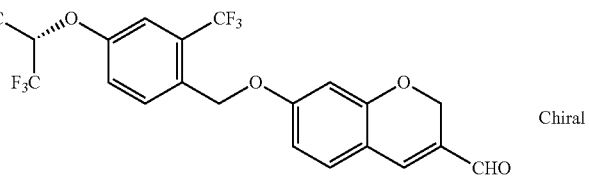  Chiral
Pr38-59 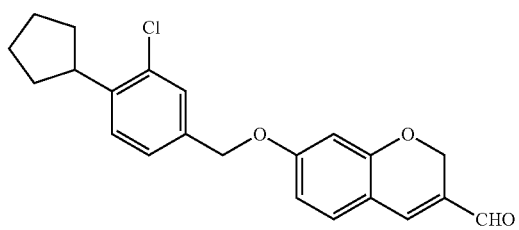
Pr38-60 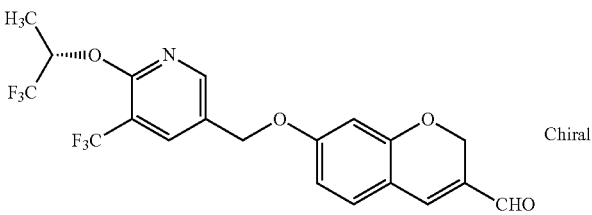  Chiral
TABLE 44
Pr38-61 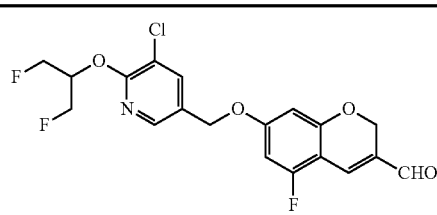
Pr39 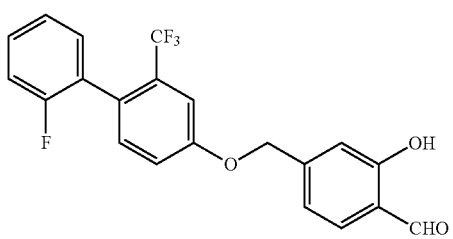
Pr39-1 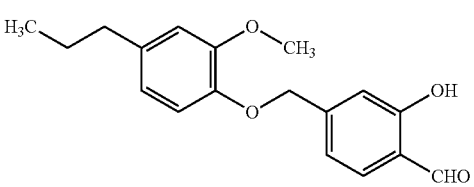
TABLE 44-continued
Pr39-2 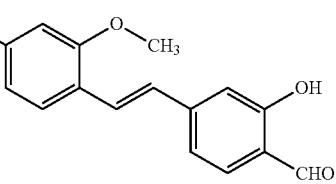
Pr39-3 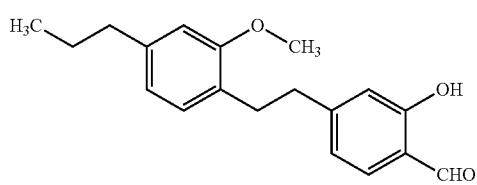
Pr39-4 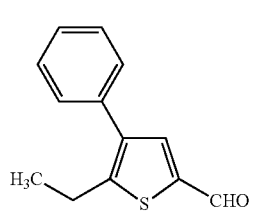

TABLE 45
| | | |
|---|---|---|
| Pr39-5 | 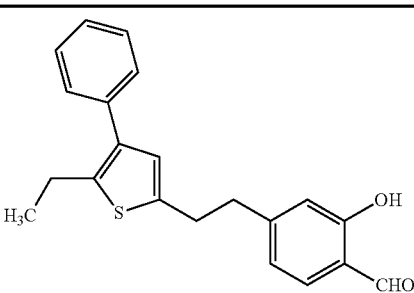 | |
| Pr39-6 | 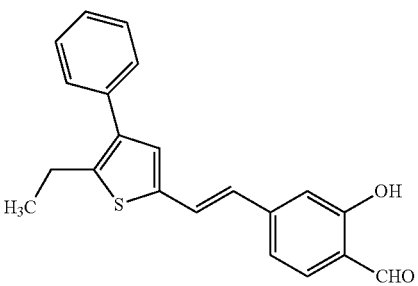 | |
| Pr40 | 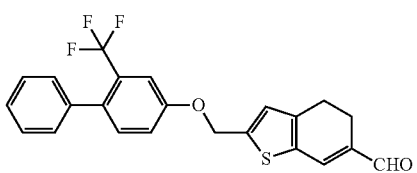 | |
| Pr41 | 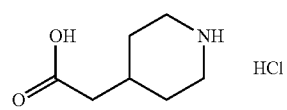 | |
| Pr41-1 | 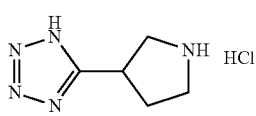 | |
| Pr41-2 | 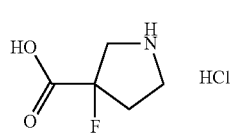 | |
| Pr41-3 | 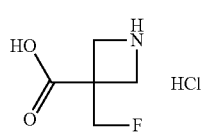 | |
TABLE 46
| | | |
|---|---|---|
| Pr41-4 | 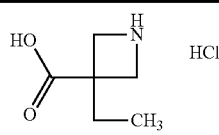 | |
| Pr41-5 | 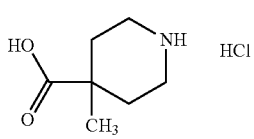 | |
TABLE 46-continued
| | | |
|---|---|---|
| Pr42 | 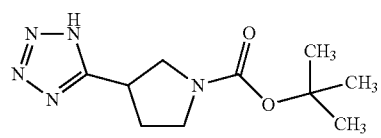 | |
| Pr43 | 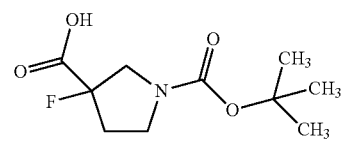 | |
| Pr44 | 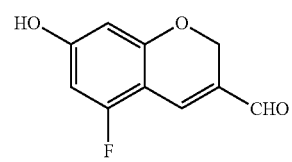 | |
| Pr44-1 | 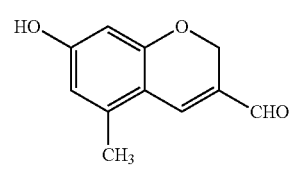 | |
| Pr44-2 | 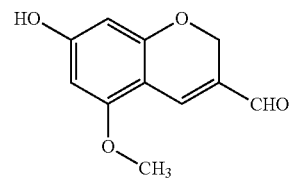 | |
| Pr44-3 | 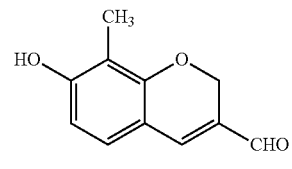 | |
| Pr44-4 | 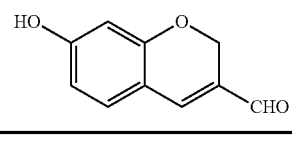 | |
TABLE 47
| | | |
|---|---|---|
| Pr44-5 | 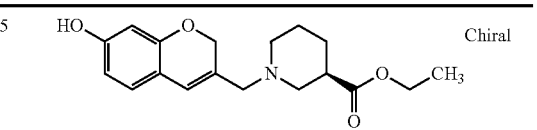 | Chiral |
| Pr44-6 | 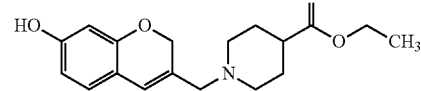 | |
| Pr45 | 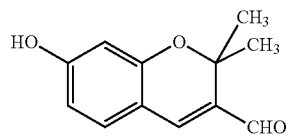 | |

TABLE 47-continued
Pr46 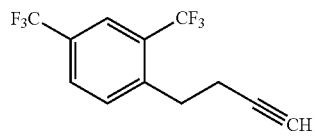
Pr47 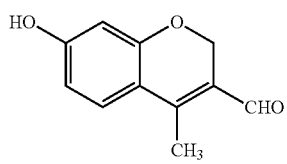
Pr47-1 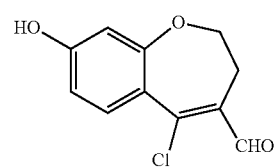
Pr47-2 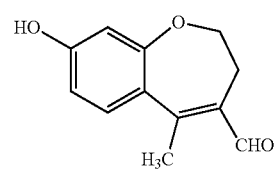
Pr48 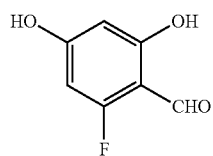
Pr48-1 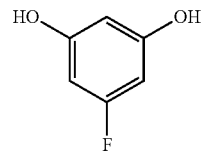
TABLE 48
Pr49 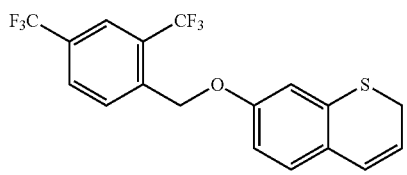
Pr50 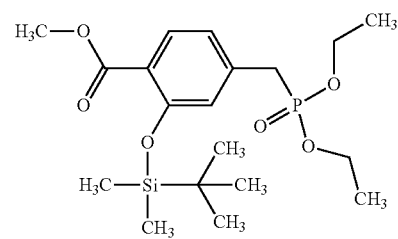
TABLE 48-continued
Pr51 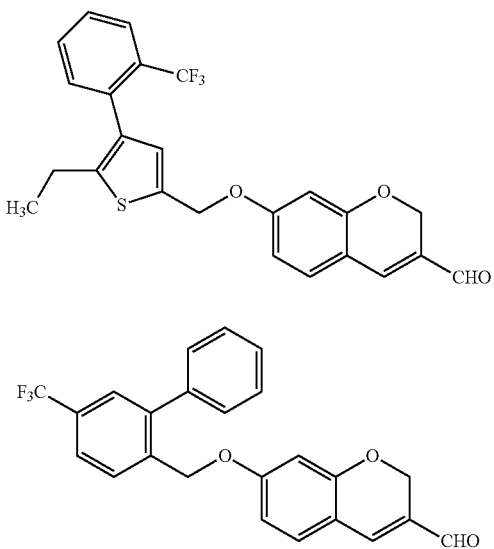
Pr51-1 
Pr51-2 
Pr51-3 
TABLE 49
Pr51-4 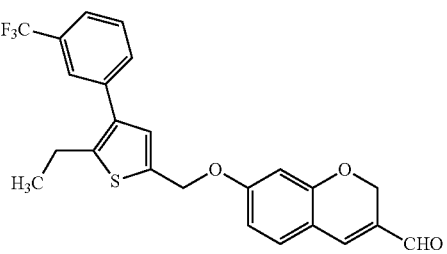
Pr51-5 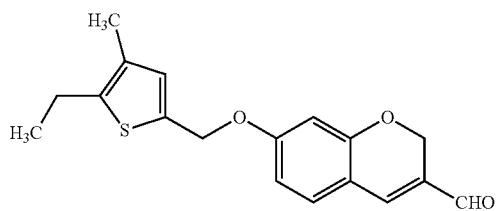

TABLE 49-continued
TABLE 50-continued
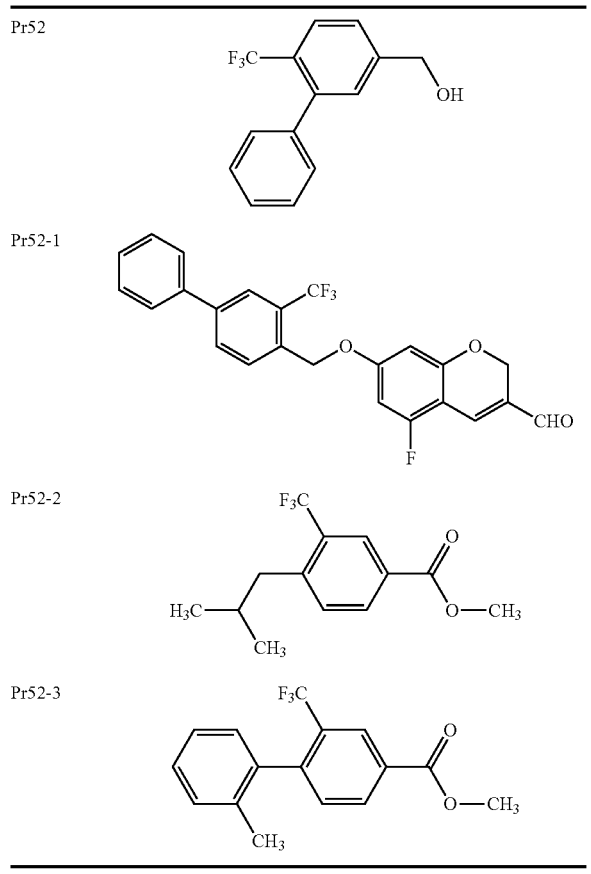
TABLE 50
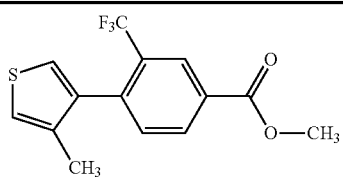
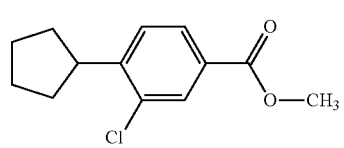
TABLE 51
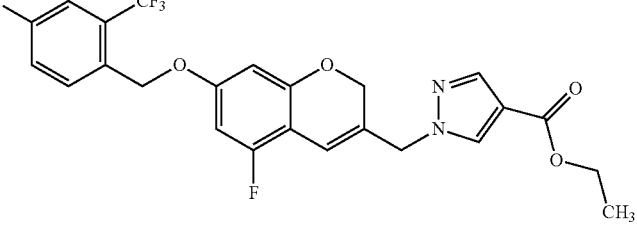
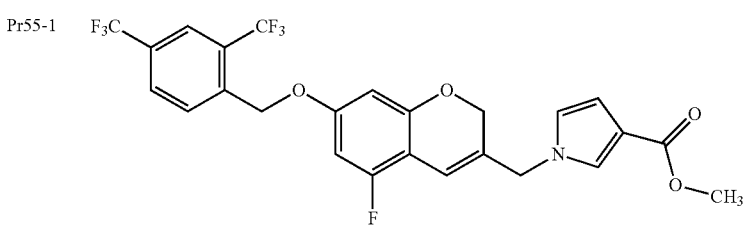

TABLE 51-continued
| | |
|---|---|
| Pr56 | 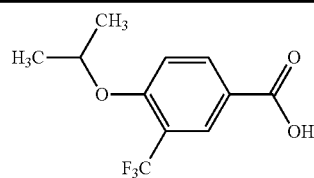 |
| Pr56-1 | 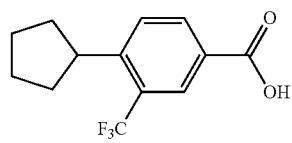 |
| Pr56-2 | 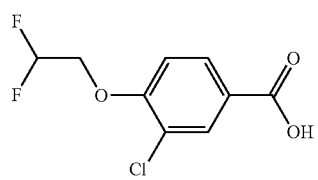 |
| Pr56-3 | 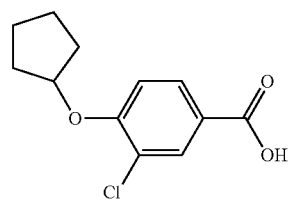 |
| Pr56-4 | 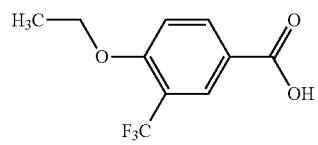 |
TABLE 52
| | |
|---|---|
| Pr56-5 | 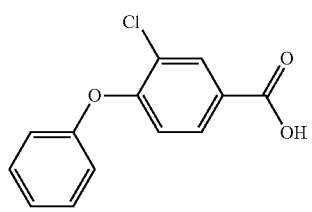 |
| Pr56-6 | 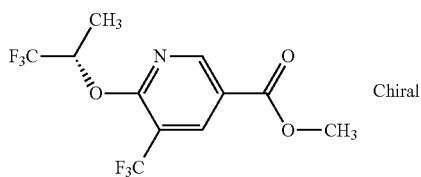 |
| Pr57 | Chiral |
TABLE 52-continued
| | |
|---|---|
| Pr58 | 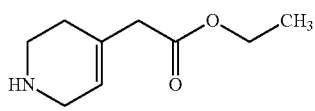 |
| Pr58-1 | 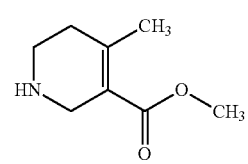 |
| Pr59 | 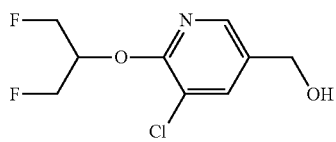 |
| Pr60 | 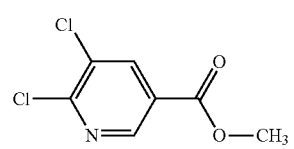 |

TABLE 53
Pr62 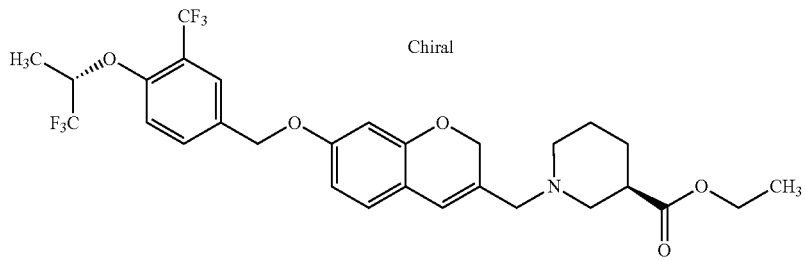
Pr62-1 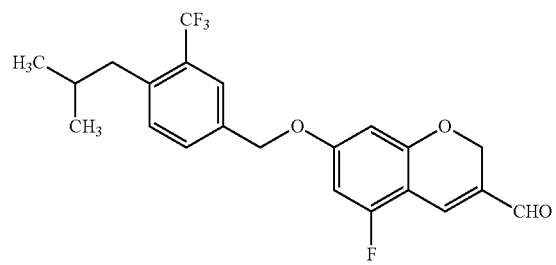
Pr62-2 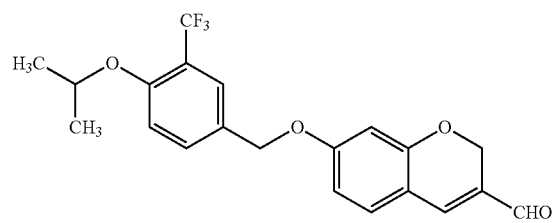
Pr62-3 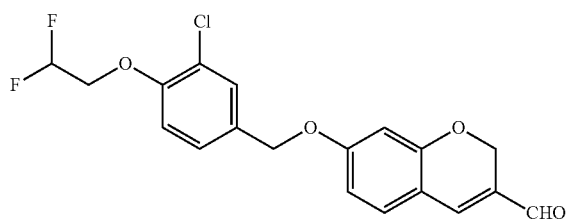
Pr62-4 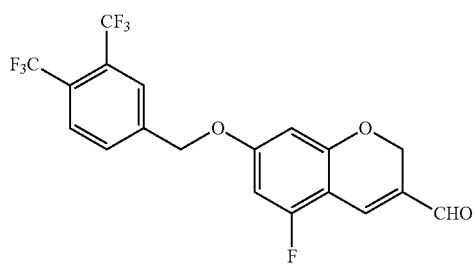
Pr62-5 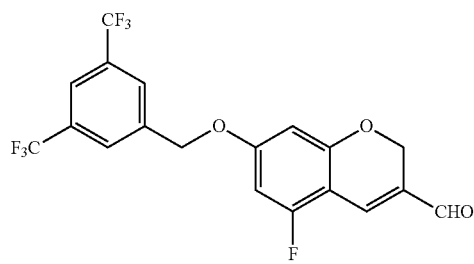

TABLE 54
Pr62-6 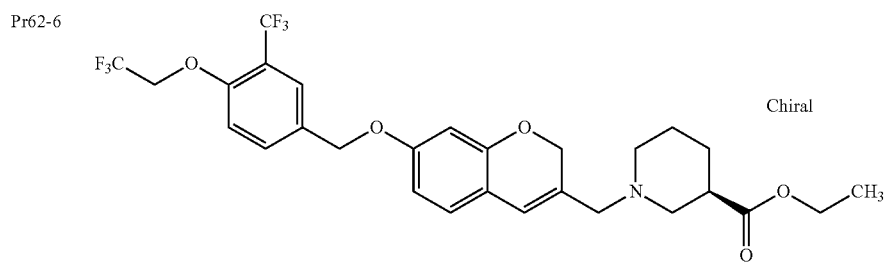 Chiral
Pr62-7 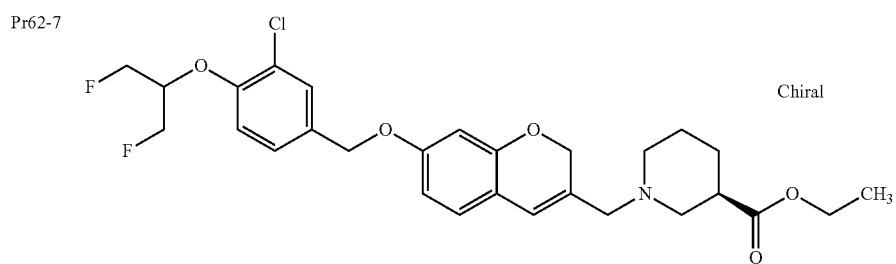 Chiral
Pr62-8 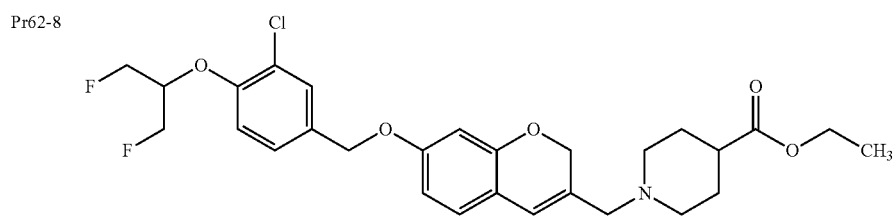
Pr62-9 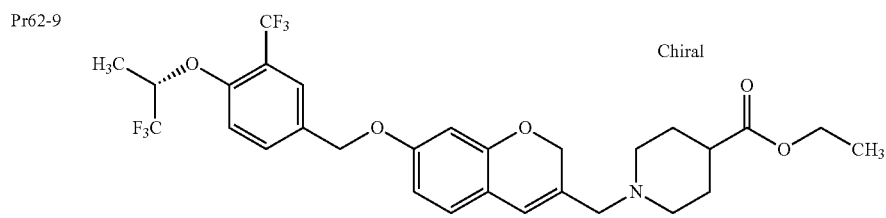 Chiral
Pr62-10 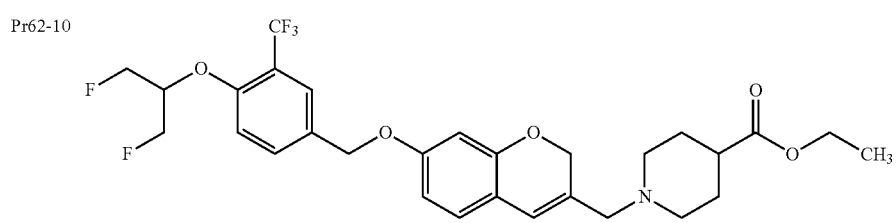
Pr62-11 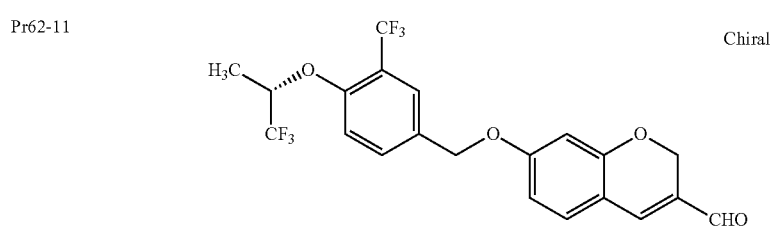 Chiral TABLE 55
Pr62-12
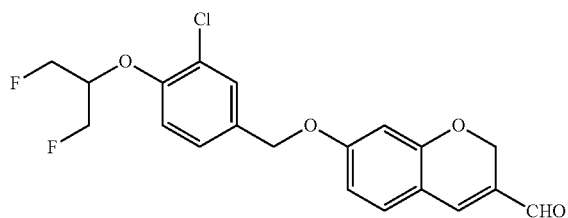
Pr62-13
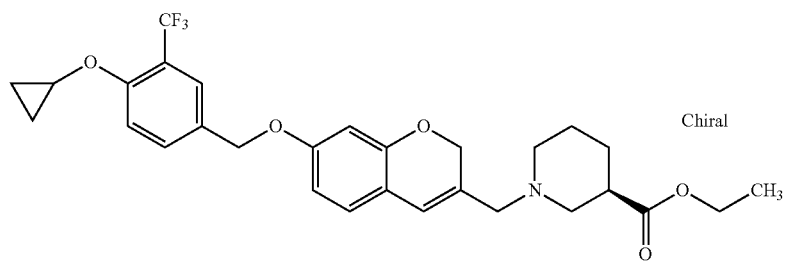
Chiral
Pr62-14
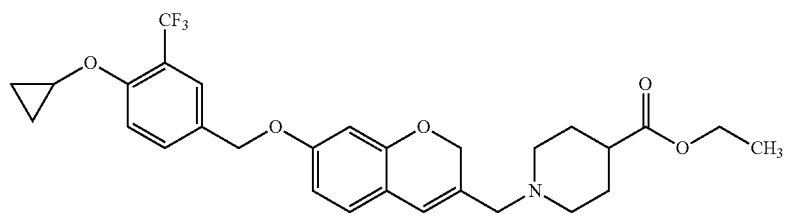
Pr62-15
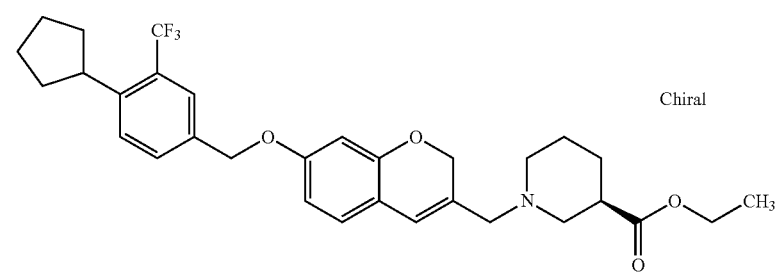
Chiral
Pr62-16
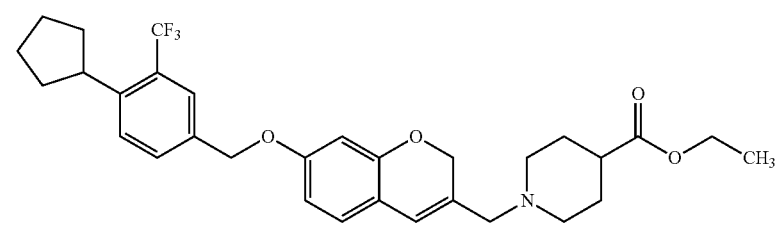
Pr62-17
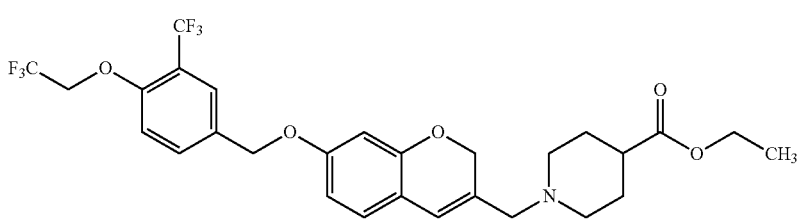

TABLE 56
Pr62-18
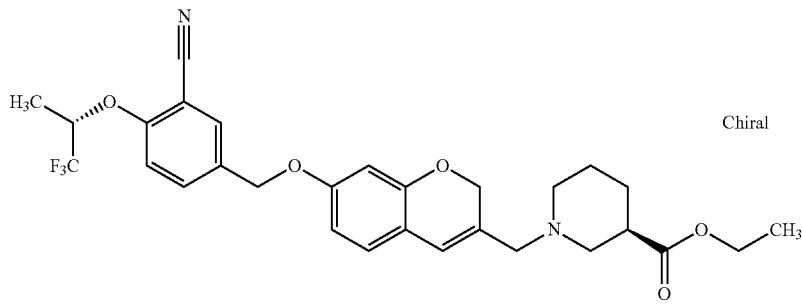
Chiral
Pr62-19
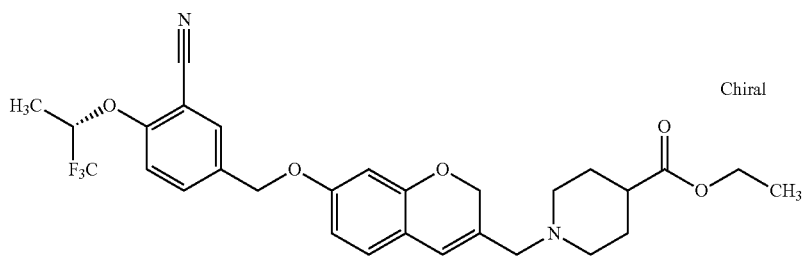
Chiral
Pr63
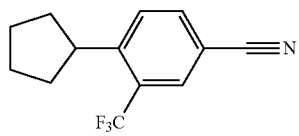
Pr64
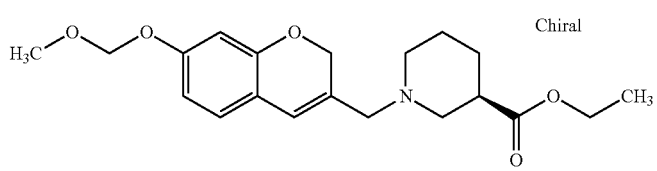
Chiral
Pr64-1
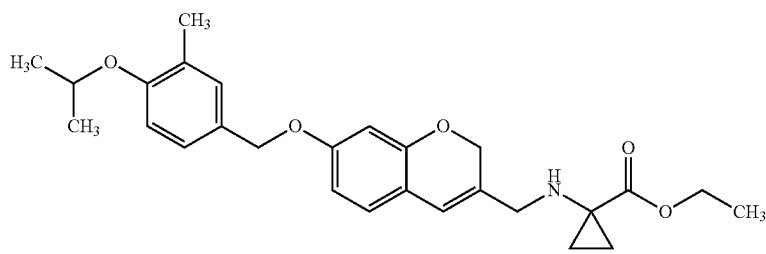
Pr64-2
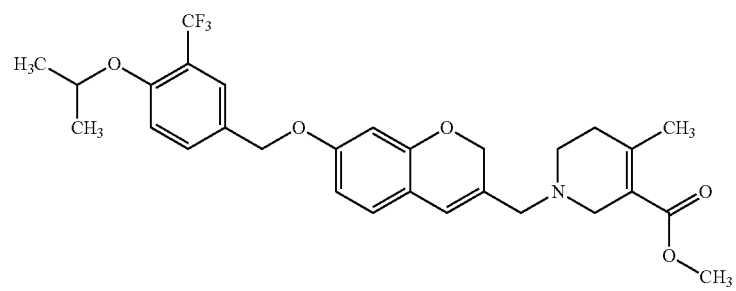

TABLE 57
Pr64-3 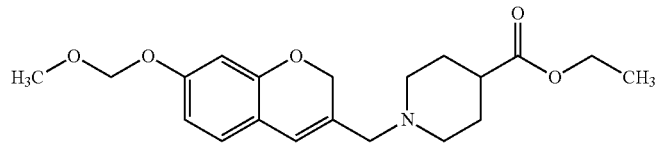
Pr64-4 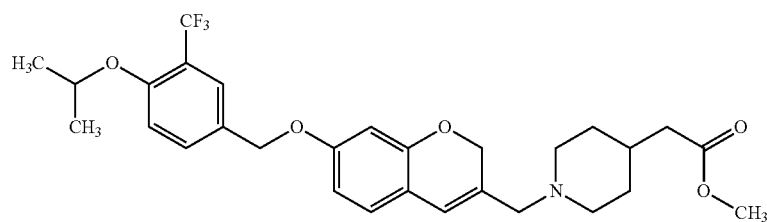
Pr64-5 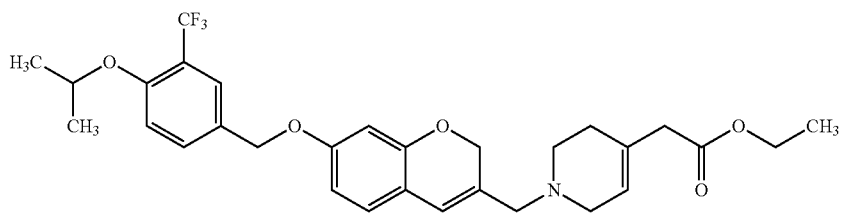
Pr64-6 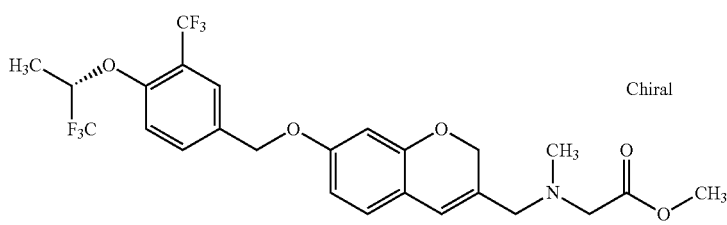
Chiral
Pr64-7 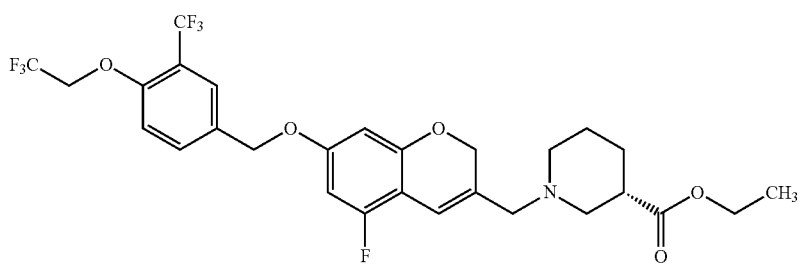
TABLE 58
| No | Str |
|---|---|
| Ex 1 | 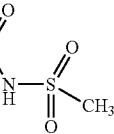 HCl |

TABLE 58-continued

| No | Str |
|---|---|
| Ex 2 | (structure: 2-(trifluoromethyl)-4-phenylthiophen-5-yl-methoxy-chromene-pyrrolidine-3-carboxylic acid) |
| Ex 3 | (structure: 2,4-bis(trifluoromethyl)phenyl-ethynyl-5-fluoro-chromene-pyrrolidine-3-carboxylic acid, HCl) |
| Ex 4 | (structure: 4-propyl-2-methoxybenzyloxy-chromene-azetidine-3-carboxylic acid) |
| Ex 5 | (structure: 4-biphenylmethoxy-chromene-azetidine-3-carboxylic acid) |
| Ex 6 | (structure: 4-propyl-2-methoxybenzyloxy-2,2-dimethyl-chromene-azetidine-3-carboxylic acid) |

TABLE 59

| Ex 7 | (structure: benzothiazol-2-ylmethoxy-chromene-azetidine-3-carboxylic acid) |
|---|---|
| Ex 8 | (structure: 3-(4-chlorophenyl)propyloxy-chromene-azetidine-3-carboxylic acid) |

TABLE 59-continued
Ex 9 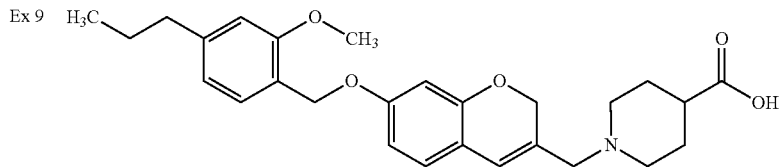
Ex 10 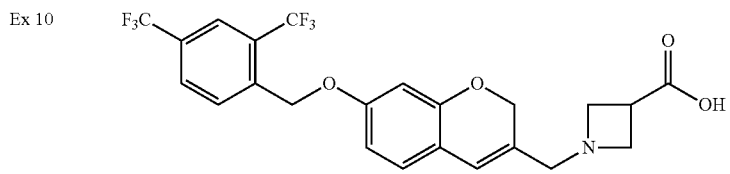
Ex 11 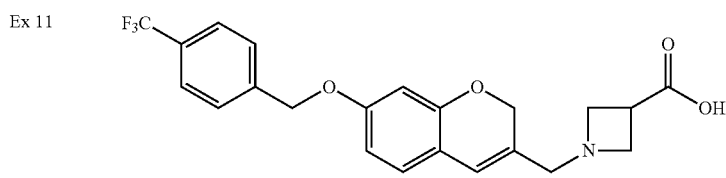
Ex 12 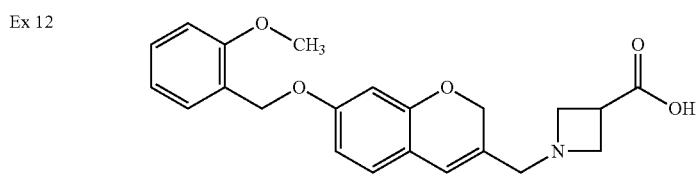
Ex 13 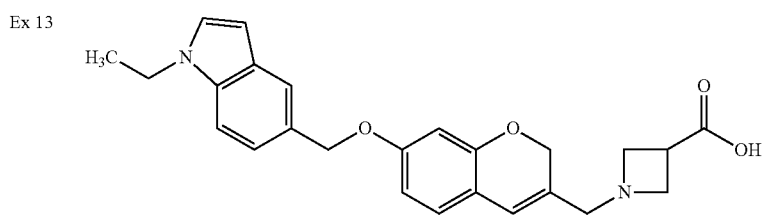
Ex 14 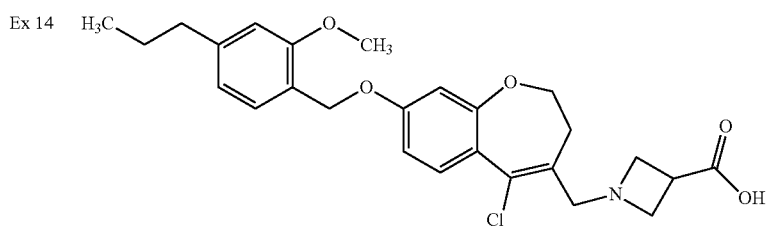
TABLE 60
Ex 15 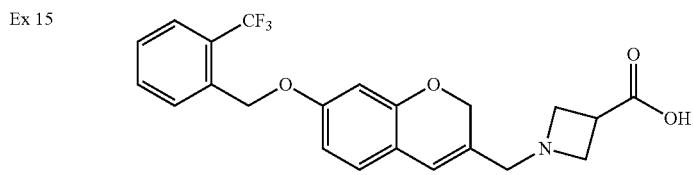

TABLE 60-continued
| Ex 16 | 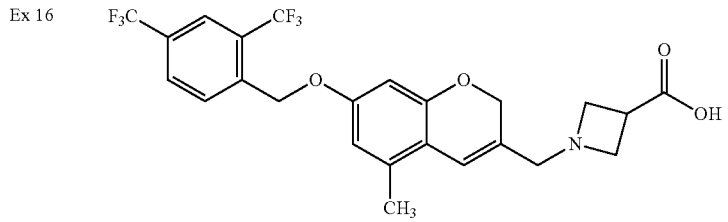 |
| Ex 17 | 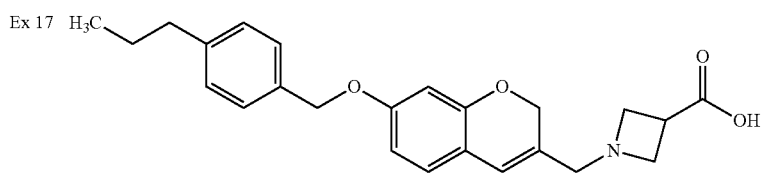 |
| Ex 18 | 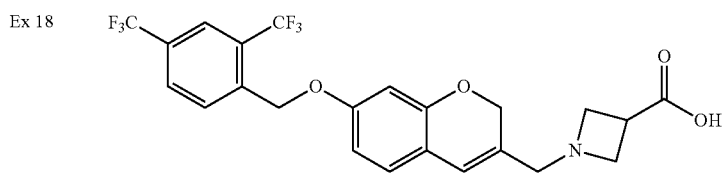 |
| Ex 19 | 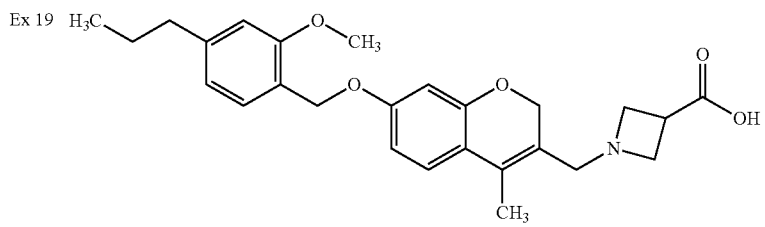 |
| Ex 20 | 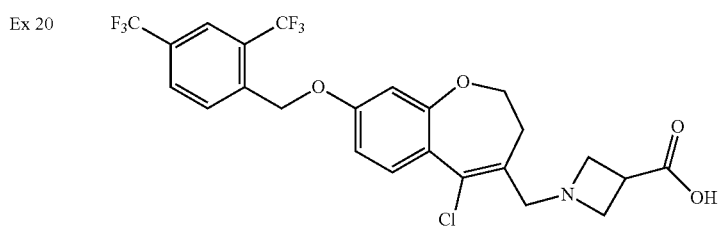 |
| Ex 21 | 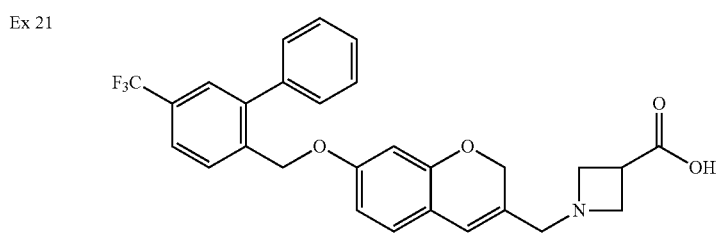 |

TABLE 61
Ex 22 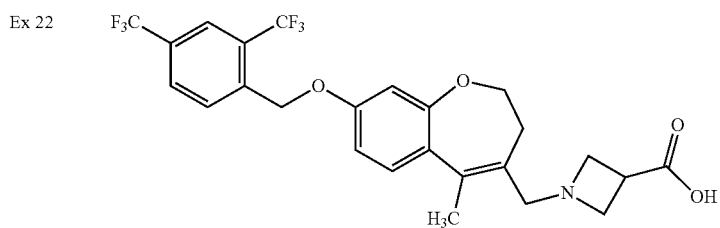
Ex 23 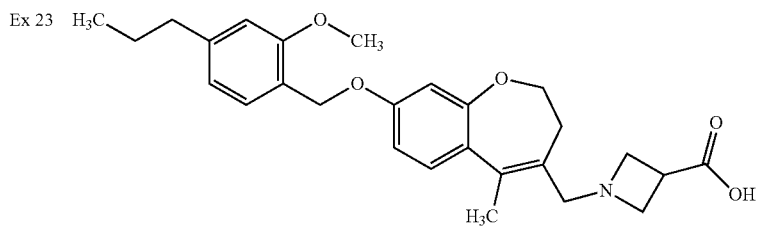
Ex 24 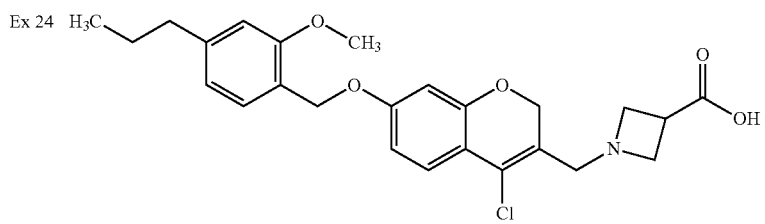
Ex 25 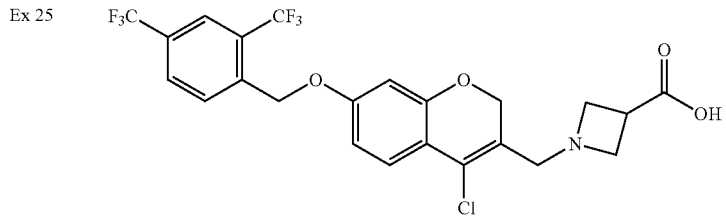
Ex 26 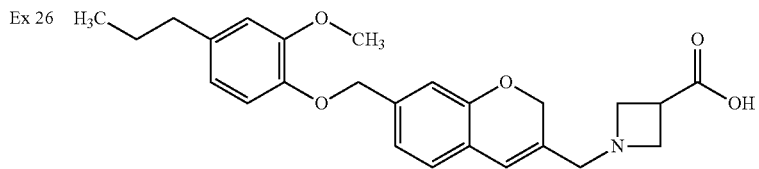
Ex 27 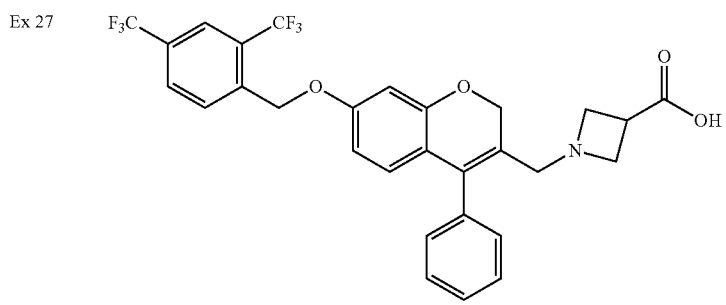

TABLE 62
Ex 28 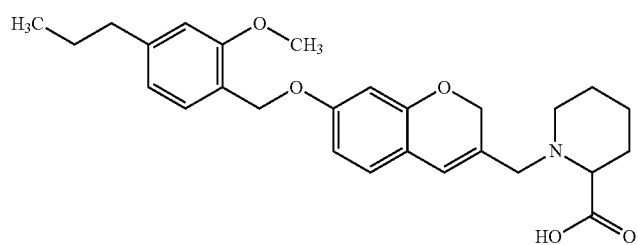
Ex 29 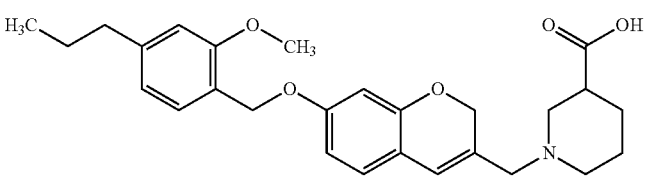
Ex 30 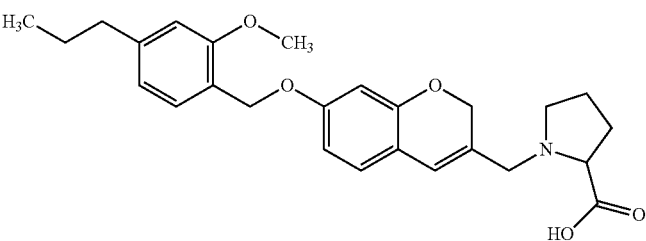
Ex 31 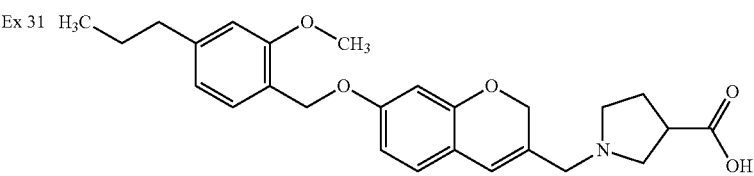
Ex 32 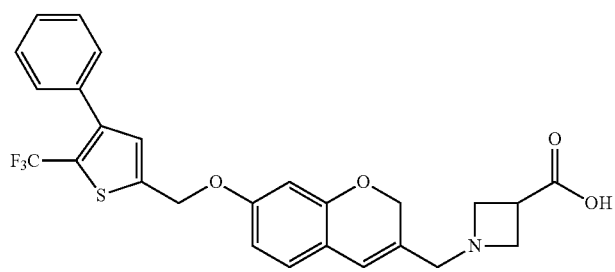
Ex 33 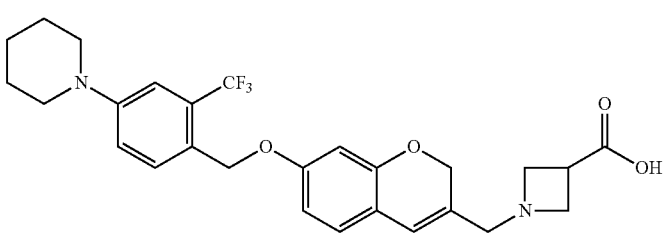

TABLE 63
Ex 34 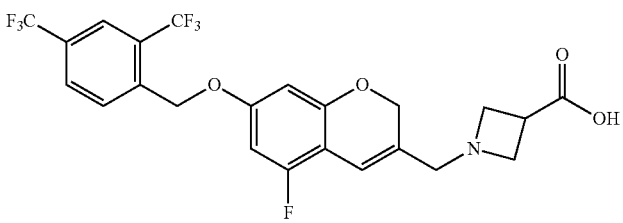
Ex 35 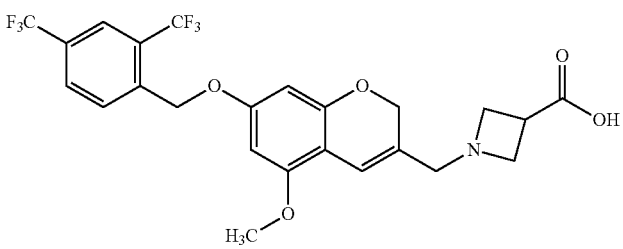
Ex 36 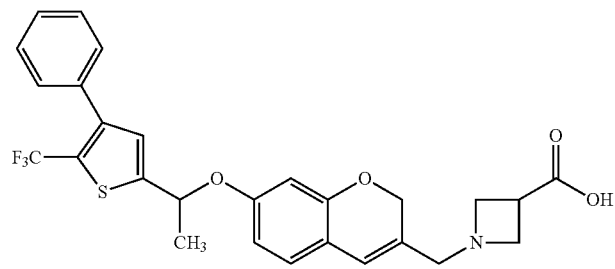
Ex 37 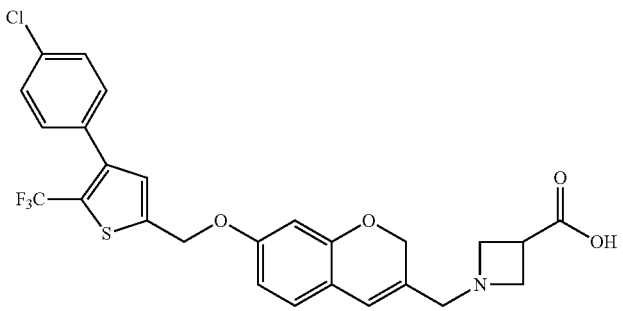
Ex 38 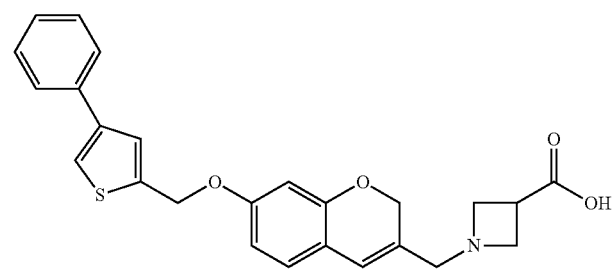

TABLE 64
Ex 39 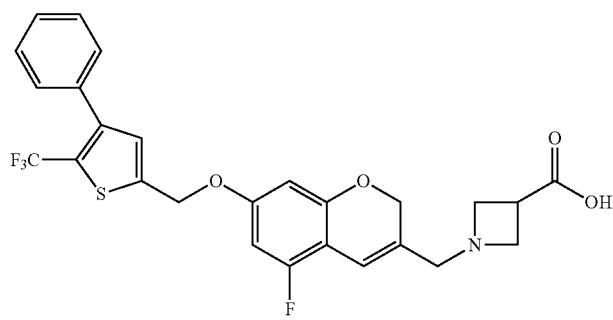
Ex 40 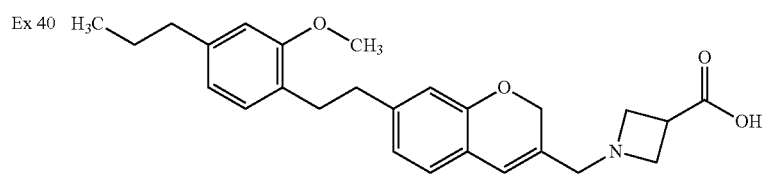
Ex 41 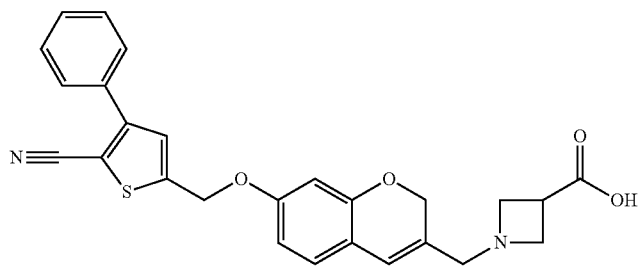
Ex 42 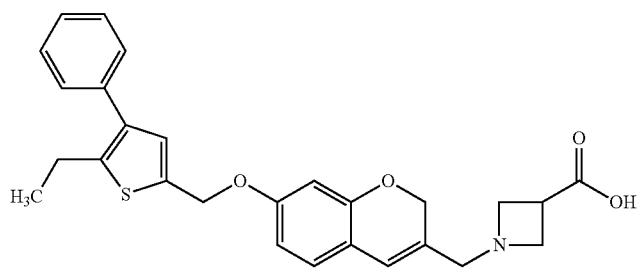
Ex 43 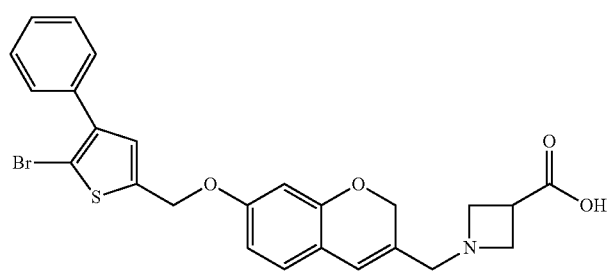

TABLE 65
Ex 44 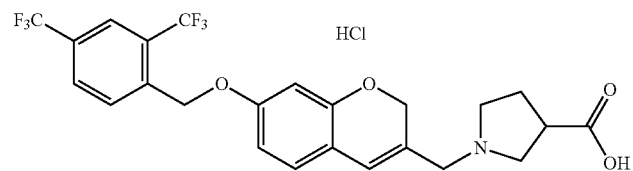
Ex 45 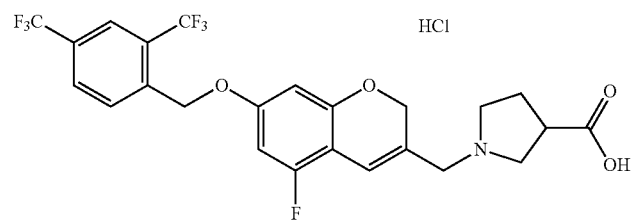
Ex 46 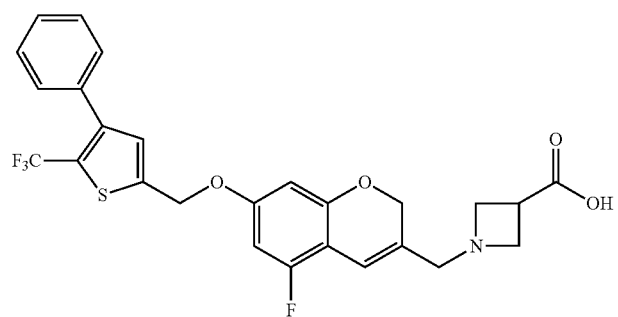
Ex 47 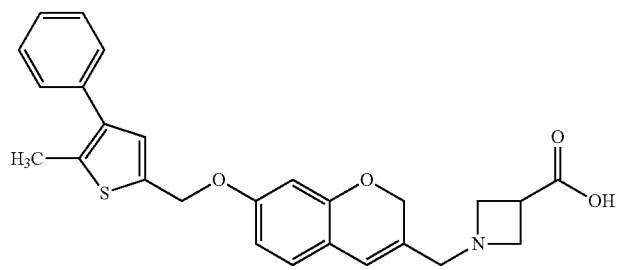
Ex 48 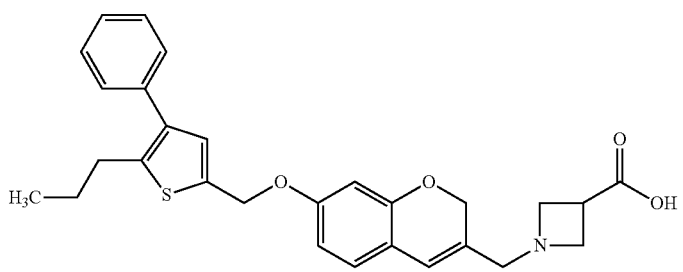

TABLE 66
Ex 49
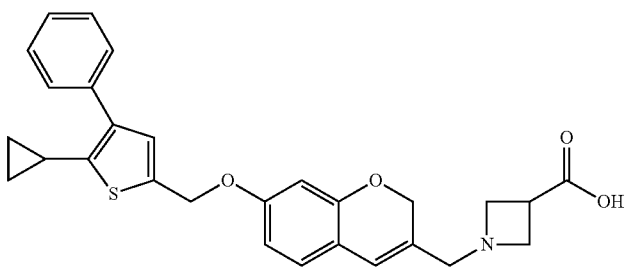
Ex 50
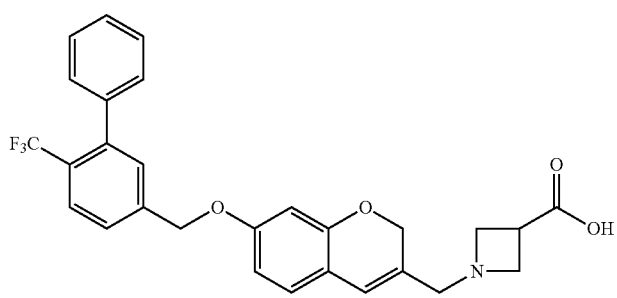
Ex 51
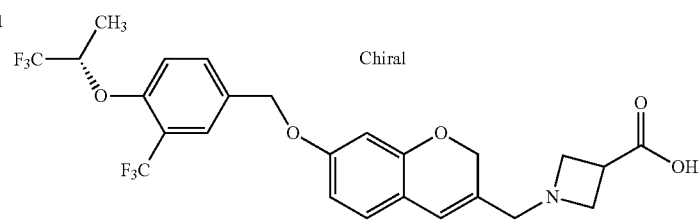
Ex 52
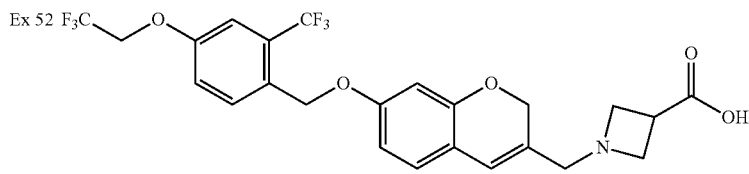
Ex 53
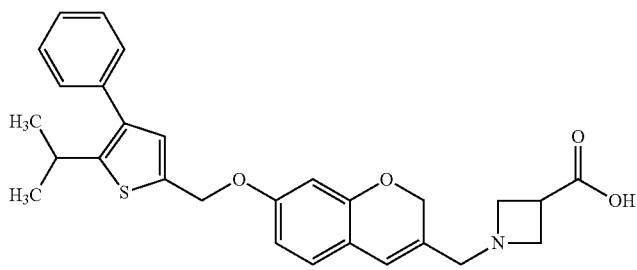
Ex 54
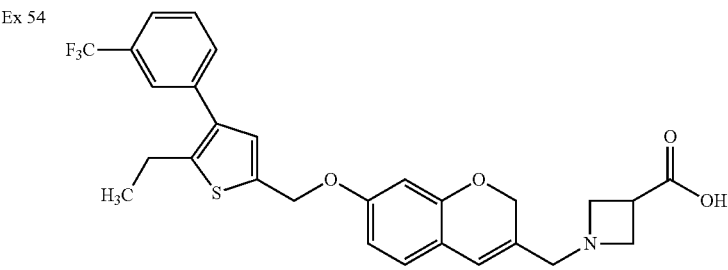

TABLE 67
Ex 55
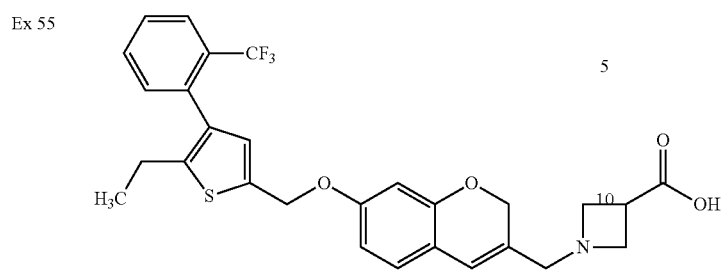
Ex 56
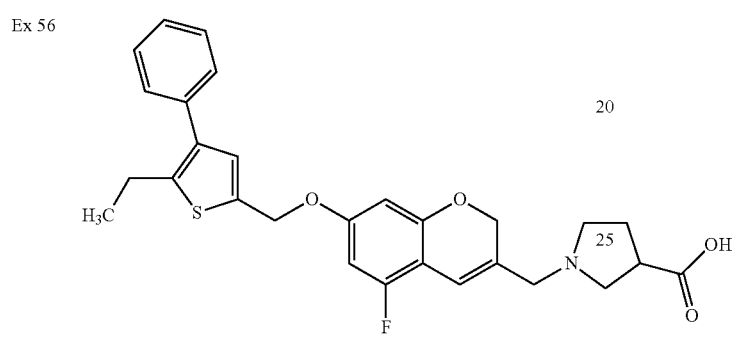
Ex 57
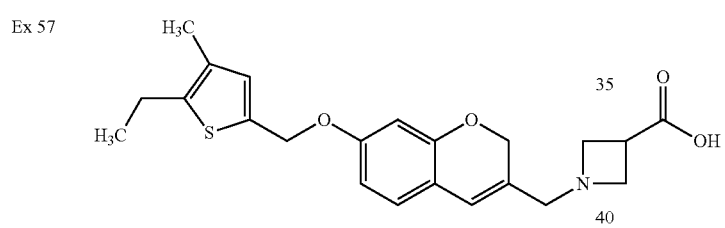
Ex 58
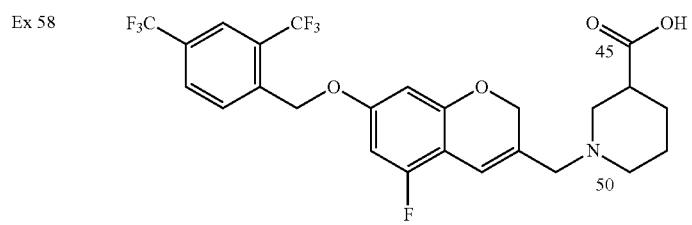
Ex 59
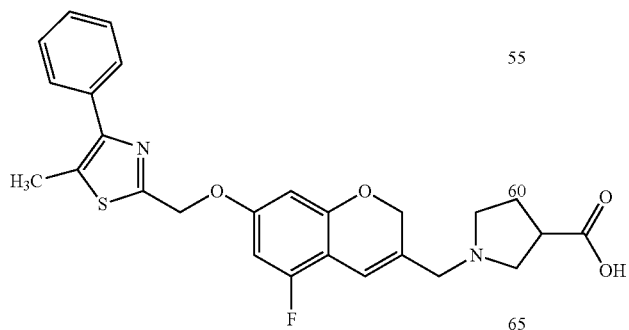

TABLE 68
Ex 60
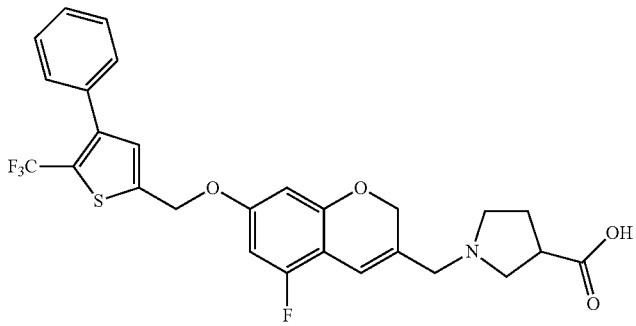
Ex 61
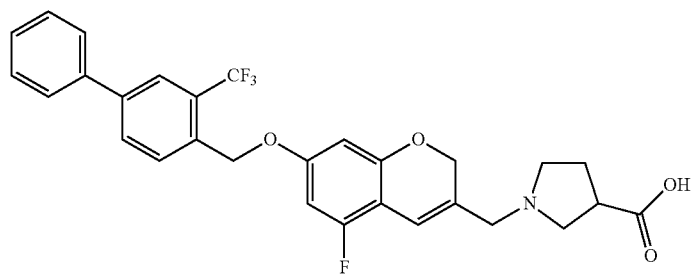
Ex 62
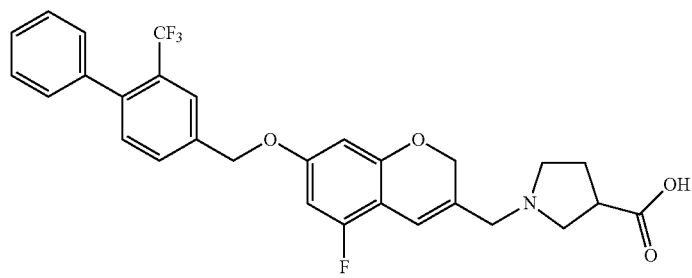
Ex 63
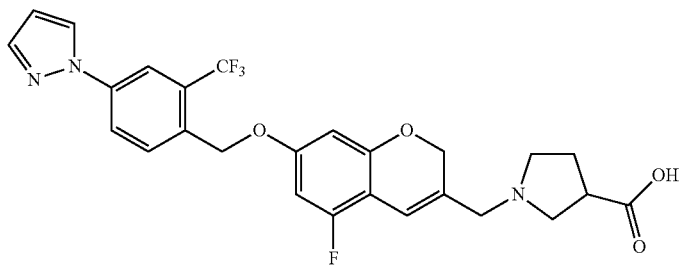
Ex 64
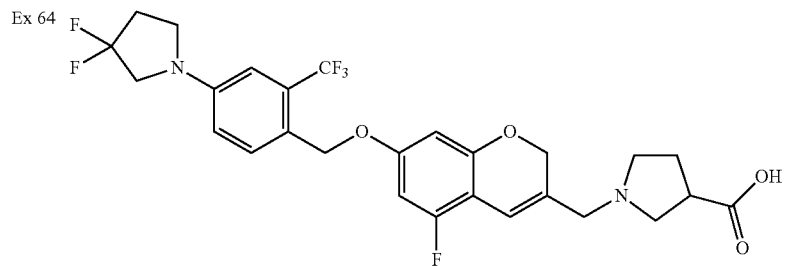

TABLE 69
Ex65
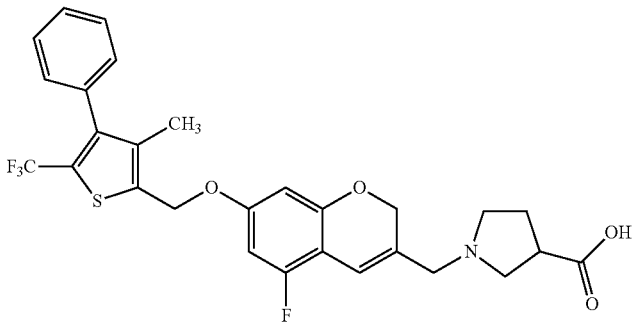
Ex66
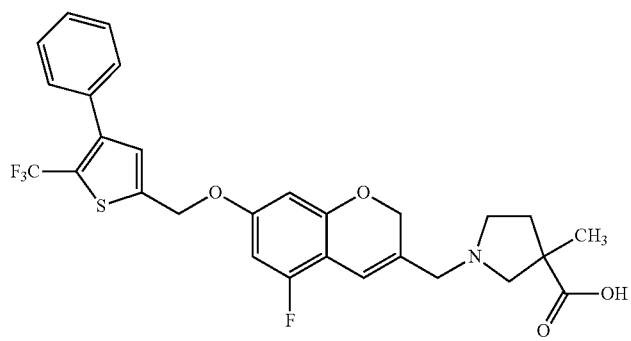
Ex67
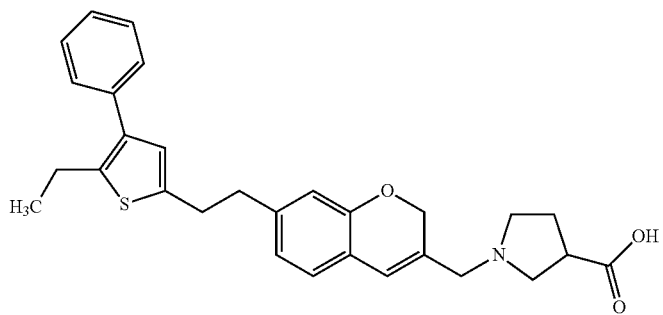
Ex68
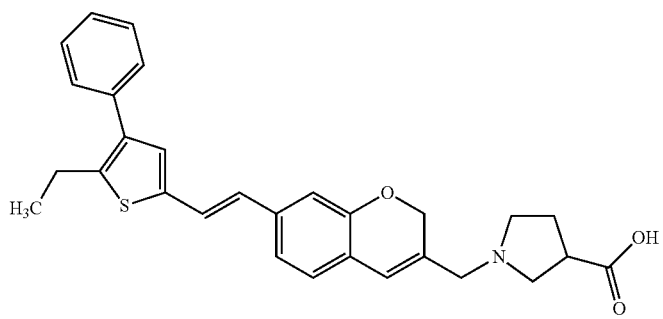

TABLE 70
Ex69 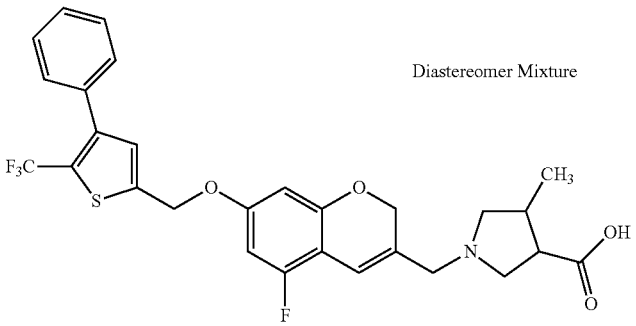
Diastereomer Mixture
Ex70 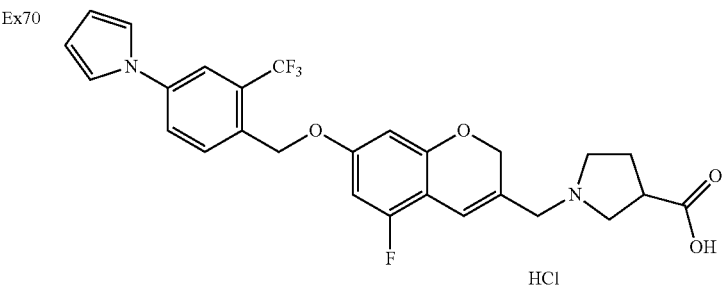
HCl
Ex71 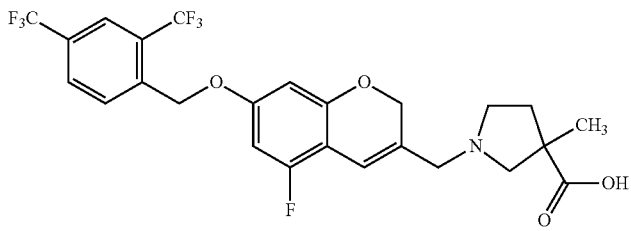
Ex72 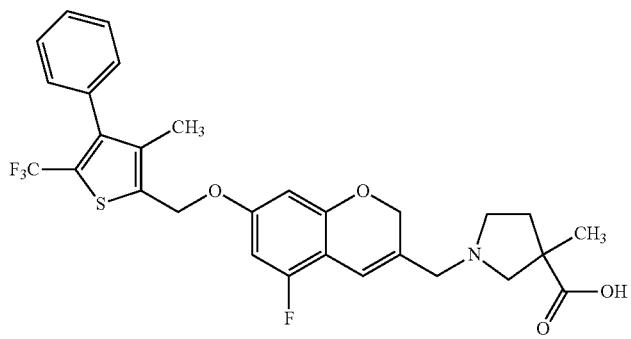
Ex73 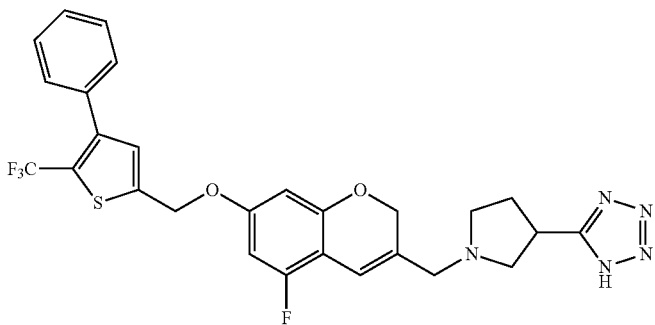

TABLE 71
Ex74
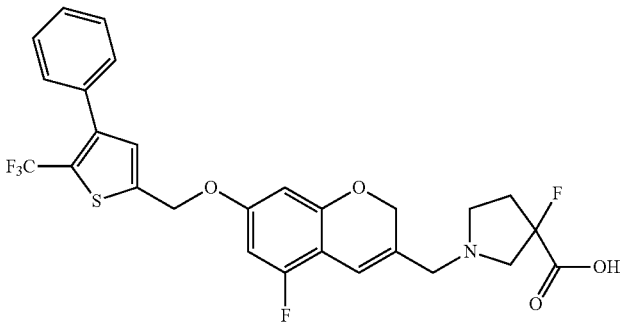
Ex75
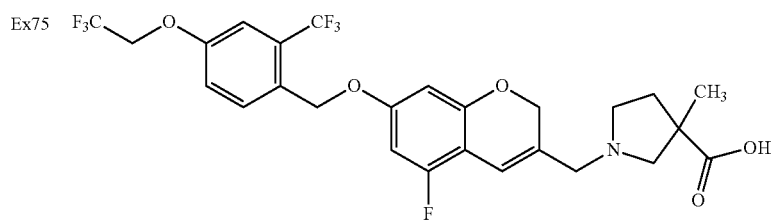
Ex76
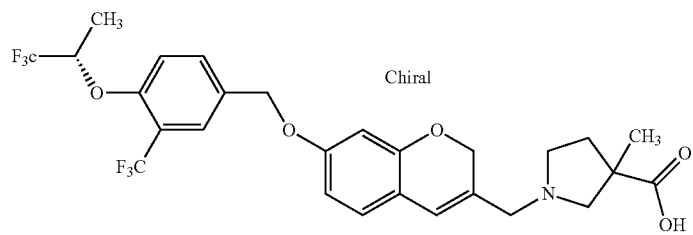
Ex77
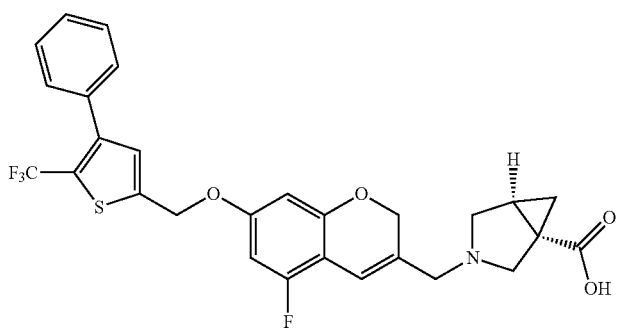
Ex78
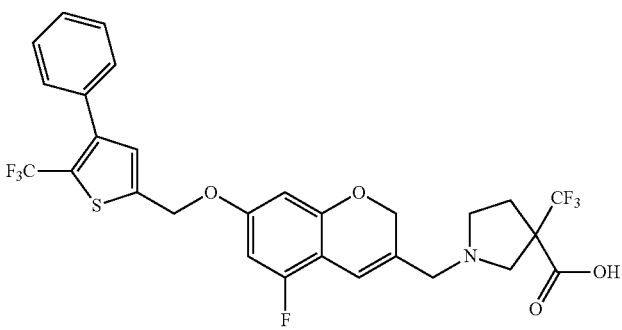

TABLE 72
Ex79 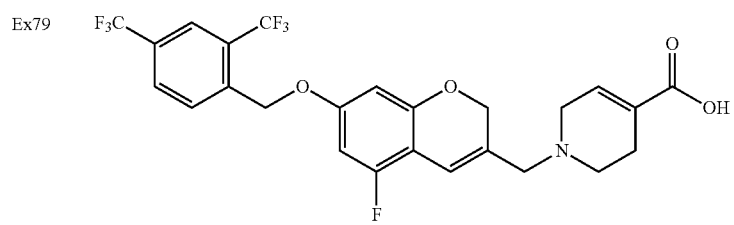
Ex80 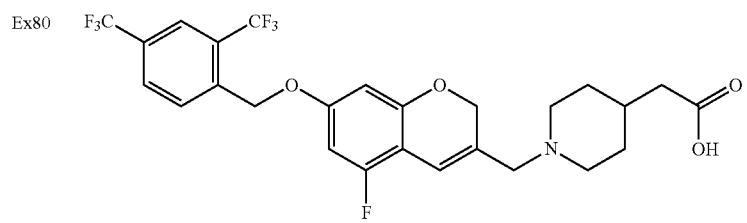
Ex81 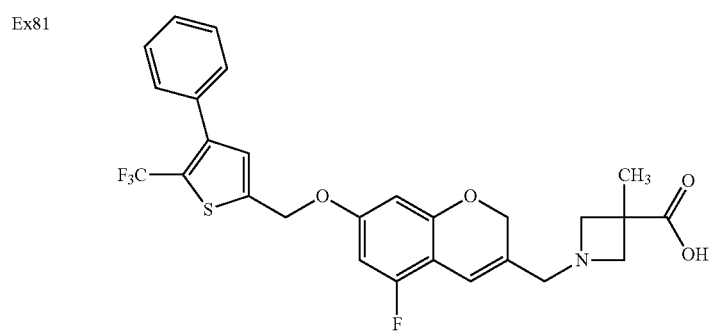
Ex82 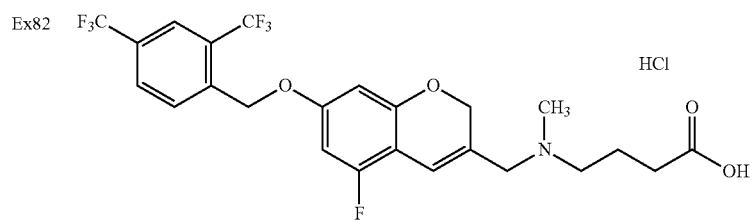
Ex83 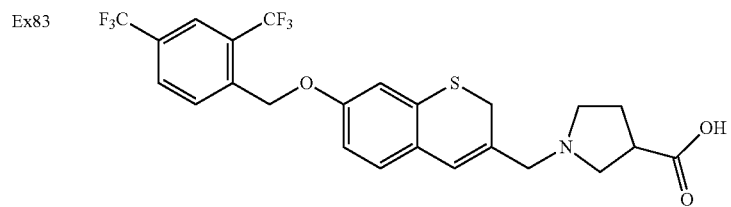
Ex84 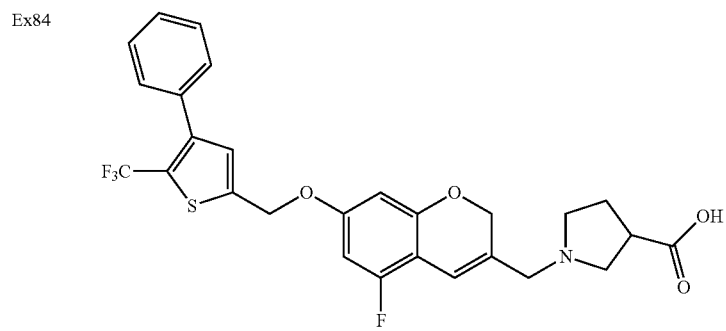

TABLE 73
Ex85 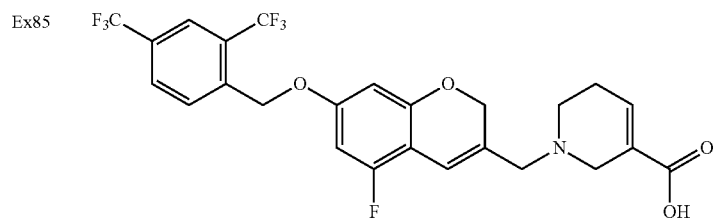
Ex86 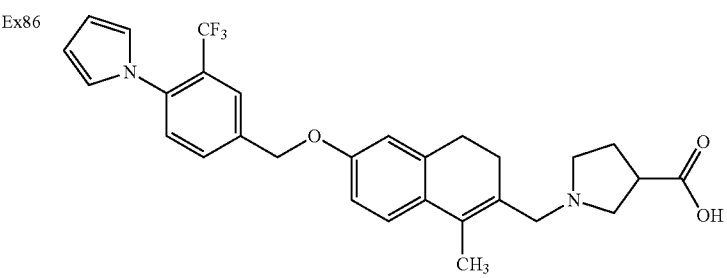
Ex87 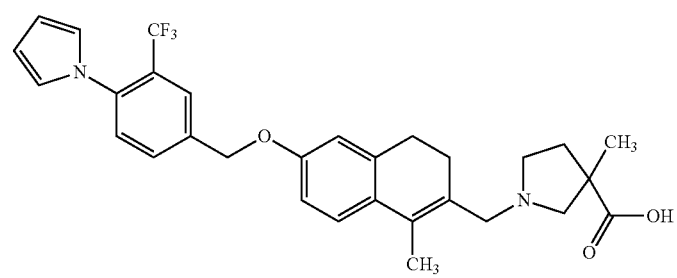
Ex88 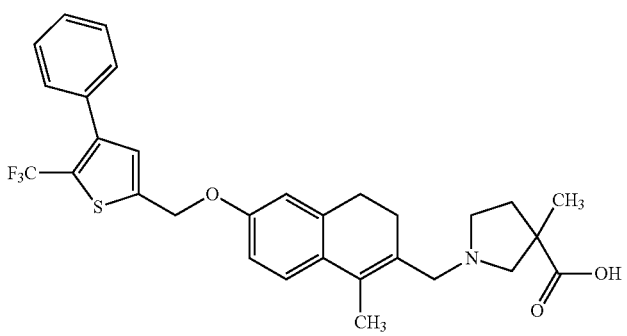
Ex89 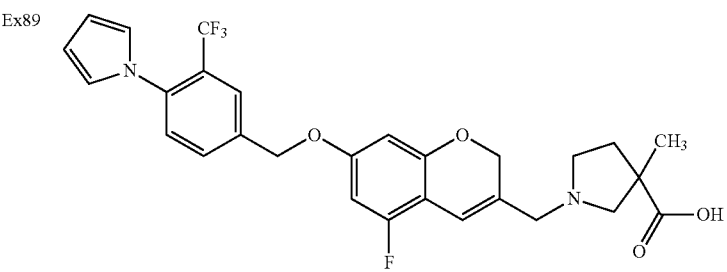

TABLE 74
Ex90
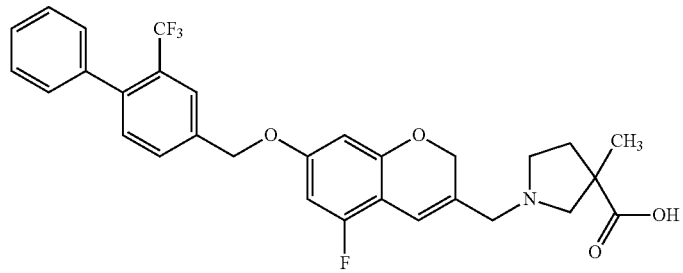
Ex91
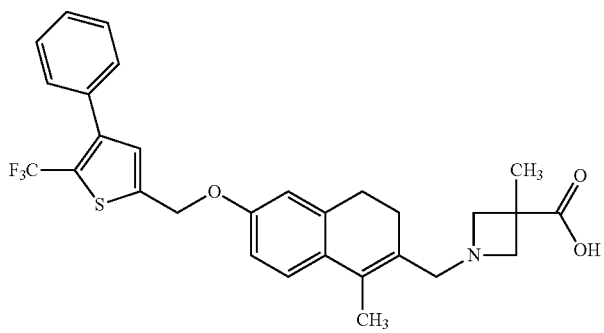
Ex92
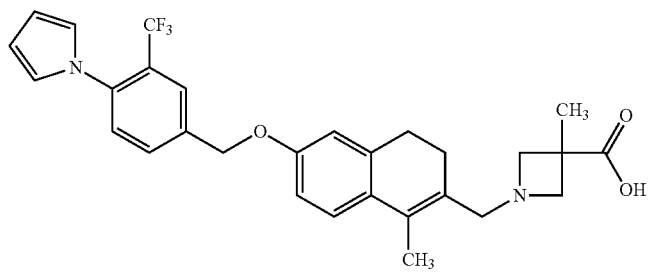
Ex93
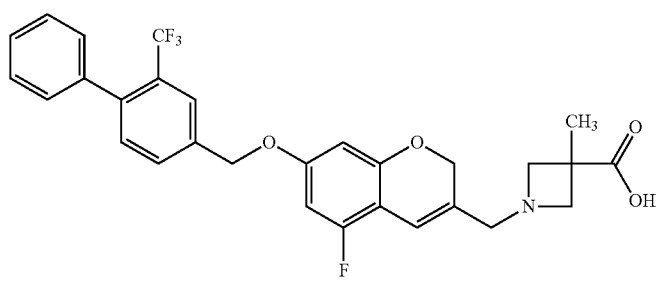
TABLE 75
Ex94
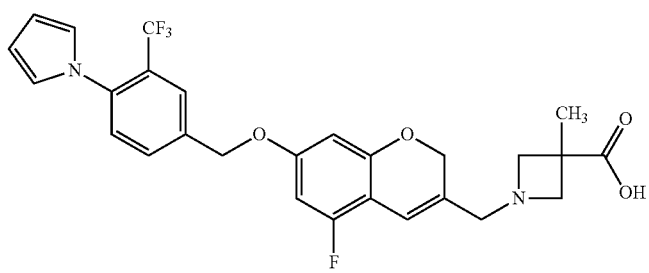

TABLE 75-continued
Ex95
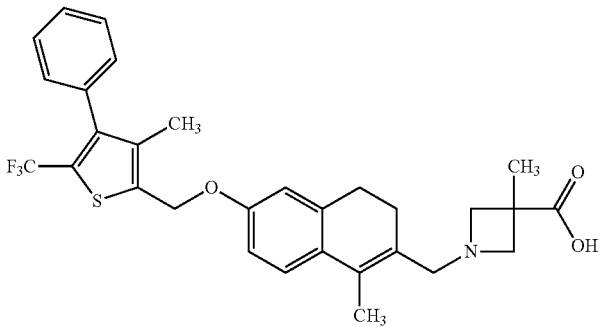
Ex96
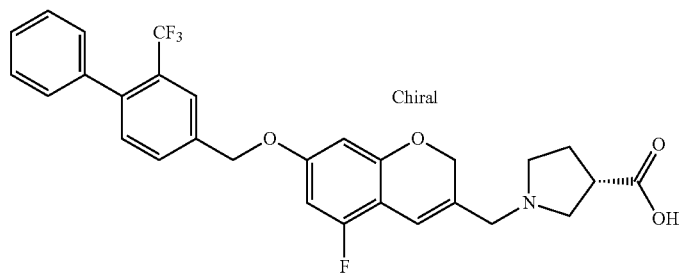
Ex97
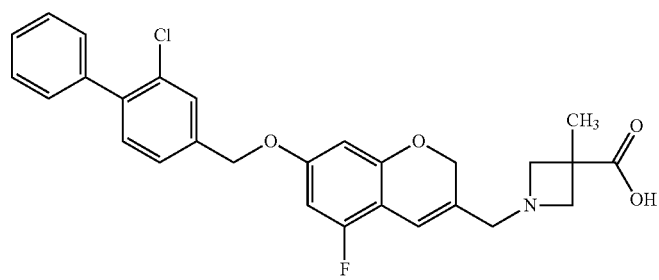
Ex98
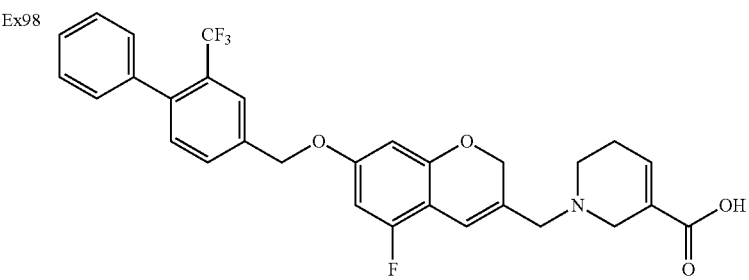
TABLE 76
Ex99
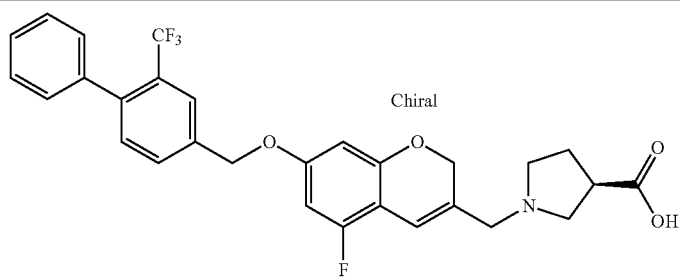

TABLE 76-continued
Ex100 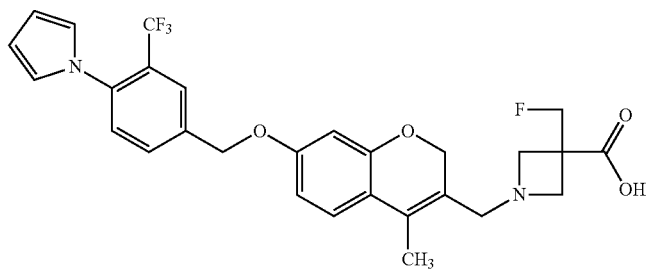
Ex101 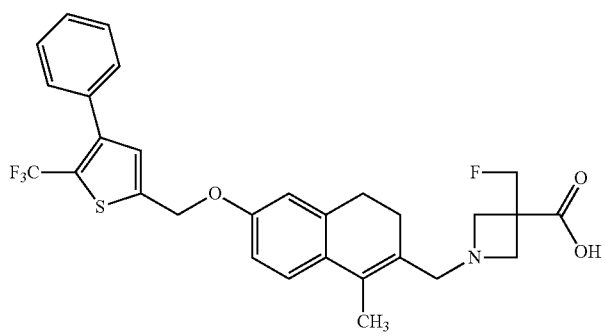
Ex102 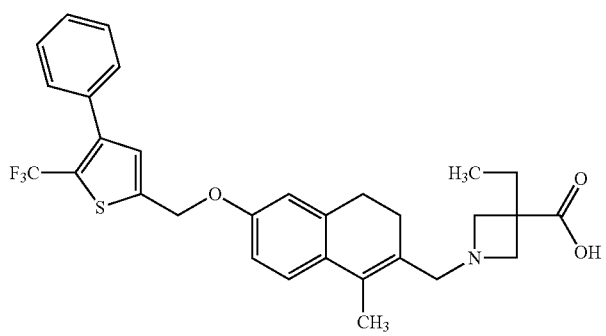
TABLE 77
Ex103 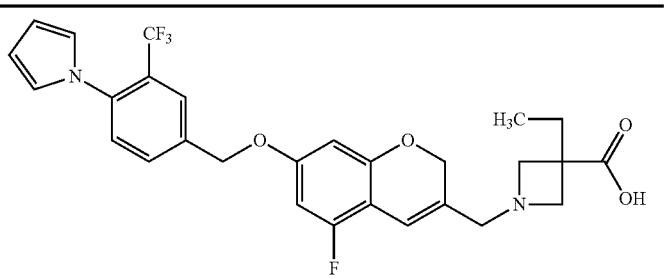
Ex104 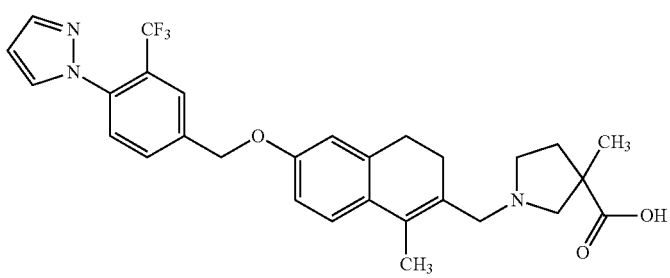

TABLE 77-continued
Ex105 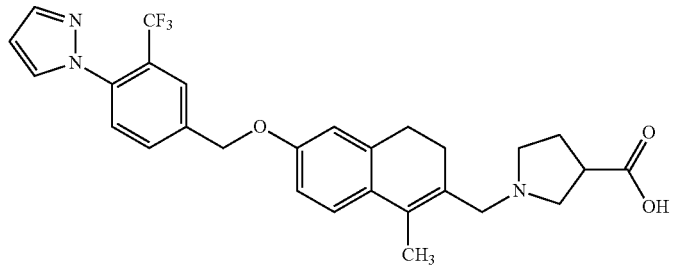
Ex106 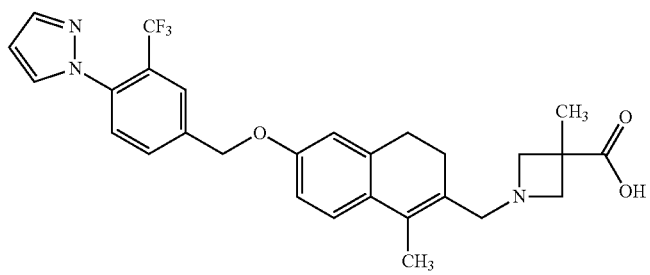
Ex107 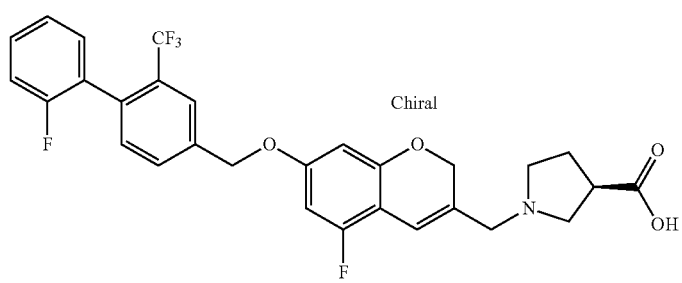
TABLE 78
Ex108 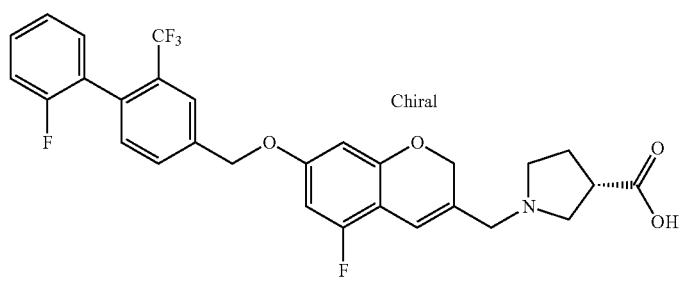
Ex109 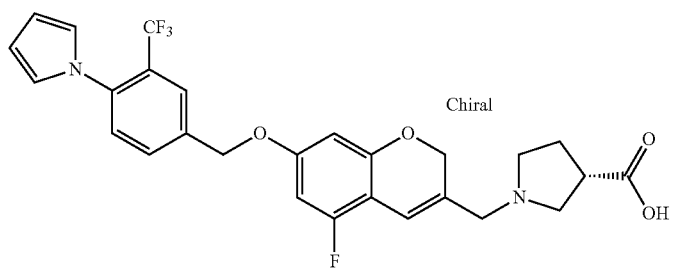

TABLE 78-continued
Ex110 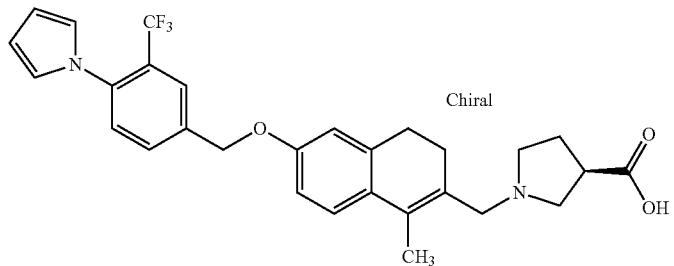
Ex111 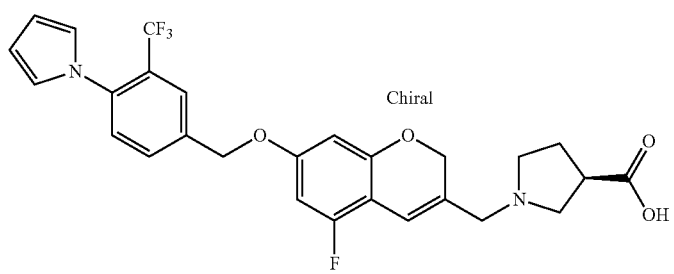
Ex112 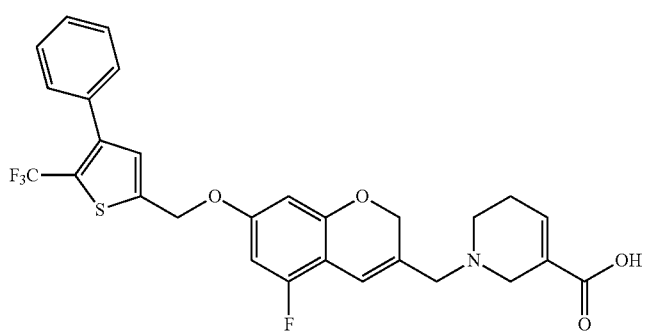
TABLE 79
Ex113 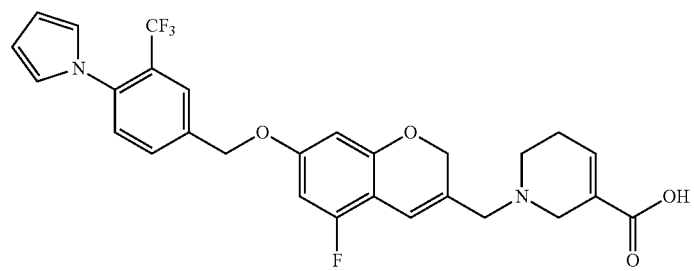
Ex114 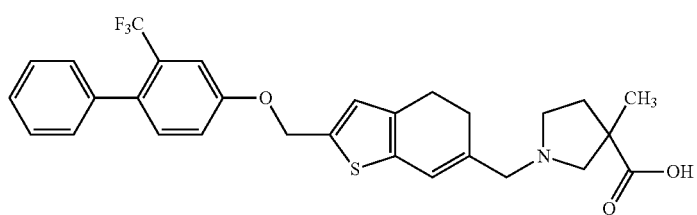

TABLE 79-continued
Ex115 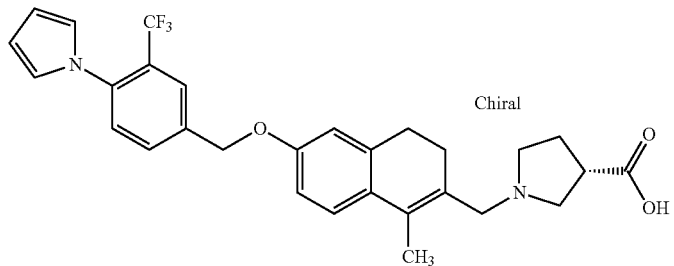
Ex116 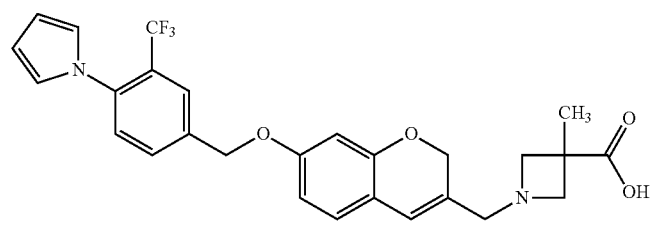
Ex117 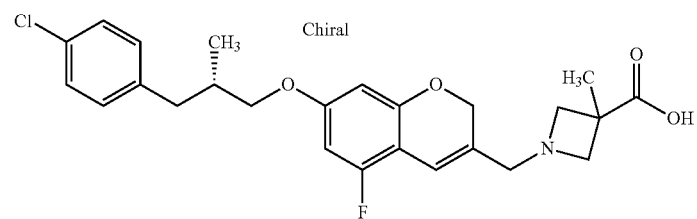
Ex118 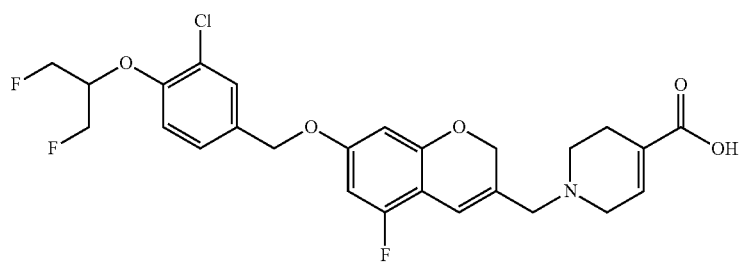
TABLE 80
Ex119 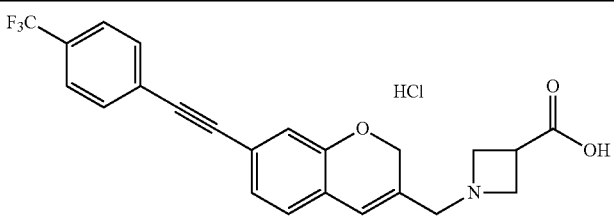
Ex120 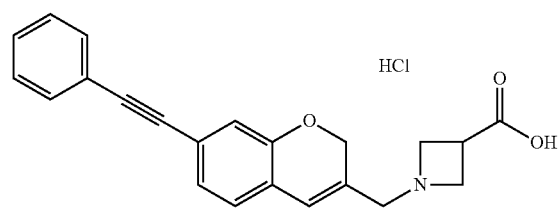

TABLE 80-continued
Ex121 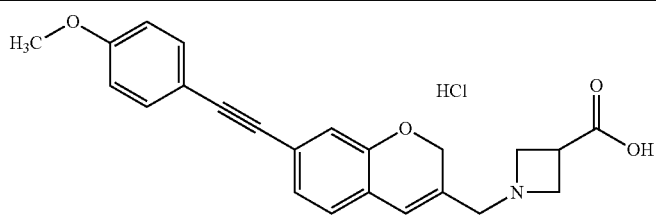
Ex122 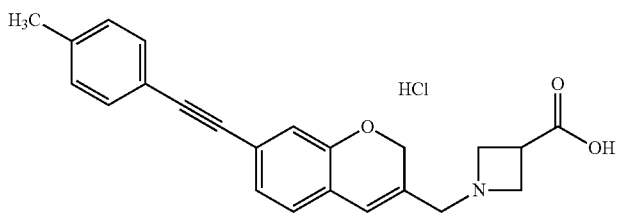
Ex123 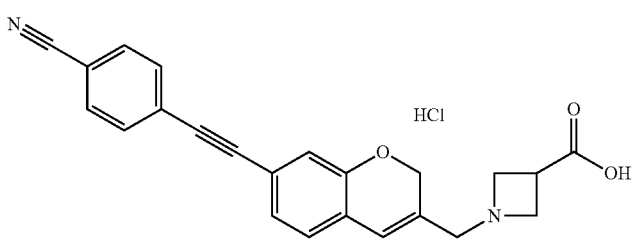
Ex124 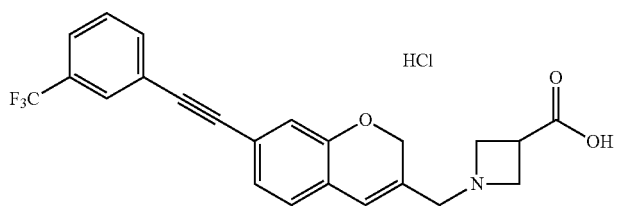
Ex125 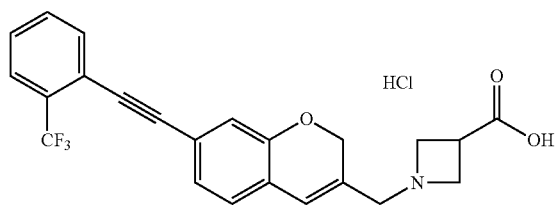
TABLE 81
Ex126 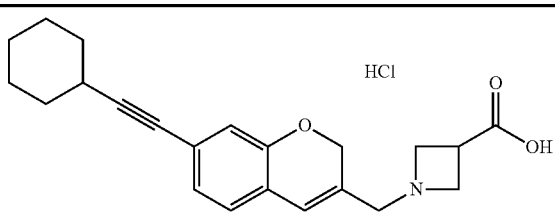
Ex127 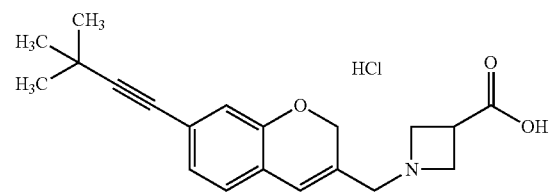

TABLE 81-continued
Ex128 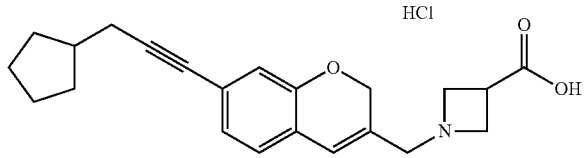
Ex129 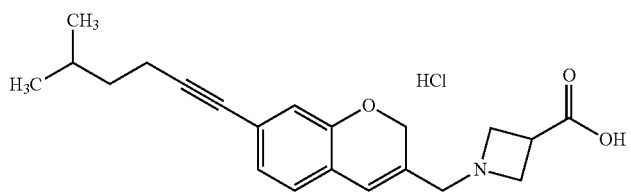
Ex130 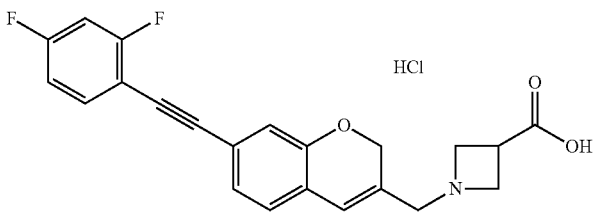
Ex131 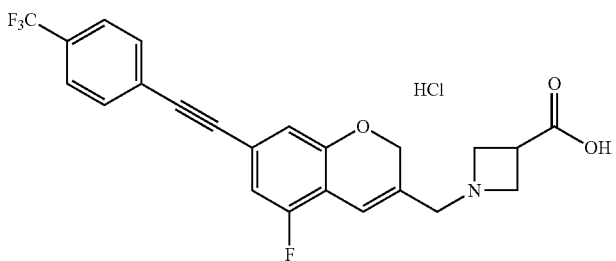
Ex132 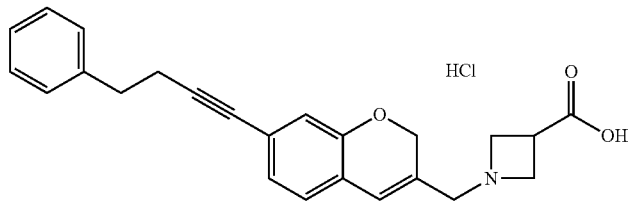
TABLE 82
Ex133 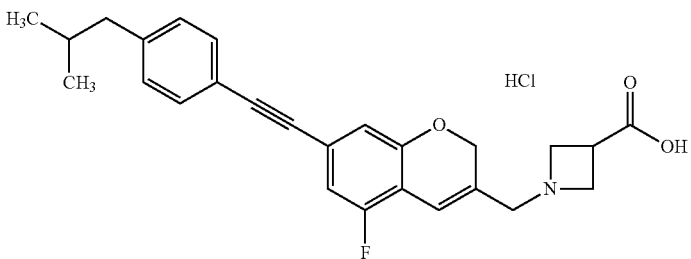

TABLE 82-continued
Ex134 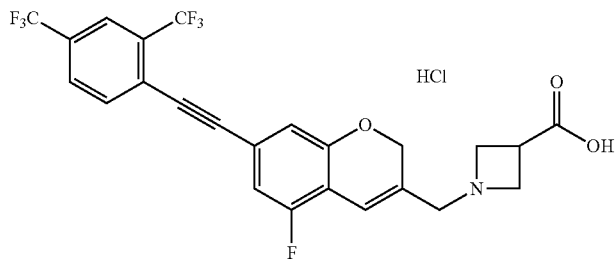
Ex135 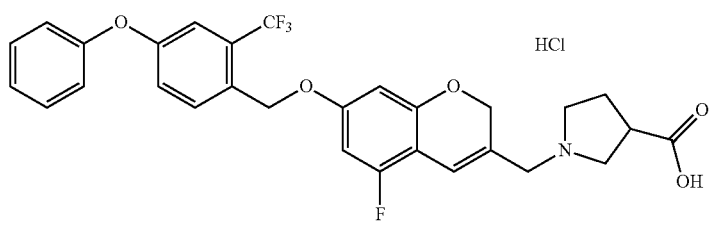
Ex136 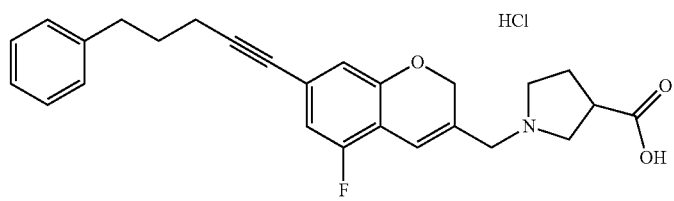
Ex137 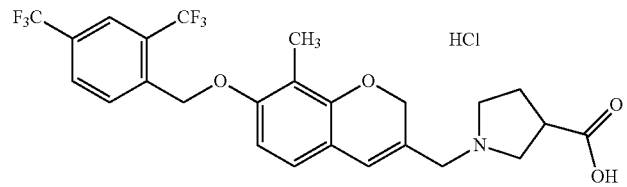
Ex138 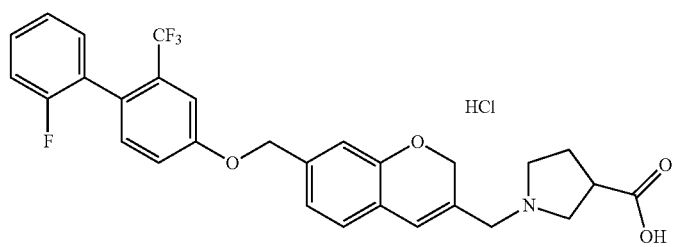
TABLE 83
Ex139 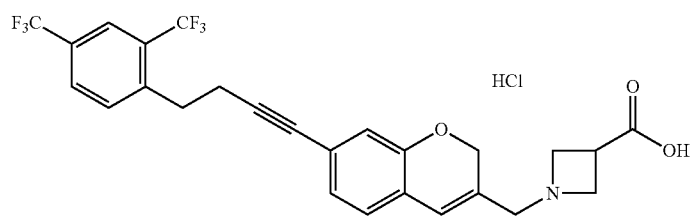

TABLE 83-continued
Ex140 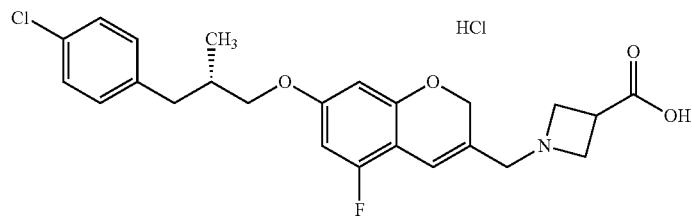
Ex141 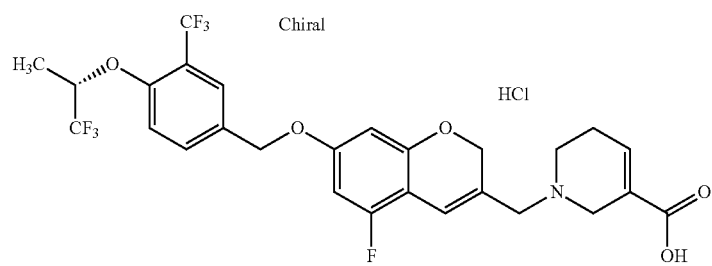
Ex142 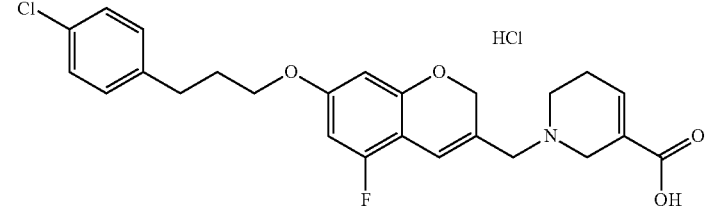
Ex143 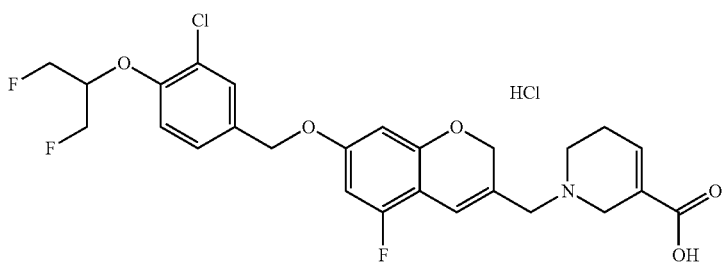
Ex144 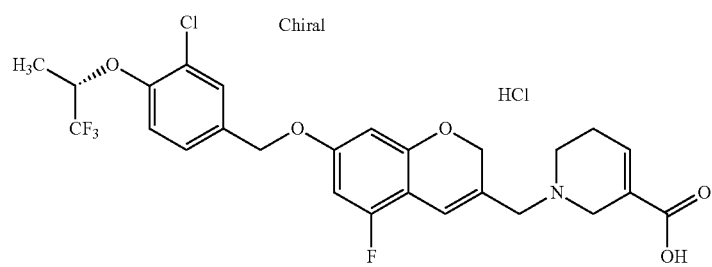

TABLE 84
Ex145 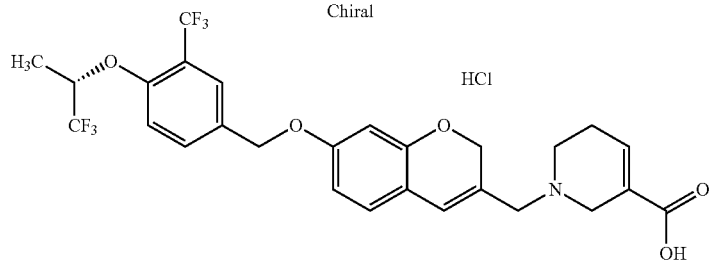
Ex146 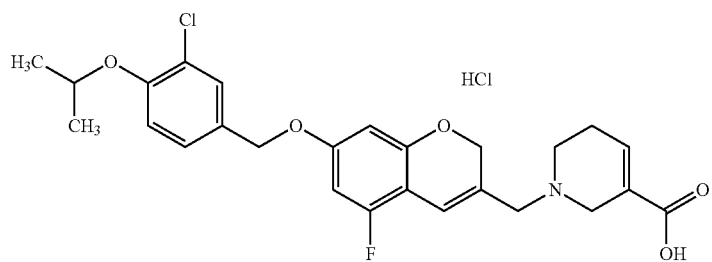
Ex147 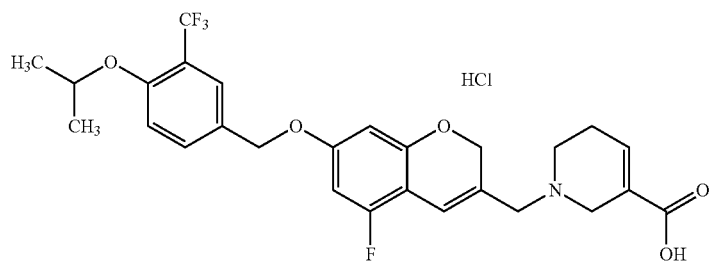
Ex148 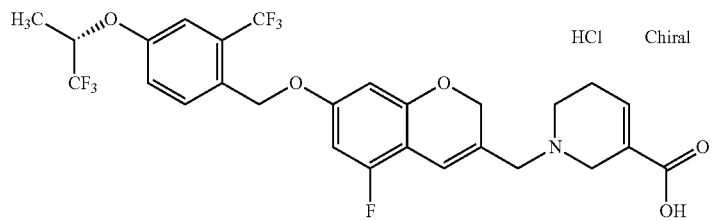
Ex149 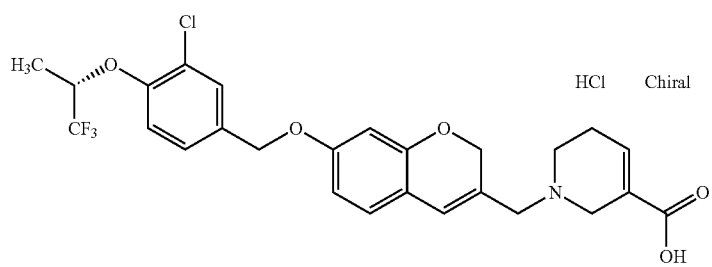
Ex150 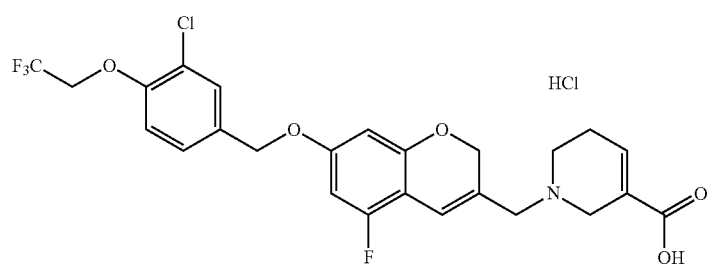

TABLE 85
Ex151 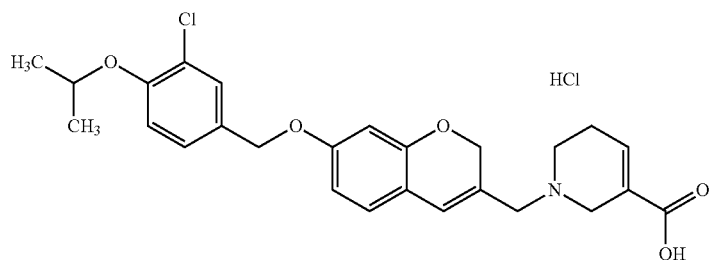
Ex152 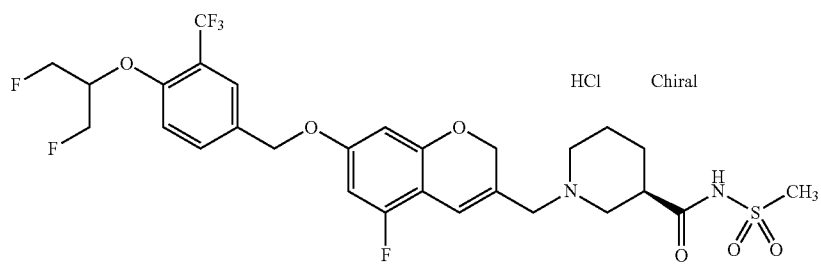
Ex153 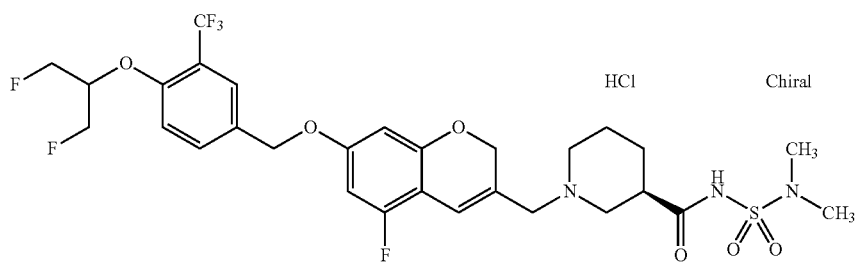
Ex154 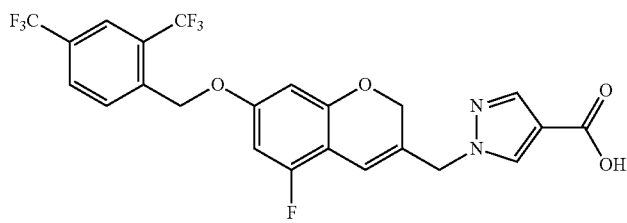
Ex155 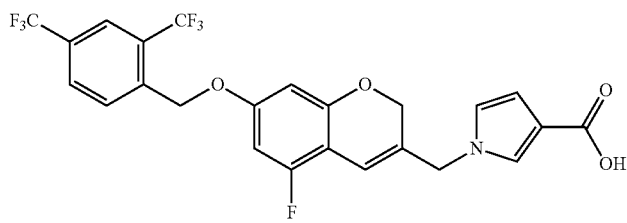
Ex156 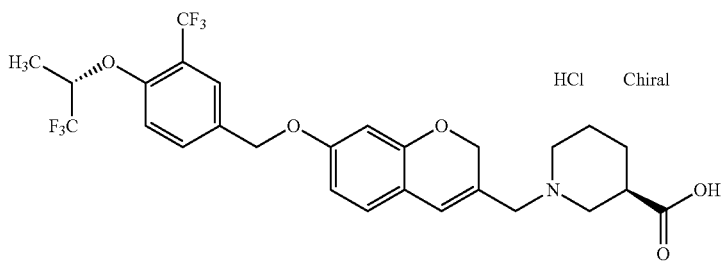

TABLE 86
Ex157 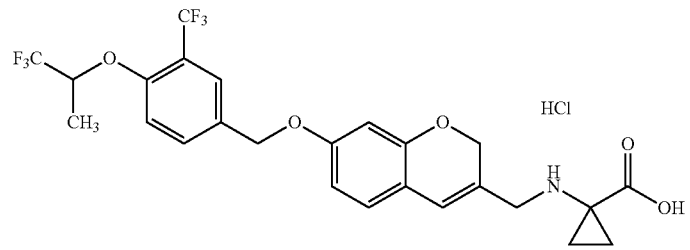
Ex158 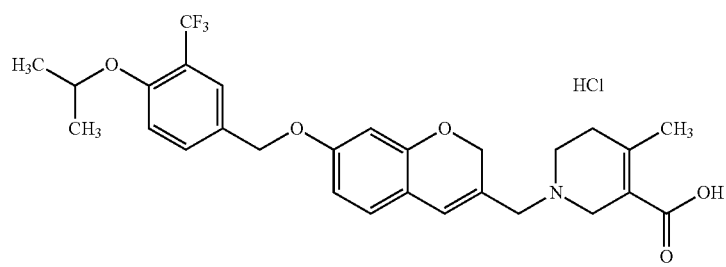
Ex159 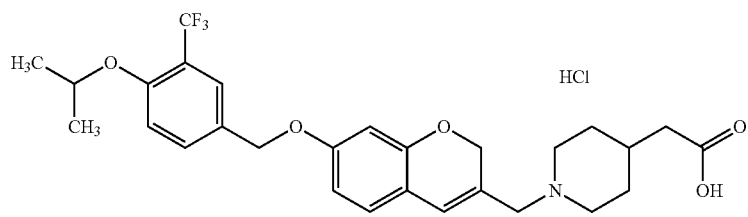
Ex160 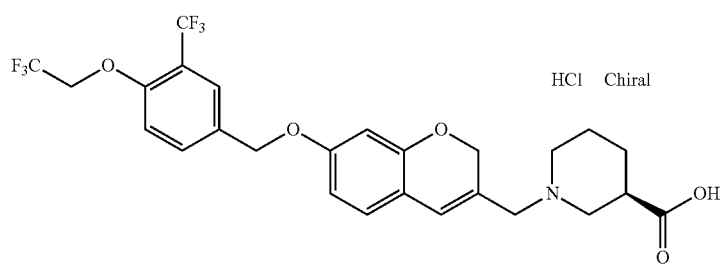
Ex161 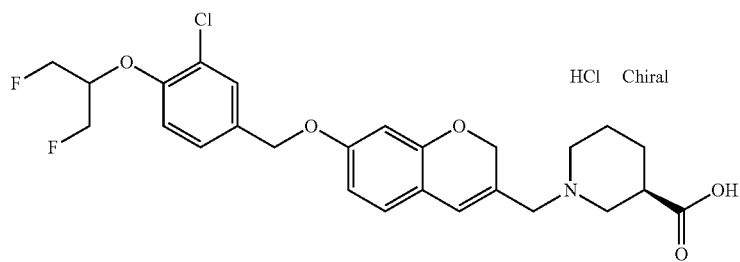
Ex162 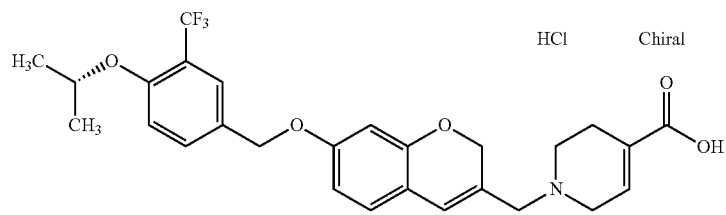

TABLE 87
Ex163 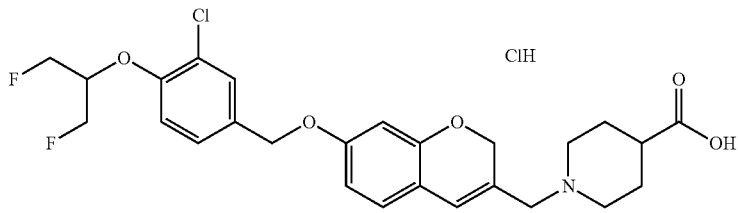
Ex164 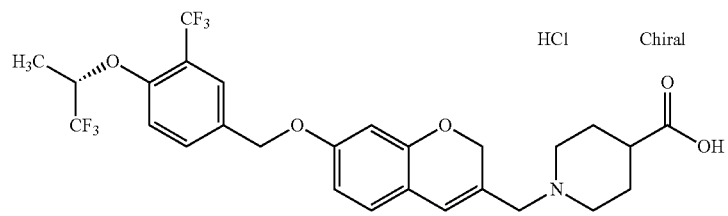
Ex165 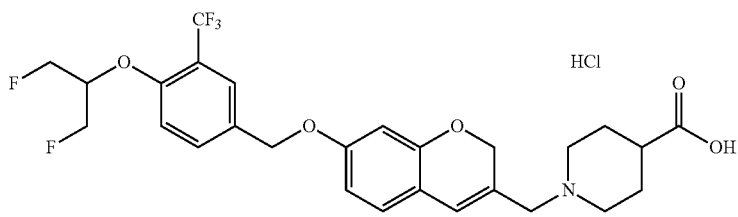
Ex166 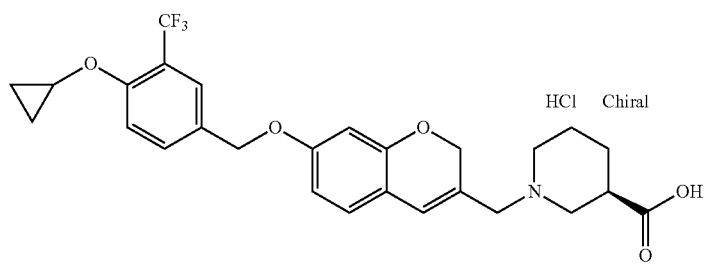
Ex167 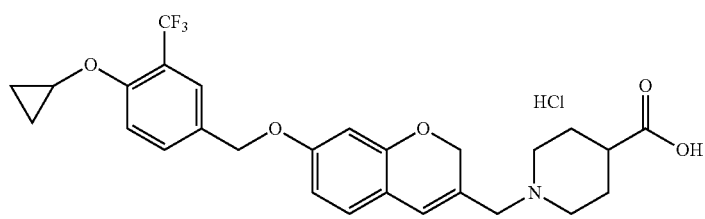
Ex168 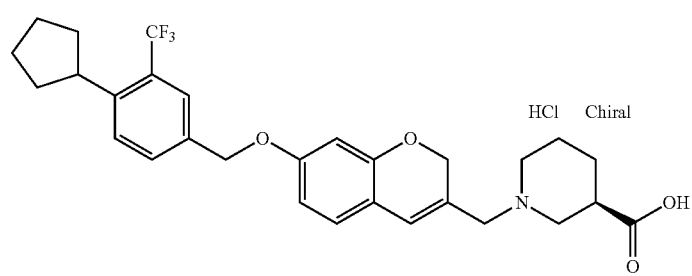

TABLE 87-continued
Ex169 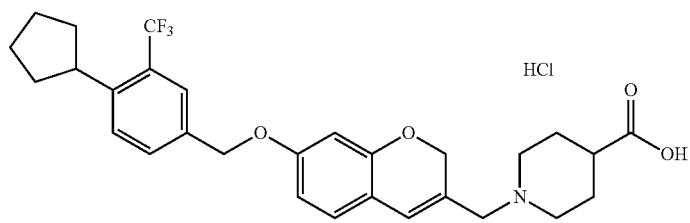
TABLE 88
Ex170 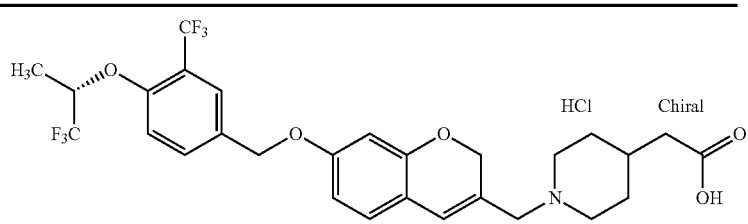
Ex171 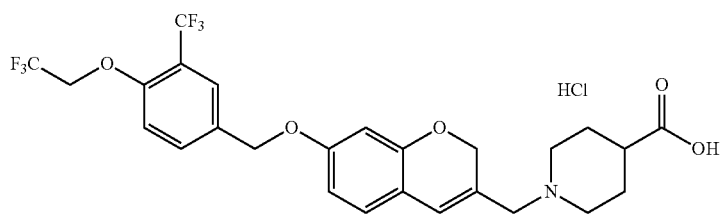
Ex172 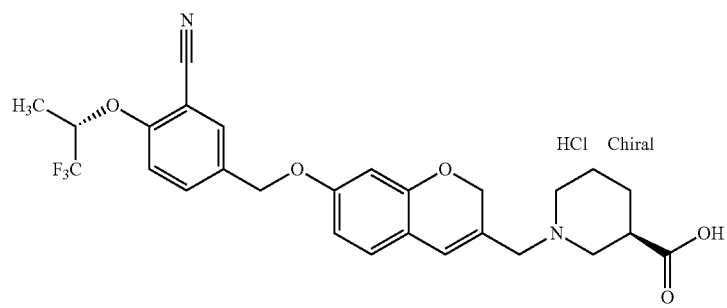
Ex173 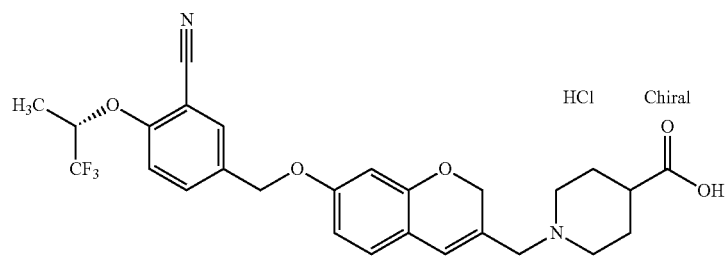
Ex174 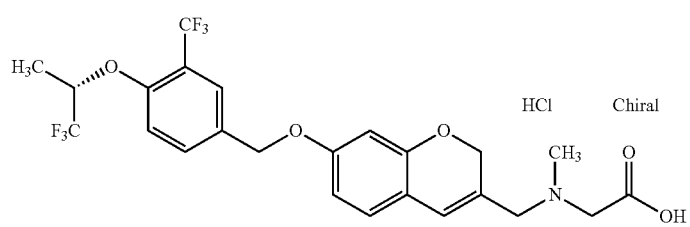

TABLE 88-continued
Ex175 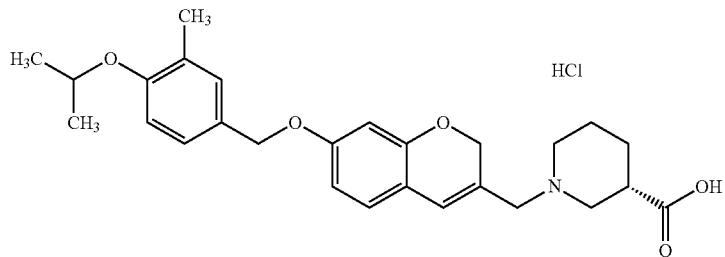 HCl
TABLE 89
Ex176 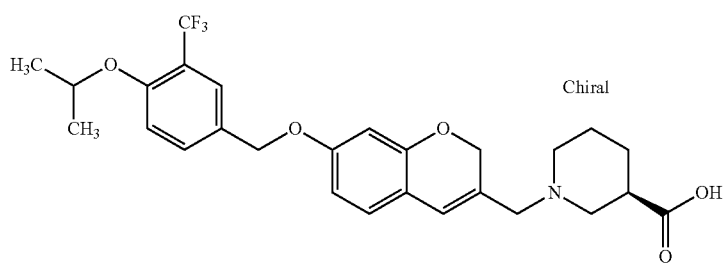 Chiral
Ex177 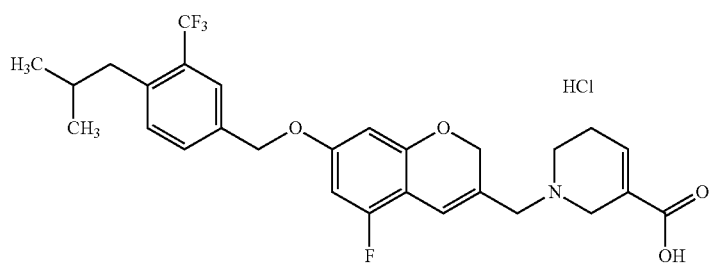 HCl
Ex178 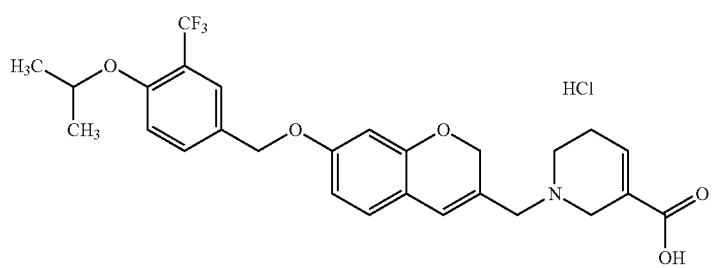 HCl
Ex179 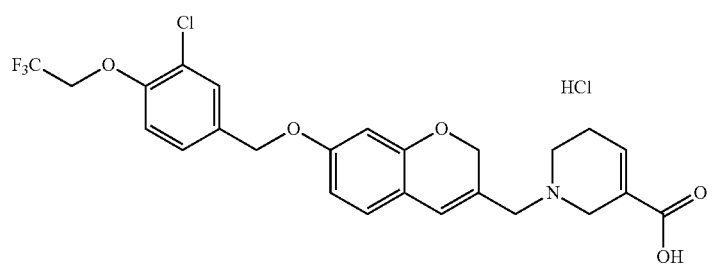 HCl TABLE 89-continued
Ex180 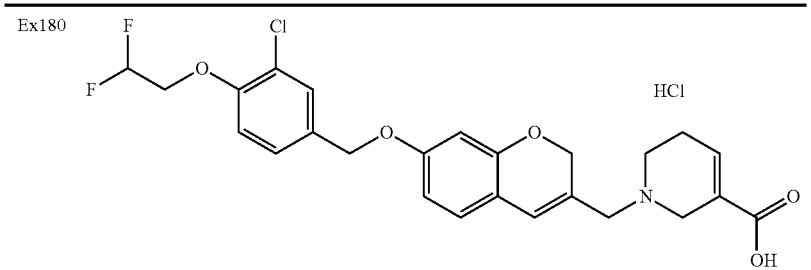
Ex181 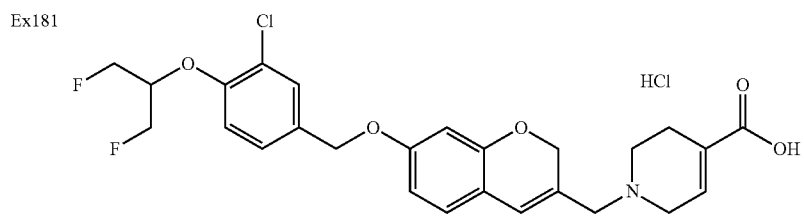
TABLE 90
Ex182 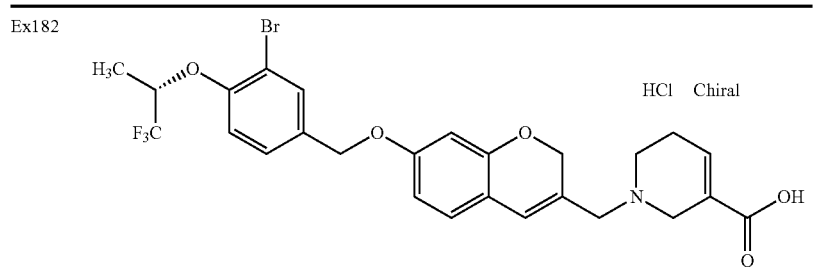
Ex183 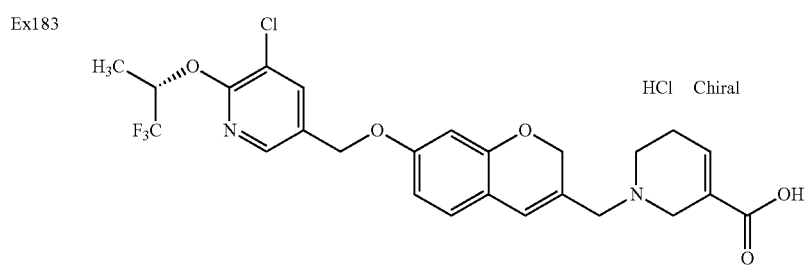
Ex184 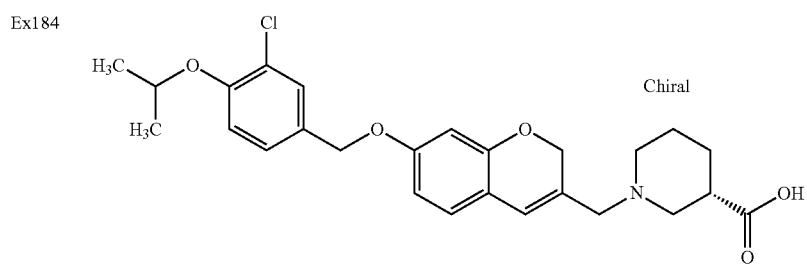
Ex185 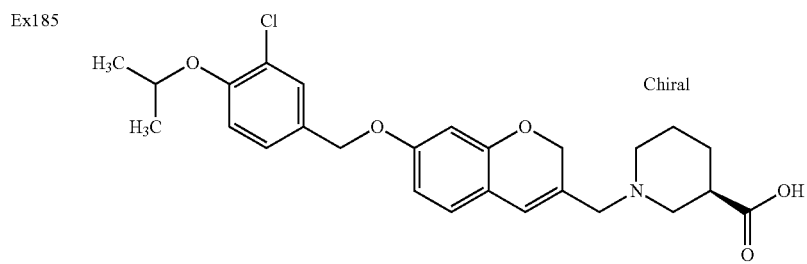

TABLE 90-continued
Ex186 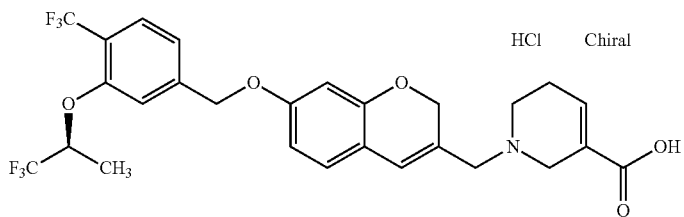 HCl Chiral
Ex187 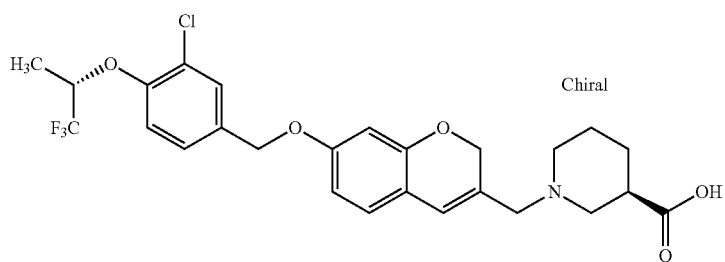 Chiral
TABLE 91
Ex188 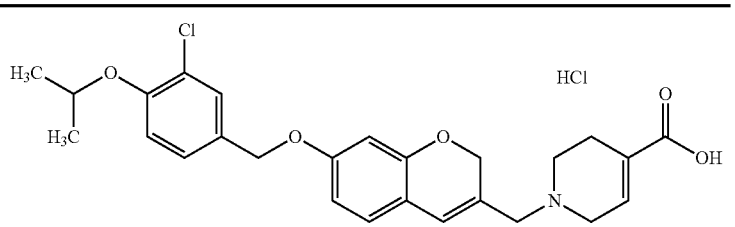 HCl
Ex189 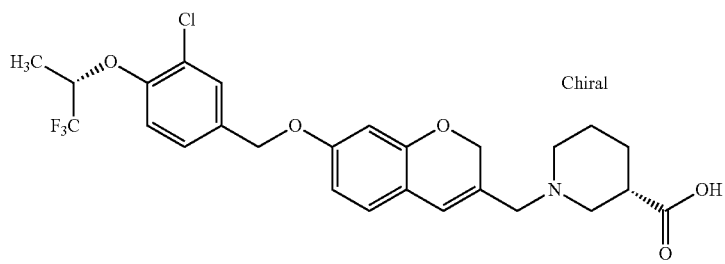 Chiral
Ex190 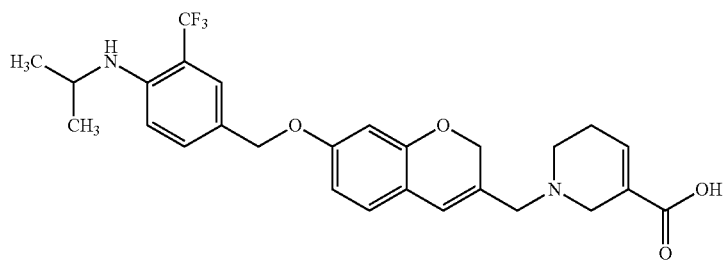
Ex191 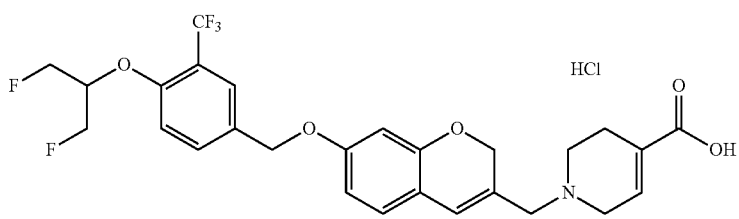 HCl TABLE 91-continued
Ex192 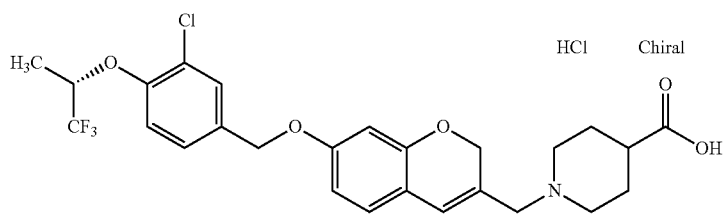 HCl Chiral
Ex193 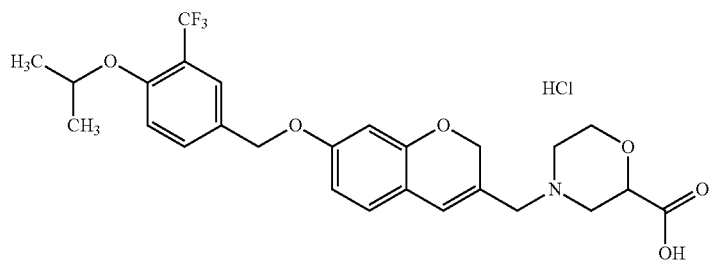 HCl
TABLE 92
Ex194 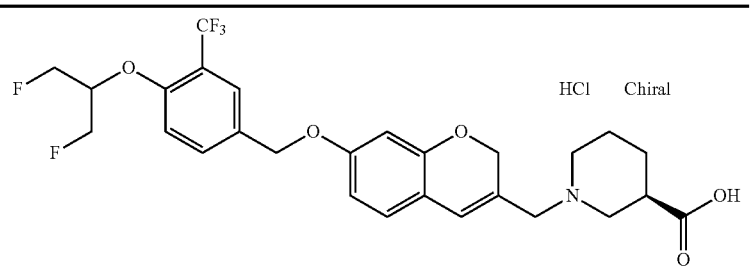 HCl Chiral
Ex195 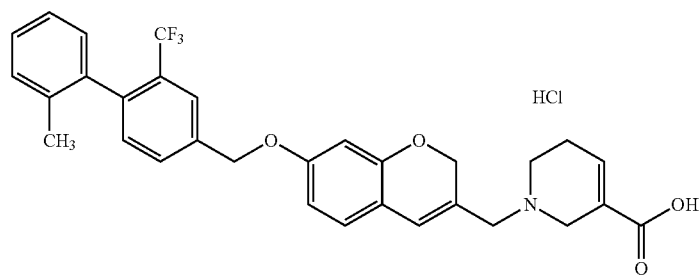 HCl
Ex196 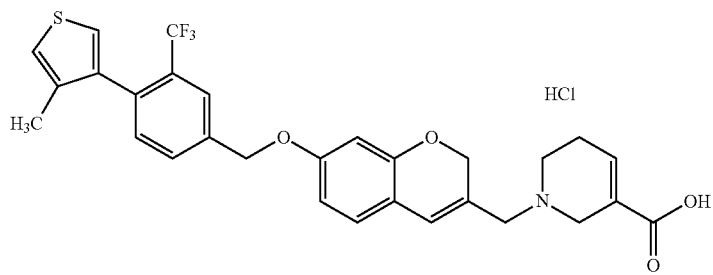 HCl
Ex197 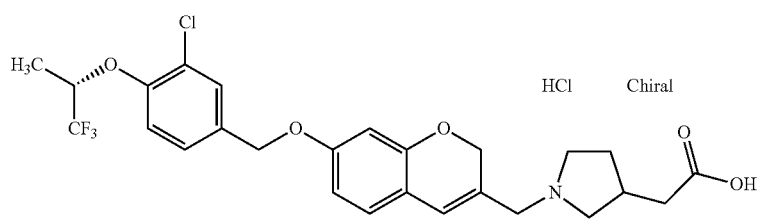 HCl Chiral TABLE 92-continued
Ex198 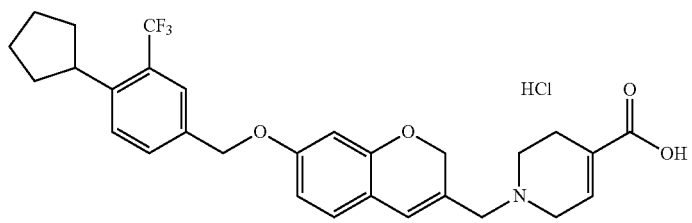
Ex199 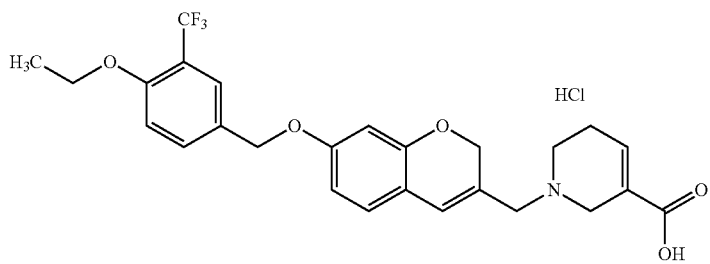
TABLE 93
Ex200 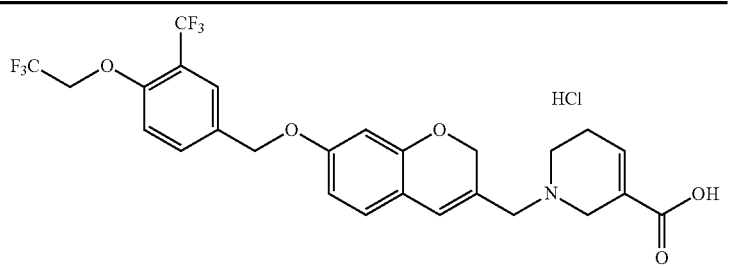
Ex201 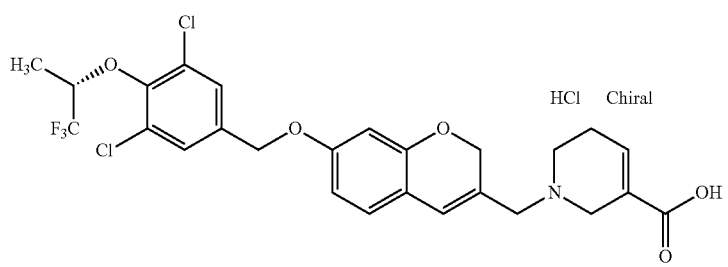
Ex202 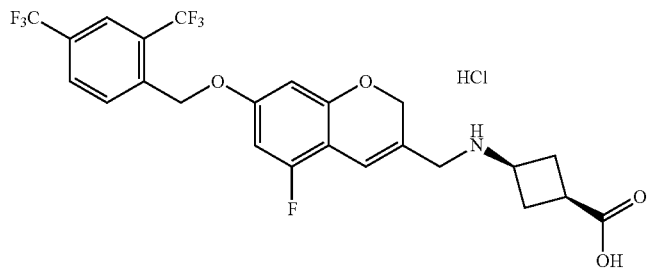
Ex203 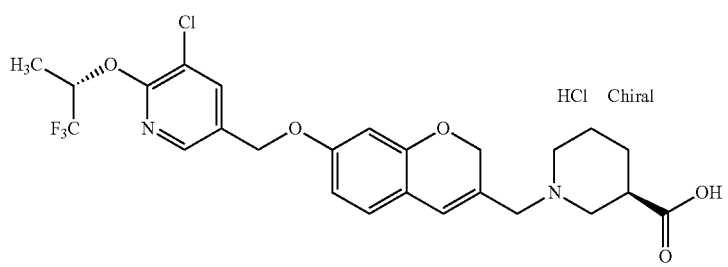

TABLE 93-continued
Ex204 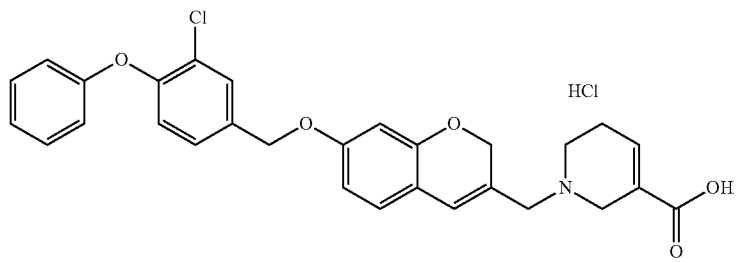
Ex205 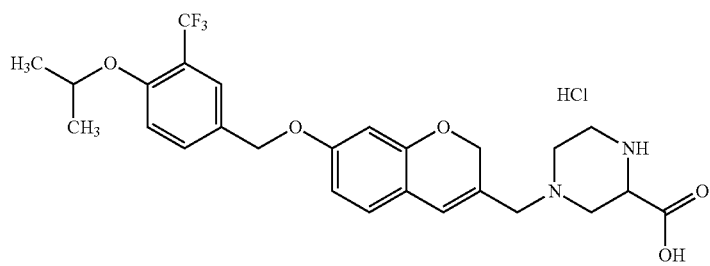
TABLE 94
Ex206 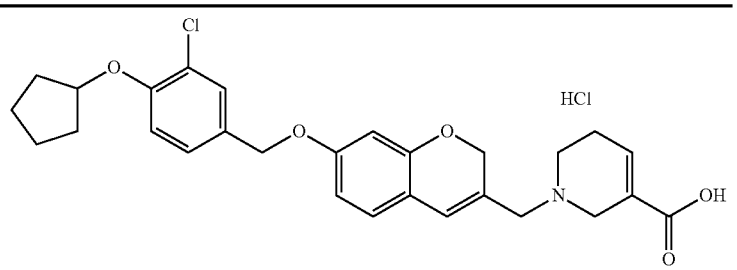
EX207 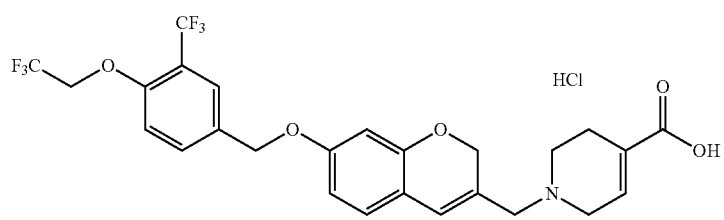
Ex208 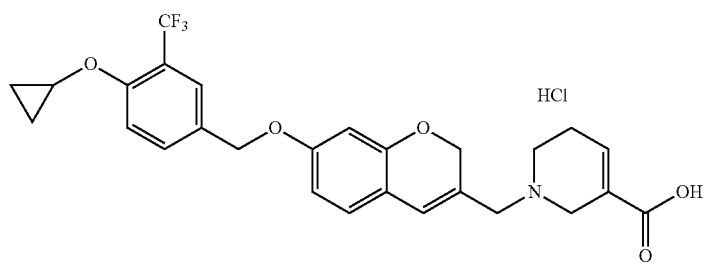
Ex209 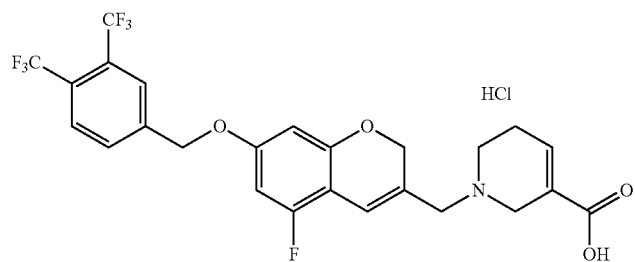

TABLE 94-continued
Ex210 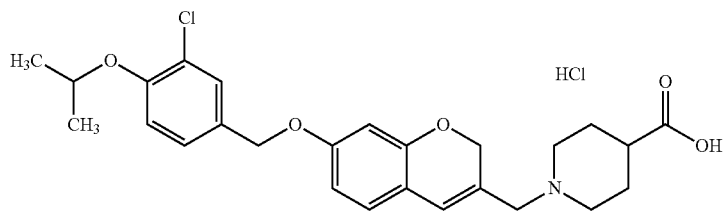
Ex211 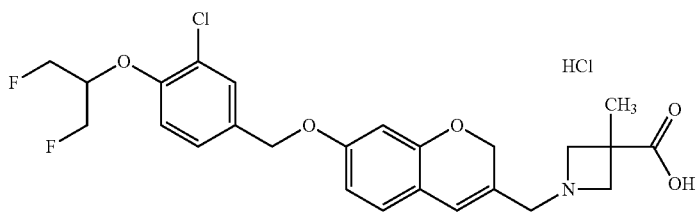
TABLE 95
Ex212 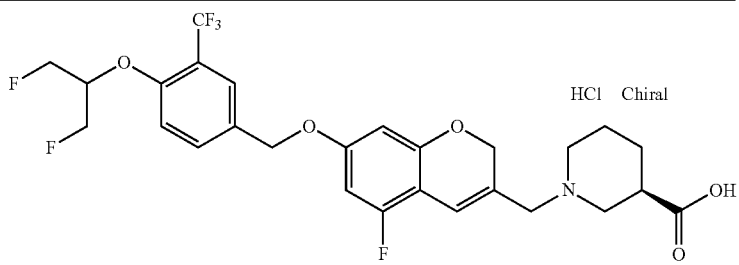
Ex213 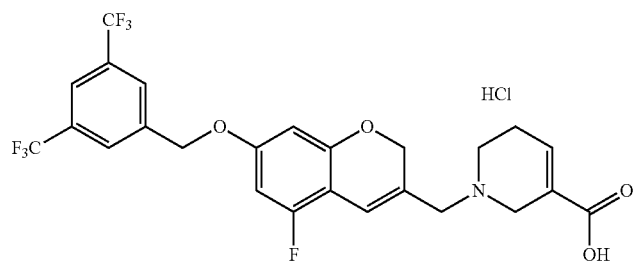
Ex214 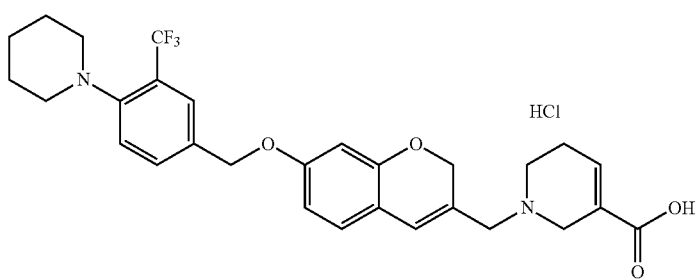
Ex215 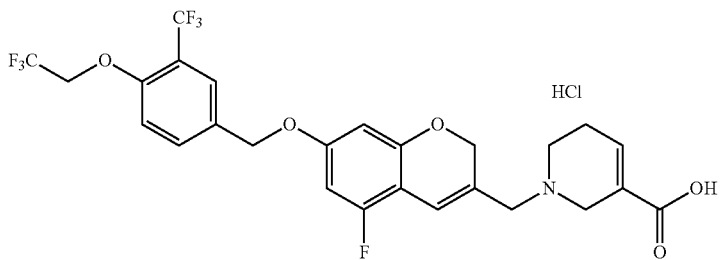

TABLE 95-continued
Ex216 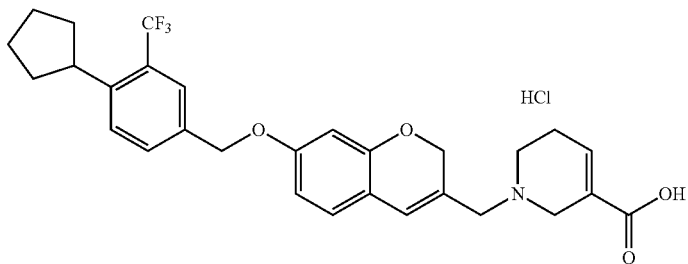
Ex217 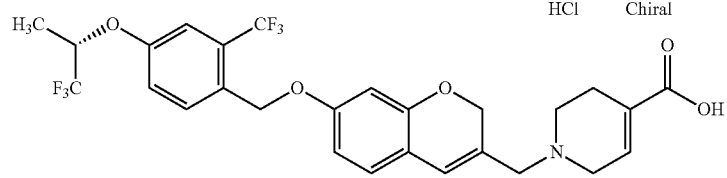
TABLE 96
Ex218 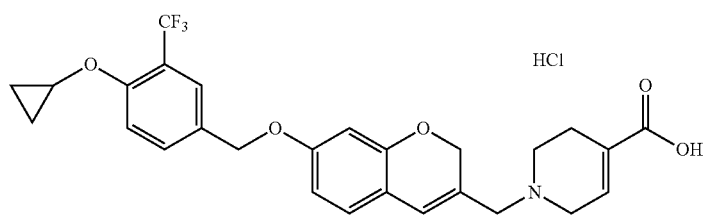
Ex219 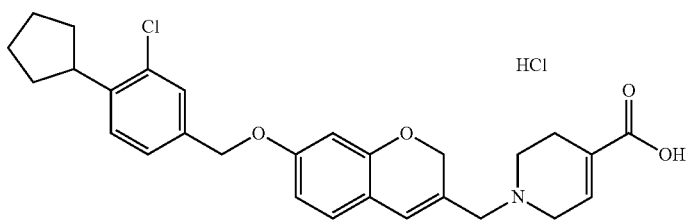
Ex220 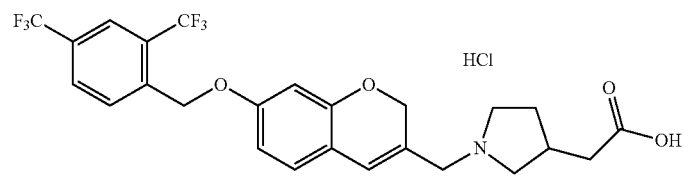
Ex221 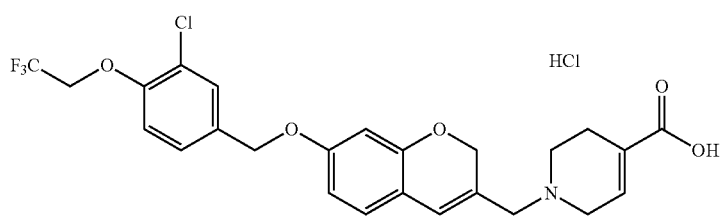

TABLE 96-continued
Ex222 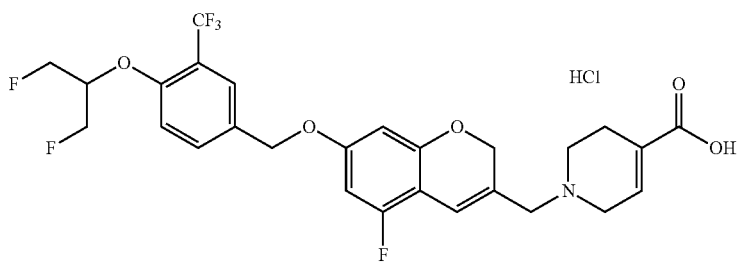
Ex223 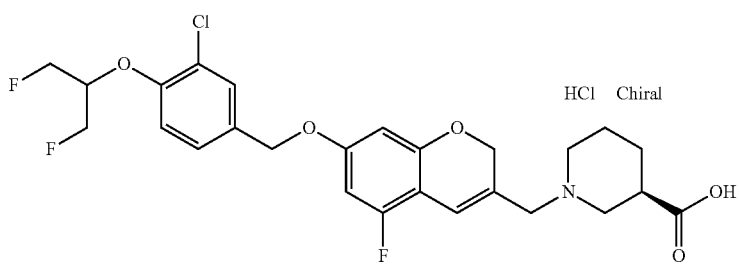
Ex224 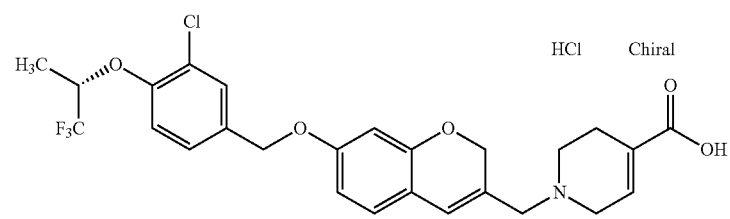
TABLE 97
Ex225 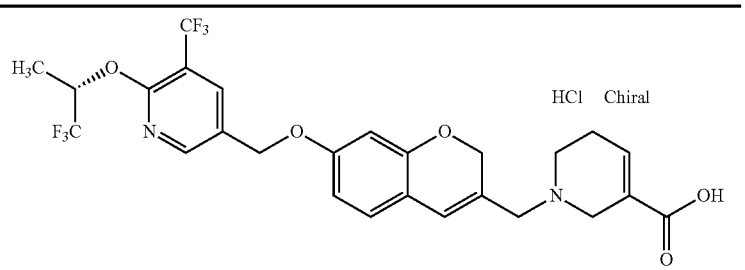
Ex226 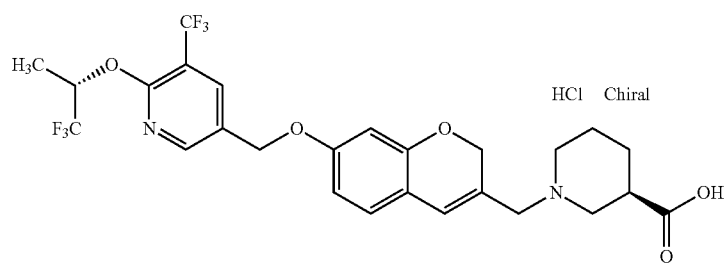
Ex227 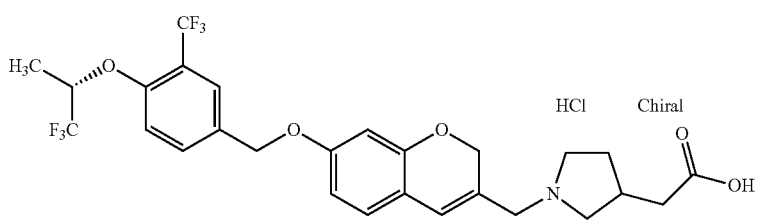

TABLE 97-continued
Ex228 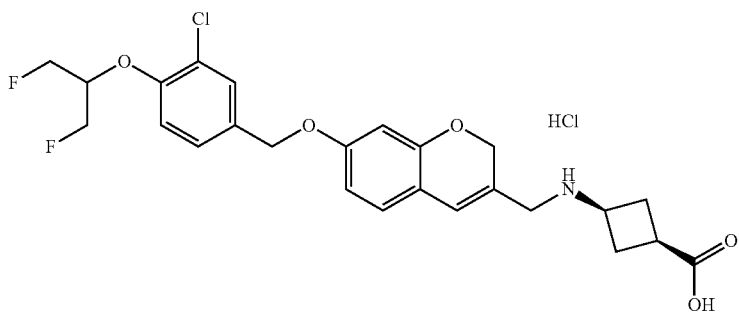
Ex229 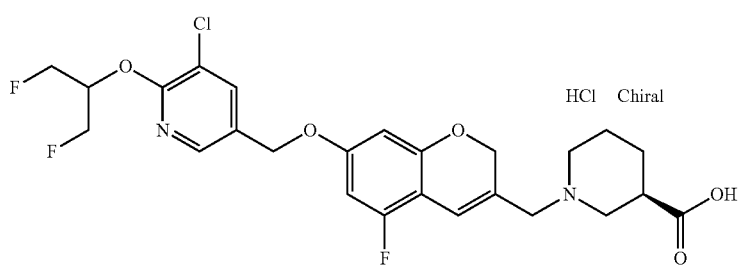
Ex230 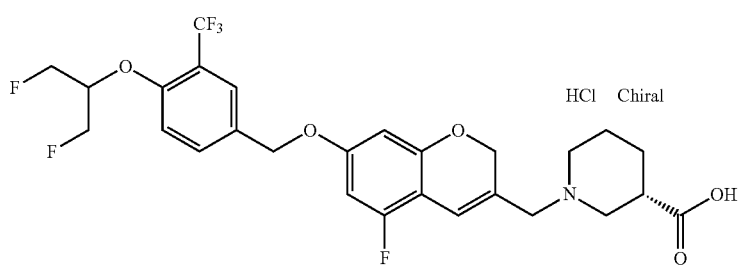
TABLE 98
Ex231 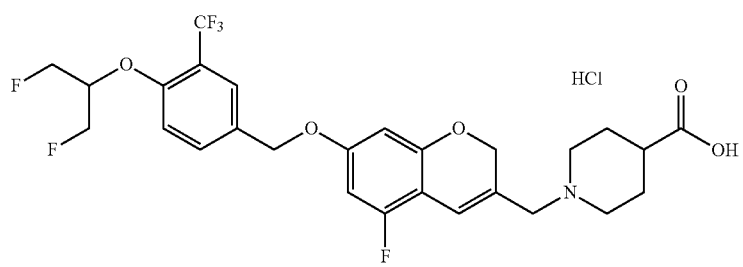
Ex232 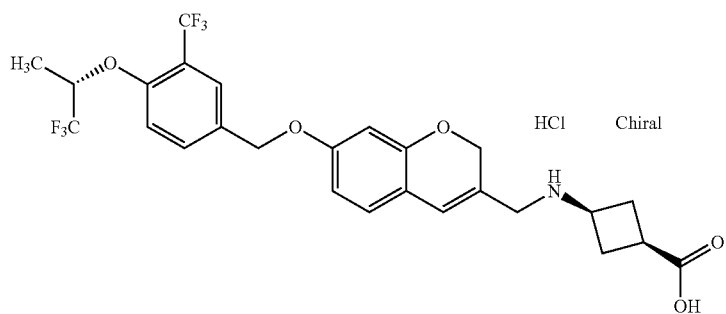

| | |
|---|---|
| Ex233 | 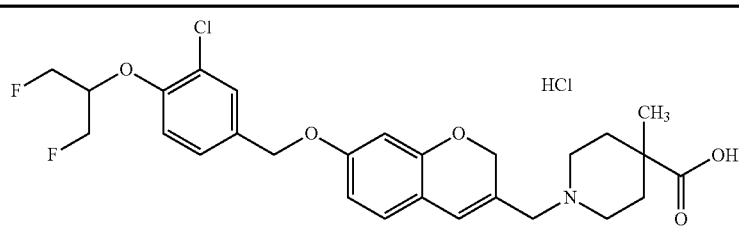 HCl |
| Ex234 | 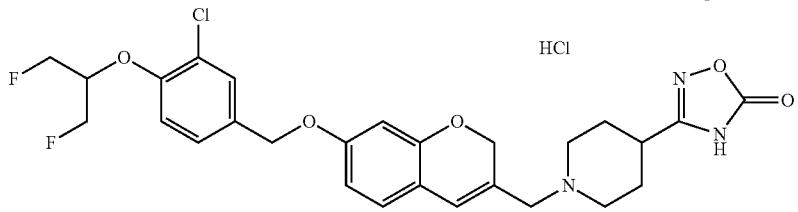 HCl |
| Ex235 | 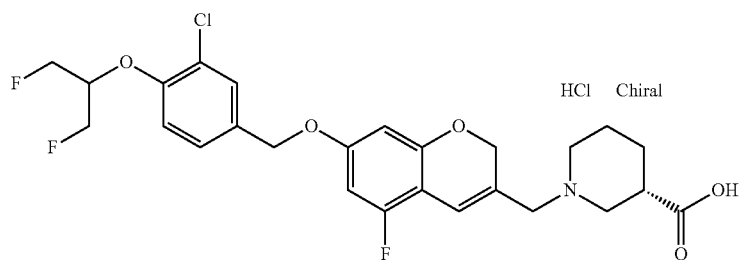 HCl Chiral |
| Ex236 | 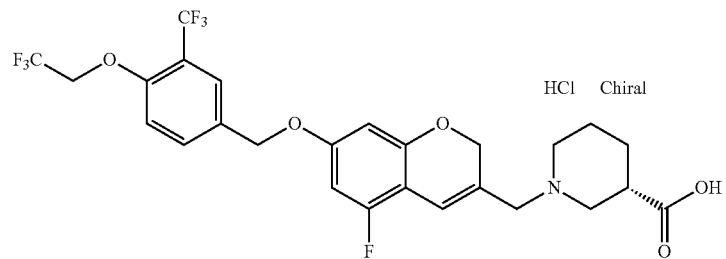 HCl Chiral |

TABLE 99

| Pr | DATA |
|---|---|
| Pr1 | MS+: 396 |
| Pr2 | MS+: 281 |
| Pr2-1 | MS+: 267 |
| Pr2-2 | MS+: 385 |
| Pr2-3 | MS+: 281 |
| Pr2-4 | MS−: 387 |
| Pr3 | NMR: 2.56 (2H, t, J = 6.0 Hz), 4.44 (2H, t, J = 6.0 Hz), 5.18 (2H, s), 5.81 (1H, d, J = 2.6 Hz), 6.98 (1H, dd, J = 2.6, 8.9 Hz), 7.32-7.48 (5H, m), 7.73 (1H, d, J = 8.9 Hz), 10.22 (1H, s) |
| Pr4 | MS−: 209 |
| Pr5 | MS+: 253 |
| Pr5-1 | MS+: 267 |
| Pr6 | MS+: 361 |
| Pr6-1 | NMR: 2.36 (3H, s), 3.36 (3H, s), 4.86 (2H, d), 5.21 (2H, s), 6.41 (1H, d), 6.56 (1H, dd), 7.76 (1H, d), 9.57 (1H, s) |
| Pr6-2 | MS+: 261 |
| Pr6-3 | MS+: 273 |
| Pr6-4 | NMR: 0.91 (3H, t), 1.55-1.66 (2H, m), 2.57 (2H, t), 3.86 (3H, s), 4.96 (2H, s), 6.81 (1H, d), 6.88 (1H, s), 7.05 (1H, s), 7.16 (1H, d), 7.21 (1H, dd), 7.38 (1H, d), 7.46 (1H, d), 7.56 (1H, d), 7.63 (1H, s), 9.57 (1H, s) |
| Pr6-5 | MS−: 335 |
| Pr6-6 | MS+: 397 |
| Pr6-7 | MS+: 395 |
| Pr6-8 | MS+: 257 |
| Pr6-9 | MS+: 451 |
| Pr6-10 | MS+: 271 |
| Pr6-11 | MS+: 221 |
| Pr7 | MS+: 256 |
| Pr8 | MS+: 237 |
| Pr9 | ESI−: 199 |
| Pr9-1 | MS−: 195 |
| Pr9-2 | MS+: 235 |
| Pr9-3 | MS−: 195 |
| Pr9-4 | MS+: 183 |
| Pr10 | MS+: 425 |
| Pr10-1 | MS+: 303 |
| Pr11 | NMR: 5.04 (2H, d, J = 1.3 Hz), 7.09-7.16 (2H, m), 7.59 (1H, d, J = 8.4 Hz), 7.67 (1H, s), 9.61 (1H, s) |
| Pr11-1 | NMR: 5.08 (2H, d), 7.04-7.07 (1H, m), 7.29 (1H, dd), 7.74-7.77 (1H, m), 9.68 (1H, s) |
| Pr12 | MS+: 303 |
| Pr12-1 | MS+: 317 |
| Pr12-2 | NMR: 3.87 (3H, s), 3.90 (3H, s), 6.51-6.56 (2H, m), 10.15 (1H, d) |
| Pr12-3 | ESI−: 151 |
| Pr12-4 | NMR: 3.67 (2H, s), 5.41 (2H, s), 6.90 (1H, dd), 7.05 (1H, d), 7.47 (1H, d), 7.56 (1H, s), 8.02 (1H, d), 8.08-8.20 (2H, m), 9.57 (1H, s) |
| Pr13 | MS+: 327 |
| Pr13-1 | MS+: 387 |

TABLE 100

| | |
|---|---|
| Pr14 | NMR: 1.31 (2H, d), 4.89-4.99 (1H, m), 7.49 (1H, d), 8.09 (1H, dd), 8.13 (1H, dd) |
| Pr14-1 | MS+: 319 |
| Pr14-2 | 4.56 (2H, dt), 6.45 (1H, tt), 7.41 (1H, d), 7.86 (1H, dd), 8.07 (1H, d) |
| Pr14-3 | ESI+: 349, 351 |
| Pr14-4 | ESI+: 284 |
| Pr14-5 | NMR: 1.46 (3H, d), 3.91 (3H, s), 5.66-5.76 (1H, m), 7.56 (1H, d), 7.85 (1H, d), 7.96 (1H, s) |
| Pr14-6 | ESI+: 283 |
| Pr14-7 | EI+: 316 |
| Pr14-8 | ESI+: 299 |
| Pr14-9 | ESI+: 222 |
| Pr14-10 | EI: 302 |
| Pr14-11 | EI: 215 |
| Pr14-12 | NMR: 1.49 (3H, d), 3.87 (3H, s), 5.12-5.21 (1H, m), 8.00 (2H, s) |
| Pr14-13 | ESI+: 230 |
| Pr14-14 | EI+: 227 |
| Pr14-15 | ESI+: 338 |
| Pr14-16 | EI: 243 |
| Pr15 | MS+: 310 |
| Pr15-1 | MS+: 293 |
| Pr15-2 | MS+: 271 |
| Pr15-3 | ESI+: 262 |
| Pr15-4 | ESI+: 274 |
| Pr16 | MS+: 226 |
| Pr17 | NMR: 3.87 (3H, s), 7.66-7.73 (1H, m), 7.80-7.87 (1H, m), 7.94-8.00 (1H, m) |
| Pr18 | NMR: 1.24 (3H, t), 2.81 (2H, q), 3.82 (3H, s), 7.72 (1H, s) |
| Pr18-1 | EI+: 223 |
| Pr18-2 | NMR: 3.87 (3H, s), 7.58 (1H, t), 7.98 (1H, ddd), 8.10 (1H, dd) |
| Pr18-3 | EI+: 222 |
| Pr18-4 | ESI+: 245 |
| Pr18-5 | ESI+: 245 |
| Pr18-6 | EI+: 238 |
| Pr19 | MS+: 270 |
| Pr20 | MS+: 319, 321 |
| Pr21 | MS+: 323 |
| Pr22 | MS+: 296 |
| Pr23 | MS+: 381, 383 |
| Pr23-1 | NMR: 0.93 (3H, d), 2.00-2.13 (1H, m), 2.46-2.53 (1H, m), 2.69 (1H, dd), 3.39 (1H, dd), 3.51 (1H, dd), 7.23 (2H, d), 7.35 (2H, d) |
| Pr24 | MS+: 235 |
| Pr25 | MS+: 292 |
| Pr25-1 | NMR: 3.93 (3H, s), 6.30 (2H, dd), 7.01 (2H, dd), 7.69 (1H, d), 8.32 (2H, s) |
| Pr26 | NMR: 0.06 (9H, s), 2.60 (2H, t), 3.02 (2H, t), 7.84 (1H, d), 7.97 (1H, s), 8.04 (1H, d) |
| Pr27 | NMR: 0.91 (3H, t, J = 7.3 Hz), 1.55-1.66 (2H, m), 2.56 (2H, t, J = 7.9 Hz), 3.81 (3H, s), 4.92 (2H, d, J = 1.0 Hz), 5.03 (2H, s), 6.54 (1H, d, J = 2.3 Hz), 6.66 (1H, dd, J = 2.4, 8.5 Hz), 6.78 (1H, dd, J = 1.3, 7.6 Hz), 6.88 (1H, d, J = 1.3 Hz), 7.26 (1H, d, J = 7.6 Hz), 7.34 (1H, d, J = 8.5 Hz), 7.58 (1H, s), 9.51 (1H, s) |
| Pr27-1 | MS+: 319 |
| Pr27-2 | MS+: 409 |

TABLE 101

| | |
|---|---|
| Pr27-3 | MS+: 375 |
| Pr27-4 | MS+: 435, 437 |
| Pr27-5 | MS+: 389 |
| Pr27-6 | MS+: 395 |
| Pr28 | MS−: 401 |
| Pr28-1 | MS+: 389 |
| Pr28-2 | MS+: 351 |
| Pr28-3 | NMR: 4.93 (2H, d), 5.28 (2H, s), 6.59 (1H, d), 6.71 (1H, dd), 7.35 (1H, d), 7.58 (1H, m), 7.66 (2H, d), 7.78 (2H, d), 9.51 (1H, s) |
| Pr28-4 | NMR: 4.93 (2H, d), 5.27 (2H, s), 6.57 (1H, d), 6.69 (1H, dd), 7.36 (1H, d), 7.58-7.63 (2H, m), 7.72-7.75 (2H, m), 7.81 (1H, d), 9.52 (1H, s) |
| Pr28-5 | MS−: 415 |
| Pr28-6 | NMR: 2.71 (2H, t, J = 6.4 Hz), 4.50 (2H, t, J = 6.4 Hz), 5.18 (2H, s), 6.63 (1H, d, J = 2.4 Hz), 6.71 (1H, dd, J = 2.4, 8.8 Hz), 7.32-7.47 (5H, m), 7.69 (1H, d, J = 8.8 Hz) |
| Pr28-7 | MS+: 439 |
| Pr28-8 | MS+: 331 |
| Pr28-9 | NMR: 2.57 (2H, t, J = 6.0 Hz), 4.50 (2H, t, J = 6.0 Hz), 5.42 (2H, s), 6.85 (1H, d, J = 2.6 Hz), 7.00 (1H, dd, J = 2.6, 8.9 Hz), 7.77 (1H, d, J = 8.9 Hz), 8.04 (1H, d, J = 8.1 Hz), 8.12 (1H, s), 8.17 (1H, d, J = 8.1 Hz), 10.23 (1H, s) |
| Pr28-10 | MS+: 431 |
| Pr28-11 | MS−: 435 |
| Pr28-12 | NMR: 4.97 (2H, d), 5.39 (2H, s), 6.48-6.51 (1H, m), 6.70 (1H, dd), 7.70 (1H, d), 8.02 (1H, d), 8.11 (1H, s), 8.17 (1H, d), 9.59 (1H, s) |
| Pr28-14 | MS+: 455 |
| Pr28-15 | MS−: 415 |
| Pr28-16 | MS−: 419 |
| Pr28-17 | MS+: 429 |
| Pr28-18 | ESI+: 469 |
| Pr28-19 | NMR: 0.91 (3H, d), 2.10-2.21 (1H, m), 2.45-2.53 (1H, m), 2.77 (1H, dd), 3.79-3.89 (2H, m), 4.95 (2H, d), 6.36-6.38 (1H, m), 6.55 (1H, dd), 7.22 (2H, d), 7.34 (2H, d), 7.69 (1H, s), 9.58 (1H, s) |
| Pr28-20 | ESI−: 429 |
| Pr28-21 | ESI+: 399 |
| Pr28-22 | ESI+: 433 |
| Pr28-23 | ESI−: 463 |
| Pr28-24 | ESI+: 435 |
| Pr28-25 | MS+: 365 |
| Pr28-26 | ESI+: 439 |
| Pr28-27 | ESI+: 381 |
| Pr29 | NMR: 5.00 (2H, s), 7.11 (1H, s), 7.21-7.28 (1H, m), 7.43-7.52 (2H, m), 7.77-7.85 (4H, m), 9.61 (1H, s) |
| Pr29-1 | NMR: 4.99 (2H, d), 7.04-7.06 (1H, m), 7.20 (1H, dd), 7.42-7.48 (5H, m), 7.55-7.59 (1H, m), 7.65-7.67 (1H, m), 9.60 (1H, s) |
| Pr29-2 | NMR: 3.80 (3H, s), 4.98 (2H, d), 6.98-7.02 (3H, m), 7.16 (1H, dd), 7.43 (1H, d), 7.51 (2H, d), 7.64-7.66 (1H, m), 9.59 (1H, s) |
| Pr29-3 | NMR: 2.34 (3H, s), 4.99 (2H, d), 7.01-7.03 (1H, m), 7.17 (1H, dd), 7.25 (2H, d), 7.44 (1H, d), 7.46 (2H, d), 7.64-7.66 (1H, m), 9.59 (1H, s) |
| Pr29-4 | NMR: 5.00 (2H, d), 7.09-7.11 (1H, m), 7.24 (1H, dd), 7.48 (1H, d), 7.65-7.68 (1H, m), 7.76 (2H, d), 7.92 (2H, d), 9.61 (1H, s) |

TABLE 102

| | |
|---|---|
| Pr29-5 | NMR: 5.00 (2H, d), 7.09-7.11 (1H, m), 7.24 (1H, dd), 7.47 (1H, d), 7.65-7.72 (2H, m), 7.81 (1H, dm), 7.88 (1H, dm), 7.93-7.96 (1H, m), 9.61 (1H, s) |
| Pr29-6 | NMR: 5.00 (2H, d), 6.99-7.03 (1H, m), 7.18 (1H, dd), 7.49 (1H, d), 7.61-7.69 (2H, m), 7.75 (1H, t), 7.84 (2H, t), 9.61 (1H, s) |
| Pr29-7 | NMR: 1.27-1.86 (10H, m), 2.58-2.71 (1H, m), 4.95 (2H, s), 6.83-6.84 (1H, m), 7.00 (1H, dd), 7.36 (1H, d), 7.61-7.63 (1H, m), 9.57 (1H, s) |
| Pr29-8 | NMR: 1.22-1.36 (2H, m), 1.46-1.68 (4H, m), 1.73-1.83 (2H, m), 2.02-2.15 (1H, m), 2.44 (2H, d), 4.95 (2H, d), 6.83-6.86 (1H, m), 7.01 (1H, dd), 7.36 (1H, d), 7.60-7.63 (1H, m), 9.57 (1H, s) |
| Pr29-9 | NMR: 1.28 (9H, s), 4.95 (2H, d), 6.80-6.82 (1H, m), 6.98 (1H, dd), 7.35 (1H, d), 7.61-7.63 (1H, m), 9.57 (1H, s) |
| Pr29-10 | NMR: 0.90 (6H, d), 1.44 (2H, q), 1.64-1.77 (1H, m), 2.44 (2H, d), 4.95 (2H, d), 6.82-6.85 (1H, m), 7.00 (1H, dd), 7.36 (1H, d), 7.60-7.63 (1H, m), 9.57 (1H, s) |
| Pr29-11 | NMR: 4.99 (2H, d), 7.04-7.06 (1H, m), 7.17-7.23 (2H, m), 7.42-7.49 (2H, m), 7.65-7.67 (1H, m), 7.69-7.77 (1H, m), 9.60 (1H, s) |
| Pr29-12 | NMR: 5.03 (2H, d), 7.02 (1H, s), 7.19 (1H, dd), 7.76-7.85 (5H, m), 9.67 (1H, s) |
| Pr29-13 | NMR: 2.72 (2H, t), 2.85 (2H, t), 4.95 (2H, d), 6.79 (1H, s), 6.97 (1H, dd), 7.19-7.26 (1H, m), 7.29-7.32 (4H, m), 7.35 (1H, d), 7.61 (1H, s), 9.57 (1H, s) |
| Pr29-14 | NMR: 1.79-1.89 (2H, m), 2.44 (2H, t), 2.72 (2H, t), 4.99 (2H, d), 6.78 (1H, s), 6.95 (1H, dd), 7.16-7.33 (5H, m), 7.72-7.75 (1H, m), 9.65 (1H, s) |
| Pr29-15 | NMR: 2.84 (2H, t), 3.13 (2H, t), 4.95 (2H, d), 6.81 (1H, s), 6.97 (1H, dd), 7.36 (1H, d), 7.61-7.64 (1H, m), 7.92 (1H, d), 8.00 (1H, s), 8.09 (1H, d), 9.56 (1H, s) |
| Pr30 | NMR: 0.24 (9H, s), 0.88 (6H, d), 1.77-1.90 (1H, m), 2.46 (2H, d), 7.07 (2H, d), 7.37 (2H, d) |
| Pr30-1 | NMR: 0.27 (9H, s), 7.69-7.75 (2H, m), 7.88 (1H, s) |
| Pr31 | NMR: 0.86 (6H, d), 1.78-1.92 (1H, m), 2.49 (2H, d), 5.02 (2H, d), 6.93 (1H, s), 7.10 (1H, dd), 7.24 (2H, d), 7.49 (2H, d), 7.76-7.77 (1H, m), 9.66 (1H, s) |
| Pr31-1 | NMR: 5.05 (2H, d), 6.96 (1H, s), 7.13 (1H, dd), 7.78-7.79 (1H, m), 8.08 (1H, d), 8.16 (1H, s), 8.17 (1H, d), 9.68 (1H, s) |
| Pr32 | NMR: 1.47 (3H, d), 4.98-5.05 (1H, m), 5.96 (1H, d), 7.10 (1H, s), 7.35-7.50 (5H, m) |
| Pr33 | MS−: 287 |
| Pr33-1 | NMR: 4.60 (1H, d), 4.85 (2H, d), 4.90 (1H, d), 5.41 (1H, t), 7.32 (1H, d), 7.38 (1H, dd), 7.70 (1H, d) |
| Pr33-2 | EI+: 226 |
| Pr33-3 | EI+: 232 |
| Pr33-4 | NMR: 4.60 (1H, d), 4.85 (2H, d), 4.90 (1H, d), 5.41 (1H, t), 7.32 (1H, d), 7.38 (1H, dd), 7.70 (1H, d) |
| Pr33-5 | EI+: 234 |
| Pr33-6 | ESI+: 259 |
| Pr33-7 | ESI+: 257 |
| Pr33-8 | ESI+: 223 |
| Pr33-9 | EI+: 288 |
| Pr33-10 | EI+: 240 |
| Pr33-11 | EI+: 210 |
| Pr33-12 | ESI+: 245 |
| Pr33-13 | EI: 244 |
| Pr33-14 | EI: 220 |

TABLE 103

| | |
|---|---|
| Pr33-15 | EI: 244 |
| Pr33-16 | ESI+: 260 |
| Pr33-17 | ESI+: 259 |
| Pr33-18 | NMR: 1.44 (3H, d), 4.44 (2H, d), 5.17-5.29 (2H, m), 7.25 (1H, dd), 7.31 (1H, d), 7.40 (1H, d) |
| Pr33-19 | ESI+: 257 |
| Pr33-20 | ESI+: 223 |
| Pr33-21 | ESI−: 287 |
| Pr34 | MS+: 206 |
| Pr34-1 | MS+: 243 |
| Pr34-2 | MS+: 198 |
| Pr34-3 | NMR: 4.72 (2H, d), 5.87 (1H, t), 7.13 (1H, d), 7.41-7.47 (2H, m), 7.52-7.58 (2H, m) |
| Pr34-4 | NMR: 4.62 (2H, d), 5.63 (1H, t), 7.03 (1H, s), 7.34-7.41 (1H, m), 7.43-7.49 (2H, m), 7.52-7.57 (2H, m) |
| Pr34-5 | NMR: 1.20 (3H, t), 2.81 (2H, q), 4.58 (2H, d), 5.39 (1H, t), 6.89 (1H, s), 7.28-7.46 (5H, m) |
| Pr34-6 | MS+: 255 |
| Pr34-7 | NMR: 1.18 (3H, t), 2.71 (2H, q), 4.54 (2H, d), 5.50 (1H, t), 6.84 (1H, s) |
| Pr34-8 | MS+: 255 |
| Pr34-9 | MS+: 304 |
| Pr34-10 | MS−: 267 |
| Pr34-11 | NMR: 4.67 (2H, d), 5.54 (1H, t), 6.29 (2H, t), 7.48 (2H, t), 7.79-7.81 (2H, m), 7.88-7.91 (1H, m) |
| Pr34-12 | NMR: 1.86 (3H, s), 4.69 (2H, d), 5.80 (1H, t), 7.22-7.27 (2H, m), 7.42-7.50 (3H, m) |
| Pr34-13 | MS+: 359 |
| Pr34-14 | MS+: 361 |
| Pr34-15 | MS−: 240 |

TABLE 103-continued

| | |
|---|---|
| Pr34-16 | MS+: 243 |
| Pr34-17 | MS+: 439 |
| Pr34-18 | EI+: 288 |
| Pr34-19 | EI+: 255 |
| Pr34-20 | NMR: 0.88 (6H, d), 1.85-1.97 (1H, m), 2.60 (2H, d), 4.54 (2H, d), 5.31 (1H, t), 7.40 (1H, d), 7.51 (1H, d), 7.61 (1H, s) |
| Pr34-21 | ESI+: 321, 323 |
| Pr34-22 | ESI+: 256 |
| Pr34-23 | ESI−: 287 |
| Pr34-24 | ESI+: 234 |
| Pr34-25 | EI+: 270 |
| Pr34-26 | EI+: 266 |
| Pr34-27 | EI+: 272 |
| Pr34-28 | EI+: 274 |
| Pr34-29 | NMR: 1.45 (3H, d), 4.47 (2H, d), 4.95-5.06 (1H, m), 5.42 (1H, t), 7.44 (2H, s) |
| Pr34-30 | ESI+: 290 |
| Pr35 | MS+: 325 |
| Pr35-1 | MS+: 321 |

TABLE 104

| | |
|---|---|
| Pr35-2 | MS+: 323 |
| Pr35-3 | ESI−: 391 |
| Pr36 | MS−: 407 |
| Pr36-1 | ESI+: 445 |
| Pr36-2 | EI: 245 |
| Pr37 | MS+: 269 |
| Pr37-1 | MS+: 283 |
| Pr37-2 | MS+: 283 |
| Pr37-3 | MS+: 367 |
| Pr38 | MS+: 382 |
| Pr38-1 | MS+: 324 |
| Pr38-2 | MS+: 356 |
| Pr38-3 | MS+: 331 |
| Pr38-4 | NMR: 4.94 (2H, d), 5.44 (2H, s), 6.44 (1H, d), 6.74 (1H, dd), 7.35-7.51 (7H, m), 7.59 (1H, s), 9.52 (1H, s) |
| Pr38-5 | MS+: 418 |
| Pr38-6 | MS+: 453 |
| Pr38-7 | MS−: 449 |
| Pr38-8 | MS+: 349 |
| Pr38-9 | NMR: 3.04 (2H, s), 4.93 (2H, s), 5.33 (2H, s), 6.62 (1H, d), 6.72 (1H, dd), 7.28-7.43 (3H, m), 7.44-7.50 (2H, m), 7.52-7.60 (3H, m), 9.52 (1H, s) |
| Pr38-10 | NMR: 1.21 (3H, t), 2.85 (2H, q), 4.93 (2H, s), 5.29 (2H, s), 6.61 (1H, d), 6.71 (1H, dd), 7.18 (1H, s), 7.31-7.48 (6H, m), 7.58 (1H, s), 9.51 (1H, s) |
| Pr38-11 | MS−: 433 |
| Pr38-12 | MS+: 391 |
| Pr38-13 | MS+: 433 |
| Pr38-14 | MS−: 445 |
| Pr38-15 | MS+: 455 |
| Pr38-16 | NMR: 1.19 (3H, t), 2.74 (2H, q), 4.93 (2H, s), 5.27 (2H, s), 6.58 (1H, d), 6.68 (1H, dd), 7.15 (1H, s), 7.34 (1H, d), 7.57 (1H, s), 9.51 (1H, s) |
| Pr38-17 | MS+: 413 |
| Pr38-18 | MS+: 417 |
| Pr38-19 | MS−: 385 |
| Pr38-20 | NMR: 4.97 (2H, s), 5.32 (2H, s), 6.54 (1H, d), 6.72 (1H, dd), 7.30-7.43 (2H, m), 7.43-7.49 (4H, m), 7.69-7.72 (1H, m), 7.74-7.80 (1H, m), 7.90-7.93 (1H, m), 9.59 (1H, s) |
| Pr38-21 | MS+: 441 |
| Pr38-22 | MS+: 480 |
| Pr38-23 | MS+: 467 |
| Pr38-24 | MS−: 447 |
| Pr38-25 | NMR: 4.96 (2H, s), 5.26 (2H, s), 6.32 (2H, t), 7.53 (2H, t), 7.69-7.71 (1H, m), 7.80-7.83 (1H, m), 7.93-7.97 (2H, m), 9.59 (1H, s) |
| Pr38-26 | MS+: 434 |
| Pr38-27 | MS−: 416 |
| Pr38-28 | MS+: 451 |

TABLE 105

| | |
|---|---|
| Pr38-29 | MS+: 417 |
| Pr38-30 | MS+: 465 |
| Pr38-31 | MS+: 435 |
| Pr38-32 | MS+: 469 |
| Pr38-33 | MS+: 467 |
| Pr38-34 | MS+: 421 |
| Pr38-35 | ESI+: 487 |
| Pr38-36 | ESI+: 369 |
| Pr38-37 | ESI+: 435 |
| Pr38-38 | ESI+: 413 |
| Pr38-39 | ESI+: 399 |
| Pr38-40 | ESI+: 395, 397 |
| Pr38-41 | ESI+: 479, 481 |
| Pr38-42 | ESI+: 436 |

TABLE 105-continued

| | |
|---|---|
| Pr38-43 | ESI+: 447 |
| Pr38-44 | ESI+: 392 |
| Pr38-45 | ESI+: 429 |
| Pr38-46 | ESI+: 425 |
| Pr38-47 | ESI+: 431 |
| Pr38-48 | ESI+: 403 |
| Pr38-49 | ESI+: 433 |
| Pr38-50 | ESI+: 379 |
| Pr38-51 | ESI+: 447 |
| Pr38-52 | ESI+: 393 |
| Pr38-53 | ESI+: 385 |

TABLE 105-continued

| | |
|---|---|
| Pr39-2 | MS−: 295 |
| Pr39-3 | MS+: 321 |
| Pr39-4 | MS+: 239 |
| Pr39-5 | MS+: 359 |
| Pr39-6 | MS+: 357 |
| Pr40 | MS+: 437 |
| Pr41 | MS−: 142 |
| Pr41-1 | MS+: 140 |
| Pr41-2 | MS−: 133 |
| Pr41-3 | MS−: 134 |
| Pr41-4 | MS−: 130 |
| Pr41-5 | ESI+: 144 |

TABLE 106

| | |
|---|---|
| Pr42 | MS+: 262 |
| Pr43 | MS+: 256 |
| Pr44 | MS−: 193 |
| Pr44-1 | NMR: 2.30 (3H, s), 4.82 (2H, d), 6.13 (1H, d), 6.32 (1H, dd), 7.71 (1H, d), 9.52 (1H, s), 10.19 (1H, brs) |
| Pr44-2 | MS−: 205 |
| Pr44-3 | ESI−: 189 |
| Pr44-4 | NMR: 4.88 (2H, d), 6.28 (1H, d), 6.44 (1H, dd), 7.22 (1H, d), 7.52 (1H, s), 9.47 (1H, s), 10.24 (1H, s) |
| Pr44-5 | MS+: 318 |
| Pr44-6 | MS+: 318 |
| Pr45 | MS−: 203 |
| Pr46 | NMR: 2.56 (2H, td), 2.87 (1H, t), 3.03 (2H, t), 7.85 (1H, d), 7.98 (1H, s), 8.06 (1H, d) |
| Pr47 | MS+: 191 |
| Pr47-1 | MS−: 223 |
| Pr47-2 | MS+: 227 |
| Pr48 | MS+: 157 |
| Pr48-1 | MS−: 127 |
| Pr49 | NMR: 3.48 (2H, dd), 5.33 (2H, s), 5.80-5.89 (1H, m), 6.47 (1H, d), 6.75 (1H, dd), 6.87 (1H, d), 7.08 (1H, d), 8.00 (1H, d), 8.10 (1H, s), 8.15 (1H, d) |
| Pr50 | MS+: 417 |
| Pr51 | MS+: 467 |
| Pr51-1 | MS+: 443 |
| Pr51-2 | MS+: 479 |
| Pr51-3 | MS+: 269 |
| Pr51-4 | MS+: 467 |
| Pr51-5 | MS+: 337 |
| Pr52 | MS+: 253 |
| Pr52-1 | MS+: 451 |
| Pr52-2 | NMR: 0.89 (6H, d), 1.91-2.03 (1H, m), 2.70 (2H, d), 3.89 (3H, s), 6.63 (1H, d), 7.65 (1H, d), 8.17 (1H, s) |
| Pr52-3 | EI+: 294 |
| Pr52-4 | EI+: 300 |
| Pr53 | NMR: 1.46 (3H, d), 4.74 (2H, s), 5.27-5.38 (1H, m), 7.37 (1H, d), 7.42 (1H, dd), 7.59 (1H, d) |
| Pr53-1 | NMR: 1.29 (6H, d), 4.64-4.73 (3H, m), 7.16 (1H, d), 7.35 (1H, dd), 7.51 (1H, d) |
| Pr53-2 | NMR: 1.28 (6H, d), 4.74-4.85 (3H, m), 7.30 (1H, d), 7.65-7.70 (2H, m) |
| Pr53-3 | NMR: 1.44 (3H, d), 4.83 (2H, s), 5.42-5.53 (1H, m), 7.42 (1H, d), 7.46 (1H, dd), 7.72 (1H, d) |
| Pr53-4 | NMR: 4.74 (2H, s), 4.87 (1H, d), 4.91 (1H, d), 7.28 (1H, d), 7.42 (1H, dd), 7.59 (1H, d) |
| Pr54 | NMR: 1.51-1.85 (7H, m), 2.00-2.09 (2H, m), 3.86 (3H, s), 7.57 (1H, s), 7.86 (1H, d), 7.91 (1H, d) |
| Pr55 | ESI+: 545 |
| Pr55-1 | ESI+: 552 |
| Pr56 | ESI−: 247 |
| Pr56-1 | MS−: 257 |
| Pr56-2 | ESI−: 235 |
| Pr56-3 | ESI+: 241 |
| Pr56-4 | EI: 234 |

TABLE 105-continued

| | |
|---|---|
| Pr38-54 | ESI+: 391 |
| Pr38-55 | ESI+: 447 |
| Pr38-56 | ESI+: 418 |
| Pr38-57 | ESI+: 451 |
| Pr38-58 | ESI+: 447 |
| Pr38-59 | ESI+: 369 |
| Pr38-60 | ESI+: 448 |
| Pr38-61 | ESI+: 414 |
| Pr39 | MS+: 413 |
| Pr39-1 | MS−: 323 |

TABLE 107

| | |
|---|---|
| Pr56-5 | ESI+: 247 |
| Pr56-6 | ESI+: 249 |
| Pr57 | EI+: 317 |
| Pr58 | ESI+: 170 |
| Pr58-1 | ESI+: 156 |
| Pr59 | ESI+: 238 |
| Pr60 | ESI+: 207 |
| Pr61 | ESI+: 184 |
| Pr62 | ESI+: 588 |
| Pr62-1 | ESI+: 431 |

TABLE 107-continued

| | |
|---|---|
| Pr62-2 | NMR: 1.29 (6H, d), 4.75-4.84 (1H, m), 4.93 (2H, d), 5.12 (2H, s), 6.57 (1H, d), 6.69 (1H, dd), 7.29-7.35 (2H, m), 7.57 (1H, s), 7.65-7.69 (2H, m), 9.51 (1H, s) |
| Pr62-3 | ESI+: 403 |
| Pr62-4 | ESI+: 421 |
| Pr62-5 | |
| Pr62-6 | ESI+: 574 |
| Pr62-7 | ESI+: 536 |
| Pr62-8 | ESI+: 536 |
| Pr62-9 | ESI+: 588 |
| Pr62-10 | ESI+: 570 |
| Pr62-11 | ESI+: 447 |
| Pr62-12 | ESI+: 395, 397 |
| Pr62-13 | ESI+: 532 |
| Pr62-14 | ESI+: 532 |
| Pr62-15 | ESI+: 544 |
| Pr62-16 | ESI+: 544 |
| Pr62-17 | ESI+: 574 |
| Pr62-18 | ESI+: 545 |
| Pr62-19 | ESI+: 545 |
| Pr63 | ESI+: 262 |
| Pr64 | MS+: 362 |
| Pr64-1 | ESI+: 528 |
| Pr64-2 | ESI+: 532 |
| Pr64-3 | ESI+: 362 |
| Pr64-4 | ESI+: 534 |
| Pr64-5 | ESI+: 546 |
| Pr64-6 | ESI+: 534 |
| Pr64-7 | ESI+: 592 |

TABLE 108

| Ex | RefEx | Data |
|---|---|---|
| Ex1 | Ex1 | NMR: 1.93-2.57 (2H, m), 3.00-3.75 (5H, m), 3.27 (3H, s), 3.96 (2H, s), 4.90 (2H, d), 5.34 (2H, s), 6.42 (1H, s), 6.59 (1H, dd), 6.88 (1H, s), 8.00 (1H, d), 8.09-8.19 (2H, m), 11.11 (1H, brs), 12.06 (1H, brs), MS+: 619 |
| Ex2 | Ex2 | NMR: 1.88-1.99 (2H, m), 2.38-2.61 (2H, m), 2.65-2.73 (1H, m), 2.84-2.96 (1H, m), 3.04-3.14 (1H, m), 3.30-3.39 (2H, m), 4.69 (2H, s), 5.36 (2H, s), 6.34 (1H, s), 6.50 (1H, d), 6.57 (1H, dd), 6.99 (1H, d), 7.37 (1H, s), 7.41-7.52 (5H, m) MS+: 538 |
| Ex3 | Ex3 | NMR: 2.00-2.40 (2H, m), 3.04-3.81 (5H, m), 3.99 (2H, s), 5.03 (2H, s), 6.89 (1H, s), 7.00 (1H, s), 7.06 (1H, dd), 8.06 (1H, d), 8.15 (1H, s), 8.16 (1H, d), 11.43 (1H, brs), 12.89 (1H, brs), MS+: 514 |
| Ex4 | Ex2 | NMR: 0.90 (3H, t, J = 7.4 Hz), 1.55-1.65 (2H, m), 2.55 (2H, t, J = 7.9 Hz), 3.03 (2H, s), 3.09-3.41 (5H, m), 3.80 (3H, s), 4.60 (2H, s), 4.94 (2H, s), 6.30 (1H, s), 6.37 (1H, d, J = 2.2 Hz), 6.75 (1H, dd, J = 2.4, 8.3 Hz), 6.77 (1H, dd, J = 1.3, 8.8 Hz), 6.87 (1H, d, J = 1.3 Hz), 6.94 (1H, d, J = 8.3 Hz), 7.23 (1H, d, J = 7.6 Hz) MS−: 422 |
| Ex5 | Ex2 | NMR: 3.04 (2H, s), 3.12-3.40 (5H, m), 4.61 (2H, s), 5.11 (2H, s), 6.30 (1H, s), 6.44 (1H, d, J = 2.3 Hz), 6.54 (1H, dd, J = 2.5, 8.2 Hz), 6.96 (1H, d, J = 8.2 Hz), 7.34-7.39 (1H, m), 7.44-7.53 (4H, m), 7.64-7.70 (4H, m) MS−: 426 |
| Ex6 | Ex2 | NMR: 0.90 (3H, t, J = 7.3 Hz), 1.34 (6H, s), 1.55-1.65 (2H, m), 2.55 (2H, t, J = 7.6 Hz), 3.06 (2H, s), 3.11-3.43 (5H, m), 3.80 (3H, s), 4.93 (2H, s), 6.24 (1H, s), 6.37 (1H, d, J = 2.2 Hz), 6.46 (1H, dd, J = 2.4, 8.3 Hz), 6.77 (1H, dd, J = 1.3, 7.6 Hz), 6.87 (1H, d, J = 1.3 Hz), 6.98 (1H, d, J = 8.3 Hz), 7.24 (1H, d, J = 7.6 Hz) MS−: 450 |
| Ex7 | Ex2 | NMR: 3.04 (2H, s), 3.11-3.41 (5H, m), 4.62 (2H, s), 5.56 (2H, s), 6.03 (1H, s), 6.51 (1H, d), 6.60 (1H, dd), 6.99 (1H, d), 7.46 (1H, ddd), 7.54 (1H, ddd), 8.00-8.03 (1H, m), 8.10-8.13 (1H, m) MS+: 431 |
| Ex8 | Ex2 | NMR: 1.92-2.00 (2H, m), 2.71 (2H, t, J = 7.4 Hz), 3.03 (2H, s), 3.10-3.42 (5H, m), 3.89 (2H, t, J = 6.3 Hz), 4.60 (2H, s), 6.30 (1H, s), 6.33 (1H, d, J = 2.3 Hz), 6.43 (1H, dd, J = 2.4, 8.3 Hz), 6.93 (1H, d, J = 8.3 Hz), 7.23-7.27 (2H, m), 7.31-7.35 (2H, m) MS−: 412 |
| Ex9 | Ex2 | NMR: 0.90 (3H, t), 1.03 (2H, d), 1.44-1.65 (4H, m), 1.73-1.83 (2H, m), 1.86-1.96 (3H, m), 2.11-2.21 (1H, m), 2.52-2.58 (2H, m), 2.70-2.79 (2H, m), 2.96 (2H, brs), 3.79 (3H, s), 4.63 (2H, s), 4.95 (2H, s), 6.37 (1H, s), 6.38 (1H, d), 6.48 (1H, dd), 6.77 (1H, d), 6.86 (1H, brs), 6.93 (1H, d), 7.23 (1H, d) MS−: 450 |
| Ex10 | Ex2 | NMR: 3.03 (2H, s), 3.10-3.41 (5H, m), 4.62 (2H, s), 5.30 (2H, s), 6.31 (1H, s), 6.42 (1H, d, J = 2.4 Hz), 6.50 (1H, dd, J = 2.6, 8.3 Hz), 6.98 (1H, d, J = 8.3 Hz), 7.98 (1H, d, J = 8.3 Hz), 8.09 (1H, s), 8.14 (1H, d, J = 8.3 Hz) MS−: 486 |
| Ex11 | Ex2 | NMR: 3.03 (2H, s), 3.11-3.40 (5H, m), 4.61 (2H, s), 5.19 (2H, s), 6.30 (1H, s), 6.44 (1H, d), 6.52 (1H, dd), 6.96 (1H, d), 7.64 (2H, d), 7.76 (2H, d) MS+: 442 |

TABLE 109

| | | |
|---|---|---|
| Ex12 | Ex2 | NMR: 3.03 (2H, s), 3.11-3.24 (3H, m), 3.38 (2H, t), 3.81 (3H, s), 4.60 (2H, s), 5.00 (2H, s), 6.30 (1H, s), 6.39 (1H, d), 6.49 (1H, dd), 6.93-6.98 (2H, m), 7.04 (1H, d), 7.30-7.38 (2H, m)<br>MS+: 404 |
| Ex13 | Ex2 | NMR: 1.34 (3H, t), 3.02 (2H, s), 3.10-3.24 (3H, m), 3.37 (2H, t), 4.20 (2H, q), 4.59 (2H, s), 5.09 (2H, s), 6.29 (1H, s), 6.38-6.44 (2H, m), 6.52 (1H, dd), 6.93 (1H, d), 7.18 (1H, dd), 7.39 (1H, d), 7.46 (1H, dd), 7.58 (1H, s)<br>MS−: 417 |
| Ex14 | Ex2 | NMR: 0.91 (3H, t, J = 7.3 Hz), 1.56-1.66 (2H, m), 2.31 (2H, t, J = 6.3 Hz), 2.56 (2H, t, J = 7.8 Hz), 3.18-3.49 (7H, m), 3.81 (3H, s), 4.43 (2H, t, J = 6.3 Hz), 5.00 (2H, s), 6.66 (1H, d, J = 2.6 Hz), 7.79 (1H, dd, J = 1.2, 7.7 Hz), 6.82 (1H, dd, J = 2.6, 8.8 Hz), 6.88 (1H, d, J = 1.3 Hz), 7.27 (1H, d, J = 7.7 Hz), 7.41 (1H, d, J = 8.8 Hz)<br>MS−: 470 |
| Ex15 | Ex2 | NMR: 3.03 (2H, s), 3.11-3.40 (5H, m), 4.62 (2H, s), 5.19 (2H, s), 6.31 (1H, s), 6.41 (1H, d), 6.50 (1H, dd), 6.97 (1H, d), 7.56-7.61 (1H, m), 7.69-7.74 (2H, m), 7.79 (1H, d)<br>MS−: 418 |
| Ex16 | Ex2 | NMR: 2.22 (3H, s), 3.08 (2H, s), 3.11-3.42 (5H, m), 4.56 (2H, s), 5.28 (2H, s), 6.28 (1H, d), 6.42-6.44 (2H, m), 7.97 (1H, d), 8.10 (1H, s), 8.14 (1H, d)<br>MS−: 500 |
| Ex17 | Ex2 | NMR: 0.88 (3H, t), 1.53-1.62 (2H, m), 2.50-2.57 (2H, m), 3.02 (2H, s), 3.10-3.40 (5H, m), 4.60 (2H, s), 5.00 (2H, s), 6.29 (1H, s), 641 (1H, d), 6.50 (1H, dd), 6.94 (1H, d), 7.19 (2H, d), 7.32 (2H, d)<br>MS−: 392 |
| Ex18 | Ex2 | NMR: 1.98 (3H, s), 3.10-3.41 (7H, m), 4.55 (2H, d, J = 1.3 Hz), 5.32 (2H, s), 6.46 (1H, d, J = 2.6 Hz), 6.57 (1H, dd, J = 2.6, 8.5 Hz), 7.17 (1H, d, J = 8.6 Hz), 7.98 (1H, d, J = 8.2 Hz), 8.10 (1H, s), 8.14 (1H, d, J = 8.2 Hz)<br>MS−: 500 |
| Ex19 | Ex2 | NMR: 0.90 (3H, t, J = 7.3 Hz), 1.55 (2H, m), 1.98 (3H, s), 2.55 (2H, t, J = 7.9 Hz), 3.10-3.41 (7H, m), 3.80 (3H, s), 4.53 (2H, d, J = 1.3 Hz), 4.96 (2H, s), 6.40 (1H, d, J = 2.6 Hz), 6.54 (1H, dd, J = 2.5, 8.5 Hz), 6.77 (1H, dd, J = 1.3, 7.5 Hz), 6.87 (1H, d, J = 1.3 Hz), 7.13 (1H, d, J = 8.5 Hz), 7.24 (1H, d, J = 7.5 Hz)<br>MS−: 436 |
| Ex20 | Ex2 | NMR: 2.32 (2H, t, J = 6.0 Hz), 3.15-3.48 (7H, m), 4.45 (2H, t, J = 6.0 Hz), 5.36 (2H, s), 6.73 (1H, d, J = 2.6 Hz), 6.87 (1H, dd, J = 2.6, 8.8 Hz), 7.46 (1H, d, J = 8.8 Hz), 8.02 (1H, d, J = 8.1 Hz), 8.11 (1H, s), 8.16 (1H, d, J = 8.1 Hz)<br>MS+: 536 |
| Ex21 | Ex2 | NMR: 3.02 (2H, s), 3.00-3.25 (3H, m), 3.36 (2H, t), 4.59 (2H, s), 4.99 (2H, s), 6.26-6.29 (2H, m), 6.36 (1H, dd), 6.91 (1H, d), 7.42-7.50 (5H, m), 7.62 (1H, s), 7.75-7.83 (2H, m)<br>MS−: 494 |
| Ex22 | Ex2 | NMR: 2.03 (3H, s), 2.12 (2H, t, J = 6.0 Hz), 3.15-3.45 (7H, m), 4.38 (2H, t, J = 6.0 Hz), 5.33 (2H, s), 6.65 (1H, d, J = 2.6 Hz), 6.79 (1H, dd, J = 2.6, 8.6 Hz), 7.25 (1H, d, J = 8.6 Hz), 8.02 (1H, d, J = 8.2 Hz), 8.10 (1H, s), 8.15 (1H, d, J = 8.2 Hz)<br>MS−: 514 |
| Ex23 | Ex2 | NMR: 0.91 (3H, t, J = 7.4 Hz), 1.55-1.66 (2H, m), 2.02 (3H, s), 2.12 (2H, t, J = 5.9 Hz), 2.56 (2H, t, J = 7.8 Hz), 3.13-3.45 (7H, m), 3.81 (3H, s), 4.37 (2H, t, J = 5.9 Hz), 4.97 (2H, s), 4.58 (1H, d, J = 2.6 Hz), 6.74 (1H, dd, J = 2.6, 8.6 Hz), 6.78 (1H, dd, J = 1.0, 7.6 Hz), 6.88 (1H, d, J = 1.0 Hz), 7.2 (1H, d, J = 8.6 Hz), 7.26 (1H, d, J = 7.6 Hz)<br>MS+: 474 |

TABLE 110

| | | |
|---|---|---|
| Ex24 | Ex2 | NMR (CDCl$_3$): 0.95 (3H, t, J = 7.3 Hz), 1.58-1.69 (2H, m), 2.58 (2H, t, J = 7.4 Hz), 3.36-4.37 (10H, m), 4.87 (2H, s), 5.03 (2H, s), 6.49 (1H, d, J = 2.3 Hz), 6.61 (1H, dd, J = 2.3, 8.7 Hz), 6.71 (1H, s), 6.77 (1H, d, J = 7.4 Hz), 7.27 (1H, d, J = 8.7 Hz), 7.36 (1H, d, J = 8.7 Hz)<br>MS−: 456 |
| Ex25 | Ex2 | NMR: 3.14-3.45 (7H, m), 4.76 (2H, s), 5.35 (2H, s), 6.56 (1H, d, J = 2.5 Hz), 6.68 (1H, dd, J = 2.5, 8.6 Hz), 7.33 (1H, d, J = 8.6 Hz), 8.00 (1H, d, J = 8.2 Hz), 8.10 (1H, s), 8.15 (1H, d, J = 8.2 Hz)<br>MS−: 520 |
| Ex26 | Ex2 | NMR: 0.88 (3H, t), 1.50-1.60 (2H, m), 2.47 (2H, t), 3.06 (2H, s), 3.12-3.25 (3H, m), 3.33-3.42 (2H, m), 3.75 (3H, s), 4.65 (2H, s), 4.93 (2H, s), 6.36 (1H, s), 6.64 (1H, dd), 6.77-6.82 (2H, m), 6.86 (1H, d), 6.89 (1H, dd), 7.03 (1H, d)<br>MS+: 446 |
| Ex27 | Ex2 | NMR: 2.91 (2H, s), 2.95 (2H, t, J = 6.8 Hz), 3.05-3.14 (1H, m), 3.27 (2H, t, J = 7.2 Hz), 4.77 (2H, s), 5.30 (2H, s), 6.38 (1H, d, J = 8.5 Hz), 6.46 (1H, dd, J = 2.5, 8.5 Hz), 6.53 (1H, d, J = 2.5 Hz), 7.12-7.17 (2H, m), 7.38-7.44 (1H, m), 7.45-7.50 (2H, m), 7.97 (1H, d, J = 8.3 Hz), 8.09 (1H, s), 8.13 (1H, d, J = 8.2 Hz)<br>MS−: 565 |
| Ex28 | Ex2 | MS−: 450 |
| Ex29 | Ex2 | NMR: 0.90 (3H, t, J = 7.3 Hz), 1.31-1.52 (2H, m), 1.53-1.68 (4H, m), 1.70-1.80 (1H, m), 1.93-2.17 (2H, m), 2.35-2.46 (1H, m), 2.55 (2H, t, J = 7.8 Hz), 2.94-3.04 (1H, m), 3.80 (3H, s), 4.65 (2H, s), 4.95 (2H, s), 6.32 (1H, s), 6.38 (1H, d, J = 2.1 Hz), 6.48 (1H, dd, J = 2.3, 8.3 Hz), 6.77 (1H, d, J = 7.5 Hz), 6.87 (1H, s), 6.94 (1H, d, J = 8.2 Hz), |

TABLE 110-continued

| | | |
|---|---|---|
| | | 7.24 (1H, d, J = 7.5 Hz)<br>MS−: 450 |
| Ex30 | Ex2 | NMR: 0.90 (3H, t, J = 7.3 Hz), 1.55-1.65 (2H, m), 1.67-1.88 (3H, m),<br>2.03-2.15 (2H, m), 2.43-2.58 (3H, m), 3.06-3.13 (1H, m), 3.18-3.25 (2H, m), 3.45 (1H, d, J = 13.5 Hz),<br>3.80 (3H, s), 4.72 (2H, s), 4.95 (2H, s), 6.38 (1H, s), 6.39 (1H, d, J = 2.4 Hz),<br>6.48 (1H, dd, J = 2.4, 8.3 Hz), 6.77 (1H, dd, J = 1.0, 7.6 Hz), 6.87 (1H, s),<br>6.95 (1H, d, J = 8.3 Hz), 7.24 (1H, d, J = 7.6 Hz)<br>MS−: 436 |
| Ex31 | Ex2 | NMR: 0.90 (3H, t, J = 7.3 Hz), 1.55-1.66 (2H, m), 1.90-1.99 (2H, m),<br>2.40-3.15 (9H, m), 3.80 (3H, s), 4.66 (2H, s), 4.95 (2H, s), 6.33 (1H, s), 6.39 (1H, d, J = 2.4 Hz),<br>6.48 (1H, dd, J = 2.4, 8.3 Hz), 6.77 (1H, dd, J = 1.3, 7.6 Hz), 6.87 (1H, d, J = 1.3 Hz),<br>6.94 (1H, d, J = 8.3 Hz), 7.24 (1H, d, J = 7.6 Hz)<br>MS−: 436 |
| Ex32 | Ex2 | NMR: 3.04 (2H, s), 3.10-3..23 (3H, m), 3.34-3.43 (2H, m), 4.62 (2H, s), 5.35 (2H,<br>s), 6.31 (1H, s), 6.49 (1H, d), 6.57 (1H, dd), 6.99 (1H, d), 7.35-7.39 (1H, m),<br>7.42-7.51 (5H, m)<br>MS+: 524 |
| Ex33 | Ex2 | NMR: 1.52-1.64 (6H, m), 3.03 (2H, s), 3.10-3.34 (9H, m), 4.61 (2H, s), 5.01 (2H,<br>s), 6.30 (1H, s), 6.37 (1H, d, J = 2.4 Hz), 6.48 (1H, dd, J = 2.4, 8.3 Hz), 6.95 (1H, d, J = 8.3 Hz),<br>7.15-7.21 (2H, m), 7.47 (1H, d, J = 8.3 Hz)<br>MS−: 501 |
| Ex34 | Ex2 | NMR: 3.08 (2H, s), 3.12-3.42 (5H, m), 4.66 (2H, s), 5.31 (2H, s), 6.32-6.34 (1H,<br>m), 6.39 (1H, s), 6.50 (1H, dd), 7.99 (1H, d), 8.09 (1H, s), 8.15 (1H, d)<br>MS−: 504 |
| Ex35 | Ex2 | NMR: 3.05 (2H, s), 3.10-3.38 (5H, m), 3.76 (3H, s), 4.56 (2H, s), 5.31 (2H, s),<br>6.08 (1H, d), 6.24 (1H, d), 6.42 (1H, s), 8.00 (1H, d), 8.09 (1H, s), 8.14 (1H, d)<br>MS−: 516 |

TABLE 111

| | | |
|---|---|---|
| Ex36 | Ex2 | NMR: 1.65 (3H, d), 3.02 (2H, s), 3.10-3.23 (3H, m), 3.34-3.40 (2H, m), 4.61 (2H,<br>s), 5.87 (1H, q), 6.29 (1H, s), 6.46 (1H, d), 6.54 (1H, dd), 6.95 (1H, d),<br>7.30-7.38 (1H, m), 7.40-7.52 (5H, m)<br>MS+: 538 |
| Ex37 | Ex2 | NMR: 3.04 (2H, s), 3.10-3.24 (3H, m), 3.32-3.42 (2H, m), 4.62 (2H, s), 5.35 (2H,<br>s), 6.31 (1H, s), 6.48 (1H, d), 6.57 (1H, dd), 6.99 (1H, d), 7.35-7.39 (1H, m),<br>7.42-7.48 (2H, m), 7.53-7.58 (2H, m)<br>MS+: 558 |
| Ex38 | Ex2 | NMR: 3.05 (2H, s), 3.12-3.26 (3H, m), 3.32-3.43 (2H, m), 4.62 (2H, s), 5.27 (2H,<br>s), 6.31 (1H, s), 6.47 (1H, d), 6.55 (1H, dd), 6.97 (1H, d), 7.21-7.33 (1H, m),<br>7.37-7.45 (2H, m), 7.62-7.72 (3H, m), 7.86 (1H, d)<br>MS+: 456 |
| Ex39 | Ex2 | NMR: 0.91 (3H, t), 1.53-1.66 (2H, m), 2.56 (2H, t), 3.07 (2H, s), 3.13-3.25 (3H,<br>m), 3.37-3.45 (2H, m), 3.84 (3H, s), 4.66 (2H, s), 6.37 (1H, s), 6.79 (1H, d),<br>6.85 (1H, s), 6.90 (1H, s), 7.00-7.10 (3H, m), 7.30 (1H, d), 7.52 (1H, d)<br>MS−: 418 |
| Ex40 | Ex2 | NMR: 0.89 (3H, t), 1.53-1.62 (2H, m), 2.51 (2H, t), 2.65-2.78 (4H, m), 3.05 (2H,<br>s), 3.10-3.23 (3H, m), 3.35-3.43 (2H, m), 3.77 (3H, s), 4.61 (2H, s), 6.32 (1H, s),<br>6.58 (1H, s), 6.63-6.71 (2H, m), 6.77 (1H, s), 6.91 (1H, d), 6.99 (1H, d)<br>MS+: 444 |
| Ex41 | Ex2 | NMR: 3.04 (2H, s), 3.10-3.22 (3H, m), 3.35-3.42 (2H, m), 4.62 (2H, s), 5.39 (2H,<br>s), 6.31 (1H, s), 6.48 (1H, d), 6.57 (1H, dd), 6.99 (1H, d), 7.47-7.59 (3H, m),<br>7.63 (1H, s), 7.70-7.76 (2H, m)<br>MS+: 481 |
| Ex42 | Ex2 | NMR: 1.21 (3H, t), 2.84 (2H, q), 3.03 (2H, s), 3.13-3.24 (3H, m), 3.32-3.43 (2H,<br>m), 4.61 (2H, s), 5.19 (2H, s), 6.30 (1H, s), 6.45 (1H, d), 6.54 (1H, dd), 6.96 (1H,<br>d), 7.14 (1H, s), 7.30-7.47 (5H, m)<br>MS−: 460 |
| Ex43 | Ex2 | NMR: 3.04 (2H, s), 3.09-3.25 (3H, m), 3.35-3.43 (2H, m), 4.62 (2H, s), 5.24 (2H,<br>s), 6.31 (1H, s), 6.46 (1H, d), 6.54 (1H, dd), 6.97 (1H, d), 7.28 (1H, s),<br>7.35-7.43 (1H, m), 7.43-7.51 (2H, m), 7.51-7.57 (2H, m)<br>MS+: 534, 536 |
| Ex44 | Ex2 | NMR: 2.01-3.73 (7H, m), 3.87 (2H, s), 4.86 (2H, s), 5.33 (2H, s), 6.51 (1H, d, J = 2.4 Hz),<br>6.59 (1H, dd, J = 2.4, 8.3 Hz), 6.72 (1H, s), 7.09 (1H, d, J = 8.3 Hz), 7.99 (1H,<br>d, J = 8.1 Hz), 8.10 (1H, s), 8.15 (1H, d, J = 8.1 Hz)<br>MS−: 500 |
| Ex45 | Ex2 | NMR: 1.96-4.01 (9H, m), 4.86 (2H, s), 5.34 (2H, s), 6.41 (1H, brs), 6.59 (1H, dd,<br>J = 2.3, 11.3 Hz), 6.85 (1H, brs), 8.00 (1H, d, J = 8.1 Hz), 8.11 (1H, s), 8.16 (1H, s, J = 8.1 Hz)<br>MS−: 518 |

TABLE 112

| | | |
|---|---|---|
| Ex46 | Ex2 | NMR: 3.08 (2H, s), 3.12-3.25 (3H, m), 3.34-3.45 (2H, m), 4.67 (2H, s), 5.37 (2H, s), 6.36-6.40 (2H, m), 6.54 (1H, dd), 7.36-7.39 (1H, m), 7.41-7.52 (5H, m)<br>MS−: 518 |
| Ex47 | Ex2 | NMR: 2.44 (3H, s), 3.03 (2H, s), 3.09-3.22 (3H, m), 3.34-3.43 (2H, m), 4.61 (2H, s), 5.19 (2H, s), 6.30 (1H, s), 6.44 (1H, d), 6.53 (1H, dd), 6.96 (1H, d), 7.19 (1H, s), 7.29-7.38 (1H, m), 7.39-7.48 (4H, m)<br>MS+: 470 |
| Ex48 | Ex2 | NMR: 0.88 (3H, t), 1.52-1.65 (2H, m), 2.78 (2H, t), 3.03 (2H, s), 3.11-3.47 (5H, m), 4.61 (2H, s), 5.19 (2H, s), 6.30 (1H, s), 6.45 (1H, d), 6.53 (1H, dd), 6.96 (1H, d), 7.13 (1H, s), 7.30-7.40 (3H, m), 7.41-7.48 (2H, m)<br>MS+: 498 |
| Ex49 | Ex2 | NMR: 0.61-0.68 (2H, m), 0.94-1.06 (2H, m), 2.10-2.19 (1H, m), 2.97-3.09 (5H, m), 3.21-3.42 (2H, m), 4.60 (2H, s), 5.15 (2H, s), 6.25 (1H, s), 6.42 (1H, d), 6.52 (1H, dd), 6.92-6.97 (1H, m), 7.19 (1H, s), 7.30-7.36 (1H, m), 7.42-7.48 (2H, m), 7.52-7.60 (2H, m)<br>MS−: 472 |
| Ex50 | Ex2 | NMR: 3.03 (2H, s), 3.08-3.24 (3H, m), 3.34-3.42 (2H, m), 4.61 (2H, s), 5.20 (2H, s), 6.30 (1H, s), 6.45 (1H, d), 6.53 (1H, dd), 6.96 (1H, d), 7.28-7.35 (2H, m), 7.40-7.49 (4H, m), 7.60-7.66 (1H, m), 7.85 (1H, d)<br>MS+: 518 |
| Ex51 | Ex2 | NMR: 1.44 (3H, d), 3.02 (2H, brs), 3.09-3.40 (5H, m), 4.60 (2H, s), 5.07 (2H, s), 5.42-5.52 (1H, m), 6.29 (1H, s), 6.43 (1H, d), 6.51 (1H, dd), 6.95 (1H, d), 7.50 (1H, d), 7.70-7.75 (2H, m)<br>MS−: 530 |
| Ex52 | Ex2 | NMR: 2.95-3.64 (7H, m), 4.61 (2H, s), 4.89 (1H, d), 4.94 (1H, d), 5.11 (2H, s), 6.28 (1H, s), 6.39 (1H, d), 6.49 (1H, dd), 6.96 (1H, d), 7.36-7.45 (2H, m), 7.68 (1H, d)<br>MS+: 540 |
| Ex53 | Ex2 | NMR: 1.22 (6H, d), 3.00 (2H, s), 3.06-3.13 (1H, m), 3.25-3.42 (5H, m), 4.62 (2H, s), 5.17 (2H, s), 6.28 (1H, s), 6.45 (1H, d), 6.53 (1H, dd), 6.96 (1H, d), 7.06 (1H, s), 7.32-7.38 (3H, m), 7.41-7.48 (2H, m)<br>MS−: 474 |
| Ex54 | Ex2 | NMR: 1.21 (3H, t), 2.84 (2H, q), 2.95-3.16 (5H, m), 3.28-3.42 (2H, m), 4.61 (2H, s), 5.19 (2H, s), 6.28 (1H, s), 6.45 (1H, d), 6.53 (1H, dd), 6.95 (1H, d), 7.23 (1H, s), 7.60-7.72 (4H, m)<br>MS+: 552 |
| Ex55 | Ex2 | NMR: 1.08 (3H, t), 3.00-3.15 (5H, m), 3.24-3.51 (4H, m), 4.61 (2H, s), 5.18 (2H, s), 6.29 (1H, s), 6.44 (1H, d), 6.52 (1H, dd), 6.91-6.97 (2H, m), 7.37 (1H, d), 7.56-7.64 (1H, m), 7.66-7.73 (1H, m), 7.81-7.87 (1H, m)<br>MS−: 528 |

TABLE 113

| | | |
|---|---|---|
| Ex56 | Ex2 | NMR: 1.21 (3H, t), 1.90-1.99 (2H, m), 2.40-2.62 (3H, m), 2.63-2.73 (1H, m), 2.80-2.96 (3H, m), 3.13 (2H, q), 4.71 (2H, s), 5.22 (2H, s), 6.38 (1H, d), 6.43 (1H, s), 6.51 (1H, dd), 7.16 (1H, s), 7.30-7.40 (3H, m), 7.40-7.48 (2H, m)<br>MS+: 516 |
| Ex57 | Ex2 | NMR: 1.16 (3H, t), 2.06 (3H, s), 2.67 (2H, q), 3.02 (2H, s), 3.09-3.20 (3H, m), 3.32-3.43 (2H, m), 4.60 (2H, s), 5.09 (2H, s), 6.29 (1H, s), 6.40 (1H, d), 6.49 (1H, dd), 6.85 (1H, s), 6.94 (1H, d)<br>MS+: 422 |
| Ex58 | Ex2 | NMR: 1.29-1.53 (2H, m), 1.55-1.80 (2H, m), 1.94-2.21 (2H, m), 2.33-2.44 (1H, m), 2.52-2.62 (1H, m), 2.74 (1H, d), 3.07 (2H, dd), 4.72 (2H, s), 5.31 (2H, s), 6.33 (1H, m), 6.42 (1H, s), 6.51 (1H, dd), 7.98 (1H, d), 8.01 (1H, s), 8.15 (1H, d)<br>MS+: 534 |
| Ex59 | Ex2 | NMR: 1.90-2.00 (2H, m), 2.41-2.54 (2H, m), 2.56 (3H, s), 2.56-2.61 (1H, m), 2.69 (1H, t), 2.85-2.96 (1H, m), 3.13 (2H, dd), 4.71 (2H, s), 5.38 (2H, s), 6.41 (1H, m), 6.43 (1H, s), 6.55 (1H, dd), 7.35-7.41 (1H, m), 7.44-7.49 (2H, m), 7.65-7.68 (2H, m)<br>MS+: 503 |
| Ex60 | Ex2 | NMR: 1.80-1.94 (2H, m), 2.41-2.62 (2H, m), 2.65-2.73 (1H, m), 2.84-2.89 (1H, m), 3.08-3.41 (3H, m), 4.72 (2H, s), 5.37 (2H, s), 6.38-6.45 (2H, m), 6.55 (1H, dd), 7.38 (1H, s), 7.40-7.53 (5H, m)<br>MS+: 556 |
| Ex61 | Ex2 | NMR: 1.88-1.99 (2H, m), 2.41-2.64 (3H, m), 2.65-2.73 (1H, m), 2.85-2.95 (1H, m), 3.04-3.21 (2H, m), 4.72 (2H, s), 5.25 (2H, s), 6.35 (1H, d), 6.43 (1H, s), 6.52 (1H, dd), 7.40-7.57 (3H, m), 7.72-7.86 (3H, m), 7.98-8.04 (2H, m)<br>MS+: 550 |
| Ex62 | Ex2 | NMR: 1.87-1.97 (2H, m), 2.41-3.24 (7H, m), 4.72 (2H, s), 5.23 (2H, s), 6.39 (1H, d), 6.43 (1H, s), 6.54 (1H, dd), 7.30-7.34 (2H, m), 7.42-7.47 (4H, m), 7.74-7.77 (1H, m), 7.86-7.89 (1H, m)<br>MS−: 526 |
| Ex63 | Ex2 | NMR: 1.79-2.00 (2H, m), 2.30-2.41 (1H, m), 2.43-2.79 (4H, m), 3.09 (2H, s), 4.71 (2H, s), 5.20 (2H, s), 6.33 (1H, d), 6.40 (1H, s), 6.48 (1H, dd), 6.60-6.63 (1H, m), 7.80-7.87 (2H, m), 8.12-8.25 (2H, m), 8.69 (1H, d)<br>MS−: 516 |
| Ex64 | Ex2 | NMR: 1.78-2.04 (2H, m), 2.30-2.79 (7H, m), 3.09 (2H, s), 3.55 (2H, t), 3.78 (2H, t), 4.70 (2H, s), 5.02 (2H, s), 6.28 (1H, s), 6.38-6.45 (2H, m), 6.84-6.89 (2H, m), |

TABLE 113-continued

| | | |
|---|---|---|
| | | 7.45-7.52 (1H, m)<br>MS−: 555 |
| Ex65 | Ex2 | NMR: 1.78-2.02 (2H, m), 1.95 (3H, s), 2.30-2.81 (5H, m), 3.08-3.19 (2H, m),<br>4.72 (2H, s), 5.32 (2H, s), 6.40-6.44 (2H, m), 6.55 (1H, dd), 7.24-7.30 (2H, m),<br>7.42-7.51 (3H, m)<br>MS+: 570 |

TABLE 114

| | | |
|---|---|---|
| Ex66 | Ex2 | NMR: 1.20 (3H, s), 1.41-1.52 (1H, m), 2.24 (1H, d), 2.22-2.36 (1H, m),<br>2.43-2.60 (2H, m), 2.86 (1H, d), 3.11 (2H, s), 4.72 (2H, s), 5.37 (2H, s), 6.38-6.42 (2H, m),<br>6.54 (1H, dd), 7.38 (1H, s), 7.41-7.52 (5H, m)<br>MS+: 570 |
| Ex67 | Ex2 | NMR: 1.18 (3H, t), 1.70-2.01 (2H, m), 2.31-3.51 (13H, m), 4.67 (2H, s), 6.34 (1H,<br>s), 6.67 (1H, s) 6.72-6.81 (2H, m), 6.94 (1H, s), 7.31-7.38 (3H, m),<br>7.39-7.44 (2H, m)<br>MS+: 496 |
| Ex68 | Ex2 | NMR: 1.24 (3H, t), 1.91-2.04 (2H, m), 2.42-2.75 (4H, m), 2.85 (2H, q),<br>2.85-3.60 (3H, m), 4.72 (2H, s), 6.41 (1H, s), 6.79 (1H, d), 6.97 (1H, s), 7.00-7.09 (2H, m),<br>7.14 (1H, s), 7.30-7.50 (6H, m)<br>MS−: 470 |
| Ex69 | Ex2 | NMR: 1.02 (3H, d), 2.04-2.09 (1H, m), 2.21-2.38 (2H, m), 2.56-2.79 (3H, m),<br>3.01-3.16 (2H, m), 4.72 (2H, s), 5.36 (2H, s), 6.37-6.44 (2H, m), 6.53 (1H, dd),<br>7.38 (1H, s), 7.40-7.53 (5H, m)<br>MS−: 546 |
| Ex70 | Ex2 | NMR: 1.94-2.49 (3H, m), 2.95-3.72 (4H, m), 3.90 (2H, brs), 4.94 (2H, s), 5.21 (2H,<br>s), 6.34 (2H, t), 6.41 (1H, brs), 6.57 (1H, dd), 6.86 (1H, brs), 7.54 (2H, t),<br>7.80 (1H, d), 7.94-7.99 (2H, m) |
| Ex71 | Ex2 | NMR: 1.19 (3H, s), 1.38-1.52 (1H, m), 2.23 (1H, d), 2.24-2.34 (1H, m),<br>2.43-2.58 (2H, m), 2.85 (1H, d), 3.10 (2H, s), 4.72 (2H, s), 5.31 (2H, s), 6.33 (1H, s),<br>6.40 (1H, d), 6.49 (1H, dd), 7.99 (1H, d), 8.09 (1H, s), 8.14 (1H, d)<br>MS+: 556 |
| Ex72 | Ex2 | NMR: 1.20 (3H, s), 1.38-1.53 (1H, m), 1.95 (3H, s), 2.24 (1H, d), 2.25-2.35 (1H,<br>m), 2.40-2.62 (2H, m), 2.86 (1H, d), 3.11 (2H, s), 4.73 (2H, s), 5.32 (2H, s),<br>6.39-6.41 (2H, m), 6.56 (1H, dd), 7.25-7.32 (2H, m), 7.42-7.55 (3H, m)<br>MS+: 584 |
| Ex73 | Ex2 | NMR: 2.01-2.23 (2H, m), 2.46-2.79 (3H, m), 2.92-3.00 (1H, m), 3.12-3.27 (2H,<br>m), 3.43-3.57 (1H, m), 4.75 (2H, s), 5.37 (2H, s), 6.40 (1H, d), 6.45 (1H, s),<br>6.55 (1H, dd), 7.35-7.42 (1H, m), 7.42-7.54 (5H, m)<br>MS+: 558 |
| Ex74 | Ex2 | NMR: 1.72-1.93 (1H, m), 2.21-2.48 (2H, m), 2.63-2.89 (3H, m), 3.16 (2H, s),<br>4.74 (2H, s), 5.37 (2H, s), 6.40 (1H, d), 6.43 (1H, s), 6.54 (1H, dd), 7.34-7.40 (1H,<br>m), 7.41-7.53 (5H, m)<br>MS+: 574 |
| Ex75 | Ex2 | NMR: 1.18 (3H, s), 1.38-1.48 (1H, m), 2.22 (1H, d), 2.26-2.68 (3H, m), 2.85 (1H,<br>d), 3.05 (2H, s), 4.68 (2H, s), 4.92 (2H, q), 5.11 (2H, s), 6.31 (1H, s), 6.39 (1H,<br>d), 6.48 (1H, dd), 6.95 (1H, d), 7.35-7.45 (2H, m), 7.69 (1H, d)<br>MS+: 568 |
| Ex76 | Ex2 | NMR: 1.19 (3H, s), 1.44 (3H, d), 2.18-2.23 (3H, m), 2.39-2.65 (2H, m),<br>2.80-2.88 (1H, m), 3.02 (2H, s), 4.68 (2H, s), 5.06 (2H, s), 5.43-5.50 (1H, m), 6.37 (1H, brs),<br>6.43 (1H, d), 6.51 (1H, dd), 6.94 (1H, d), 7.49 (1H, d), 7.69-7.75 (2H, m)<br>MS+582 |
| Ex77 | Ex2 | NMR: 0.92-1.06 (2H, m), 1.52-1.63 (1H, m), 2.27-2.35 (1H, m), 2.53-2.64 (1H,<br>m), 2.78-2.85 (2H, m), 3.12 (2H, s), 4.67 (2H, s), 5.37 (2H, s), 6.37-6.43 (2H, m),<br>6.54 (1H, dd), 7.35-7.40 (1H, m), 7.41-7.53 (5H, m)<br>MS−: 544 |

TABLE 115

| | | |
|---|---|---|
| Ex78 | Ex2 | NMR: 1.70-1.82 (1H, m), 2.38-2.70 (3H, m), 3.04-3.14 (2H, m), 3.23-3.43 (2H,<br>m), 4.71 (2H, s), 5.37 (2H, s), 6.39 (1H, d), 6.43 (1H, s), 6.55 (1H, dd),<br>7.35-7.39 (1H, m), 7.41-7.56 (5H, m)<br>MS−: 600 |
| Ex79 | Ex2 | NMR: 2.17-2.27 (2H, m), 2.39-2.47 (2H, m), 2.92-2.99 (2H, m), 3.10 (2H, s),<br>4.72 (2H, s), 5.31 (2H, s), 6.35 (1H, s), 6.42-6.56 (3H, m), 7.99 (1H, d), 8.09 (1H,<br>s), 8.14 (1H, d),<br>MS−: 530 |
| Ex80 | Ex2 | NMR: 1.09-1.24 (2H, m), 1.56-1.68 (3H, m), 1.87 (2H, t), 2.12 (2H, d), 2.77 (2H,<br>dm), 3.01 (2H, s), 4.70 (2H, s), 5.32 (2H, s), 6.33-6.35 (1H, m), 6.40 (1H, s),<br>6.50 (1H, dd), 7.99 (1H, d), 8.10 (1H, s), 8.15 (1H, d), MS−: 546 |
| Ex81 | Ex2 | NMR: 1.38 (3H, s), 2.96 (2H, d), 3.07 (2H, s), 3.31 (2H, d), 4.46 (2H, s), 5.36 (2H,<br>s), 6.32-6.42 (2H, m), 6.54 (1H, dd), 7.34-7.40 (1H, m), 7.40-7.52 (5H, m)<br>MS+: 556 |
| Ex82 | Ex2 | NMR: 1.84-1.95 (2H, m), 2.32 (2H, t), 2.59 (3H, s), 2.82-3.08 (2H, m), 3.73 (2H,<br>brs), 4.89 (2H, s), 5.34 (2H, s), 6.40-6.43 (1H, m), 6.57 (1H, dd), 6.77-6.85 (1H, |

TABLE 115-continued

| | | |
|---|---|---|
| | | m), 8.00 (1H, d), 8.11 (1H, s), 8.16 (1H, d), 11.11 (1H, brs), 11.99 (1H, brs), MS−: 520 |
| Ex83 | Ex2 | NMR: 1.76-2.02 (2H, m), 2.31-2.85 (5H, m), 3.12 (2H, s), 3.43 (2H, s), 5.32 (2H, s), 6.37 (1H, s), 6.73 (1H, s), 6.87 (1H, d), 7.07 (1H, d), 8.02 (1H, d), 8.05-8.15 (2H, m) MS+: 518 |
| Ex84 | Ex2 | NMR: 1.21-1.78 (5H, m), 1.77-2.00 (1H, m), 2.20-2.38 (2H, m), 2.37-2.51 (1H, m), 2.64-2.78 (2H, m), 3.02 (2H, s), 4.72 (2H, s), 5.37 (2H, s), 6.34-6.58 (3H, m), 7.38 (1H, s), 7.41-7.53 (5H, m) MS+: 574 |
| Ex85 | Ex2 | NMR: 2.10-2.21 (2H, m), 2.35-2.43 (2H, m), 2.99 (2H, s), 3.13 (2H, s), 4.72 (2H, s), 5.31 (2H, s), 6.33-6.36 (1H, m), 6.44 (1H, s), 6.47-6.58 (2H, m), 7.99 (1H, d), 8.09 (1H, d), 8.14 (1H, d), MS−: 530 |
| Ex86 | Ex2 | NMR: 1.89-1.97 (2H, m), 2.01 (3H, s), 2.18-2.28 (2H, m), 2.43-3.20 (9H, m), 5.26 (2H, s), 6.24 (2H, dd), 6.83-6.89 (2H, m), 6.90-6.95 (2H, m), 7.17-7.25 (1H, m), 7.53 (1H, d), 7.84 (1H, d), 7.96 (1H, d) MS+: 533 |
| Ex87 | Ex2 | NMR: 1.20 (3H, s), 1.40-1.53 (1H, m), 2.01 (3H, s), 2.19-2.35 (4H, m), 2.42-2.70 (4H, m), 2.84 (1H, d), 3.18 (2H, s), 5.26 (2H, s), 6.24 (2H, dd), 6.83-6.89 (2H, m), 6.91-6.96 (2H, m), 7.19 (1H, d), 7.53 (1H, d), 7.83 (1H, d), 7.95 (1H, s) MS+: 525 |
| Ex88 | Ex2 | NMR: 1.20 (3H, s), 1.40-1.54 (1H, m), 2.01 (3H, s), 2.20-2.38 (4H, m), 2.40-2.69 (4H, m), 2.85 (1H, d), 3.18 (2H, s), 5.38 (2H, s), 6.83-6.90 (2H, m), 7.20 (1H, d), 7.38 (1H, s), 7.43-7.52 (5H, m) MS+: 542 |
| Ex89 | Ex2 | NMR: 1.18 (3H, s), 1.38-1.48 (1H, m), 2.23 (1H, d), 2.25-2.35 (1H, m), 2.38-2.53 (2H, m), 2.84 (1H, d), 3.09 (2H, s), 4.72 (2H, s), 5.24 (2H, s), 6.23 (2H, dd), 6.36-6.43 (2H, d), 6.52 (1H, dd), 6.93 (2H, s), 7.53 (1H, d), 7.82 (1H, d), 7.94 (1H, s) MS+: 553 |

TABLE 116

| | | |
|---|---|---|
| Ex90 | Ex2 | NMR: 1.19 (3H, s), 1.38-1.51 (1H, m), 2.23 (1H, d), 2.24-2.36 (1H, m), 2.42-2.57 (2H, m), 2.84 (1H, d), 3.11 (2H, s), 4.72 (2H, s), 5.24 (2H, s), 6.37-6.43 (2H, m), 6.53 (1H, dd), 7.30-7.37 (2H, m), 7.41-7.48 (4H, m), 7.76 (1H, d), 7.89 (1H, s) MS+: 542 |
| Ex91 | Ex2 | NMR: 1.38 (3H, s), 2.01 (3H, s), 2.18 (2H, t), 2.16 (2H, t), 2.97 (2H, d), 3.19 (2H, s), 3.33 (2H, d), 5.38 (2H, s), 6.84-6.90 (2H, m), 7.19 (1H, d), 7.38 (1H, s), 7.41-7.54 (5H, m) MS+: 550 |
| Ex92 | Ex2 | NMR: 1.40 (3H, s), 2.02 (3H, s), 2.18 (2H, t), 2.61 (2H, t), 3.00 (2H, d), 3.21 (2H, s), 3.34 (2H, d), 5.26 (2H, s), 6.24 (2H, dd), 6.82-6.89 (2H, m), 6.91-6.95 (2H, m), 7.19 (1H, d), 7.53 (1H, d), 7.83 (1H, dd), 7.96 (1H, d) MS+: 533 |
| Ex93 | Ex2 | NMR: 1.34 (3H, s), 2.91 (2H, d), 3.05 (2H, s), 3.27 (2H, d), 4.66 (2H, s), 5.22 (2H, s), 6.34-6.39 (2H, m), 6.52 (1H, d), 7.28-7.35 (2H, m), 7.40-7.48 (4H, m), 7.75 (1H, d), 7.88 (1H, s) MS+: 550 |
| Ex94 | Ex2 | NMR: 1.34 (3H, s), 2.91 (2H, d), 3.05 (2H, s), 3.29 (2H, d), 4.66 (2H, s), 5.23 (2H, s), 6.23 (2H, dd), 6.33-6.39 (2H, m), 6.51 (1H, d), 6.91-6.95 (2H, m), 7.52 (1H, d), 7.81 (1H, d), 7.93 (1H, d) MS+: 539 |
| Ex95 | Ex2 | NMR: 1.35 (3H, s), 1.97 (3H, s), 2.02 (3H, s), 2.19 (2H, t), 2.62 (2H, t), 2.90-2.95 (2H, m), 3.18 (2H, s), 3.26-3.36 (2H, m), 5.33 (2H, s), 6.85-6.93 (2H, m), 7.20 (1H, d), 7.25-7.32 (2H, m), 7.41-7.54 (3H, m) MS+: 564 |
| Ex96 | Ex2 | NMR: 1.68-2.01 (2H, m), 2.31-2.42 (1H, m), 2.46-2.62 (2H, m), 2.63-2.78 (2H, m), 3.04-3.18 (2H, m), 4.72 (2H, s), 5.23 (2H, s), 6.40 (2H, d), 6.53 (1H, dd), 7.26-7.36 (2H, m), 7.40-7.49 (4H, m), 7.75 (1H, d), 7.88 (1H, s) MS+: 550 |
| Ex97 | Ex2 | NMR: 1.35 (3H, s), 2.88-2.94 (2H, m), 3.06 (2H, s), 3.25-3.36 (2H, m), 4.66 (2H, s), 5.14 (2H, s), 6.54 (2H, d), 6.51 (1H, dd), 7.38-7.50 (7H, m), 7.62 (1H, s) MS+: 516 |
| Ex98 | Ex2 | NMR: 2.23-2.30 (2H, m), 2.42-2.53 (2H, m), 3.03 (2H, s), 3.18 (2H, s), 4.72 (2H, s), 5.24 (2H, s), 6.41 (1H, d), 6.48 (1H, s), 6.55 (1H, dd), 6.82-6.88 (1H, m), 7.28-7.35 (2H, m), 7.40-7.48 (4H, m), 7.76 (1H, d), 7.89 (1H, s) MS+: 562 |
| Ex99 | Ex2 | NMR: 1.70-2.01 (2H, m), 2.32-2.42 (1H, m), 2.47-2.62 (2H, m), 2.63-2.70 (1H, m), 2.71-2.87 (1H, m), 3.04-3.18 (2H, m), 4.72 (2H, s), 5.23 (2H, s), 6.41 (2H, d), 6.53 (1H, dd), 7.26-7.36 (2H, m), 7.40-7.48 (4H, m), 7.75 (1H, d), 7.88 (1H, s) MS+: 550 |
| Ex100 | Ex2 | NMR: 2.03 (3H, s), 2.18 (2H, t), 2.61 (2H, t), 3.11-3.19 (2H, m), 3.24 (2H, s), 3.31-3.37 (2H, m), 4.64 (2H, s), 5.26 (2H, s), 6.24 (2H, dd), 6.82-6.88 (2H, m), 6.91-6.95 (2H, m), 7.17-7.23 (1H, m), 7.53 (1H, d), 7.80-7.86 (1H, m), |

TABLE 116-continued

| | | |
|---|---|---|
| | | 7.93-7.97 (1H, m)<br>MS+: 551 |
| Ex101 | Ex2 | NMR: 2.02 (3H, s), 2.18 (2H, t), 2.61 (2H, t), 3.12-3.20 (2H, m), 3.24 (2H, s), 3.28-3.38 (2H, m), 4.65 (2H, d), 5.38 (2H, s), 6.83-6.91 (2H, m), 7.20 (1H, d), 7.38 (1H, s), 7.40-7.53 (5H, m)<br>MS−: 544 |

TABLE 117

| | | |
|---|---|---|
| Ex102 | Ex2 | NMR: 0.79 (3H, t), 1.81 (2H, q), 2.02 (3H, s), 2.17 (2H, t), 2.61 (2H, t), 3.00-3.08 (2H, m), 3.20 (2H, s), 3.26-3.35 (2H, m), 5.38 (2H, s), 6.83-6.88 (2H, m), 7.20 (1H, d), 7.38 (1H, d), 7.40-7.54 (5H, m)<br>MS+: 564 |
| Ex103 | Ex2 | NMR: 0.80 (3H, t), 1.80 (2H, q), 2.97-3.05 (2H, m), 3.08 (2H, s), 3.34-3.32 (2H, m), 4.66 (2H, s), 5.24 (2H, s), 6.24 (2H, dd), 6.35-6.41 (2H, m), 6.53 (1H, dd), 6.91-6.96 (2H, m), 7.53 (1H, d), 7.82 (1H, d), 7.94 (1H, s)<br>MS+: 553 |
| Ex104 | Ex2 | NMR: 1.20 (3H, s), 1.42-1.53 (1H, m), 2.01 (3H, s), 2.18-2.38 (4H, m), 2.41-2.70 (4H, m), 2.80-2.88 (1H, m), 3.19 (2H, s), 5.29 (2H, s), 6.52 (1H, dd), 6.84-6.90 (2H, m), 7.17-7.24 (1H, m), 7.60-7.66 (1H, d), 7.75 (1H, d), 7.85-7.92 (1H, m), 7.99 (1H, d), 8.05 (1H, d)<br>MS+: 548 |
| Ex105 | Ex2 | NMR: 1.81-2.02 (2H, m), 2.01 (3H, s), 2.19-2.27 (2H, m), 2.41-2.85 (7H, m), 3.18 (2H, s), 5.29 (2H, s), 6.52 (1H, dd), 6.82-6.90 (2H, m), 7.17-7.24 (1H, m), 7.63 (1H, d), 7.75 (1H, d), 7.85-7.90 (1H, m), 7.96-8.01 (1H, m), 8.05 (1H, d)<br>MS+: 534 |
| Ex106 | Ex2 | NMR: 1.37 (3H, s), 2.01 (3H, s), 2.18 (2H, t), 2.61 (2H, t), 2.93-3.01 (2H, m), 3.19 (2H, s), 3.28-3.35 (2H, m), 5.28 (2H, s), 6.52 (1H, dd), 6.80-6.88 (2H, m), 7.14-7.24 (1H, m), 7.60-7.67 (1H, m), 7.75 (1H, d), 7.85-7.92 (1H, m), 7.97-8.02 (1H, d), 8.04 (1H, d)<br>MS+: 534 |
| Ex107 | Ex2 | NMR: 1.70-2.01 (2H, m), 2.30-2.73 (5H, m), 3.09 (2H, s), 4.72 (2H, s), 5.24 (2H, s), 6.36-6.46 (2H, m), 6.53 (1H, dd), 7.24-7.37 (3H, m), 7.42-7.56 (2H, m), 7.78 (1H, d), 7.91 (1H, s)<br>MS+: 568 |
| Ex108 | Ex2 | NMR: 1.70-2.01 (2H, m), 2.30-2.73 (5H, m), 3.09 (2H, s), 4.72 (2H, s), 5.24 (2H, s), 6.36-6.46 (2H, m), 6.53 (1H, dd), 7.24-7.37 (3H, m), 7.42-7.56 (2H, m), 7.78 (1H, d), 7.91 (1H, s)<br>MS+: 568 |
| Ex109 | Ex2 | NMR: 1.76-2.00 (2H, m), 2.28-2.58 (3H, m), 2.60-2.80 (2H, m), 3.07-3.17 (2H, m), 4.72 (2H, s), 5.24 (2H, s), 6.20-6.26 (2H, m), 6.37-6.45 (2H, m), 6.53 (1H, dd), 6.89-6.97 (2H, m), 7.53 (1H, d), 7.76-7.85 (1H, m), 7.90-7.97 (1H, m)<br>MS+: 539 |
| Ex110 | Ex2 | NMR: 1.80-2.01 (2H, m), 2.01 (3H, s), 2.23 (2H, t), 2.35-2.96 (7H, m), 3.17 (2H, s), 5.26 (2H, s), 6.21-6.27 (2H, m), 6.83-6.90 (2H, m), 6.90-6.98 (2H, m), 7.15-7.25 (1H, m), 7.53 (1H, d), 7.81-7.88 (1H, m), 7.92-7.97 (1H, m)<br>MS+: 533 |
| Ex111 | Ex2 | NMR: 1.76-2.00 (2H, m), 2.28-2.58 (3H, m), 2.60-2.80 (2H, m), 3.07-3.17 (2H, m), 4.72 (2H, s), 5.24 (2H, s), 6.20-6.26 (2H, m), 6.37-6.45 (2H, m), 6.53 (1H, dd), 6.89-6.97 (2H, m), 7.53 (1H, d), 7.76-7.85 (1H, m), 7.90-7.97 (1H, m)<br>MS+: 539 |

TABLE 118

| | | |
|---|---|---|
| Ex112 | Ex2 | NMR: 2.10-2.24 (2H, m), 2.32-2.43 (2H, m), 2.99 (2H, s), 3.13 (2H, s), 4.72 (2H, s), 5.37 (2H, s), 6.37-6.47 (2H, m), 6.55 (1H, dd), 7.38 (1H, s), 7.40-7.54 (6H, m)<br>MS−: 544 |
| Ex113 | Ex2 | NMR: 2.13-2.25 (2H, m), 2.31-2.50 (2H, m), 2.97-3.04 (2H, m), 3.16 (2H, s), 4.72 (2H, s), 5.25 (2H, s), 6.21-6.28 (2H, m), 6.38-6.42 (1H, m), 6.43-6.46 (2H, m), 6.54 (1H, dd), 6.90-6.98 (2H, m), 7.53 (1H, d), 7.80-7.85 (1H, m), 7.92-7.97 (1H, m)<br>MS+: 551 |
| Ex114 | Ex2 | NMR: 1.22 (3H, s), 1.46-1.54 (1H, m), 2.41-2.48 (4H, m), 2.47-2.61 (1H, m), 2.67 (2H, t), 2.83-2.89 (1H, m), 3.05-3.10 (2H, m), 3.23-3.27 (1H, m), 5.35 (2H, s), 6.37 (1H, s), 7.02 (1H, d), 7.24-7.47 (8H, m)<br>MS+: 528 |
| Ex115 | Ex2 | NMR: 1.80-2.01 (2H, m), 2.01 (3H, s), 2.23 (2H, t), 2.35-2.96 (7H, m), 3.17 (2H, s), 5.26 (2H, s), 6.21-6.27 (2H, m), 6.83-6.90 (2H, m), 6.90-6.98 (2H, m), 7.15-7.25 (1H, m), 7.53 (1H, d), 7.81-7.88 (1H, m), 7.92-7.97 (1H, m)<br>MS+: 533 |
| Ex116 | Ex2 | NMR: 1.35 (3H, s), 2.87-2.95 (2H, m), 3.02 (2H, s), 3.20-3.32 (2H, s), 4.62 (2H, s), 5.23 (2H, s), 6.20-6.26 (2H, m), 6.24-6.30 (1H, m), 6.46 (1H, d), 6.55 (1H, dd), 6.90-7.00 (3H, m), 7.52 (1H, d), 7.76-7.85 (1H, m), 7.90-7.97 (1H, m)<br>MS+: 521 |

TABLE 118-continued

| | | |
|---|---|---|
| Ex117 | Ex2 | NMR: 0.89 (3H, d), 1.40 (3H, s), 2.07-2.18 (1H, m), 2.47 (1H, dd), 2.76 (1H, dd), 2.99 (2H, d), 3.08 (2H, s), 3.32 (2H, d), 3.71-3.80 (2H, m), 4.64 (2H, s), 6.21-6.23 (1H, m), 6.33-6.39 (2H, m), 7.21 (2H, d), 7.33 (2H, d)<br>ESI−: 458 |
| Ex118 | Ex2 | NMR: 2.16-2.22 (2H, m), 2.39-2.46 (2H, m), 2.91-2.97 (2H, m), 3.08-3.13 (2H, m), 4.61-4.84 (6H, m), 4.92-5.08 (3H, m), 6.32-6.40 (2H, m), 6.43 (1H, s), 6.47 (1H, dd), 7.31 (1H, d), 7.37 (1H, dd), 7.53 (1H, d)<br>ESI−: 522 |
| Ex119 | Ex3 | NMR: 3.53-3.70 (1H, m), 3.80-4.41 (5H, m), 4.79 (2H, s), 6.72 (1H, brs), 7.01 (1H, s), 7.16 (1H, dd, J = 1.4, 7.8 Hz), 7.20 (1H, d, J = 7.8 Hz), 7.76 (2H, d, J = 8.6 Hz), 7.80 (4H, d, J = 8.6 Hz)<br>MS−: 412 |
| Ex120 | Ex3 | NMR: 3.57-3.71 (1H, m), 3.87-3.99 (2H, m), 4.08-4.32 (4H, m), 4.83 (2H, s), 6.74-6.78 (1H, m), 6.94-6.97 (1H, m), 7.11 (1H, dd), 7.12 (1H, d), 7.40-7.45 (3H, m), 7.52-7.57 (2H, m), 11.31 (1H, brs), 13.14 (1H, brs)<br>MS−: 344 |
| Ex121 | Ex3 | NMR: 3.59-3.69 (1H, m), 3.79 (3H, s), 3.89-3.97 (2H, m), 4.07-4.31 (4H, m), 4.82 (2H, s), 6.73-6.77 (1H, m), 6.90-6.92 (1H, m), 6.99 (2H, d), 7.07 (1H, dd), 7.15 (1H, d), 7.48 (2H, d), 11.28 (1H, brs), 13.06 (1H, brs)<br>MS−: 374 |

TABLE 119

| | | |
|---|---|---|
| Ex122 | Ex3 | NMR: 2.34 (3H, s), 3.59-3.71 (1H, m), 3.87-4.00 (2H, m), 4.06-4.34 (4H, m), 4.82 (2H, s), 6.71-6.79 (1H, m), 6.92-6.94 (1H, m), 7.09 (1H, dd), 7.16 (1H, d), 7.24 (2H, d), 7.43 (2H, d), 11.13 (1H, brs), 13.11 (1H, brs)<br>MS−: 358 |
| Ex123 | Ex3 | NMR: 1.24-1.56 (6H, m), 1.57-1.73 (2H, m), 1.75-1.86 (2H, m), 2.57-2.70 (1H, m), 3.55-3.70 (1H, m), 3.83-3.98 (2H, m), 4.02-4.34 (4H, m), 4.76 (2H, s), 6.68-6.76 (2H, m), 6.91 (1H, dd), 7.08 (1H, d), 10.94 (1H, brs), 13.08 (1H, brs)<br>MS−: 350 |
| Ex124 | Ex3 | NMR: 3.57-3.72 (1H, m), 3.85-4.01 (2H, m), 4.04-4.38 (4H, m), 4.85 (2H, s), 6.74-6.79 (1H, m), 7.00-7.02 (1H, m), 7.15 (1H, dd), 7.20 (1H, d), 7.68 (1H, t), 7.79 (1H, d), 7.86 (1H, d), 7.91 (1H, s), 11.31 (1H, brs), 13.13 (1H, brs)<br>MS−: 412 |
| Ex125 | Ex3 | NMR: 3.57-3.70 (1H, m), 3.89-4.02 (2H, m), 4.09-4.35 (4H, m), 4.84 (2H, s), 6.74-6.79 (1H, m), 6.91-6.94 (1H, m), 7.1 (1H, dd), 7.21 (1H, d), 7.63 (1H, t), 7.73 (1H, t), 7.80 (1H, d), 7.84 (1H, d), 11.13 (1H, brs), 1311 (1H, brs)<br>MS−: 412 |
| Ex126 | Ex3 | NMR: 1.24-1.56 (6H, m), 1.57-1.73 (2H, m), 1.75-1.86 (2H, m), 2.57-2.70 (1H, m), 3.55-3.70 (1H, m), 3.83-3.98 (2H, m), 4.02-4.34 (4H, m), 4.76 (2H, s), 6.68-6.76 (2H, m), 6.91 (1H, dd), 7.08 (1H, d), 10.94 (1H, brs), 13.08 (1H, brs)<br>MS−: 350 |
| Ex127 | Ex3 | NMR: 1.27 (9H, s), 3.56-3.68 (1H, m), 3.84-3.96 (2H, m), 4.06-4.33 (4H, m), 4.77 (2H, s), 6.68-6.74 (2H, m), 6.89 (1H, dd), 7.07 (1H, d), 11.04 (1H, brs), 13.11 (1H, brs)<br>MS−: 324 |
| Ex128 | Ex3 | NMR: 1.23-1.34 (2H, m), 1.46-1.67 (4H, m), 1.72-1.82 (2H, m), 2.00-2.13 (1H, m), 2.41 (2H, d), 3.57-3.68 (1H, m), 3.86-3.96 (2H, m), 4.04-4.32 (4H, m), 4.78 (2H, s), 6.70-6.72 (1H, m), 6.74-6.76 (1H, m), 6.92 (1H, dd), 7.08 (1H, d), 11.13 (1H, brs), 13.09 (1H, brs)<br>MS−: 350 |
| Ex129 | Ex3 | NMR: 0.89 (6H, d), 1.43 (2H, q), 1.62-1.76 (1H, m), 2.41 (2H, t), 3.57-3.69 (1H, m), 3.86-3.96 (2H, m), 4.06-4.33 (4H, m), 4.78 (2H, s), 6.69-6.78 (2H, m), 6.91 (1H, dd), 7.08 (1H, d), 11.13 (1H, brs), 13.11 (1H, brs)<br>MS−: 338 |
| Ex130 | Ex3 | NMR: 3.57-3.69 (1H, m), 3.86-4.00 (2H, m), 4.06-4.35 (4H, m), 4.82 (2H, s), 6.73-6.78 (1H, m), 6.94-6.97 (1H, m), 7.12 (1H, d), 7.18 (1H, d), 7.19 (1H, dt), 7.44 (1H, dt), 7.67-7.74 (1H, m), 11.13 (1H, brs), 13.09 (1H, brs)<br>MS−: 380 |
| Ex131 | Ex3 | NMR: 3.56-3.68 (1H, m), 3.88-4.33 (6H, m), 4.86 (2H, s), 6.89 (1H, s), 6.93 (1H, s), 7.10 (1H, dd), 7.77 (2H, d), 7.82 (2H, d), 10.94 (1H, brs), 13.09 (1H, brs):<br>MS−: 430 |
| Ex132 | Ex3 | NMR: 2.69 (2H, t), 2.84 (2H, t), 3.57-3.68 (1H, m), 3.91 (2H, s), 4.04-4.30 (4H, m), 4.78 (2H, s), 6.69-6.72 (2H, m), 6.88 (1H, dd), 7.07 (1H, dd), 7.19-7.25 (1H, m), 7.28-7.32 (4H, m), 11.11 (1H, brs), 13.13 (1H, brs),<br>MS−: 372 |

TABLE 120

| | | |
|---|---|---|
| Ex133 | Ex3 | NMR: 0.86 (6H, d), 1.79-1.90 (1H, m), 2.48 (2H, d), 3.57-3.69 (1H, m), 3.97 (2H, s), 4.08-4.31 (4H, m), 4.86 (2H, s), 6.84 (1H, s), 6.90 (1H, s), 7.01 (1H, dd), 7.23 (2H, d), 7.46 (2H, d), 11.13 (1H, brs), 13.11 (1H, brs), MS−: 418 |
| Ex134 | Ex3 | NMR: 3.53-3.66 (1H, m), 3.90 (2H, s), 3.99-4.25 (4H, m), 4.89 (2H, s), 6.84-6.90 (2H, m), 7.05 (1H, dd), 8.06 (1H, d), 8.15 (1H, s), 8.17 (1H, d), 11.31 (1H, brs), 12.89 (1H, brs), MS−: 498 |
| Ex135 | Ex3 | NMR: 2.03-2.38 (2H, m), 2.95-4.05 (7H, m), 4.86 (2H, s), 5.16 (2H, s), 6.39 (1H, s), 6.55 (1H, dd), 6.85 (1H, s), 7.12-7.17 (2H, m), 7.21-7.32 (2H, m), 7.38 (1H, d), 7.43-7.49 (2H, m), 7.74 (1H, d), 10.85 (1H, brs), 12.95 (1H, brs) MS+: 566 |
| Ex136 | Ex3 | NMR: 1.79-1.88 (2H, m), 2.02-2.30 (2H, m), 2.42 (2H, t), 2.71 (2H, t), 3.03-3.76 (5H, m), 3.95 (2H, s), 4.93 (2H, s), 6.72 (1H, s), 6.86 (1H, dd), 6.93 (1H, s), 7.16-7.33 (5H, m), 11.06 (1H, brs), 12.94 (1H, brs), MS+: 420 |
| Ex137 | Ex3 | NMR: 2.04 (3H, s), 2.09-2.35 (2H, m), 2.92-3.73 (5H, m), 3.83 (2H, s), 4.89 (2H, s), 5.35 (2H, s), 6.59 (1H, d), 6.70 (1H, s), 6.96 (1H, d), 8.02 (1H, d), 8.11 (1H, s), 8.16 (1H, d), 11.33 (1H, brs), 12.89 (1H, brs), MS−: 514 |
| Ex138 | Ex3 | NMR: 2.00-2.34 (2H, m), 2.99-3.72 (5H, m), 3.87 (2H, brs), 4.91 (2H, s), 5.20 (2H, s), 6.77 (1H, s), 6.94 (1H, s), 7.04 (1H, dd), 7.17 (1H, d), 7.22-7.51 (7H, m), 11.23 (1H, brs), 12.89 (1H, brs), MS−: 526 |
| Ex139 | Ex3 | NMR: 2.80 (2H, t), 3.12 (2H, t), 2.96-3.66 (5H, m), 3.74 (2H, brs), 4.72 (2H, s), 6.52 (1H, brs), 6.68 (1H, s), 6.85 (1H, dd), 7.03 (1H, d), 7.91 (1H, d), 8.00 (1H, s), 8.09 (1H, d) |
| Ex140 | Ex3 | NMR: 0.90 (3H, d), 2.08-2.19 (1H, m), 2.48 (1H, dd), 2.76 (1H, dd), 3.51-3.65 (1H, m), 3.72-3.89 (4H, m), 3.96-4.19 (4H, m), 4.78 (2H, m), 6.27 (1H, s), 6.42 (1H, dd), 6.74-6.82 (1H, m), 7.21 (2H, d), 7.33 (2H, d) ESI−: 444 |
| Ex141 | Ex3 | NMR: 1.45 (3H, d), 2.50-2.61 (1H, m), 2.65-2.83 (1H, m), 2.94-3.11 (1H, m), 3.43-3.57 (1H, m), 3.63-3.77 (1H, m), 3.82-4.04 (3H, m), 4.87-5.06 (2H, m), 5.13 (2H, s), 5.44-5.55 (1H, m), 6.43 (1H, s), 6.57 (1H, d), 6.86-6.95 (1H, m), 6.99-7.06 (1H, m), 7.52 (1H, d), 7.71-7.77 (2H, m), 11.31 (1H, brs), 12.97 (1H, brs) ESI−: 574 |
| Ex142 | Ex3 | NMR: 1.93-2.02 (2H, m), 2.51-2.62 (1H, m), 2.65-2.81 (3H, m), 2.96-3.09 (1H, m), 3.44-3.55 (1H, m), 3.64-3.77 (1H, m), NMR: 3.84-4.03 (5H, m), 4.84-5.04 (2H, m), 6.32 (1H, s), 6.45 (1H, dd), 6.86-6.93 (1H, m), 6.99-7.06 (1H, m), 7.25 (2H, d), 7.34 (2H, d), 11.21 (1H, brs), 12.99 (1H, brs) ESI−: 456 |
| Ex143 | Ex3 | NMR: 2.43-2.76 (2H, m), 2.97-3.10 (1H, m), 3.46-3.55 (1H, m), 3.65-3.77 (1H, m), 3.88-4.04 (3H, m), 4.59-5.11 (9H, m), 6.41 (1H, s), 6.56 (1H, d), 6.87-6.93 (1H, m), 6.99-7.06 (1H, m), 7.31 (1H, d), 7.37 (1H, dd), 7.54 (1H, d), 10.84 (1H, brs), 13.00 (1H, brs) ESI−: 522 |

TABLE 121

| | | |
|---|---|---|
| Ex144 | Ex3 | NMR: 1.45 (3H, d), 2.43-2.82 (2H, m), 2.95-3.09 (1H, m), 3.44-3.58 (1H, m), 3.62-3.78 (1H, m), 3.83-4.07 (3H, m), 4.34-5.02 (2H, m), 5.06 (2H, s), 5.26-5.37 (1H, m), 6.41 (1H, s), 6.55 (1H, d), 6.83-7.08 (2H, m), 7.36-7.43 (2H, m), 7.56-7.57 (1H, m), 11.03 (1H, brs), 13.00 (1H, brs) ESI−: 540 |
| Ex145 | Ex3 | NMR: 1.45 (3H, d), 2.51-2.60 (1H, m), 2.66-2.82 (1H, m), 2.97-3.12 (1H, m), 3.43-3.54 (1H, m), 3.64-3.76 (1H, m), 3.83-4.00 (3H, m), 4.83-5.00 (2H, m), 5.11 (2H, s), 5.44-5.55 (1H, m), 6.52 (1H, d), 6.60 (1H, dd), 6.71-6.81 (1H, m), 6.99-7.06 (1H, m), 7.09 (1H, d), 7.52 (1H, d), 7.71-7.76 (2H, m), 11.20 (1H, brs), 12.99 (1H, brs) ESI−: 556 |
| Ex146 | Ex3 | NMR: 1.29 (6H, d), 2.52-2.61 (1H, m), 2.63-2.77 (1H, m), 2.95-3.10 (1H, m), 3.46-3.55 (1H, m), 3.65-3.77 (1H, m), 3.86-4.04 (3H, m), 4.62-4.72 (1H, m), 4.85-4.96 (2H, m), 5.02 (2H, s), 6.41 (1H, s), 6.55 (1H, d), 6.86-6.94 (1H, m), 6.98-7.07 (1H, m), 7.18 (1H, d), 7.34 (1H, dd), 7.49 (1H, d), 10.89 (1H, brs), 13.00 (1H, brs) ESI−: 486 |
| Ex147 | Ex3 | NMR: 1.29 (6H, d), 2.53-2.62 (1H, m), 2.64-2.80 (1H, m), 2.96-3.10 (1H, m), 3.44-3.57 (1H, m), 3.65-3.79 (1H, m), 3.84-4.06 (3H, m), 4.75-4.85 (1H, m), 4.87-5.01 (2H, m), 5.09 (2H, s), 6.42 (1H, s), 6.56 (1H, dd), 6.85-6.95 (1H, m), 6.99-7.07 (1H, m), 7.32 (1H, d), 7.63-7.68 (2H, m), 11.04 (1H, brs), 13.00 (1H, brs) ESI−: 520 |
| Ex148 | Ex3 | NMR: 1.44 (3H, d), 2.52-2.61 (1H, m), 2.66-2.81 (1H, m), 2.96-3.09 (1H, m), 3.46-3.55 (1H, m), 3.65-3.77 (1H, m), 3.85-4.04 (3H, m), 4.86-5.05 (2H, m), 5.15 (2H, s), 5.42-5.55 (1H, m), 6.41 (1H, s), 6.56 (1H, dd), 6.88-6.94 (1H, m), 7.00-7.06 (1H, m), 7.43-7.48 (2H, m), 7.71 (1H, d), 11.19 (1H, |

TABLE 121-continued

| | | |
|---|---|---|
| | | brs), 13.01 (1H, brs)<br>ESI−: 574 |
| Ex149 | Ex3 | NMR: 1.45 (3H, d), 2.50-2.61 (1H, m), 2.61-2.77 (1H, m), 2.94-3.13 (1H, m), 3.42-3.57 (1H, m), 3.64-3.77 (1H, m), 3.84-4.02 (3H, m), 4.78-4.95 (2H, m), 5.05 (2H, s), 5.25-5.36 (1H, m), 6.51 (1H, d), 6.59 (1H, dd), 6.72-6.79 (1H, m), 7.00-7.06 (1H, m), 7.09 (1H, d), 7.36-7.42 (2H, m), 7.56 (1H, d), 10.75 (1H, brs), 13.02 (1H, brs)<br>ESI−: 522 |
| Ex150 | Ex3 | NMR: 2.53-2.61 (1H, m), 2.63-2.77 (1H, m), 2.95-3.10 (1H, m), 3.46-3.55 (1H, m), 3.65-3.77 (1H, m), 3.88-4.04 (3H, m), 4.85-4.99 (4H, m), 5.07 (2H, s), 6.39-6.45 (1H, m), 6.56 (1H, dd), 6.84-6.94 (1H, m), 6.99-7.07 (1H, m), 7.23 (1H, d), 7.42 (1H, dd), 7.57 (1H, d), 10.80 (1H, brs), 13.03 (1H, brs)<br>ESI−: 526 |
| Ex151 | Ex3 | NMR: 1.29 (6H, d), 2.53-2.61 (1H, m), 2.63-2.77 (1H, m), 2.97-3.11 (1H, m), 3.45-3.55 (1H, m), 3.65-3.77 (1H, m), 3.84-4.01 (3H, m), 4.62-4.72 (1H, m), 4.81-4.95 (2H, m), 5.01 (2H, s), 6.51 (1H, d), 6.58 (1H, dd), 6.72-6.79 (1H, m), 7.00-7.06 (1H, m), 7.08 (1H, d), 7.17 (1H, d), 7.34 (1H, dd), 7.49 (1H, d), 10.80 (1H, brs), 13.01 (1H, brs)<br>ESI−: 468 |

TABLE 122

| | | |
|---|---|---|
| Ex152 | Ex1 | NMR: 1.34-1.51 (1H, m), 1.79-1.96 (2H, m), 2.00-2.10 (1H, m), 2.73-3.10 (3H, m), 3.24 (3H, s), 3.30-3.54 (2H, m), 3.79-3.96 (2H, m), 4.59-4.85 (4H, m), 4.85-4.99 (2H, m), 5.09-5.25 (1H, m), 5.11 (2H, s), 6.42 (1H, s), 6.56 (1H, dd), 6.85 (1H, s), 7.44 (1H, d), 7.67-7.74 (2H, m), 10.72 (1H, br s), 12.06 (1H, brs)<br>ESI+: 637 |
| Ex153 | Ex1 | NMR: 1.36-1.51 (1H, m), 1.80-1.94 (2H, m), 1.98-2.12 (1H, m), 2.73-2.86 (1H, m), 2.79 (6H, s), 2.87-3.07 (2H, m), 3.28-3.52 (2H, m), 3.85 (2H, s), 4.59-4.85 (4H, m), 4.86-4.97 (2H, m), 5.10-5.25 (1H, m), 5.12 (2H, s), 6.42 (1H, s), 6.56 (1H, dd), 6.84 (1H, s), 7.44 (1H, d), 7.67-7.73 (2H, m), 10.65 (1H, brs), 11.72 (1H, brs)<br>ESI+: 666 |
| EX154 | — | NMR: 4.67 (2H, s), 4.93 (2H, s), 5.32 (2H, s), 6.37 (1H, s), 6.44 (1H, s), 6.54 (1H, dd), 7.85 (1H, s), 7.99 (1H, d), 8.09 (1H, s), 8.14 (1H, d), 8.31 (1H, s), 12.41 (1H, brs)<br>ESI+: 517 |
| Ex155 | Ex154 | NMR: 4.64 (2H, s), 4.71 (2H, s), 5.31 (2H, s), 6.36 (2H, s), 6.41 (1H, dd), 6.53 (1H, dd), 6.84 (1H, t), 7.42 (1H, t), 7.99 (1H, d), 8.09 (1H, s), 8.14 (1H, d), 11.77 (1H, brs)<br>ESI+: 538 |
| Ex156 | — | NMR: 1.35-1.52 (4H, m), 1.65-2.02 (3H, m), 2.72-3.08 (3H, m), 3.20-3.60 (2H, m), 3.72-3.95 (2H, m), 4.79-4.96 (2H, m), 5.11 (2H, s), 5.42-5.55 (1H, m), 6.52 (1H, d, J = 2.4 Hz), 6.59 (1H, dd, J = 2.4, 8.4 Hz), 6.71 (1H, s), 7.09 (1H, d, J = 8.4 Hz), 7.51 (1H, d, J = 9.3 Hz), 7.69-7.78 (2H, m), 10.71 (1H, bs), 12.85 (1H, bs)<br>ESI+: 560 |
| Ex157 | Ex156 | NMR: 1.28 (6H, d), 1.38-1.44 (2H, m), 1.58-1.65 (2H, m), 3.79 (2H, brs), 4.74-4.83 (1H, m), 4.82 (2H, s), 5.06 (2H, s), 6.49 (1H, d), 6.57 (1H, dd), 6.62 (1H, s), 7.05 (1H, d), 7.31 (1H, d), 7.63-7.68 (2H, m), 9.88 (1H, brs)<br>FAB−: 476 |
| Ex158 | Ex156 | NMR: 1.28 (6H, d), 2.12 (3H, s), 2.40-2.56 (1H, m), 2.62-2.76 (1H, m), 2.97-3.12 (1H, m), 3.40-3.51 (1H, m), 3.62-3.74 (1H, m), 3.84-3.99 (3H, m), 4.75-4.83 (1H, m), 4.86 (2H, s), 5.07 (2H, s), 6.51 (1H, d), 6.59 (1H, dd), 6.74 (1H, s), 7.09 (1H, d), 7.31 (1H, d), 7.62-7.68 (2H, m), 10.59 (1H, brs), 12.97 (1H, brs)<br>ESI+: 518 |
| Ex159 | Ex156 | NMR: 1.28 (6H, d), 1.50-1.71 (2H, m), 1.81-1.95 (3H, m), 2.20 (1.6H, d), 2.38 (0.4H, d), 2.82-2.97 (2H, m), 3.40 (2H, d), 3.76 (1.6H, d), 3.87 (0.4H, d), 4.74-4.84 (1H, m), 4.85 (2H, s), 5.07 (2H, s), 6.51 (1H, d), 6.58 (1H, dd), 6.69 (0.8H, s), 6.73 (0.2H, s), 7.07 (1H, d), 7.31 (1H, d), 7.63-7.67 (2H, m), 10.17 (0.8H, brs), 10.35 (0.2H, brs), 12.21 (1H, brs); two rotamers (4:1)<br>ESI+: 520 |
| Ex160 | Ex156 | NMR: 1.35-1.53 (2H, m), 1.65-2.12 (3H, m), 2.70-3.06 (2H, m), 3.25-3.60 (2H, m), 3.72-3.94 (2H, m), 4.88 (2H, bs), 4.95 (2H, q, J = 8.8 Hz), 5.12 (2H, s), 6.52 (1H, d, J = 2.2 Hz), 6.59 (1H, dd, J = 2.4, 8.4 Hz), 6.71 (1H, s), 7.08 (1H, d, J = 8.4 Hz), 7.41 (1H, d, J = 9.2 Hz), 7.68-7.81 (2H, m), 10.62 (1H, bs), 12.83 (1H, bs)<br>ESI+: 546 |

TABLE 123

| | | |
|---|---|---|
| Ex161 | Ex156 | NMR: 1.35-1.56 (1H, m), 1.60-2.14 (3H, m), 2.70-3.12 (3H, m), 3.25-3.60 (2H, m), 3.66-4.00 (2H, m), 4.59-5.16 (9H, m), 6.50 (1H, d, J = 2.3 Hz), 6.58 (1H, dd, J = 2.4, 8.4 Hz), 6.71 (1H, s), 7.08 (1H, d, J = 8.4 Hz), 7.31 (1H, d, J = 8.6 Hz), 7.37 (1H, dd, J = 2.0, 8.5 Hz), 7.53 (1H, d, J = 2.0 Hz), 10.69 (1H, bs), 12.84 (1H, bs)<br>ESI+: 508 |
| Ex162 | Ex156 | NMR: 1.28 (6H, d), 2.25-2.35 (1H, m), 2.44-2.60 (1H, m), 3.00-3.14 (3H, m), 3.44-3.53 (1H, m), 3.53-3.64 (1H, m), 3.69-3.79 (1H, m), 3.81-3.91 (2H, m), 4.74-4.85 (1H, m), 4.84 (2H, brs), 5.07 (2H, s), 5.58 (1H, brs), 6.51 (1H, d), 6.59 (1H, dd), 6.71 (1H, s), 7.07 (1H, d), 7.31 (1H, d), 7.63-7.68 (2H, m), 10.35 (1H, brs), 12.40 (1H, brs)<br>ESI+: 518 |
| Ex163 | Ex156 | NMR: 1.88-2.15 (4H, m), 2.44-2.56 (0.8H, m), 2.72-2.81 (0.2H, m), 2.82-3.00 (2H, m), 3.38-3.50 (2H, m), 3.68-3.86 (2H, m), 4.60-4.85 (4H, m), 4.90 (2H, s), 4.92-5.09 (3H, m), 6.50 (1H, d), 6.57 (1H, dd), 6.70 (0.8H, s), 6.74 (0.2H, s), 7.01-7.09 (1H, m), 7.31 (1H, d), 7.37 (1H, dd), 7.53 (1H, d), 10.78 (0.8H, brs), 10.87 (0.2H, brs), 12.54 (1H, brs); two rotamers (4:1)<br>ESI+: 508 |
| Ex164 | Ex156 | NMR: 1.44 (3H, d), 1.83-1.99 (2H, m), 1.99-2.13 (2H, m), 2.43-2.53 (0.8H, m), 2.73-2.82 (0.2H, m), 2.83-3.00 (2H, m), 3.23-3.38 (0.4H, m), 3.39-3.50 (1.6H, m), 3.68-3.87 (2H, m), 4.88 (2H, s), 5.11 (2H, s), 5.42-5.54 (1H, m), 6.51 (1H, d), 6.59 (1H, dd), 6.70 (0.8H, s), 6.74 (0.2H, s), 7.03-7.10 (1H, m), 7.51 (1H, d), 7.71-7.77 (2H, m), 10.49 (0.8H, brs), 10.59 (0.2H, brs), 12.54 (1H, brs); two rotamers (4:1)<br>ESI+: 560 |
| Ex165 | Ex156 | NMR: 1.84-1.99 (2H, m), 1.99-2.13 (2H, m), 2.45-2.54 (0.8H, m), 2.74-2.81 (0.2H, m), 2.82-3.00 (2H, m), 3.25-3.37 (0.4H, m), 3.38-3.49 (1.6H, m), 3.70-3.86 (2H, m), 4.58-4.66 (1H, m), 4.66-4.77 (2H, m), 4.78-4.85 (1H, m), 4.88 (2H, s), 5.10 (2H, s), 5.10-5.24 (1H, m), 6.51 (1H, d), 6.59 (1H, dd), 6.70 (0.8H, s), 6.74 (0.2H, s), 7.02-7.10 (1H, m), 7.43 (1H, d), 7.65-7.73 (2H, m), 10.53 (0.8H, brs), 10.62 (0.2H, brs), 12.54 (1H, brs); two rotamers (4:1)<br>ESI+: 542 |
| Ex166 | Ex156 | NMR: 3.60 (2H, m), 3.69-3.92 (2H, m), 4.01-4.08 (1H, m), 4.89 (2H, s), 5.09 (2H, s), 6.51 (1H, d, J = 2.3 Hz), 6.59 (1H, dd, J = 2.4, 8.4 Hz), 6.71 (1H, s), 7.08 (1H, d, J = 8.4 Hz), 7.55 (1H, d, J = 8.6 Hz), 7.67 (1H, d, J = 1.8 Hz), 7.72 (1H, dd, J = 1.8, 8.6 Hz), 10.71 (1H, bs), 12.84 (1H, bs)<br>ESI+: 504 |
| Ex167 | Ex156 | NMR: 0.64-0.70 (2H, m), 0.81-0.88 (2H, m), 1.85-2.13 (4H, m), 2.41-2.57 (0.8H, m), 2.73-2.80 (0.2H, m), 3.21-3.50 (4H, m), 3.71-3.87 (2H, m), 4.01-4.08 (1H, m), 4.88 (2H, s), 5.09 (2H, s), 6.51 (1H, d), 6.59 (1H, dd), 6.70 (0.8H, s), 6.74 (0.2H, s), 7.02-7.10 (1H, m), 7.55 (1H, d), 7.67 (1H, d), 7.72 (1H, dd), 10.50-10.75 (1H, m), 12.55 (1H, brs); two rotamers (4:1)<br>ESI+: 504 |
| Ex168 | Ex156 | NMR: 1.38-1.55 (1H, m), 1.54-1.73 (4H, m), 1.77-2.15 (7H, m), 2.72-3.08 (2H, m), 3.18-3.58 (4H, m), 3.81 (2H, s), 4.90 (2H, s), 5.15 (2H, s), 6.52 (1H, d), 6.60 (1H, dd), 6.71 (1H, s), 7.08 (1H, d), 7.60-7.72 (3H, m), 10.82 (1H, brs), 12.84 (1H, brs)<br>ESI+: 516 |

TABLE 124

| | | |
|---|---|---|
| EX169 | Ex156 | NMR: 1.54-1.75 (4H, m), 1.77-2.13 (8H, m), 2.83-2.98 (2H, m), 3.19-3.49 (4H, m), 3.72-3.86 (2H, m), 4.89 (2H, s), 5.15 (2H, s), 6.51 (1H, d), 6.59 (1H, dd), 6.70 (0.8H, s), 6.74 (0.2H, s), 7.02-7.10 (1H, m), 7.61-7.72 (3H, m), 10.61-10.81 (1H, m), 12.54 (1H, brs); two rotamers (4:1)<br>ESI+: 516 |
| Ex170 | Ex156 | NMR: 1.45 (3H, d), 1.51-1.71 (2H, m), 1.80-1.96 (3H, m), 2.20 (2H, d), 2.82-2.96 (2H, m), 3.35-3.44 (2H, m), 3.72-3.78 (1.6H, m), 3.84-3.89 (0.4H, m), 4.87 (2H, s), 5.11 (2H, s), 5.43-5.54 (1H, m), 6.51 (1H, d), 6.59 (1H, dd), 6.69 (0.8H, s), 6.73 (0.2H, s), 7.07 (1H, d), 7.51 (1H, d), 7.71-7.75 (2H, m), 10.36 (0.8H, brs), 10.53 (0.2H, brs), 12.20 (1H, brs); two rotamers (4:1)<br>ESI+: 574 |
| Ex171 | Ex156 | NMR: 1.80-2.12 (4H, m), 2.83-2.99 (2H, m), 3.26-3.49 (3H, m), 3.73-3.86 (2H, m), 4.87 (2H, s), 4.95 (2H, q), 5.12 (2H, s), 6.51 (1H, d), 6.59 (1H, dd), 6.70 (0.8H, s), 6.74 (0.2H, s), 7.03-7.10 (1H, m), 7.41 (1H, d), 7.72-7.78 (2H, m), 10.38-10.57 (1H, m), 12.54 (1H, brs); two rotamers (4:1)<br>ESI+: 546 |
| Ex172 | Ex156 | NMR: 1.49 (3H, d), 1.78-1.99 (2H, m), 2.00-2.12 (1H, m), 2.70-3.15 (3H, m), 3.30-3.47 (2H, m), 3.49-3.57 (1H, m), 3.82 (2H, s), 4.89 (2H, s), 5.07 (2H, s), 5.43-5.54 (1H, m), 6.52 (1H, d), 6.59 (1H, dd), 6.71 (1H, s), 7.09 (1H, d), 7.51 (1H, d), 7.77 (1H, dd), 7.86 (1H, d), 10.69 (1H, brs), 12.84 (1H, brs)<br>ESI+: 517 |
| Ex173 | Ex156 | NMR: 1.49 (3H, d), 1.85-2.12 (4H, m), 2.82-3.00 (2H, m), 3.25-3.50 (3H, m), 3.72-3.86 (2H, m), 4.88 (2H, s), 5.07 (2H, s), 5.43-5.54 (1H, m), |

TABLE 124-continued

| | | |
|---|---|---|
| | | 6.51 (1H, d), 6.59 (1H, dd), 6.70 (0.8H, s), 6.74 (0.2H, s), 7.03-7.09 (1H, m), 7.51 (1H, d), 7.77 (1H, dd), 7.86 (1H, d), 10.45-10.70 (1H, m), 12.55 (1H, brs); two rotamers (4:1) ESI+: 517 |
| Ex174 | Ex156 | NMR: 1.45 (3H, d), 2.81 (3H, s), 3.87 (2H, s), 4.06 (2H, s), 4.83 (2H, s), 5.11 (2H, s), 5.43-5.55 (1H, m), 6.51 (1H, d), 6.59 (1H, dd), 6.71 (1H, s), 7.08 (1H, d), 7.52 (1H, d), 7.68-7.77 (2H, m) ESI+: 520 |
| Ex175 | Ex2 | NMR: 1.20-1.31 (1H, m), 1.28 (6H, d), 1.34-1.47 (1H, m), 1.54-1.64 (1H, m), 1.71-1.81 (1H, m), 1.81-2.01 (2H, m), 2.10-2.22 (1H, m), 2.58-2.65 (1H, m), 2.75-2.83 (1H, m), 2.95 (2H, s), 4.66 (2H, s), 4.74-4.83 (1H, m), 5.03 (2H, s), 6.31 (1H, s), 6.43 (1H, d), 6.51 (1H, dd), 6.95 (1H, d), 7.30 (1H, d), 7.61-7.67 (2H, m); (CO$_2$H too broad to be seen) ESI+: 528 (M + Na)+ |
| Ex176 | Ex2 | NMR: 1.17-1.30 (1H, m), 1.28 (6H, d), 1.33-1.47 (1H, m), 1.53-1.63 (1H, m), 1.71-1.96 (3H, m), 2.04-2.19 (1H, m), 2.57-2.68 (1H, m), 2.76-2.83 (1H, m), 2.95 (2H, s), 4.66 (2H, s), 4.74-4.83 (1H, m), 5.03 (2H, s), 6.31 (1H, s), 6.43 (1H, d), 6.51 (1H, dd), 6.95 (1H, d), 7.30 (1H, d), 7.62-7.67 (2H, m); (CO$_2$H too broad to be seen) ESI+: 528 |
| Ex177 | Ex3 | NMR: 0.89 (6H, d), 1.84-1.99 (1H, m), 2.46-2.78 (2H, m), 2.63 (2H, d), 2.96-3.10 (1H, m), 3.43-3.56 (1H, m), 3.64-3.77 (1H, m), 3.84-4.04 (3H, m), 4.91 (1H, d), 4.99 (1H, d), 5.17 (1H, s), 6.44 (1H, s), 6.58 (1H, dd), 6.91 (1H, s), 7.03 (1H, d), 7.49 (1H, d), 7.66 (1H, s), 7.74 (1H, s), 11.09 (1H, brs), 13.01 (1H, brs) ESI−: 518 |

TABLE 125

| | | |
|---|---|---|
| Ex178 | Ex3 | NMR: 1.28 (6H, d), 2.50-2.60 (1H, m), 2.65-2.83 (1H, m), 2.97-3.10 (1H, m), 3.43-3.54 (1H, m), 3.64-3.75 (1H, m), 3.85-3.98 (3H, m), 4.74-4.83 (1H, m), 4.86 (1H, d), 4.93 (1H, d), 5.07 (2H, s), 6.52 (1H, d), 6.59 (1H, d), 6.76 (1H, s), 7.03 (1H, s), 7.09 (1H, d), 7.31 (1H, d), 7.63-7.69 (2H, m), 10.96 (1H, brs), 12.99 (1H, brs) ESI−: 502 |
| Ex179 | Ex3 | NMR: 2.53-2.62 (1H, m), 2.62-2.77 (1H, m), 2.98-3.11 (1H, m), 3.45-3.55 (1H, m), 3.66-3.77 (1H, m), 3.87-4.00 (3H, m), 4.79-4.93 (4H, m), 5.05 (2H, s), 6.51 (1H, s), 6.59 (1H, d), 6.75 (1H, s), 7.03 (1H, s), 7.09 (1H, d), 7.29 (1H, d), 7.41 (1H, dd), 7.56 (1H, d), 10.53 (1H, brs), 13.04 (1H, brs) ESI−: 508 |
| Ex180 | Ex3 | NMR: 2.55-2.61 (1H, m), 2.64-2.77 (1H, m), 2.98-3.10 (1H, m), 3.45-3.55 (1H, m), 3.65-3.77 (1H, m), 3.85-3.98 (3H, m), 4.42 (2H, dt), 4.85 (1H, d), 4.91 (1H, d), 5.04 (2H, s), 6.42 (1H, tt), 6.51 (1H, d), 6.59 (1H, dd), 6.75 (1H, s), 7.00-7.05 (1H, m), 7.08 (1H, d), 7.24 (1H, d), 7.38 (1H, dd), 7.54 (1H, d), 10.77 (1H, brs), 13.01 (1H, brs) ESI−: 490 |
| Ex181 | Ex3 | NMR: 2.53-2.63 (2H, m), 3.03-3.13 (1H, m), 3.49-3.58 (1H, m), 3.72-3.83 (1H, m), 3.86-4.00 (3H, m), 4.60-4.88 (6H, m), 4.93-5.08 (1H, m), 5.04 (2H, s), 6.50 (1H, s), 6.59 (1H, d), 6.74 (1H, s), 6.77 (1H, s), 7.07 (1H, d), 7.31 (1H, d), 7.37 (1H, dd), 7.53 (1H, d), 10.50 (1H, brs), 12.82 (1H, brs) ESI+: 528 |
| Ex182 | Ex3 | NMR: 1.45 (3H, d), 2.42-2.65 (2H, m), 2.98-3.14 (1H, m), 3.47-3.58 (1H, m), 3.66-3.78 (1H, m), 3.88-4.02 (3H, m), 4.80 (1H, d), 4.86 (1H, d), 5.05 (2H, s), 5.26-5.36 (1H, m), 6.51 (1H, s), 6.59 (1H, d), 6.75 (1H, s), 7.04 (1H, s), 7.10 (1H, d), 7.35 (1H, d), 7.44 (1H, dd), 7.70 (1H, d), 10.17 (1H, brs), 13.02 (1H, brs) ESI−: 566 |
| Ex183 | Ex3 | NMR: 1.49 (3H, d), 2.53-2.72 (2H, m), 2.98-3.13 (1H, m), 3.46-3.56 (1H, m), 3.65-3.78 (1H, m), 3.88-4.02 (3H, m), 4.81 (1H, d), 4.88 (1H, d), 5.09 (2H, s), 5.87-5.98 (1H, m), 6.54 (1H, s), 6.62 (1H, d), 6.76 (1H, s), 7.04 (1H, s), 7.11 (1H, d), 8.10 (1H, d), 8.27 (1H, d), 10.26 (1H, brs), 13.02 (1H, brs) ESI+: 547 |
| Ex184 | Ex3 | NMR: 1.21-1.34 (1H, m), 1.29 (6H, d), 1.35-1.48 (1H, m), 1.56-1.64 (1H, m), 1.72-1.81 (1H, m), 1.84-2.05 (2H, m), 2.17-2.29 (1H, m), 2.57-2.65 (1H, m), 2.73-2.85 (1H, m), 2.96 (2H, s), 4.60-4.71 (1H, m), 4.65 (2H, s), 4.97 (2H, s), 6.31 (1H, s), 6.41 (1H, d), 6.50 (1H, dd), 6.95 (1H, d), 7.16 (1H, d), 7.33 (1H, dd), 7.48 (1H, d); (CO$_2$H too broad to be seen) ES1+: 494 (M + Na)+ |
| Ex185 | Ex3 | NMR: 1.20-1.34 (1H, m), 1.29 (6H, d), 1.33-1.47 (1H, m), 1.53-1.65 (1H, m), 1.71-1.81 (1H, m), 1.83-2.03 (2H, m), 2.14-2.27 (1H, m), 2.57-2.65 (1H, m), 2.74-2.83 (1H, m), 2.96 (2H, s), 4.60-4.72 (1H, m), 4.65 (2H, s), 4.97 (2H, s), 6.31 (1H, s), 6.42 (1H, d), 6.50 (1H, dd), 6.94 (1H, d), 7.16 (1H, d), 7.33 (1H, dd), 7.47 (1H, d); (CO$_2$H too broad to be seen) ESI+: 494 |
| Ex186 | Ex3 | NMR: 1.45 (3H, d), 2.46-2.76 (2H, m), 2.99-3.11 (1H, m), 3.45-3.55 (1H, m), 3.66-3.77 (1H, m), 3.87-3.99 (3H, m), 4.84 (1H, d), 4.91 (1H, d), 5.18 (2H, s), 5.43-5.54 (1H, m), 6.54 (1H, d), 6.62 (1H, dd), 6.76 (1H, s), 7.04 (1H, |

TABLE 125-continued s), 7.11 (1H, d), 7.24 (1H, d), 7.57 (1H, s), 7.68 (1H, d), 10.61 (1H, brs), 13.02 (1H, brs)
ESI−: 556

TABLE 126

| Ex187 | Ex3 | NMR: 1.19-1.31 (1H, m), 1.33-1.48 (1H, m), 1.45 (3H, d), 1.54-1.64 (1H, m), 1.72-1.99 (3H, m), 2.12-2.23 (1H, m), 2.58-2.67 (1H, m), 2.77-2.86 (1H, m), 2.96 (2H, m), 4.66 (2H, s), 5.00 (2H, s), 5.23-5.34 (1H, m), 6.30 (1H, s), 6.42 (1H, d), 6.50 (1H, dd), 6.94 (1H, d), 7.34-7.41 (2H, m), 7.54 (1H, s); ($CO_2H$ too broad to be seen)<br>ESI+: 526 |
|---|---|---|
| Ex188 | Ex3 | NMR: 1.29 (6H, d), 2.45-2.72 (2H, m), 3.01-3.15 (1H, m), 3.48-3.58 (1H, m), 3.70-3.83 (1H, m), 3.83-3.99 (3H, m), 4.61-4.72 (1H, m), 4.86 (1H, d), 4.92 (1H, d), 5.01 (2H, s), 6.50 (1H, d), 6.58 (1H, dd), 6.72-6.79 (2H, m), 7.06 (1H, d), 7.17 (1H, d), 7.34 (1H, dd), 7.48 (1H, d), 10.95 (1H, brs), 12.79 (1H, brs)<br>FAB+: 470 |
| Ex189 | Ex3 | NMR: 1.19-1.30 (1H, m), 1.33-1.47 (1H, m), 1.45 (3H, d), 1.53-1.64 (1H, m), 1.72-1.99 (3H, m), 2.10-2.21 (1H, m), 2.58-2.69 (1H, m), 2.76-2.85 (1H, m), 2.95 (2H, s), 4.66 (2H, s), 5.00 (2H, s), 5.23-5.34 (1H, m), 6.30 (1H, s), 6.42 (1H, d), 6.50 (1H, dd), 6.95 (1H, d), 7.34-7.41 (2H, m), 7.54 (1H, s); ($CO_2H$ too broad to be seen)<br>ESI+: 526 |
| Ex190 | Ex3 | NMR: 1.19 (6H, d), 2.08-2.15 (2H, m), 2.32-2.39 (2H, m), 2.93-2.99 (2H, m), 3.07 (2H, s), 3.70-3.81 (1H, m), 4.57 (1H, d), 4.66 (2H, s), 4.93 (2H, s), 6.23-6.39 (2H, m), 6.42 (1H, d), 6.50 (1H, dd), 6.89 (1H, d), 6.96 (1H, d), 7.44-7.50 (2H, m); ($CO_2H$ too broad to be seen)<br>ESI+: 503 |
| Ex191 | Ex3 | NMR: 2.53-2.72 (2H, m), 3.00-3.15 (1H, m), 3.46-3.59 (1H, m), 3.70-3.84 (1H, m), 3.83-3.98 (3H, m), 4.59-4.96 (6H, m), 5.07-5.25 (1H, m), 5.10 (2H, s), 6.51 (1H, d), 6.59 (1H, dd), 6.71-6.81 (2H, m), 7.06 (1H, d), 7.44 (1H, d), 7.66-7.74 (2H, m), 11.05 (1H, brs), 12.67 (1H, brs)<br>ESI+: 540 |
| Ex192 | Ex3 | NMR: 1.45 (3H, d), 1.85-2.14 (4H, m), 2.73-3.01 (3H, m), 3.37-3.49 (2H, m), 3.65-3.87 (2H, m), 4.89 (2H, s), 5.05 (2H, s), 5.24-5.36 (1H, m), 6.50 (1H, d), 6.58 (1H, dd), 6.66-6.77 (1H, m), 7.01-7.10 (1H, m), 7.36-7.43 (2H, m), 7.55 (1H, s), 10.76 (1H, brs), 12.51 (1H, brs)<br>ESI+: 526 |
| Ex193 | Ex3 | NMR: 1.28 (6H, d), 2.77-3.17 (1H, m), 3.2-3.63 (4H, m), 3.68-4.13 (3H, m), 4.49-4.69 (1H, m), 4.73-4.83 (1H, m), 4.83-4.98 (2H, m), 5.06 (2H, s), 6.50 (1H, d), 6.58 (1H, dd), 6.69 (1H, brs), 7.06 (1H, d), 7.31 (1H, d), 7.63-7.68 (2H, m), 11.90 (1H, brs), 13.31 (1H, brs)<br>ESI+: 508 |
| Ex194 | Ex3 | NMR: 1.36-1.53 (2H, m), 1.73-1.93 (2H, m), 1.99-2.09 (1H, m), 2.73-3.05 (3H, m), 3.49-3.59 (1H, m), 3.81 (2H, s), 4.58-4.85 (4H, m), 4.88 (2H, s), 5.06-5.25 (1H, m), 5.10 (2H, s), 6.51 (1H, d), 6.59 (1H, dd), 6.71 (1H, s), 7.08 (1H, d), 7.44 (1H, d), 7.66-7.74 (2H, m), 10.60 (1H, brs), 12.83 (1H, brs)<br>ESI+: 542 |
| Ex195 | Ex3 | NMR: 1.97 (3H, s), 2.55-2.62 (1H, m), 2.65-2.78 (1H, m), 2.99-3.13 (1H, m), 3.46-3.55 (1H, m), 3.66-3.77 (1H, m), 3.87-4.00 (3H, m), 4.87 (1H, d), 4.94 (1H, d), 5.26 (2H, s), 6.58 (1H, d), 6.66 (1H, dd), 6.78 (1H, s), 7.03 (1H, s), 7.10 (1H, d), 7.12 (1H, d), 7.20-7.26 (1H, m), 7.28-7.33 (2H, m), 7.35 (1H, d), 7.76 (1H, d), 7.90 (1H, s), 10.86 (1H, brs), 13.00 (1H, brs)<br>ESI+: 536 |

TABLE 127

| Ex196 | Ex3 | NMR: 1.93 (3H, s), 2.56-2.76 (2H, m), 2.98-3.13 (1H, m), 3.46-3.57 (1H, m), 3.66-3.78 (1H, m), 3.87-4.01 (3H, m), 4.84 (1H, d), 4.91 (1H, d), 5.25 (2H, s), 6.57 (1H, d), 6.65 (1H, d), 6.77 (1H, s), 7.04 (1H, s), 7.13 (1H, d), 7.25-7.27 (1H, m), 7.36 (1H, d), 7.39 (1H, d), 7.75 (1H, d), 7.88 (1H, s), 10.59 (1H, brs), 13.00 (1H, brs)<br>ESI+: 542 |
|---|---|---|
| Ex197 | Ex3 | NMR: 1.45 (3H, d), 1.55-1.75 (2H, m), 2.10-2.24 (2H, m), 2.55-2.76 (2H, m), 2.99-3.23 (2H, m), 3.73-3.94 (3H, m), 4.86 (2H, s), 5.04 (2H, s), 5.24-5.35 (1H, m), 6.49 (1H, d), 6.57 (1H, dd), 6.69 (1H, s), 7.04 (1H, d), 7.35-7.42 (2H, m), 7.55 (1H, s), 10.95 (1H, brs), 12.29 (1H, brs)<br>ESI+: 526 |
| Ex198 | Ex3 | NMR: 1.51-1.73 (5H, m), 1.78-1.90 (2H, m), 1.93-2.08 (2H, m), 2.52-2.59 (1H, m), 2.61-2.74 (1H, m), 3.01-3.14 (1H, m), 3.20-3.32 (1H, m), 3.48-3.56 (1H, m), 3.71-3.83 (1H, m), 3.84-3.96 (2H, m), 4.89 (1H, d), 4.95 (1H, d), 5.15 (2H, s), 6.52 (1H, d), 6.60 (1H, dd), 6.73-6.79 (2H, m), 7.07 (1H, d), 7.61-7.71 (3H, m), 11.21 (1H, brs), 12.79 (1H, brs)<br>ESI+: 514 |

TABLE 127-continued

| | | |
|---|---|---|
| Ex199 | Ex3 | NMR: 1.34 (3H, t), 2.52-2.62 (1H, m), 2.64-2.83 (1H, m), 2.94-3.12 (1H, m), 3.43-3.56 (1H, m), 3.63-3.78 (1H, m), 3.81-4.00 (3H, m), 4.18 (2H, q), 4.81-4.98 (2H, m), 5.08 (2H, s), 6.51 (1H, s), 6.58 (1H, d), 6.69-6.79 (1H, brs), 7.01 (1H, s), 7.07 (1H, d), 7.27 (1H, d), 7.64-7.70 (2H, m), 11.21 (1H, brs), 12.90 (1H, brs)<br>ESI+: 490 |
| Ex200 | Ex3 | NMR: 2.54-2.75 (2H, m), 2.98-3.11 (1H, m), 3.43-3.56 (1H, m), 3.65-3.77 (1H, m), 3.86-4.00 (3H, m), 4.83 (1H, d), 4.90 (1H, d), 4.93 (1H, d), 4.98 (1H, d), 5.12 (2H, s), 6.52 (1H, d), 6.60 (1H, dd), 6.75 (1H, s), 7.03 (1H, s), 7.09 (1H, d), 7.41 (1H, d), 7.72-7.77 (2H, m), 10.61 (1H, brs), 13.01 (1H, brs)<br>ESI+: 544 |
| Ex201 | Ex3 | NMR: 1.46 (3H, d), 2.55-2.76 (2H, m), 2.99-3.11 (1H, m), 3.45-3.56 (1H, m), 3.65-3.77 (1H, m), 3.86-4.00 (3H, m), 4.85 (1H, d), 4.92 (1H, d), 4.99-5.11 (1H, m), 5.09 (2H, s), 6.53 (1H, d), 6.61 (1H, dd), 6.76 (1H, s), 7.03 (1H, s), 7.10 (1H, d), 7.61 (2H, s), 10.75 (1H, brs), 13.01 (1H, brs)<br>ESI+: 558 |
| Ex202 | Ex3 | NMR: 2.26-2.45 (4H, m), 2.82-2.94 (1H, m), 3.53-3.63 (2H, m), 4.27-4.39 (1H, m), 4.82 (2H, s), 5.33 (2H, s), 6.40 (1H, s), 6.57 (1H, dd), 6.76 (1H, s), 8.00 (1H, d), 8.10 (1H, s), 8.16 (1H, d), 10.07 (1H, brs)<br>ESI+: 520 |
| Ex203 | Ex3 | NMR: 1.37-1.51 (1H, m), 1.49 (3H, d), 1.77-2.10 (4H, m), 2.73-3.05 (3H, m), 3.46-3.56 (1H, m), 3.81 (2H, s), 4.89 (2H, s), 5.09 (2H, s), 5.85-5.98 (1H, m), 6.53 (1H, d), 6.60 (1H, dd), 6.71 (1H, s), 7.08 (1H, d), 8.10 (1H, d), 8.26 (1H, d), 10.78 (1H, brs), 12.83 (1H, brs)<br>ESI+: 527 |
| Ex204 | Ex3 | NMR: 2.53-2.78 (2H, m), 2.99-3.12 (1H, m), 3.44-3.56 (1H, m), 3.66-3.77 (1H, m), 3.87-3.99 (3H, m), 4.85 (1H, d), 4.92 (1H, d), 5.10 (2H, s), 6.54 (1H, d), 6.61 (1H, dd), 6.76 (1H, s), 6.97 (2H, d), 7.03 (1H, s), 7.11 (2H, d), 7.15 (1H, t), 7.36-7.44 (3H, m), 7.67 (1H, d), 10.67 (1H, brs), 12.99 (1H, brs)<br>ESI+: 504 |

TABLE 128

| | | |
|---|---|---|
| Ex205 | Ex3 | NMR: 1.28 (6H, d), 2.50-2.59 (1H, m), 2.62-2.73 (1H, m), 2.75-2.84 (1H, m), 2.97-3.14 (1H, m), 3.15-3.38 (4H, m), 4.19-4.25 (1H, m), 4.69 (2H, s), 4.74-4.84 (1H, m), 5.04 (2H, s), 6.41-6.47 (2H, m), 6.54 (1H, dd), 6.98 (1H, d), 7.31 (1H, d), 7.62-7.67 (2H, m)<br>ESI+: 507 |
| Ex206 | Ex3 | NMR: 1.47-1.98 (8H, m), 2.53-2.78 (2H, m), 2.97-3.11 (1H, m), 3.44-3.55 (1H, m), 3.64-3.76 (1H, m), 3.84-3.99 (3H, m), 4.81-4.95 (3H, m), 5.01 (2H, s), 6.50 (1H, d), 6.58 (1H, dd), 6.75 (1H, s), 7.03 (1H, s), 7.08 (1H, d), 7.15 (1H, d), 7.34 (1H, dd), 7.48 (1H, d), 10.86 (1H, brs), 12.95 (1H, brs)<br>ESI+: 496 |
| Ex207 | Ex3 | NMR: 2.54-2.63 (2H, m), 3.04-3.14 (1H, m), 3.50-3.59 (1H, m), 3.73-3.83 (1H, m), 3.86-4.00 (3H, m), 4.86 (2H, d), 4.93 (1H, d), 4.98 (1H, d), 5.12 (2H, s), 6.52 (1H, d), 6.60 (1H, dd), 6.74 (1H, s), 6.77 (1H, s), 7.08 (1H, d), 7.41 (1H, d), 7.71-7.78 (2H, m), 10.57 (1H, brs), 12.81 (1H, brs)<br>ESI+: 544 |
| Ex208 | Ex3 | NMR: 0.64-0.70 (2H, m), 0.81-0.88 (2H, m), 2.56-2.76 (2H, m), 2.99-3.12 (1H, m), 3.45-3.56 (1H, m), 3.65-3.78 (1H, m), 3.87-4.00 (3H, m), 4.01-4.08 (1H, m), 4.83 (1H, d), 4.90 (1H, d), 5.10 (2H, s), 6.52 (1H, d), 6.60 (1H, dd), 6.76 (1H, s), 7.03 (1H, s), 7.09 (1H, d), 7.56 (1H, d), 7.67 (1H, d), 7.73 (1H, dd), 10.61 (1H, brs), 13.00 (1H, brs)<br>ESI+: 502 |
| Ex209 | Ex3 | NMR: 2.41-2.61 (1H, m), 2.63-2.84 (1H, m), 2.90-3.14 (1H, m), 3.35-3.58 (1H, m), 3.61-3.80 (1H, m), 3.77-4.07 (3H, m), 4.85-5.06 (2H, m), 5.35 (2H, s), 6.45 (1H, s), 6.51 (1H, s), 6.60 (1H, d), 7.01 (1H, s), 7.96 (1H, d), 8.06-8.13 (2H, m), 11.43 (1H, brs), 12.97 (1H, brs)<br>ESI+: 532 |
| Ex210 | Ex3 | NMR: 1.29 (6H, d), 1.82-2.12 (4H, m), 2.73-3.01 (3H, m), 3.39-3.49 (2H, m), 3.72-3.80 (1.6H, m), 3.80-3.86 (0.4H, m), 4.61-4.72 (1H, m), 4.85 (2H, s), 5.01 (2H, s), 6.46-6.51 (1H, m), 6.54-6.60 (1H, m), 6.70 (0.8H, s), 6.73 (0.2H, s), 7.01-7.08 (1H, m), 7.17 (1H, d), 7.33 (1H, dd), 7.48 (1H, d), 10.27 (0.8H, brs), 10.37 (0.2H, brs), 12.52 (1H, brs); two rotaners (4:1)<br>ESI+: 472 |
| Ex211 | Ex3 | NMR: 1.56 (3H, s), 3.76-3.93 (4H, m), 4.10-4.27 (2H, m), 4.59-4.85 (6H, m), 4.92-5.08 (1H, m), 5.02 (2H, s), 6.47 (1H, d), 6.56 (1H, dd), 6.67 (1H, s), 7.03 (1H, d), 7.31 (1H, d), 7.36 (1H, dd), 7.53 (1H, d); (CO$_2$H too broad to be seen)<br>ESI+: 494 |
| Ex212 | Ex3 | NMR: 1.36-1.52 (2H, m), 1.76-2.12 (3H, m), 2.70-3.08 (3H, m), 3.45-3.62 (1H, m), 3.76-3.96 (2H, m), 4.59-4.85 (4H, m), 4.92 (2H, s), 5.09-5.25 (1H, m), 5.11 (2H, s), 6.41 (1H, s), 6.55 (1H, dd), 6.84 (1H, s), 7.44 (1H, s), 7.67-7.73 (2H, m), 10.86 (1H, brs), 12.81 (1H, brs)<br>ESI+: 560 |
| Ex213 | Ex3 | NMR: 2.45-2.62 (1H, m), 2.65-2.82 (1H, m), 2.96-3.10 (1H, m), 3.42-3.56 (1H, m), 3.64-3.78 (1H, m), 3.83-4.05 (3H, m), 4.94 (1H, d), 5.01 (1H, d), |

TABLE 128-continued 5.32 (2H, s), 6.48 (1H, s), 6.62 (1H, d), 6.91 (1H, s), 7.03 (1H, s), 8.11 (1H, s), 8.16 (2H, s), 11.27 (1H, brs), 12.99 (1H, brs)
ESI+: 532

TABLE 129

| Ex214 | Ex3 | NMR: 1.46-1.66 (6H, m), 2.55-2.72 (2H, m), 2.76-2.84 (4H, m), 2.98-3.10 (1H, m), 3.45-3.55 (1H, m), 3.65-3.78 (1H, m), 3.87-4.02 (3H, m), 4.82 (1H, d), 4.88 (1H, d), 5.13 (2H, s), 6.53 (1H, d), 6.61 (1H, dd), 6.76 (1H, s), 7.04 (1H, s), 7.10 (1H, d), 7.52 (1H, d), 7.66-7.75 (2H, m), 10.42 (1H, brs), 13.01 (1H, brs)<br>ESI+: 529 |
|---|---|---|
| Ex215 | Ex3 | NMR: 2.54-2.78 (2H, m), 2.96-3.08 (1H, m), 3.45-3.55 (1H, m), 3.65-3.77 (1H, m), 3.85-4.05 (3H, m), 4.85-5.01 (4H, m), 5.14 (2H, s), 6.43 (1H, s), 6.57 (1H, dd), 6.90 (1H, s), 7.03 (1H, s), 7.42 (1H, d), 7.73-7.79 (2H, m), 10.96 (1H, s), 13.00 (1H, brs)<br>ESI+: 562 |
| Ex216 | Ex3 | NMR: 1.51-2.09 (9H, m), 2.53-2.62 (1H, m), 2.62-2.76 (1H, m), 2.97-3.12 (1H, m), 3.45-3.56 (1H, m), 3.64-3.77 (1H, m), 3.85-4.00 (3H, m), 4.84 (1H, d), 4.90 (1H, d), 5.15 (2H, s), 6.52 (1H, s), 6.60 (1H, d), 6.75 (1H, s), 7.03 (1H, s), 7.10 (1H, d), 7.61-7.72 (3H, m), 10.67 (1H, brs), 12.96 (1H, brs)<br>ESI+: 514 |
| Ex217 | Ex3 | NMR: 1.44 (3H, d), 2.54-2.68 (2H, m), 3.02-3.15 (1H, m), 3.49-3.59 (1H, m), 3.71-3.84 (1H, m), 3.84-4.00 (3H, m), 4.86 (1H, d), 4.91 (1H, d), 5.14 (2H, s), 5.41-5.52 (1H, m), 6.49 (1H, s), 6.57 (1H, d), 6.73-6.80 (2H, m), 7.08 (1H, d), 7.42-7.49 (2H, m), 7.69 (1H, d), 10.79 (1H, brs), 12.82 (1H, brs)<br>ESI+: 558 |
| Ex218 | Ex3 | NMR: 0.64-0.70 (2H, m), 0.81-0.88 (2H, m), 2.54-2.63 (2H, m), 3.04-3.14 (1H, m), 3.50-3.59 (1H, m), 3.72-3.83 (1H, m), 3.86-3.99 (3H, m), 4.01-4.07 (1H, m), 4.83 (1H, d), 4.89 (1H, d), 5.09 (2H, s), 6.52 (1H, s), 6.60 (1H, d), 6.74 (1H, s), 6.77 (1H, s), 7.08 (1H, d), 7.55 (1H, d), 7.67 (1H, d), 7.72 (1H, dd), 10.52 (1H, brs), 12.83 (1H, brs)<br>ESI+: 502 |
| Ex219 | Ex3 | NMR: 1.48-1.84 (7H, m), 1.96-2.06 (2H, m), 2.48-2.68 (2H, m), 3.02-3.14 (1H, m), 3.48-3.58 (1H, m), 3.69-3.83 (1H, m), 3.84-3.98 (3H, m), 4.84 (1H, d), 4.90 (1H, d), 5.07 (2H, s), 6.50 (1H, d), 6.58 (1H, dd), 6.74 (1H, s), 6.77 (1H, s), 7.07 (1H, d), 7.34 (1H, dd), 7.42 (1H, d), 7.46 (1H, d), 10.74 (1H, brs), 12.83 (1H, brs)<br>ESI+: 480 |
| Ex220 | Ex3 | NMR: 1.54-1.73 (2H, m), 2.07-2.23 (2H, m), 2.54-2.70 (1H, m), 2.92-3.60 (4H, m), 3.83 (2H, s), 4.87 (2H, s), 5.33 (2H, s), 6.50 (1H, d), 6.58 (1H, dd), 6.70 (1H, s), 7.08 (1H, d), 7.99 (1H, d), 8.10 (1H, s), 8.14 (1H, d), 10.93 (1H, brs), 12.29 (1H, brs)<br>ESI+: 516 |
| Ex221 | Ex3 | NMR: 2.54-2.72 (2H, m), 3.01-3.13 (1H, m), 3.47-3.57 (1H, m), 3.70-3.82 (1H, m), 3.83-3.91 (3H, m), 4.83-4.95 (4H, m), 5.05 (2H, s), 6.50 (1H, d), 6.58 (1H, dd), 6.74 (1H, s), 6.77 (1H, s), 7.06 (1H, d), 7.29 (1H, d), 7.41 (1H, dd), 7.56 (1H, d), 10.98 (1H, brs), 12.77 (1H, brs)<br>ESI+: 510 |
| Ex222 | Ex3 | NMR: 2.53-2.66 (2H, m), 3.01-3.12 (1H, m), 3.49-3.58 (1H, m), 3.71-3.85 (1H, m), 3.86-4.01 (3H, m), 4.58-4.85 (4H, m), 4.89 (1H, d), 4.96 (1H, d), 5.08-5.25 (1H, m), 5.11 (2H, s), 6.47 (1H, s), 6.56 (1H, dd), 6.76 (1H, s), 6.89 (1H, s), 7.44 (1H, d), 7.67-7.74 (2H, m), 10.86 (1H, brs), 12.79 (1H, brs)<br>ESI+: 558 |

TABLE 130

| Ex223 | Ex3 | NMR: 1.36-1.53 (1H, m), 1.79-1.95 (2H, m), 2.00-2.09 (1H, m), 2.72-3.04 (3H, m), 3.32-3.44 (1H, m), 3.49-3.58 (1H, m), 3.86 (2H, s), 4.60-4.84 (4H, m), 4.93 (2H, s), 4.93-5.09 (1H, m), 5.05 (2H, s), 6.40 (1H, d), 6.54 (1H, dd), 6.84 (1H, s), 7.31 (1H, d), 7.37 (1H, dd), 7.54 (1H, d), 10.80 (1H, brs), 12.83 (1H, brs)<br>ESI+: 526 |
|---|---|---|
| Ex224 | Ex3 | NMR: 1.45 (3H, d), 2.39-2.68 (2H, m), 3.01-3.14 (1H, m), 3.46-3.59 (1H, m), 3.69-3.99 (2H, m), 3.89 (2H, s), 4.85 (1H, d), 4.91 (1H, d), 5.05 (2H, s), 5.24-5.36 (1H, m), 6.51 (1H, d), 6.59 (1H, dd), 6.72-6.80 (2H, m), 7.07 (1H, d), 7.35-7.43 (2H, m), 7.54-7.57 (1H, m), 10.84 (1H, brs), 12.82 (1H, brs)<br>ESI+: 524 |
| Ex225 | Ex3 | NMR: 1.50 (3H, d), 2.39-2.76 (2H, m), 2.96-3.12 (1H, m), 3.44-3.57 (1H, m), 3.64-3.78 (1H, m), 3.84-4.00 (3H, m), 4.88 (2H, s), 5.14 (2H, s), 5.94-6.09 (1H, m), 6.47-6.66 (2H, m), 6.77 (1H, s), 6.97-7.14 (2H, m), 8.29 (1H, d), 8.58 (1H, d), 10.73 (1H, brs), 12.91 (1H, brs)<br>ESI+: 559 |

TABLE 130-continued

| | | |
|---|---|---|
| Ex226 | Ex3 | NMR: 1.38-1.54 (1H, m), 1.50 (3H, d), 1.78-2.11 (3H, m), 2.72-3.09 (3H, m), 3.30-3.44 (1H, m), 3.46-3.57 (1H, m), 3.81 (2H, s), 4.91 (2H, s), 5.16 (2H, s), 5.96-6.08 (1H, m), 6.52-6.57 (1H, m), 6.61 (1H, dd), 6.72 (1H, s), 7.09 (1H, d), 8.30 (1H, d), 8.58 (1H, d), 10.93 (1H, brs), 12.73 (1H, brs)<br>ESI+: 561 |
| Ex227 | Ex3 | NMR: 1.44 (3H, d), 1.51-1.71 (2H, m), 2.06-2.20 (2H, m), 2.38-2.64 (2H, m), 2.95-3.46 (3H, m), 3.56-3.92 (2H, m), 4.80 (2H, s), 5.10 (2H, s), 5.42-5.53 (1H, m), 6.49 (1H, d), 6.57 (1H, dd), 6.57-6.67 (1H, m), 7.04 (1H, d), 7.51 (1H, d), 7.70-7.76 (2H, m), 10.61 (1H, brs), 12.27 (1H, brs)<br>ESI+: 560 |
| Ex228 | Ex3 | NMR: 2.27-2.49 (4H, m), 2.82-2.97 (1H, m), 3.56 (2H, s), 3.57-3.70 (1H, m), 4.59-4.85 (4H, m), 4.75 (2H, s), 4.91-5.08 (1H, m), 5.03 (2H, s), 6.49 (1H, d), 6.57 (1H, dd), 6.62 (1H, s), 7.04 (1H, d), 7.31 (1H, d), 7.37 (1H, dd), 7.53 (1H, d), 8.85-9.21 (2H, m), 12.38 (1H, brs)<br>ESI+: 494 |
| Ex229 | Ex3 | NMR: 1.36-1.52 (1H, m), 1.59-1.96 (3H, m), 1.99-2.11 (1H, m), 2.72-2.96 (2H, m), 3.36-3.46 (1H, m), 3.50-3.60 (1H, m), 3.88 (2H, s), 4.67-4.86 (4H, m), 4.90 (2H, s), 5.09 (2H, s), 5.61-5.78 (1H, m), 6.44 (1H, d), 6.58 (1H, dd), 6.82 (1H, s), 8.06 (1H, d), 8.23 (1H, d), 10.29 (1H, brs), 12.84 (1H, brs)<br>ESI+: 527 |
| Ex230 | Ex3 | NMR: 1.37-1.52 (1H, m), 1.62-1.93 (3H, m), 1.99-2.10 (1H, m), 2.71-2.97 (2H, m), 3.36-3.45 (1H, m), 3.49-3.62 (1H, m), 3.88 (2H, s), 4.58-4.86 (4H, m), 4.89 (2H, s), 5.08-5.25 (1H, m), 5.11 (2H, s), 6.42 (1H, s), 6.56 (1H, dd), 6.84 (1H, s), 7.44 (1H, d), 7.65-7.73 (2H, m), 10.37 (1H, brs), 12.83 (1H, brs)<br>ESI+: 560 |
| Ex231 | Ex3 | NMR: 1.74-1.94 (2H, m), 1.95-2.14 (3H, m), 2.81-3.01 (2H, m), 3.40-3.51 (2H, m), 3.84 (1.4H, d), 3.89 (0.6H, d), 4.58-4.86 (4H, m), 4.88 (2H, s), 5.08-5.25 (1H, m), 5.11 (2H, s), 6.42 (1H, s), 6.53-6.60 (1H, m), 6.84 (0.7H, s), 6.89 (0.3H, s), 7.44 (1H, d), 7.66-7.74 (2H, m), 10.08 (0.7H, brs), 10.18 (0.3H, brs), 12.52 (1H, brs); two rotamers (7:3)<br>ESI+: 560 |

TABLE 131

| | | |
|---|---|---|
| Ex232 | Ex3 | NMR: 1.45 (3H, d), 2.30-2.47 (4H, m), 2.83-2.97 (1H, m), 3.54 (2H, s), 3.56-3.67 (1H, m), 4.79 (2H, s), 5.10 (2H, s), 5.44-5.54 (1H, m), 6.50 (1H, d), 6.58 (1H, dd), 6.64 (1H, s), 7.04 (1H, d), 7.52 (1H, d), 7.70-7.76 (2H, m), 9.16-9.55 (2H, brs), 12.38 (1H, brs)<br>ESI+: 546 |
| Ex233 | Ex3 | NMR: 1.17 (2.1H, s), 1.26 (0.9H, s), 1.71-1.90 (2H, m), 2.05-2.22 (2H, m), 2.72-2.90 (1.4H, m), 2.99-3.14 (0.6H, m), 3.21-3.45 (2H, m), 3.70-3.90 (2H, m), 4.60-4.90 (6H, m), 4.92-5.08 (3H, m), 6.49 (1H, d), 6.57 (1H, dd), 6.71 (1H, s), 7.01-7.08 (1H, m), 7.31 (1H, d), 7.36 (1H, dd), 7.53 (1H, d), 10.26-10.50 (1H, m), 12.73 (1H, brs); two rotamers (7:3)<br>ESI+: 522 |
| Ex234 | Ex3 | NMR: 1.86-2.03 (2H, m), 2.08-2.20 (2H, m), 2.85-3.13 (3H, m), 3.14-3.30 (1H, m), 3.46-3.57 (1H, m), 3.73-3.90 (2H, m), 4.60-4.83 (4H, m), 4.84 (2H, s), 4.92-5.09 (1H, m), 5.04 (2H, s), 6.50 (1H, d), 6.58 (1H, dd), 6.71 (1H, s), 7.07 (1H, d), 7.31 (1H, d), 7.37 (1H, dd), 7.53 (1H, d), 10.10-10.43 (1H, m), 12.44 (1H, brs)<br>ESI+: 548 |
| Ex235 | Ex3 | NMR: 1.37-1.52 (1H, m), 1.81-1.93 (2H, m), 1.99-2.10 (1H, m), 2.72-3.04 (3H, m), 3.31-3.44 (1H, m), 3.49-3.59 (1H, m), 3.87 (2H, s), 4.61-4.85 (4H, m), 4.92 (2H, s), 4.94-5.09 (1H, m), 5.05 (2H, s), 6.41 (1H, s), 6.55 (1H, dd), 6.85 (1H, s), 7.31 (1H, d), 7.37 (1H, dd), 7.54 (1H, d), 10.67 (1H, brs), 12.80 (1H, brs)<br>ESI+: 526 |
| Ex236 | Ex156 | NMR: 1.36-1.52 (1H, m), 1.79-2.10 (3H, m), 2.72-3.06 (3H, m), 3.31-3.44 (1H, m), 3.48-3.59 (1H, m), 3.86 (2H, s), 4.88-5.01 (4H, m), 5.13 (2H, s), 6.42 (1H, d), 6.56 (1H, dd), 6.85 (1H, s), 7.42 (1H, d), 7.72-7.78 (2H, m), 10.89 (1H, brs), 12.84 (1H, brs)<br>ESI+: 564 |

Industrial Applicability

The compound of the present invention has an $S1P_1$ agonist action and can be used for prevention or treatment of diseases induced by undesirable lymphocyte infiltration, for example, autoimmune diseases or inflammatory diseases such as graft rejection or graft-versus-host diseases during organ, bone marrow, or tissue transplantation, rheumatoid arthritis, multiple sclerosis, systemic lupus erythematosus, nephrotic syndrome, encephalomeningitis, myasthenia gravis, pancreatitis, hepatitis, nephritis, diabetes, lung disorders, asthma, atopic dermatitis, inflammatory bowel disease, arteriosclerosis, ischemic reperfusion disorder, and diseases induced by abnormal proliferation or accumulation of cells, for example, cancer, leukemia, and the like.

The invention claimed is:

1. A 2H-chromene compound represented by the following formula (I):

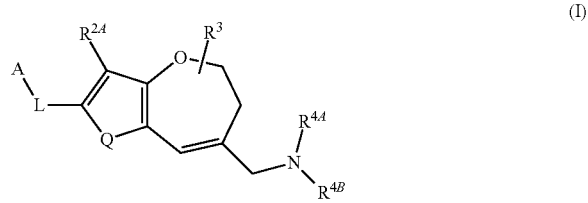

(wherein A represents lower alkyl, cycloalkyl, aryl, or heteroaryl, wherein aryl and heteroaryl may respectively be substituted with one to five $R^1$s which are the same as or different from each other;

$R^1$ represents halogen, —CN, —$NO_2$, lower alkyl, lower alkenyl, lower alkynyl, halogeno-lower alkyl, aryl, heteroaryl, cycloalkyl, —OH, —O-(lower alkyl), —O-(halogeno-lower alkyl), —O-(aryl), —O-(cycloalkyl), —O-(heteroaryl), —$NH_2$, —NH(lower alkyl), —NH(halogeno-lower alkyl), —N(lower alkyl)$_2$, or cyclic amino, wherein aryl, heteroaryl, cycloalkyl, and cyclic amino may respectively be substituted with one to five substituents which are the same as or different from each other and selected from the group consisting of halogen, —CN, lower alkyl and halogeno-lower alkyl;

L represents lower alkylene, lower alkenylene, lower alkynylene, -(lower alkylene)-O—, —O-(lower alkylene)-, or -(lower alkylene)-O-(lower alkylene)-;

Q represents —C($R^{2B}$)=C($R^{2C}$)—;

$R^{2A}$, $R^{2B}$, and $R^{2C}$ independently represent —H, halogen, lower alkyl, halogeno-lower alkyl, —O-(lower alkyl), or —O-(halogeno-lower alkyl);

$R^3$ represents —H, halogen, lower alkyl, halogeno-lower alkyl, or aryl;

$R^{4A}$ represents —H or lower alkyl;

$R^{4B}$ represents lower alkyl substituted with a group selected from Group G or cycloalkyl substituted with a group selected from Group G;

or $R^{4A}$ and $R^{4B}$ are combined with N to which they bind to form cyclic amino substituted with a group selected from Group G, in which the cyclic amino may further contain one to four substituents which are the same as or different from each other and selected from the group consisting of halogen, lower alkyl, and halogeno-lower alkyl; and Group G represents, —C(=O)OH, tetrazolyl, —C(=O)NHS(=O)$_2$(lower alkyl), -(lower alkylene)-C(=O)OH, or

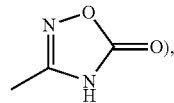

or a salt thereof.

2. The 2H-chromene compound or a salt thereof as described in claim 1, wherein $R^{4A}$ and $R^{4B}$ are combined with N to which they bind to form azetidinyl, pyrrolidinyl, piperidinyl or tetrahydropyridyl, which is substituted with a group selected from Group G, and which may further be substituted with lower alkyl or halogen.

3. The 2H-chromene compound or a salt thereof as described in claim 2, wherein Group G is —C(=O)OH or —C(=O) NHS(=O)$_2$CH$_3$.

4. The 2H-chromene compound or a salt thereof as described in claim 3, wherein A is phenyl, pyridyl, or thienyl, substituted with one to three $R^1$s which are the same as or different from each other.

5. The 2H-chromene compound or a salt thereof as described in claim 4, wherein L is -(lower alkylene)-O—, lower alkenylene, or lower alkynylene.

6. The 2H-chromene compound or a salt thereof as described in claim 5, wherein $R^{2A}$ is —H or lower alkyl; $R^{2B}$ is —H; $R^{2C}$ is —H or halogen; $R^3$ is —H or halogen; $R^1$ is halogen, lower alkyl, halogeno-lower alkyl, phenyl, pyrrolyl, cycloalkyl, —O-(lower alkyl), or —O-(halogeno-lower alkyl); and L is —$CH_2$—O—, —CH=CH—, or 3-butynylene.

7. The 2H-chromene compound or a salt thereof as described in claim 6, wherein $R^{4A}$ and $R^{4B}$ are combined with N to which they bind to form piperidinyl or tetrahydropyridyl, which is substituted with —C(=O)OH, L is —$CH_2$—O—; $R^{2A}$ and $R^{2B}$ are —H; $R^{2C}$ is —H or halogen; $R^3$ is —H; A is phenyl or pyridyl, which is substituted with two $R^1$s which are independently halogen, halogeno-lower alkyl, —O-(lower alkyl) or —O-(halogeno-lower alkyl).

8. The 2H-chromene compound or a salt thereof as described in claim 7, wherein $R^{4A}$ and $R^{4B}$ are combined with N to which they bind to form piperidinyl which is substituted with —C(=O)OH; and A is phenyl which is substituted with two $R^1$s which are the same as or different from each other.

9. The 2H-chromene compound or a salt thereof as described in claim 7, wherein $R^{4A}$ and $R^{4B}$ are combined with N to which they bind to form tetrahydropyridyl which is substituted with —C(=O)OH; and A is pyridyl which is substituted with two $R^1$s which are the same as or different from each other.

10. A 2H-chromene compound of:
1-{[7-({3-chloro-4-[(1S)-2,2,2-trifluoro-1-methylethoxy]benzyl}oxy)-2H-chromen-3-yl]methyl}-1,2,5,6-tetrahydropyridine-3-carboxylic acid,
1-({7-[(3-chloro-4-isopropylbenzyl)oxy]-2H-chromen-3-yl}methyl)-1,2,5,6-tetrahydropyridine-3-carboxylic acid,
1-[(7-{[4-isopropoxy-3-(trifluoromethyl)benzyl]oxy}-2H-chromen-3-yl)methyl]-1,2,5,6-tetrahydropyridine-3-carboxylic acid,
1-{[7-({3-chloro-4-[2-fluoro-1-(fluoromethyl)ethoxy]benzyl}oxy)-2H-chromen-3-yl]methyl}-1,2,3,6-tetrahydropyridine-4-carboxylic acid,
1-{[7-({5-chloro-6-[(1S)-2,2,2-trifluoro-1-methylethoxy]pyridin-3-yl}methoxy)-2H-chromen-3-yl]methyl}-1,2,5,6-tetrahydropyridine-3-carboxylic acid, (3R)-1-{[7-({4-[(1,3-difluoropropan-2-yl)oxy]-3-(trifluoromethyl)benzyl}oxy)-5-fluoro-2H-chromen-3-yl]methyl}piperidine-3-carboxylic acid, 1-[(7-{[4-cyclopentyl-3-(trifluoromethyl)benzyl]oxy}-2H-chromen-3-yl)methyl]-1,2,5,6-tetrahydropyridine-3-carboxylic acid, (3R)-1-{[7-({3-chloro-4-[(1,3-difluoropropan-2-yl)oxy]benzyl}oxy)-5-fluoro-2H-chromen-3-yl]methyl}piperidine-3-carboxylic acid, (3S)-1-{[7-({4-[(1,3-difluoropropan-2-yl)oxy]-3-(trifluoromethyl)benzyl}oxy)-5-fluoro-2H-chromen-3-yl]methyl}piperidine-3-carboxylic acid, (3R)-1-[(7-{[4-(2,2,2-trifluoroethoxy)-3-(trifluoromethyl)benzyl]oxy}-2H-chromen-3-yl)methyl]piperidine-3-carboxylic acid, (3R)-1-[(7-{[3-(trifluoromethyl)-4-{[(2S)-1,1,1-trifluoropropan-2-yl]oxy}benzyl]oxy}-2H-chromen-3-yl)methyl]piperidine-3-carboxylic acid, (3S)-1-[(7-{[4-(2,2,2-trifluoroethoxy)-3-(trifluoromethyl)benzyl]oxy}-5-fluoro-2H-chromen-3-yl)methyl]piperidine-3-carboxylic acid, (3R)-1-{[7-({4-[(1,3-difluoropropan-2-yl)oxy]-3-(trifluoromethyl)benzyl}oxy)-5-fluoro-2H-chromen-3-yl]methyl}-N-(methylsulfonyl)piperidine-3-carboxamide, or 1-[(7-{[4-(2,2,2-trifluoroethoxy)-3-(trifluoromethyl)benzyl]oxy}-2H-chromen-3-yl)methyl]piperidine-4-carboxylic acid, or a pharmaceutically acceptable salt thereof.

11. A pharmaceutical composition comprising the 2H-chromene compound, or a salt thereof as described in claim 1 and a pharmaceutically acceptable excipient.

12. The pharmaceutical composition as described in claim 11, which is an S1P$_1$ agonist.

13. A compound of the formula

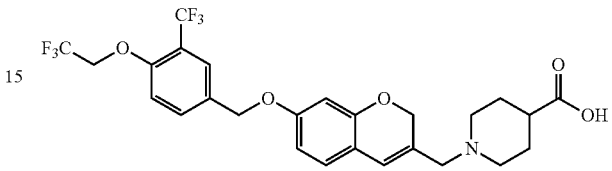

or a pharmaceutically salt thereof.

14. A pharmaceutical compostion comprising the 2H-chromene Compound, or a salt thereof as described in claim 13 and a pharmaceutically acceptable excipent.

* * * * *

UNITED STATES PATENT AND TRADEMARK OFFICE
CERTIFICATE OF CORRECTION

PATENT NO. : 8,193,378 B2
APPLICATION NO. : 13/131343
DATED : June 5, 2012
INVENTOR(S) : Hironori Harada et al.

It is certified that error appears in the above-identified patent and that said Letters Patent is hereby corrected as shown below:

COLUMN 1:

Line 33, "binds" should read --bind--.

COLUMN 7:

Line 42, "Ws" should read --$R^1$s--.

COLUMN 8:

Line 45, "(3R)-1-[7-" should read --(3R)-1-{[7- --;
    Line 46, "zyl" should read --zyl}--;
    Line 52, "benzyl}oxy]" should read --benzyl}oxy)--;
    Line 54, "(3R)-1-[(7-[3-" should read --(3R)-1-(7-{[3- --; and
    Line 55, "oxy]benzyl}oxy)" should read --oxy}benzyl]oxy}--.

COLUMN 17:

Line 42, "Jr O R," should read --Jr OR,--.

COLUMN 18:

Line 50, "can employ" should read --employing--; and
    Line 61, "condition" should read --condition,--.

COLUMN 19:

Line 44, "1,400×10mM," should read --1,400×10 min,--; and
    Line 48, "50:M" should read --50pM--.

Signed and Sealed this
Twelfth Day of February, 2013

Teresa Stanek Rea
*Acting Director of the United States Patent and Trademark Office*

CERTIFICATE OF CORRECTION (continued)
U.S. Pat. No. 8,193,378 B2

COLUMN 20:

Line 25, "left" should read --left to--; and
    Line 50, "were" should read --was--.

COLUMN 23:

Line 24, "be" should read --have--.

COLUMN 31:

Line 50, "were added, and" should read --,--; and
    Line 51, "thereto" should be deleted.

COLUMN 39:

Line 2, "liquid" should read --liquid.--.

COLUMN 46:

Tab 4 Pr 6, " 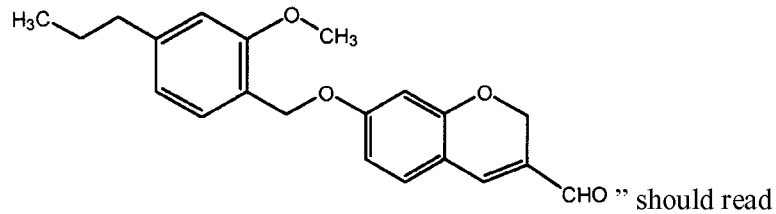 " should read

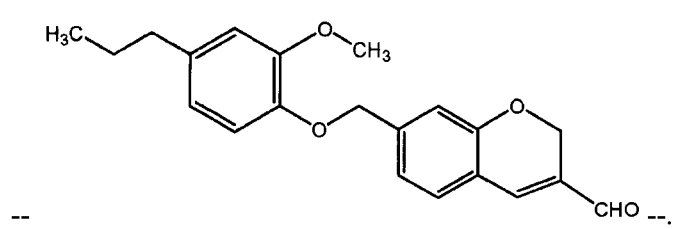

--                                                                    --.

COLUMNS 127-128:

Line numbers 5-65 should be deleted.

CERTIFICATE OF CORRECTION (continued)
U.S. Pat. No. 8,193,378 B2

COLUMN 135:

Ex 75,

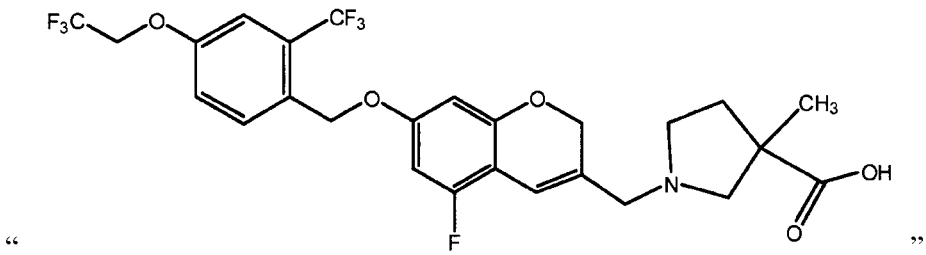

" "

should read

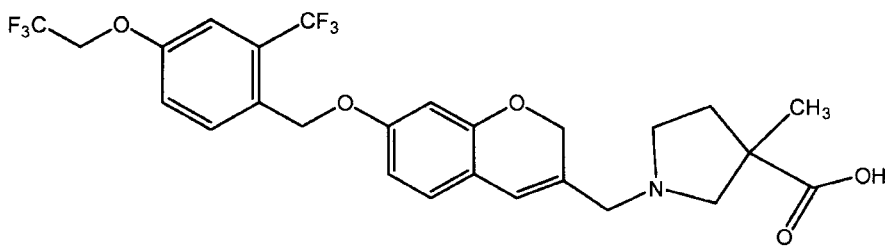

-- --.

COLUMN 137:

Ex 84,

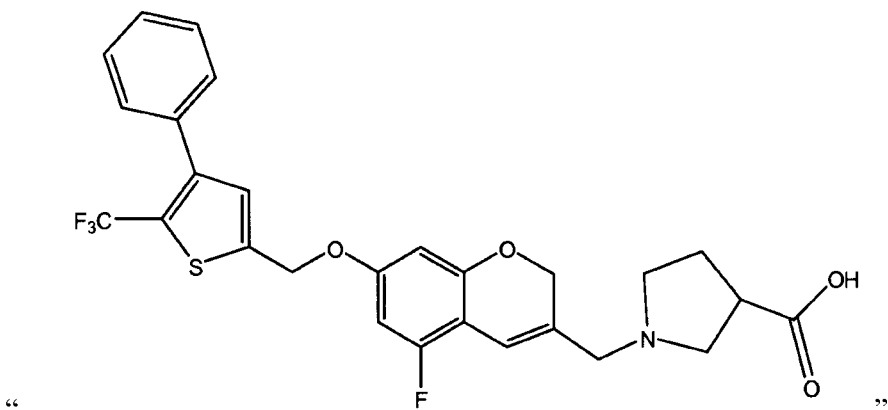

" "

should read

CERTIFICATE OF CORRECTION (continued)
U.S. Pat. No. 8,193,378 B2

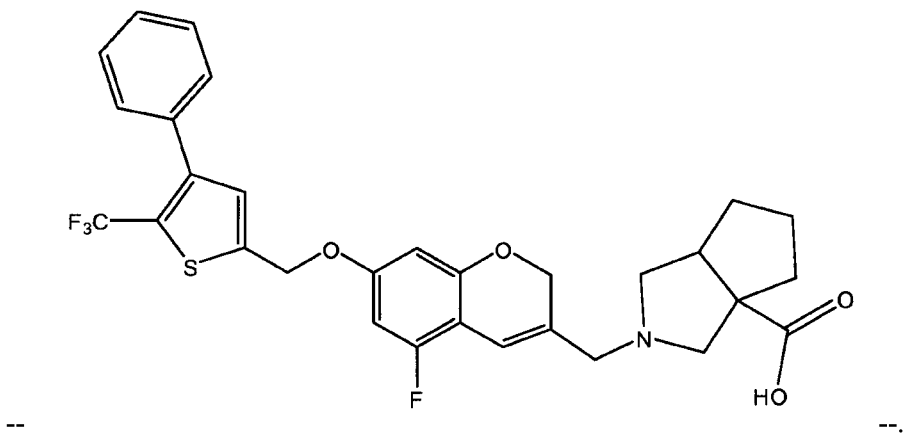

-- --.

COLUMN 227:

Ex 210 Ex3, "rotaners" should read --rotamers--.

COLUMN 234:

Claim 7, Line 36, "-C(=O)OH," should read --C(=O)OH;--; and
Claim 7, Line 37, "-H; A" should read -- -H; and A--.

COLUMN 236:

Claim 11, Line 7, "claim 1" should read --claim 1,--;
Claim 13, Line 10, "formula" should read --formula:--; and
Claim 14, Line 23, "claim 13" should read --claim 13,--.

UNITED STATES PATENT AND TRADEMARK OFFICE
CERTIFICATE OF CORRECTION

PATENT NO. : 8,193,378 B2
APPLICATION NO. : 13/131343
DATED : June 5, 2012
INVENTOR(S) : Harada et al.

It is certified that error appears in the above-identified patent and that said Letters Patent is hereby corrected as shown below:

In the claims

COLUMN 233:

Line 25, Claim 1,

"
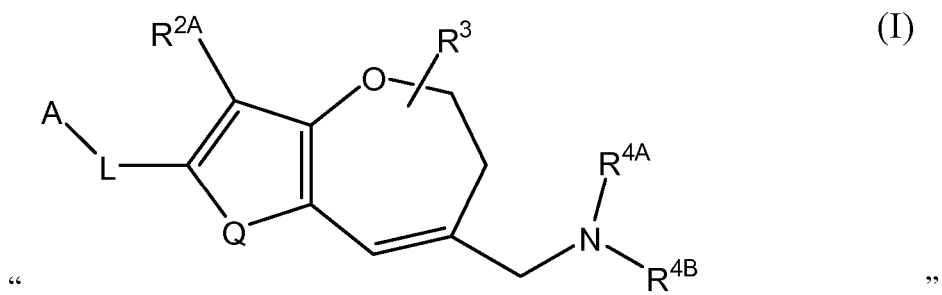
(I)
"

should read

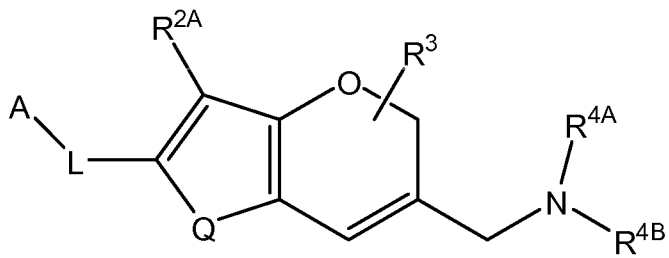
(I)

--    --.

Signed and Sealed this
Twenty-ninth Day of March, 2016

Michelle K. Lee
*Director of the United States Patent and Trademark Office*